(12) United States Patent
Barrett et al.

(10) Patent No.: US 7,465,808 B2
(45) Date of Patent: *Dec. 16, 2008

(54) CCK-1 RECEPTOR MODULATORS

(75) Inventors: Terrance D. Barrett, Encinitas, CA (US); J. Guy Breitenbucher, Escondido, CA (US); Laurent Gomez, San Diego, CA (US); Michael D. Hack, San Diego, CA (US); Liming Huang, San Diego, CA (US); Kelly J. McClure, San Diego, CA (US); Magda F. Morton, San Diego, CA (US); Clark A. Sehon, West Chester, PA (US); Nigel P. Shankley, Solana Beach, CA (US)

(73) Assignee: Janssen Pharmaceutica, N.V., Beerse (BE)

( * ) Notice: Subject to any disclaimer, the term of this patent is extended or adjusted under 35 U.S.C. 154(b) by 240 days.

This patent is subject to a terminal disclaimer.

(21) Appl. No.: 11/230,200

(22) Filed: Sep. 19, 2005

(65) Prior Publication Data

US 2006/0014817 A1 Jan. 19, 2006

Related U.S. Application Data

(63) Continuation of application No. 10/612,150, filed on Jul. 2, 2003, now Pat. No. 7,037,931.

(60) Provisional application No. 60/393,493, filed on Jul. 3, 2002.

(51) Int. Cl.
*C07D 231/12* (2006.01)
*A61K 31/415* (2006.01)
*A61K 31/4155* (2006.01)

(52) U.S. Cl. ............... 548/377.1; 548/364.1; 548/364.4; 514/406

(58) Field of Classification Search ............... 548/364.1, 548/364.4, 377.1; 514/406
See application file for complete search history.

(56) References Cited

U.S. PATENT DOCUMENTS

| | | | |
|---|---|---|---|
| 4,826,868 A | 5/1989 | Wachter et al. | |
| 5,051,518 A | 9/1991 | Murray et al. | |
| 5,164,381 A | 11/1992 | Wachter et al. | |
| 6,750,230 B2 | 6/2004 | Corbau et al. | |
| 6,750,239 B2 | 6/2004 | Hale et al. | |
| 6,784,185 B2 | 8/2004 | Allerton et al. | |
| 6,815,428 B2 | 11/2004 | Ohsumi et al. | |
| 6,838,458 B2 | 1/2005 | Sakya | |
| 6,846,838 B2 | 1/2005 | Slusarchyk et al. | |
| 6,849,653 B2 | 2/2005 | Clare et al. | |
| 6,852,717 B2 | 2/2005 | Cirillo et al. | |
| 6,875,789 B2 | 4/2005 | Tang et al. | |
| 7,037,931 B2 * | 5/2006 | Barrett et al. ............... | 514/406 |

FOREIGN PATENT DOCUMENTS

| | | |
|---|---|---|
| EP | 0 467 614 | 1/1992 |
| EP | 0293220 | 8/1994 |
| WO | WO 95/04720 | 2/1995 |
| WO | WO 97/11704 | 4/1997 |
| WO | WO 97/46534 | 11/1997 |
| WO | WO 97/46534 | 12/1997 |
| WO | WO 01/66539 | 9/2001 |
| WO | WO 01/85723 | 11/2001 |
| WO | WO 01/85724 | 11/2001 |
| WO | WO 01/90078 | 11/2001 |
| WO | WO 03/24958 A2 | 3/2003 |
| WO | WO 03/024958 A2 | 3/2003 |
| WO | WO 04/007463 A1 | 1/2004 |
| WO | WO 2004/007463 A1 | 1/2004 |

OTHER PUBLICATIONS

Gigoux, V. et al. Arginine 336 and Asparagine 333 of the Human Cholecystokinin-A Receptor Binding Site Interact with the Penultimate Aspartic Acid and the C-terminal Amide of Cholecystokinin. J. Biol. Chem. 1999, 274(29):20457-20464.

Harper, E.A. et al. Analysis of Variation in L-365,260 Competition Curves in Radioligand Binding Assays. Br. J. Pharmacol. 1996, 118:1717-1726.

Hull, R.A. et al. 2-Naphthalenesulphonyl L-aspartyl-(2-phenethyl)amide (2-NAP)-A Selective Cholecystokinin CCKA-Receptor Antagonist. Br. J. Pharmacol. 1993, 108:734-740.

Klapars, A. et al. A General and Efficient Copper Catalyst for the Amidation of Aryl Halides and the N-Arylation of Nitrogen Heterocycles. J. Am. Chem. Soc. 2001, 123(31):7727-7729.

Klausner, Y.S. and Bodanszky, M. The Azide Method in Peptide Synthesis: Its Scope and Limitations. Synthesis 1974, 8:549-559.

Moradi, W.A. and Buchwald, S.L. Palladium-Catalyzed alpha-Arylation of Esters. J. Am. Chem. Soc. 2001, 123(33):7996-8002.

Morton, M.F. et al. Pharmacological Comparison of the Alternatively Spliced Short and Long CCK2 Receptors. Br. J. Pharmacol. 2003, 140(1):218-224.

Murray, W.V. et al. Synthesis of 3-(1,5-Diphenyl-3-pyrazolyl)aryl Propanates. J. Heterocycl. Chem. 1990, 27:1933-1940

Penning, T.D. et al. Synthesis and Biological Evaluation of the 1,5-Diarylpyrazole Class of Cyclooxygenase-2 Inhibitors: Identification of 4-[5-(4-Methylphenyl)-3-(trifluoromethyl)-1H-pyrazol-1-yl]benzenesulfo- namide (SC-58635, Celecoxib). J. Med. Chem. 1997, 40(9):1347-1365.

Saito, T. et al. Total Synthesis of the Furaquinocins. J. Am. Chem. Soc. 1998, 120(45):11633-11644.

Shen, D.-M. et al. Versatile and Efficient Solid-Phase Syntheses of Pyrazoles and Isoxazoles. Organic Letters 2000, 2(18):2789-2792.

Tullio, P. et al. Therapeutic and Chemical Developments of Cholecystokinin Receptor Ligands. Exp. Opin. Invest. Drugs 2000, 9(1):129-146.

Wang, Z. et al. A New Synthesis for Methyl 2-Benzyloxyphenylacetate. Synth. Commun. 1999, 29(13):2361-2364.

Wolfe, J.P. et al. Simple Efficient Catalyst System for the Palladium-Catalyzed Amination of Aryl Chlorides, Bromides, and Triflates. J. Org. Chem. 2000, 65(4):1158-1174.

(Continued)

*Primary Examiner*—Kamal Saeed
*Assistant Examiner*—Jason M Nolan

(57) ABSTRACT

There are provided by the present invention certain pyrazole based CCK-1 receptor modulators.

3 Claims, No Drawings

OTHER PUBLICATIONS

Kirby et al., Journal of Organic Chemistry, 1963, vol. 28(9), pp. 2266-2271.
Alberola et al Synth Commun 1986 vol. 16(6) pp. 673-680.
Alberola et al Heterocycles 2001 vol. 55(2) pp. 331-351.
Bohrisch et al Synthesis 1991 vol. 12 pp. 1153-1156.
Buchwald J Org Chem 2000 vol. 65 pp. 1158-1174.
Cabarrocas et al Tetrahedron Assymetry 2000 pp. 11(12) pp. 2483-2493.
Cheng and Prusoff Biochem Pharmacol 1973 vol. 22 pp. 3099-3108.
Chowdhury et al Tetrahedron 1999 vol. 55(22) pp. 7011-7016.
De La Cal et al Synth Commun 1989 vol. 19(5) pp. 1039-1045.
De Tullio et al Exp Opinion Invest Drugs 2000 vol. 9(1) pp. 129-146.
Evans et al., J Am Chem Soc 1990 vol. 112(10) pp. 4011-4030.
Gonzales et al Synth Commun 1995 vol. 275(7) pp. 1005-1014.
Huang et al Org Lett 2000 vol. 2(18) pp. 2833-2836.
Jeong et al Tetrahedron Lett 2002 vol. 43(4) pp. 7171-7174.
Karpov et al Synthesis 2003 vol. 18 pp. 2815-2826.
Larsen et al J Am Chem Soc 1989 vol. 111(19) pp. 7650-7651.
Michael et al Pure Appl Chem 1999 vol. 71(6) pp. 979-988.
Miller et al J. Heterocyl Chem 1993 vol. 30 pp. 755-763.
Molteni et al Synthesis 2002 vol. 12 pp. 1669-1674.
Moradi et al J Am Chem Soc 2001 vol. 123 pp. 7996-8002.
Murray et al J Heterocycl Chem 1989 vol. 26 pp. 1389-1392.
Nahm et al Tetrahedron Lett 1981 vol. 22(39) pp. 3815-3818.
Ochiai et al J Chem Soc Chem Commun 1990 vol. 2 pp. 118-119.
Saito et al. J. Am. Chem. Soc. 1998 vol. 120 p. 11633.
Seko et al Tetrahedron Lett 1996 vol. 39(44) pp. 8117-8120.
Sibi et al Org Prep Proced Int 1993 vol. 25(1) pp. 15-40.
Smirnova et al Russ Chem Rev (Engl Transl) 2000 vol. 69(12) pp. 1021-1036.
Wang et al Tetrahedron Lett 2000 vol. 41(24) pp. 4713-4716.

\* cited by examiner

CCK-1 RECEPTOR MODULATORS

This application is a continuation of U.S. Ser. No. 10/612,150 filed on Jul. 2, 2003, now U.S. Pat. No. 7,037,931 which claims priority to U.S. Ser. No. 60/393,493 filed Jul. 3, 2002. The complete disclosures of the aforementioned related U.S. patent applications are hereby incorporated herein by reference for all purposes.

This invention relates to CCK-1 receptor modulators for the treatment of gastrointestinal and CNS disorders. More particularly, this invention relates to certain pyrazole compounds useful as selective agonists or antagonists of the CCK-1 receptor as well as methods for making such compounds.

BACKGROUND OF THE INVENTION

Cholecystokinin (CCK) is a brain-gut peptide hormone located both in the gastrointestinal system and in the central nervous system. The actions of CCK are mediated by two G-protein coupled receptors: CCK-1 (formerly CCK-A) and CCK-2 (formerly CCK-B/gastrin). These CCK receptors are expressed throughout the gastrointestinal system and in different parts of the central nervous system including the cortex, the striatum, the hypothalamus, the hippocampus, the olfactory bulb, the vagal afferent neurones, in different enteric nerves and in the genital tract.

CCK has a number of biological actions. CCK is the primary hormonal regulator of gall bladder contraction in response to a meal. CCK stimulates pancreatic and biliary secretions and regulates GI motility and specifically gut and colonic motility. CCK promotes protein synthesis and cell growth, especially in the GI system and in the pancreas. CCK is involved in mediating satiety after a meal. CCK is an important neuromodulator and neurotransmitter involved in anxiety and panic disorder. CCK modulates the release of dopamine. CCK is also known to antagonize morphine and beta-endorphin induced analgesia and the action on nociception. A review of CCK receptors, ligands and the activities thereof may be found in P. Tullio et al., Exp. Opin. Invest. Drugs (2000) 9(1), pp 129-146.

A number of CCK-1 receptor antagonists are presently in clinical trials including, tarazepide, devazepide and lintitript. Phase III equivalent trials are in progress by Rotta Research Group and Forest Laboratories on dexloxiglumide, a CCK-1 antagonist for the treatment of constipation, irritable bowel syndrome and non-ulcer dyspepsia.

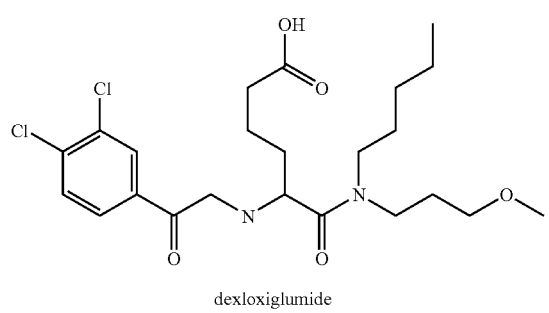

dexloxiglumide

Also, Kaken Pharmaceuticals and Mitsubishi-Tokyo Pharmaceuticals are awaiting registration in Japan on loxiglumide, a CCK-1 receptor antagonist for the treatment of GI cancers and pancreatitis. Loxiglumide is the racemate of dexloxiglumide.

A number of CCK-1 receptor agonists are under preclinical investigation. Glaxo Smith Kline, Inc is investigating GW 5823, GW 7854, GW 7178 and GW 8573, 1,5-benzodiaepines for the treatment of gallstones, gastrointestinal disease and obesity.

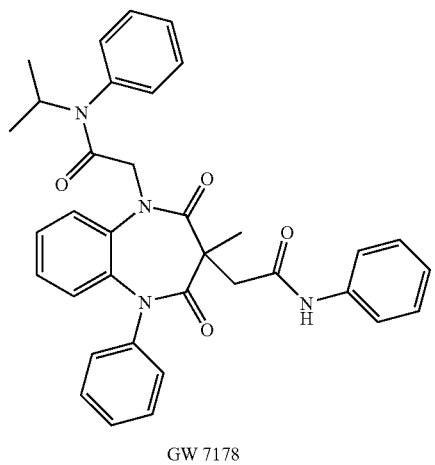

GW 7178

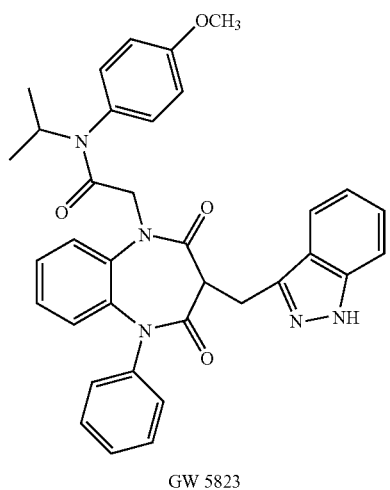

GW 5823

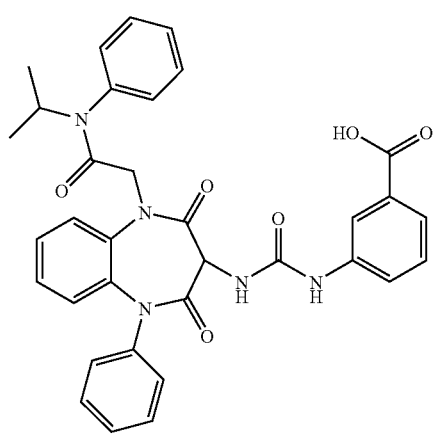

GW 7854

Also, Pfizer is investigating the CCK-1 receptor agonist, PD 170292, for 15 obesity.

In U.S. Pat. Nos. 4,826,868 and 5,164,381 there are disclosed certain pyrazoles for alleviating inflammation and treating cardiovascular disorders in mammals having the general formula:

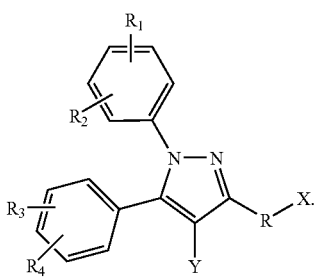

These compounds are not taught to be CCK-1 receptor modulators nor suggested to be useful in the treatment of disease states mediated by CCK-1 receptor activity.

In U.S. Pat. No. 5,051,518 there are disclosed certain pyrazoles for alleviating inflammation and treating cardiovascular disorders in mammals having the general formula:

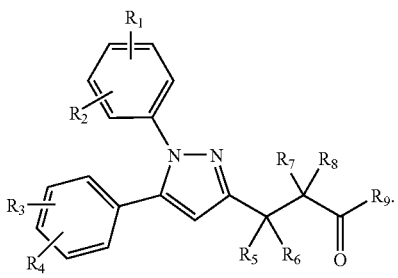

These compounds are not taught to be CCK-1 receptor modulators nor suggested to be useful in the treatment of disease states mediated by CCK-1 receptor activity.

Applicants have now discovered that certain pyrazoles as described below are useful CCK-1 receptor modulators, agonists and antagonists, and most particularly antagonists. As such, these compounds are useful to treat a number of disease states mediated by CCK.

SUMMARY OF THE INVENTION

There are provided by the present invention CCK-1 receptor antagonists which have the general formula:

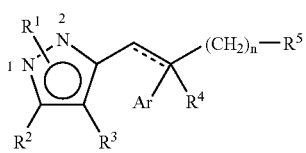

(I)

wherein, $R^1$ is a 1- or 2-position substituent selected from the group consisting of hydrogen, a) phenyl, optionally mono-, di- or tri-substituted with $R^p$ or di-substituted on adjacent carbons with —$OC_{1-4}$alkyleneO—, —$(CH_2)_{2-3}NH$—, —$(CH_2)_{1-2}NH(CH_2)$—, —$(CH_2)_{2-3}N(C_{1-4}alkyl)$- or —$(CH_2)_{1-2}N(C_{1-4}alkyl)(CH_2)$—;

$R^p$ is selected from the group consisting of —OH, —$C_{1-6}$alkyl, —$OC_{1-6}$alkyl, phenyl, —Ophenyl, benzyl, —Obenzyl, —$C_{3-6}$cycloalkyl, —$OC_{3-6}$cycloalkyl, —CN, —$NO_2$, —$N(R^y)R^z$ (wherein $R^y$ and $R^z$ are independently selected from H, $C_{1-6}$alkyl or $C_{1-6}$alkenyl, or $R^y$ and $R^z$ may be taken together with the nitrogen of attachment to form an otherwise aliphatic hydrocarbon ring, said ring having 4 to 7 members, optionally having one carbon replaced with >O, =N—, >NH or >$N(C_{1-4}$alkyl), optionally having one carbon substituted with —OH, and optionally having one or two unsaturated bonds in the ring), —(C=O)$N(R^y)R^z$, —(N—$R^t$)$COR^t$, —(N—$R^t$)$SO_2C_{1-6}$alkyl (wherein $R^t$ is H or $C_{1-6}$alkyl or two $R^t$ in the same substituent may be taken together with the amide of attachment to form an otherwise aliphatic hydrocarbon ring, said ring having 4 to 6 members), —(C=O)$C_{1-6}$alkyl, —$(S=O)_n$)—$C_{1-6}$alkyl (wherein n is selected from 0, 1 or 2), —$SO_2N(R^y)R^z$, —$SCF_3$, halo, —$CF_3$, —$OCF_3$, —COOH and —$COOC_{1-6}$alkyl;

b) phenyl or pyridyl fused at two adjacent ring members to a three membered hydrocarbon moiety to form a fused five membered aromatic ring, which moiety has one carbon atom replaced by >O, >S, >NH or >$N(C_{1-4}$alkyl) and which moiety has up to one additional carbon atom optionally replaced by N, the fused rings optionally mono-, di- or tri-substituted with $R^p$;

c) phenyl fused at two adjacent ring members to a four membered hydrocarbon moiety to form a fused six membered aromatic ring, which moiety has one or two carbon atoms replaced by N, the fused rings optionally mono-, di- or tri-substituted with $R^p$;

d) naphthyl, optionally mono-, di- or tri-substituted with $R^p$;

e) a monocyclic aromatic hydrocarbon group having five ring atoms, having a carbon atom which is the point of attachment, having one carbon atom replaced by >O, >S, >NH or >$N(C_{1-4}$alkyl), having up to two additional carbon atoms optionally replaced by N, optionally mono- or di-substituted with $R^p$ and optionally benzo fused on the condition that two or fewer of said carbon ring atoms are replaced by a heteroatom, where the benzo fused moiety is optionally mono- di- or tri-substituted with $R^p$;

f) a monocyclic aromatic hydrocarbon group having six ring atoms, having a carbon atom which is the point of attachment, having one or two carbon atoms replaced by N, having one N optionally oxidized to the N-oxide, optionally mono- or di-substituted with $R^p$ and optionally benzo fused, where the benzo fused moiety is optionally mono- or di-substituted with $R^p$;

g) adamantanyl or monocyclic $C_{5-7}$cycloalkyl, optionally having one or two carbon members optionally replaced with >O, >NH or >$N(C_{1-4}$alkyl) and optionally having one or two unsaturated bonds in the ring and optionally having one of the ring atoms substituted with —OH, =O or —$CH_3$;

h) a $C_{1-8}$alkyl;

i) $C_{1-4}$alkyl, mono-substituted by a substituent selected from the group consisting of any one of a) to g);

$R^2$ is selected from the group consisting of:
  i) phenyl, optionally mono-, di- or tri- substituted with $R^q$ or di-substituted on adjacent carbons with —$OC_{1-4}$alkyleneO—, —$(CH_2)_{2-3}$NH—, —$(CH_2)_{1-2}$NH($CH_2$)—, —$(CH_2)_{2-3}$N($C_{1-4}$alkyl)- or —$(CH_2)_{1-2}$N($C_{1-4}$alkyl)($CH_2$)—;
    $R^q$ is selected from the group consisting of —OH, —$C_{1-6}$ alkyl, —$OC_{1-6}$alkyl, phenyl, —Ophenyl, benzyl, —Obenzyl, —$C_{3-6}$cycloalkyl, —$OC_{3-6}$cycloalkyl, —CN, —$NO_2$, —N($R^y$)$R^z$ (wherein $R^y$ and $R^z$ are independently selected from H, $C_{1-6}$alkyl, $C_{1-6}$alkenyl, or $R^y$ and $R^z$ may be taken together with the nitrogen of attachment to form an otherwise aliphatic hydrocarbon ring, said ring having 4 to 7 members, optionally having one carbon replaced with >O, =N—, >NH or >N($C_{1-4}$alkyl), optionally having one carbon substituted with —OH, and optionally having one or two unsaturated bonds in the ring), —(C=O)N($R^y$)$R^z$, —(N—$R^t$)COR$^t$, —(N—$R^t$)$SO_2C_{1-6}$alkyl (wherein $R^t$ is H or $C_{1-6}$alkyl or two $R^t$ in the same substituent may be taken together with the amide of attachment to form an otherwise aliphatic hydrocarbon ring, said ring having 4 to 6 members), —(C=O)$C_{1-6}$alkyl, —(S=(O)$_n$)—$C_{1-6}$alkyl (wherein n is selected from 0, 1 or 2), —$SO_2$N($R^y$)$R^z$, —$SCF_3$, halo, —$CF_3$, —$OCF_3$, —COOH and —$COOC_{1-6}$alkyl;
  ii) phenyl or pyridyl fused at two adjacent ring members to a three membered hydrocarbon moiety to form a fused five membered aromatic ring, which moiety has one carbon atom replaced by >O, >S, >NH or >N($C_{1-4}$alkyl) and which moiety has up to one additional carbon atom optionally replaced by N, the fused rings optionally mono-, di- or tri-substituted with $R^q$;
  iii) phenyl fused at two adjacent ring members to a four membered hydrocarbon moiety to form a fused six membered aromatic ring, which moiety has one or two carbon atoms replaced by N, the fused rings optionally mono-, di- or tri-substituted with $R^q$;
  iv) naphthyl, optionally mono-, di- or tri-substituted with $R^q$;
  v) a monocyclic aromatic hydrocarbon group having five ring atoms, having a carbon atom which is the point of attachment, having one carbon atom replaced by >O, >S, >NH or >N($C_{1-6}$alkyl), having up to one additional carbon atoms optionally replaced by N, optionally mono- or di-substituted with $R^q$ and optionally benzo fused on the condition that two or fewer of said carbon ring atoms are replaced by a heteroatom, where the benzo fused moiety is optionally mono- di- or tri-substituted with $R^q$; and
  vi) a monocyclic aromatic hydrocarbon group having six ring atoms, having a carbon atom which is the point of attachment, having one or two carbon atoms replaced by N, having one N optionally oxidized to the N-oxide, optionally mono- or di-substituted with $R^p$ and optionally benzo fused, where the benzo fused moiety is optionally mono- or di-substituted with $R^q$;

$R^3$ is selected from the group consisting of H, halo, and $C_{1-6}$alkyl;

n is selected from 0,1, or 2, with the proviso that where $R^5$ is attached through —S—, the n is 1 or 2;

$R^4$ is selected from the group consisting of H, halo or $C_{1-6}$alkyl or a covalent bond in the case where the a double bond is present in the above structure;

Ar is selected from the group consisting of:
  A) phenyl, optionally mono-, di- or tri-substituted with $R^r$ or di-substituted on adjacent carbons with —$OC_{1-4}$alkyleneO—, —$(CH_2)_{2-3}$NH—, —$(CH_2)_{1-2}$NH($CH_2$)—, —$(CH_2)_{2-3}$N($C_{1-4}$alkyl)- or —$(CH_2)_{1-2}$N($C_{1-4}$alkyl)($CH_2$)—;
    $R^r$ is selected from the group consisting of —OH, —$C_{1-6}$ alkyl, —$OC_{1-6}$alkyl, phenyl, —Ophenyl, benzyl, —Obenzyl, —$C_{3-6}$cycloalkyl, —$OC_{3-6}$cycloalkyl, —CN, —$NO_2$, —N($R^y$)$R^z$ (wherein $R^y$ and $R^z$ are independently selected from H, $C_{1-6}$alkyl or $C_{1-6}$alkenyl, or $R^y$ and $R^z$ may be taken together with the nitrogen of attachment to form an otherwise aliphatic hydrocarbon ring, said ring having 4 to 7 members, optionally having one carbon replaced with >O, =N—, >NH or >N($C_{1-4}$alkyl), optionally having one carbon substituted with —OH, and optionally having one or two unsaturated bonds in the ring), —(C=O)N($R^y$)$R^z$, —(N—$R^t$)COR$^t$, —(N—$R^t$)$SO_2C_{1-6}$alkyl (wherein $R^t$ is H or $C_{1-6}$alkyl or two $R^t$ in the same substituent may be taken together with the amide of attachment to form an otherwise aliphatic hydrocarbon ring, said ring having 4 to 6 members), —(C=O)$C_{1-6}$alkyl, —(S=(O)$_n$)—$C_{1-6}$alkyl (wherein n is selected from 0, 1 or 2), —$SO_2$N($R^y$)$R^z$, —$SCF_3$, halo, —$CF_3$, —$OCF_3$, —COOH and —$COOC_{1-6}$alkyl;
  B) phenyl or pyridyl fused at two adjacent ring members to a three membered hydrocarbon moiety to form a fused five membered aromatic ring, which moiety has one carbon atom replaced by >O, >S, >NH or >N($C_{1-4}$alkyl) and which moiety has up to one additional carbon atom optionally replaced by N, the fused rings optionally mono-, di- or tri-substituted with $R^r$;
  C) phenyl fused at two adjacent ring members to a four membered hydrocarbon moiety to form a fused six membered aromatic ring, which moiety has one or two carbon atoms replaced by N, the fused rings optionally mono-, di- or tri-substituted with $R^r$;
  D) naphthyl, optionally mono-, di- or tri-substituted with $R^r$;
  E) a monocyclic aromatic hydrocarbon group having five ring atoms, having a carbon atom which is the point of attachment, having one carbon atom replaced by >O, >S, >NH or >N($C_{1-4}$alkyl), having up to one additional carbon atoms optionally replaced by N, optionally mono- or di-substituted with $R^r$ and optionally benzo fused on the condition that two or fewer of said carbon ring atoms are replaced by a heteroatom, where the benzo fused moiety is optionally mono- di- or tri-substituted with $R^r$; and
  F) a monocyclic aromatic hydrocarbon group having six ring atoms, having a carbon atom which is the point of attachment, having one or two carbon atoms replaced by N, having one N optionally oxidized to the N-oxide, optionally mono- or di-substituted with $R^r$ and optionally benzo fused, where the benzo fused moiety is optionally mono- or di-substituted with $R^r$;

$R^5$ is selected from the group consisting of;
  I) —$COOR^6$, where $R^6$ is selected from the group consisting of H and —$C_{1-4}$alkyl,
  II) —$CONR^7R^8$, where $R^7$ and $R^8$ are independently selected from the group consisting of hydrogen, $C_{1-6}$alkyl and $C_{3-6}$cycloalkyl optionally hydroxy substituted, or $R^7$ and $R^8$ may be taken together with the nitrogen of attachment to form an otherwise aliphatic hydrocarbon ring, said ring having 5 to 7 members, optionally having one carbon replaced with >O, =N—, >NH or >N($C_{1-4}$alkyl) and optionally having one or two unsaturated bonds in the ring; and III) tetrazolyl, [1,2,4]triazol-3-ylsulfanyl, [1,2,4]triazol-3-ylsulfonyl, [1,2,4]triazole-3-sulfinyl and [1,2,3]triazol-4-ylsulfanyl, [1,2,3]triazol-4-ylsulfonyl, [1,2,3]triazol-4-sulfinyl.

and enantiomers, diastereomers and pharmaceutically acceptable salts and esters thereof.

DETAILED DESCRIPTION OF THE INVENTION

Considering the above referenced U.S. Pat. No. 5,051,518, columns 20 and 21, Applicant's invention does not include compounds of the following formula, and/or racemic mixtures of such compounds and/or pharmaceutical compositions containing such compounds or racemic mixtures thereof:

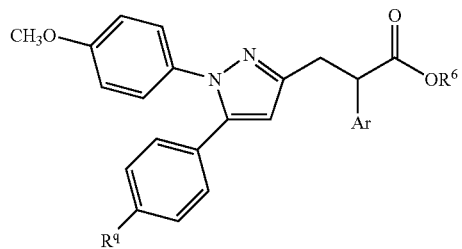

where $R^q$ Ar and $R^6$ are selected concurrently from the groups consisting of:

| CP# | $R^q$ | Ar | $R^6$ |
|---|---|---|---|
| R1 | —Cl | phenyl- | —CH$_2$CH$_3$ |
| R2 | —Cl | 3,4-diMeO-phenyl | —CH$_2$CH$_3$ |
| R3 | —Cl | 4-MeO-phenyl- | —CH$_2$CH$_3$ |
| R4 | —CH$_3$ | 2-naphthyl- | —CH$_2$CH$_3$ |
| R5 | —CH$_3$ | 1-naphthyl- | —CH$_2$CH$_3$ |
| R6 | —CH$_3$ | 2-MeO-phenyl- | —CH$_2$CH$_3$ |
| R7 | —CH$_3$ | 2-pyridyl- | —CH$_2$CH$_3$ |
| R8 | —CH$_3$ | 2-carboxymethyl-phenyl- | —CH$_2$CH$_3$ |
| R9 | —CH$_3$ | 3-pyridyl- | —CH$_2$CH$_3$ |
| R10 | —Cl | 4-MeO-phenyl- | —H |
| R11 | —Cl | 3,4-diMeO-phenyl | —H |
| R12 | —CH$_3$ | 2-naphthyl- | —H |
| R13 | —CH$_3$ | 1-naphthyl- | —H |
| R14 | —CH$_3$ | 2-MeO-phenyl- | —H |
| R15 | —CH$_3$ | 2-carboxy-phenyl- | —H |
| R16 | —CH$_3$ | 4-biphenyl | —CH$_2$CH$_3$ |
| R17 | —CH$_3$ | 4-biphenyl | —H |

The instant invention does include the use of such compounds and/or racemic mixtures thereof and/or pharmaceutical compositions containing such compounds or racemic mixtures thereof to treat patients (humans and other mammals) with disorders related to the modulation of the CCK-1 receptor. The instant invention also includes methods of making such compounds and/or racemic mixtures thereof.

Preferably $R^1$, optionally substituted with $R^p$ as described above, is selected from the group consisting of hydrogen:

a) phenyl, 5-, 6-, 7-, 8-benzo-1,4-dioxanyl, 4-, 5-, 6-, 7-benzo-1,3-dioxolyl, 4-, 5-, 6-, 7-indolinyl, 4-, 5-, 6-, 7-isoindolinyl, 1,2,3,4-tetrahydro-quinolin-4, 5, 6 or 7-yl, 1,2,3,4-tetrahydro-isoquinolin-4, 5, 6 or 7-yl, b) 4-, 5-, 6- or 7-benzoxazolyl, 4-, 5-, 6- or 7-benzothiophenyl, 4-, 5-, 6- or 7-benzofuranyl, 4-, 5-, 6- or 7-indolyl, 4-, 5-, 6- or 7-benzthiazolyl, 4-, 5-, 6- or 7-benzimidazolyl, 4-, 5-, 6- or 7-indazolyl, imidazo[1,2-a]pyridin-5, 6, 7 or 8-yl, pyrazolo[1,5-a]pyridin-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4, 5 or 7-yl, 1H-pyrrolo[3,2-b]pyridin-5, 6 or 7-yl, c) 5-, 6-, 7- or 8-isoquinolinyl, 5-, 6-, 7- or 8-quinolinyl, 5-, 6-, 7- or 8-quinoxalinyl, 5-, 6-, 7- or 8-quinazolinyl, d) naphthyl, e) furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, 3-indoxazinyl, 2-benzoxazolyl, 2- or 3-benzothiophenyl, 2- or 3-benzofuranyl, 2- or 3-indolyl, 2-benzthiazolyl, 2-benzimidazolyl, 3-indazolyl, f) pyridinyl, pyridinyl-N-oxide, pyrazinyl, pyrimidinyl, pyridazinyl, 1-, 3- or 4-isoquinolinyl, 2-, 3- or 4-quinolinyl, 2- or 3-quinoxalinyl, 2- or 4-quinazolinyl, 1-oxy-pyridin-2, 3, or 4-yl, g) cyclopentyl, cyclohexyl, cycloheptyl, piperidin-2,3 or 4-yl, 2-pyrrolin-2, 3, 4 or 5-yl, 3-pyrrolin-2 or 3-yl, 2-pyrazolin-3, 4 or 5-yl, morpholin-2, 3, 5 or 6-yl, thiomorpholin-2, 3, 5 or 6-yl, piperazin-2, 3, 5 or 6-yl, pyrrolidin-2 or 3-yl, homopiperidinyl, adamantanyl, h) methyl, ethyl, n-propyl, i-propyl, n-butyl, i-butyl, t-butyl, n-pentyl, pent-2-yl, hexyl, hex-2-yl, and i) —C$_{1-2}$alkyl mono-substituted with any one of the preferred substituents of a) to g).

Most preferably $R^1$, optionally substituted with $R^p$ as described above, is selected from the group consisting of H, methyl, phenyl, benzyl, cyclohexyl, cyclohexylmethyl, pyridinyl, pyridinylmethyl and pyridinyl-N-oxide. Specific $R^1$ are selected from the group consisting of phenyl, 2-methoxy-phenyl, 3-methoxy-phenyl, 4-methoxy-phenyl, 2,3-dimethoxy-phenyl, 3,4-dimethyoxy-phenyl, 2-chloro-phenyl, 3-chloro-phenyl, 4-chloro-phenyl, 2,4-dicloro-phenyl, 3,4-dichlorophenyl, 2,4-dichlorophenyl, 2,5-dichlorophenyl, 2-methyl-phenyl, 3-methyl-phenyl, 4-methyl-phenyl, 2,5-dimethyl-phenyl, 2-trifluoromethyl-phenyl, 3-trifluoromethyl-phenyl, 4-trifluoromethyl-phenyl, 3-trifluoromethoxy-phenyl, 4-trifluoromethoxy-phenyl, 4-t-butyl-phenyl, benzyl, cyclohexyl, pyridin-2-yl, pyridin-3-yl, pyridin-4-yl, 4-triflouromethyl-2-pyridyl, 2-pyridyl-N-oxide, 4-methanesulfonyl-phenyl, 4-phenoxy-phenyl, 4-isopropyl-phenyl, 4-ethoxy-phenyl, 4-hydroxy-phenyl, 4-pyridinyl-methyl, benzo[1,3]diox-5-yl, 2,3-diydro benzo[1,4]dioxin-6-yl and cyclohexylmethyl.

Preferably $R^p$ is selected from the group consisting of —OH, —CH$_3$, —CH$_2$CH$_3$, i-propyl, t-butyl, —OCH$_3$, —OCH$_2$CH$_3$, —OCH(CH$_3$)$_2$, cyclopropyl, cyclobutyl, cyclopentyl, cyclohexyl, —Ocyclopentyl, —Ocyclohexyl, phenyl, —Ophenyl, benzyl, —Obenzyl, —CN, —NO$_2$, —C(O)NH$_2$, —C(O)N(CH$_3$)$_2$, —C(O)NH(CH$_3$), —NH(CO)H, —NHCOCH$_3$, —NCH$_3$(CO)H, —NCH$_3$COCH$_3$, —NHSO$_2$CH$_3$, —NCH$_3$SO$_2$CH$_3$, —C(O)CH$_3$, —SOCH$_3$, —SO$_2$CH$_3$, —SO$_2$NH$_2$, —SO$_2$NHCH$_3$, —SO$_2$N(CH$_3$)$_2$, —SCF$_3$, —F, —Cl, —Br, I, —CF$_3$, —OCF$_3$, —COOH, —COOCH$_3$, —COOCH$_2$CH$_3$, —NH$_2$, —NHCH$_3$, —NHCH$_2$CH$_3$, —NH(CH$_2$CH$_2$CH$_3$), —NH(CH(CH$_3$) CH$_2$CH$_3$), —NH(allyl), —NH(CH$_2$(CH$_3$)$_2$), —N(CH$_3$)$_2$, —N(CH$_2$CH$_3$)$_2$, —NCH$_3$(CH$_2$CH$_2$CH$_3$), —NCH$_3$ (CH$_2$CH$_3$), —NCH$_3$(CH(CH$_3$)$_2$), pyrrolidin-2-one-1-yl, azetidinyl, piperidin-1-yl, 2- or 3-pyrrolin-1-yl, morpholin-4-yl, thiomorpholin-4-yl, piperazin-1-yl, pyrrolidin-1-yl, homopiperidin-1-yl.

Most preferably $R^p$ is selected from the group consisting of hydrogen, methyl, methoxy, ethoxy, chloro, fluoro, trifluoromethyl, trifluoromethoxy, t-butyl, methanesulfonyl, phenoxy, isopropyl and hydroxy. Preferably $R^2$, optionally substituted with $R^1$ as described above, is selected from the group consisting of:
i) phenyl, 5-, 6-, 7-, 8-benzo-1,4-dioxanyl, 4-, 5-, 6-, 7-benzo-1,3-dioxolyl, 4-, 5-, 6-, 7-indolinyl, 4-, 5-, 6-, 7-isoindolinyl, 1,2,3,4-tetrahydro-quinolin-4, 5, 6 or 7-yl, 1,2,3,4-tetrahydro-isoquinolin-4, 5, 6 or 7-yl,
ii) 4-, 5-, 6- or 7-benzoxazolyl, 4-, 5-, 6- or 7-benzothiophenyl, 4-, 5-, 6- or 7-benzofuranyl, 4-, 5-, 6- or 7-indolyl, 4-, 5-, 6- or 7-benzthiazolyl, 4-, 5-, 6or 7-benzimidazolyl, 4-, 5-, 6- or 7-indazolyl, imidazo[1,2-a]pyridin-5, 6, 7 or 8-yl, pyrazolo[1,5-a]pyridin-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4, 5 or 7-yl, 1H-pyrrolo[3,2-b]pyridin-5, 6 or 7-yl,
iii) 5-, 6-, 7- or 8-isoquinolinyl, 5-, 6-, 7- or 8-quinolinyl, 5-, 6-, 7- or 8-quinoxalinyl, 5-, 6-, 7- or 8-quinazolinyl,
iv) naphthyl,
v) furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, 3-indoxazinyl, 2-benzoxazolyl, 2- or 3-benzothiophenyl, 2- or 3-benzofuranyl, 2- or 3-indolyl, 2-benzthiazolyl, 2-benzimidazolyl, 3-indazolyl, and
vi) pyridinyl, pyridinyl-N-oxide, pyrazinyl, pyrimidinyl, pyridazinyl, 1-, 3- or 4-isoquinolinyl, 2-, 3- or 4-quinolinyl, 2- or 3-quinoxalinyl, 2- or 4-quinazolinyl, Most preferably $R^2$, optionally substituted with $R^q$ as described above, is selected from the group consisting of phenyl, naphthalenyl, pyridinyl, thiophenyl, benzothiophenyl, furanyl, benzofuranyl, indolyl, indolinyl, isoquinolinyl and quinolinyl. Specific $R^2$ are selected from the group consisting of 4-methyl-phenyl, 2-chloro-phenyl, 3-chloro-phenyl, 4-chloro-phenyl, 3,4-dichloro-phenyl, benzo[1,3]dioxol-5-yl, 2,3-diydro benzo[1,4]dioxin-6-yl, 4-methoxy-phenyl, phenyl, 4-phenoxy-phenyl, naphthalen-2-yl, pyridin-3-yl, 2-chloro-pyridin-3-yl, pyridin-4-yl methyl, 4-benzyloxy-phenyl, 4-dimethylamino-phenyl, 4-bromo-3-methyl-phenyl, 3-methoxy-4-methyl-phenyl, 3-cyclopentyloxy-4-methoxy-phenyl, 4-bromo-2-chloro-phenyl, 4-bromo-phenyl, 3-dimethylamino-phenyl, 4-morpholin-1-yl-phenyl, 4-pyrrolidin-1-yl-phenyl, 4-(N-propylamino)-phenyl, 4-(N-isobutylamino)-phenyl, 4-diethylamino-phenyl, 4-(N-allylamino)-phenyl, 4-(N-isopropylamino)-phenyl, 4-(N-methyl-N-propylamino)-phenyl, 4-(N-methyl-N-isopropylamino)-phenyl, 4-(N-methyl-N-ethylamino)-phenyl, 4-amino-phenyl, 4-(N-methyl-N-propylamino)-2-chloro-phenyl, 4-(N-ethyl-N-methylamino)-2-chloro-phenyl, 4-pyrrolidin-1-yl)-2-chloro-phenyl, 4-azetidinyl-phenyl, 4-(pyrrolidin-2-one-1-yl)-phenyl, 4-bromo-3-methyl-phenyl, 4-chloro-3-methyl-phenyl, 1-methyl-5-indolinyl, 5-indolinyl, 5-isoquinolinyl, 6-quinolinyl, benzo[1,3]diox-5-yl and 7-methoxy-benzofuran-2-yl.

Preferably $R^q$ is selected from the group consisting of —OH, —CH$_3$, —CH$_2$CH$_3$, i-propyl, t-butyl, —OCH$_3$, —OCH$_2$CH$_3$, —OCH(CH$_3$)$_2$, cyclopropyl, cyclobutyl, cyclopentyl, cyclohexyl, —Ocyclopentyl, —Ocyclohexyl, phenyl, —Ophenyl, benzyl, —Obenzyl, —CN, —NO$_2$, —C(O)NH$_2$, —C(O)N(CH$_3$)$_2$, —C(O)NH(CH$_3$), —NH(CO)H, —NHCOCH$_3$, —NCH$_3$(CO)H, —NCH$_3$COCH$_3$, —NHSO$_2$CH$_3$, —NCH$_3$SO$_2$CH$_3$, —C(O)CH$_3$, —SOCH$_3$, —SO$_2$CH$_3$, —SO$_2$NH$_2$, —SO$_2$NHCH$_3$, —SO$_2$N(CH$_3$)$_2$, —SCF$_3$, —F, —Cl, —Br, I, —CF$_3$, —OCF$_3$, —COOH, —COOCH$_3$, —COOCH$_2$CH$_3$, —NH$_2$, —NHCH$_3$, —NHCH$_2$CH$_3$, —NH(CH$_2$CH$_2$CH$_3$), —NH(CH(CH$_3$)CH$_2$CH$_3$), —NH(allyl), —NH(CH$_2$(CH$_3$)$_2$), —N(CH$_3$)$_2$, —N(CH$_2$CH$_3$)$_2$, —NCH$_3$(CH$_2$CH$_2$CH$_3$), —NCH$_3$(CH$_2$CH$_3$), —NCH$_3$(CH(CH$_3$)$_2$), pyrrolidin-2-one-1-yl, azetidinyl, piperidin-1-yl, 2- or 3-pyrrolin-1-yl, morpholin-4-yl, thiomorpholin-4-yl, piperazin-1-yl, pyrrolidin-1-yl, homopiperidin-1-yl.

Most preferably $R^q$ is selected from the group consisting of methyl, bromo, chloro, methoxy, cyclopentyloxy, phenoxy, benzyloxy, pyrrolidinyl, N-methyl-N-ethylamino and dimethylamino. Preferably, there are 0, 1 or 2 $R^q$ substituents.

Preferably $R^3$ is selected from the group consisting of —H, —F, Cl, Br and —CH$_3$.

Most preferably $R^3$ is H.

Preferably n is 0, or 1.

Preferably $R^4$ is selected from the group consisting of —H, —F and —CH$_3$.

Most preferably $R^4$ is H.

In one preferred embodiment of the invention, the Ar attached carbon is saturated and has the configuration

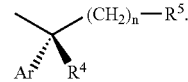

In another preferred embodiment of the present invention, the Ar attached carbon is unsaturated and has the configuration

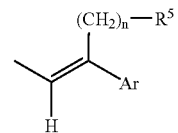

Preferably Ar, optionally substituted with $R^r$ as described above, is selected from the group consisting of:
A) phenyl, 5-, 6-, 7-, 8-benzo-1,4-dioxanyl, 4-, 5-, 6-, 7-benzo-1,3-dioxolyl, 4-, 5-, 6-, 7-indolinyl, 4-, 5-, 6-, 7-isoindolinyl, 1,2,3,4-tetrahydro-quinolin-4, 5, 6 or 7-yl, 1,2,3,4-tetrahydro-isoquinolin-4, 5, 6 or 7-yl,
B) 4-, 5-, 6- or 7-benzoxazolyl, 4-, 5-, 6- or 7-benzothiophenyl, 4-, 5-, 6- or 7-benzofuranyl, 4-, 5-, 6- or 7-indolyl, 4-, 5-, 6- or 7-benzthiazolyl, 4-, 5-, 6- or 7-benzimidazolyl, 4-, 5-, 6- or 7-indazolyl, imidazo[1,2-a]pyridin-5, 6, 7 or 8-yl, pyrazolo[1,5-a]pyridin-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4, 5 or 7-yl, 1H-pyrrolo[3,2-b]pyridin-5, 6 or 7-yl,
C) 5-, 6-, 7- or 8-isoquinolinyl, 5-, 6-, 7- or 8-quinolinyl, 5-, 6-, 7- or 8-quinoxalinyl, 5-, 6-, 7- or 8-quinazolinyl,
D) naphthyl,
E) furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, 3-indoxazinyl, 2-benzoxazolyl, 2- or 3-benzothiophenyl, 2- or 3-benzofuranyl, 2- or 3-indolyl, 2-benzthiazolyl, 2-benzimidazolyl, 3-indazolyl, and F) pyridinyl, pyridinyl-N-oxide, pyrazinyl, pyrimidinyl, pyridazinyl, 1-, 3- or 4-isoquinolinyl, 2-, 3- or 4-quinolinyl, 2- or 3-quinoxalinyl, 2- or 4-quinazolinyl.

Most preferably Ar, optionally substituted with $R^r$ as described above, is selected from the group consisting of phenyl, naphthalenyl, benzofuran-3-yl, 4, 5, 6 or 7-benzothiophenyl, 4, 5, 6 or 7-benzo[1,3]dioxolyl, 8-quinolinyl, 2-indolyl, 3-indolyl and pyridinyl. Specific Ar are selected from the group consisting of phenyl, 2-methyl-phenyl, 3-methyl-phenyl, 4-methyl-phenyl, 2,5-dimethyl-phenyl, 2-trifluoromethyl-phenyl, 3-trifluoromethyl-phenyl, 2-fluoro-3-trifluoromethyl-phenyl, 2-fluoro-phenyl, 2,3-difluoro-phenyl, 2-chloro-phenyl, 3-chloro-phenyl, 4-chloro-phenyl, 2,3-dicloro-phenyl, 3,4-dichlorophenyl, 2,6-dichlorophenyl, 3-iodo-phenyl, 2-chloro-4-fluoro-phenyl, benzofuran-3-yl, 2-methoxy-phenyl, 3-methoxy-phenyl, 4-methoxy-phenyl, 2,3-dimethoxy-phenyl, 3-trifluoromethoxy-phenyl, 4-trifluoromethoxy-phenyl, 3-ethoxy-phenyl, 3-trifluoromethylsulfanyl-phenyl, naphthalen-1-yl, naphthalen-2-yl, benzo[b]thiophen-4-yl, 3-nitro-phenyl, benzo[1,3]dioxol-5-yl, pyridin-3-yl and pyridin-4-yl, 3-indolyl, 1-methyl-indol-3-yl, 4-biphenyl, 3,5-dimethyl-phenyl, 3-isopropoxy-phenyl, 3-dimethylamino-phenyl, 2-flouro-5-methyl-phenyl, 2-methyl-3-triflouromethyl-phenyl. Preferably, there are 0, 1 or 2 $R^r$ substituents.

Preferably $R^r$ is selected from the group consisting of —OH, —CH₃, —CH₂CH₃, -propyl, -t-butyl, —OCH₃, —OCH₂CH₃, —OCH(CH₃)₂, cyclopropyl, cyclobutyl, cyclopentyl, cyclohexyl, —Ocyclopentyl, —Ocyclohexyl, phenyl, —Ophenyl, benzyl, —Obenzyl, —CN, —NO₂, —C(O)NH₂, —C(O)N(CH₃)₂, —C(O)NH(CH₃), —NH(CO)H, —NHCOCH₃, —NCH₃(CO)H, —NCH₃COCH₃, —NHSO₂CH₃, —NCH₃SO₂CH₃, —C(O)CH₃, —SOCH₃, —SO₂CH₃, —SO₂NH₂, —SO₂NHCH₃, —SO₂N(CH₃)₂, —SCF₃, —F, —Cl, —Br, I, —CF₃, —OCF₃, —COOH, —COOCH₃, —COOCH₂CH₃, —NH₂, —NHCH₃, —NHCH₂CH₃, —NH(CH₂CH₂CH₃), —NH(CH(CH₃)CH₂CH₃), —NH(allyl), —NH(CH₂(CH₃)₂), —N(CH₃)₂, —N(CH₂CH₃)₂, —NCH₃(CH₂CH₂CH₃), —NCH₃(CH₂CH₃), —NCH₃(CH(CH₃)₂), pyrrolin-2-one-1-yl, azetidinyl, piperidin-1-yl, 2- or 3-pyrrolin-1-yl, morpholin-4-yl, thiomorpholin-4-yl, piperazin-1-yl, pyrrolidin-1-yl, homopiperidin-1-yl.

Most preferably $R^r$ is selected from the group consisting of methyl, methoxy, ethoxy, isopropoxy, dimethylamino, fluoro, chloro, iodo, trifluoromethyl, trifluoromethoxy, nitro, phenyl and trifluoromethylsulfanyl.

Preferably $R^5$ is selected from the group consisting of:
I) —COOH, —COOCH₃, —COOCH₂CH₃,
II) —CONH(CH₃), —CONH(CH₂CH₃), —CONH(CH₂CH₂CH₃), —CONH(CH(CH₃)₂), —CONH(CH₂CH₂CH₂CH₃), —CONH(CH(CH₃)CH₂CH₃), —CONH(C(CH₃)₃), —CONH(cyclohexyl), —CONH(2-hydroxy-cyclohexyl), —CON(CH₃)₂, —CONCH₃(CH₂CH₃), —CONCH₃(CH₂CH₂CH₃), —CONCH₃(CH(CH₃)₂), —CONCH₃(CH₂CH₂CH₂CH₃), —CONCH₃(CH(CH₃)CH₂CH₃), —CONCH₃(C(CH₃)₃), —CON(CH₂CH₃)₂, —CO-piperidin-1-yl, —CO-morpholin-4-yl, —CO-piperazin-1-yl, —CO-imidazolidin-1-yl, —CO-pyrrolidin-1-yl, —CO-2-pyrrolin-1-yl, —CO-3-pyrrolin-1-yl, —CO-2-imidazolin-1-yl, —CO-piperidin-1-yl, and
III) -tetrazolyl, 1H-[1,2,4]triazol-5-ylsulfinyl, 1H-[1,2,4]triazol-5-ylsulfonyl, 1H-[1,2,4]triazol-5-ylsulfanyl, Most preferably $R^5$ is selected from the group consisting of —COOH and tetrazol-5-yl.

The "pharmaceutically acceptable salts and esters thereof" refer to those salt and ester forms of the compounds of the present invention which would be apparent to the pharmaceutical chemist, i.e., those which are non-toxic and which would favorably affect the pharmacokinetic properties of said compounds of the present invention. Those compounds having favorable pharmacokinetic properties would be apparent to the pharmaceutical chemist, i.e., those which are non-toxic and which possess such pharmacokinetic properties to provide sufficient palatability, absorption, distribution, metabolism and excretion. Other factors, more practical in nature, which are also important in the selection, are cost of raw materials, ease of crystallization, yield, stability, hygroscopicity and flowability of the resulting bulk drug. In addition, acceptable salts of carboxylates include sodium, potassium, calcium and magnesium. Examples of suitable cationic salts include hydrobromic, hydroiodic, hydrochloric, perchloric, sulfuric, maleic, fumaric, malic, tartatic, citric, benzoic, mandelic, methanesulfonic, hydroethanesulfonic, benzenesulfonic, oxalic, palmoic, 2-naphthalenesulfonic, p-toluenesulfonic, cyclohexanesulfamic and saccharic. Examples of suitable esters include such esters where one or more carboxyl substituents is replaced with p-methoxybenzyloxycarbonyl, 2,4,6-trimethylbenzyloxycarbonyl, 9-anthryloxycarbonyl, CH₃SCH₂COO—, tetrahydrofur-2-yloxycarbonyl, tetrahydropyran-2-yloxycarbonyl, fur-2-uloxycarbonyl, benzoylmethoxycarbonyl, p-nitrobenzyloxycarbonyl, 4-pyridylmethoxycarbonyl, 2,2,2-trichloroethoxycarbonyl, 2,2,2-tribromoethoxycarbonyl, t-butyloxycarbonyl, t-amyloxycarbonyl, diphenylmethoxycarbonyl, triphenylmethoxycarbonyl, adamantyloxycarbonyl, 2-benzyloxyphenyloxycarbonyl, 4-methylthiophenyloxycarbonyl, or tetrahydropyran-2-yloxycarbonyl.

Preferred compounds of Table 1a, which were made according to the synthetic methods outlined in Scheme A and as described in Method 2, are given by the formula:

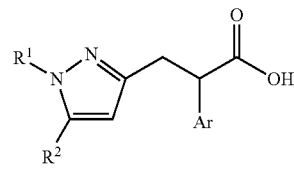

where $R^2$, $R^1$ and Ar are selected concurrently from the groups consisting of:

TABLE 1a

| EX | $R^2$ | $R^1$ | Ar | $[M + H]^+$ |
|---|---|---|---|---|
| 1 | (3,4-Dichloro-phenyl)- | (4-Methoxy-phenyl)- | (3-Methyl-phenyl)- [(S) enantiomer, Na⁺ salt] | 481.1 |
| 2 | (3,4-Dichloro-phenyl)- | (4-Methoxy-phenyl)- | (3-Methyl-phenyl)- | 481.1 |

TABLE 1a-continued

| EX | R² | R¹ | Ar | [M + H]⁺ |
|---|---|---|---|---|
| 3 | (3,4-Dichloro-phenyl)- | (4-Methoxy-phenyl)- | (3-Methyl-phenyl)-[(R) enantiomer] | 481.1 |
| 4 | (3,4-Dichloro-phenyl)- | (4-Methoxy-phenyl)- | (3-Methyl-phenyl)-[(S) enantiomer, TFA salt] | 481.1 |
| 5 | (4-Methyl-phenyl)- | (4-Methoxy-phenyl)- | (4-Methoxy-phenyl)- | 443.2 |
| 6 | (4-Methyl-phenyl)- | (4-Methoxy-phenyl)- | (3-Methoxy-phenyl)- | 443.2 |
| 7 | (4-Methyl-phenyl)- | (4-Methoxy-phenyl)- | (3-Chloro-phenyl)- | 447.2 |
| 8 | (4-Methyl-phenyl)- | (4-Methoxy-phenyl)- | (4-Methyl-phenyl)- | 427.2 |
| 9 | (4-Methyl-phenyl)- | (4-Methoxy-phenyl)- | (4-Chloro-phenyl)- | 447.2 |
| 10 | (2-Chloro-phenyl)- | (4-Methoxy-phenyl)- | Naphthalen-1-yl- | 483.1 |
| 11 | (2-Chloro-phenyl)- | (4-Methoxy-phenyl)- | (3-Chloro-phenyl)- | 467.1 |
| 12 | (3,4-Dichloro-phenyl)- | (4-Methoxy-phenyl)- | Phenyl- | 467.1 |
| 13 | Benzo[1,3]dioxol-5-yl- | (4-Methoxy-phenyl)- | (3-Methoxy-phenyl)- | 473.2 |
| 15 | Phenyl- | (4-Methoxy-phenyl)- | Naphthalen-2-yl- | 449.2 |
| 16 | (4-Phenoxy-phenyl)- | (4-Methoxy-phenyl)- | (3-Nitro-phenyl)- | 536.2 |
| 17 | Benzo[1,3]dioxol-5-yl- | (4-Methoxy-phenyl)- | Benzo[1,3]dioxol-5-yl- | 487.2 |
| 18 | (3,4-Dichloro-phenyl)- | (4-Methoxy-phenyl)- | (2,3-Difluoro-phenyl)- | 503.1 |
| 19 | (3,4-Dichloro-phenyl)- | (4-Methoxy-phenyl)- | (2-Trifluoromethyl-phenyl)- | 535.1 |
| 20 | (3,4-Dichloro-phenyl)- | (4-Methoxy-phenyl)- | (3-Ethoxy-phenyl)- | 511.1 |
| 21 | (4-Methyl-phenyl)- | (3,4-Dichloro-phenyl)- | (2-Fluoro-3-trifluoromethyl-phenyl)- | 537.1 |
| 22 | (4-Phenoxy-phenyl)- | (4-Methoxy-phenyl)- | (4-Trifluoromethoxy-phenyl)- | 575.2 |
| 23 | Benzo[1,3]dioxol-5-yl- | (4-Methoxy-phenyl)- | (3-Trifluoromethoxy-phenyl)- | 527.1 |
| 24 | (4-Methyl-phenyl)- | (3,4-Dichloro-phenyl)- | (3-Iodo-phenyl)- | 577.0 |
| 25 | (4-Methyl-phenyl)- | (3,4-Dichloro-phenyl)- | (3,5-Dimethyl-phenyl)- | 479.1 |
| 26 | (4-Methyl-phenyl)- | (3,4-Dichloro-phenyl)- | (3-Trifluoromethyl-sulfanyl-phenyl)- | 551.0 |
| 27 | Benzo[1,3]dioxol-5-yl- | (4-Methoxy-phenyl)- | Naphthalen-1-yl- | 493.2 |
| 28 | Benzo[1,3]dioxol-5-yl- | (4-Methoxy-phenyl)- | Naphthalen-1-yl-[(R) enantiomer] | 493.2 |
| 29 | Benzo[1,3]dioxol-5-yl- | (4-Methoxy-phenyl)- | Naphthalen-1-yl-[(S) enantiomer] | 493.2 |
| 30 | (4-Methoxy-phenyl)- | (4-Methoxy-phenyl)- | (3-Methoxy-phenyl)- | 459.2 |
| 31 | (4-Methoxy-phenyl)- | (4-Methoxy-phenyl)- | (3-Methoxy-phenyl)-[(R) enantiomer] | 459.2 |
| 32 | (4-Methoxy-phenyl)- | (4-Methoxy-phenyl)- | (3-Methoxy-phenyl)-[(S) enantiomer] | 459.2 |
| 33 | (4-Chloro-phenyl)- | (4-Methoxy-phenyl)- | Biphenyl-4-yl- | 509.2 |
| 34 | (4-Chloro-phenyl)- | (4-Methoxy-phenyl)- | (4-Methyl-phenyl)- | 447.2 |
| 35 | (4-Chloro-phenyl)- | (4-Methoxy-phenyl)- | (3-Methyl-phenyl)- | 447.1 |
| 36 | (4-Chloro-phenyl)- | (4-Methoxy-phenyl)- | (3-Methoxy-phenyl)- | 463.1 |
| 37 | (4-Chloro-phenyl)- | (4-Methoxy-phenyl)- | (3-Chloro-phenyl)- | 467.2 |
| 38 | (4-Methyl-phenyl)- | (4-Chloro-phenyl)- | Naphthalen-1-yl- | 467.1 |
| 39 | (4-Methyl-phenyl)- | (3-Chloro-phenyl)- | (3-Chloro-phenyl)- | 451.0 |
| 40 | (4-Methyl-phenyl)- | (3-Methyl-phenyl)- | (3-Methyl-phenyl)- | 411.1 |
| 41 | (4-Methyl-phenyl)- | (4-Trifluoromethyl-phenyl)- | Phenyl- | 451.0 |
| 42 | (4-Methyl-phenyl)- | (3,4-Dichloro-phenyl)- | (3-Methoxy-phenyl)- | 481.0 |

TABLE 1a-continued

| EX | R² | R¹ | Ar | [M + H]⁺ |
|---|---|---|---|---|
| 43 | (4-Methyl-phenyl)- | Benzyl- | (2-Chloro-phenyl)- | 431.0 |
| 44 | (4-Methyl-phenyl)- | Benzyl- | (3-Trifluoromethyl-phenyl)- | 465.0 |
| 45 | (4-Methyl-phenyl)- | Benzyl- | Naphthalen-2-yl- | 447.1 |
| 46 | (4-Methyl-phenyl)- | (3,4-Dichloro-phenyl)- | (2,3-Dichloro-phenyl)- | 519.0 |
| 142 | (4-Methyl-phenyl)- | (4-Methoxy-phenyl)- | (2-Methyl-phenyl)- | 427.5 |
| 143 | (4-Methyl-phenyl)- | (4-Methoxy-phenyl)- | (2-Fluoro-phenyl)- | 431.2 |
| 144 | (4-Methyl-phenyl)- | (4-Methoxy-phenyl)- | (2,6-Dichloro-phenyl)- | 481.1 |
| 145 | (4-Methyl-phenyl)- | (4-Methoxy-phenyl)- | (3-Methoxy-phenyl)- | 443.2 |
| 146 | (4-Methyl-phenyl)- | (4-Methoxy-phenyl)- | (2,3-Dimethoxy-phenyl)- | 473.2 |
| 147 | (4-Methyl-phenyl)- | (4-Methoxy-phenyl)- | (2-Chloro-phenyl)- | 447.1 |
| 148 | (4-Methyl-phenyl)- | (4-Methoxy-phenyl)- | (3-Methyl-phenyl)- | 427.2 |
| 149 | (4-Methyl-phenyl)- | (4-Methoxy-phenyl)- | (3,4-Dichloro-phenyl)- | 481.1 |
| 150 | (4-Methyl-phenyl)- | (4-Methoxy-phenyl)- | Phenyl- | 413.2 |
| 151 | (4-Methyl-phenyl)- | (4-Methoxy-phenyl)- | Naphthalen-1-yl- [(R) enantiomer] | 463.2 |
| 152 | (4-Methyl-phenyl)- | (4-Methoxy-phenyl)- | Naphthalen-1-yl- [(S) enantiomer] | 463.2 |
| 153 | (4-Methyl-phenyl)- | (4-Methoxy-phenyl)- | Benzo[b]thiophen-4-yl- | 469.1 |
| 154 | (4-Methyl-phenyl)- | (4-Chloro-phenyl)- | (3-Chloro-phenyl)- | 451.0 |
| 155 | (4-Methyl-phenyl)- | (4-Chloro-phenyl)- | (3-Methyl-phenyl)- | 431.0 |
| 156 | (4-Methyl-phenyl)- | (4-Chloro-phenyl)- | Phenyl- | 417.1 |
| 157 | (4-Methyl-phenyl)- | (4-Chloro-phenyl)- | (3-Methoxy-phenyl)- | 447.1 |
| 158 | (4-Methyl-phenyl)- | (4-Chloro-phenyl)- | (2-Chloro-phenyl)- | 451.0 |
| 159 | (4-Methyl-phenyl)- | (4-Chloro-phenyl)- | (3-Trifluoromethyl-phenyl)- | 485.0 |
| 160 | (4-Methyl-phenyl)- | (4-Chloro-phenyl)- | Naphthalen-2-yl- | 467.1 |
| 161 | (4-Methyl-phenyl)- | (3-Chloro-phenyl)- | Naphthalen-1-yl- | 467.1 |
| 162 | (4-Methyl-phenyl)- | (3-Chloro-phenyl)- | Phenyl- | 417.1 |
| 163 | (4-Methyl-phenyl)- | (3-Chloro-phenyl)- | (3-Methoxy-phenyl)- | 447.1 |
| 164 | (4-Methyl-phenyl)- | (3-Chloro-phenyl)- | (2-Chloro-phenyl)- | 451.0 |
| 165 | (4-Methyl-phenyl)- | (3-Chloro-phenyl)- | (3-Trifluoromethyl-phenyl)- | 485.0 |
| 166 | (4-Methyl-phenyl)- | (3-Chloro-phenyl)- | Naphthalen-2-yl- | 467.1 |
| 167 | (4-Methyl-phenyl)- | (4-Methyl-phenyl)- | Naphthalen-1-yl- | 447.1 |
| 168 | (4-Methyl-phenyl)- | (4-Methyl-phenyl)- | (3-Chloro-phenyl)- | 431.0 |
| 169 | (4-Methyl-phenyl)- | (4-Methyl-phenyl)- | Phenyl- | 397.1 |
| 170 | (4-Methyl-phenyl)- | (4-Methyl-phenyl)- | (3-Methoxy-phenyl)- | 427.1 |
| 171 | (4-Methyl-phenyl)- | (4-Methyl-phenyl)- | (2-Chloro-phenyl)- | 431.0 |
| 172 | (4-Methyl-phenyl)- | (4-Methyl-phenyl)- | (3-Trifluoromethyl-phenyl)- | 466.1 |
| 173 | (4-Methyl-phenyl)- | (4-Methyl-phenyl)- | Naphthalen-2-yl- | 447.1 |
| 174 | (4-Methyl-phenyl)- | (4-Trifluoromethyl-phenyl)- | Naphthalen-1-yl- | 501.1 |
| 175 | (4-Methyl-phenyl)- | (4-Trifluoromethyl-phenyl)- | (3-Chloro-phenyl)- | 485.0 |
| 176 | (4-Methyl-phenyl)- | (4-Trifluoromethyl-phenyl)- | (3-Methyl-phenyl)- | 465.1 |
| 177 | (4-Methyl-phenyl)- | (4-Trifluoromethyl-phenyl)- | (3-Methoxy-phenyl)- | 481.1 |
| 178 | (4-Methyl-phenyl)- | (4-Trifluoromethyl-phenyl)- | (2-Chloro-phenyl)- | 485.0 |
| 179 | (4-Methyl-phenyl)- | (4-Trifluoromethyl-phenyl)- | (3-Trifluoromethyl-phenyl)- | 519.1 |
| 180 | (4-Methyl-phenyl)- | (4-Trifluoromethyl-phenyl)- | Naphthalen-2-yl- | 501.1 |
| 181 | (4-Methyl-phenyl)- | (3,4-Dichloro-phenyl)- | Naphthalen-1-yl- | 501.0 |
| 182 | (4-Methyl-phenyl)- | (3,4-Dichloro-phenyl)- | (3-Chloro-phenyl)- | 485.0 |
| 183 | (4-Methyl-phenyl)- | (3,4-Dichloro-phenyl)- | (3-Methyl-phenyl)- | 465.1 |
| 184 | (4-Methyl-phenyl)- | (3,4-Dichloro-phenyl)- | Phenyl- | 451.0 |
| 185 | (4-Methyl-phenyl)- | (3,4-Dichloro-phenyl)- | (2-Chloro-phenyl)- | 485.0 |

TABLE 1a-continued

| EX | R² | R¹ | Ar | [M + H]⁺ |
|---|---|---|---|---|
| 186 | (4-Methyl-phenyl)- | (3,4-Dichloro-phenyl)- | (3-Trifluoromethyl-phenyl)- | 519.0 |
| 187 | (4-Methyl-phenyl)- | (3,4-Dichloro-phenyl)- | Naphthalen-2-yl- | 501.0 |
| 188 | (4-Methyl-phenyl)- | (3,4-Dichloro-phenyl)- | (3-Nitro-phenyl)- | 496.1 |
| 189 | (4-Methyl-phenyl)- | (3,4-Dichloro-phenyl)- | Benzo[1,3]dioxol-5-yl- | 495.1 |
| 190 | (4-Methyl-phenyl)- | (3,4-Dichloro-phenyl)- | Benzo[b]thiophen-4-yl- | 507.0 |
| 191 | (4-Methyl-phenyl)- | (3,4-Dichloro-phenyl)- | (2,3-Difluoro-phenyl)- | 487.1 |
| 192 | (4-Methyl-phenyl)- | (3,4-Dichloro-phenyl)- | (2-Trifluoromethyl-phenyl)- | 519.1 |
| 193 | (4-Methyl-phenyl)- | (3,4-Dichloro-phenyl)- | (4-Trifluoromethoxy-phenyl)- | 535.0 |
| 194 | (4-Methyl-phenyl)- | (3,4-Dichloro-phenyl)- | (3-Trifluoromethoxy-phenyl)- | 535.1 |
| 195 | (4-Methyl-phenyl)- | Benzyl- | Naphthalen-1-yl- | 447.1 |
| 196 | (4-Methyl-phenyl)- | Benzyl- | (3-Chloro-phenyl)- | 431.0 |
| 197 | (4-Methyl-phenyl)- | Benzyl- | (3-Methyl-phenyl)- | 411.1 |
| 198 | (4-Methyl-phenyl)- | Benzyl- | Phenyl- | 398.1 |
| 199 | (4-Methyl-phenyl)- | Benzyl- | (3-Methoxy-phenyl)- | 427.1 |
| 200 | (4-Chloro-phenyl)- | (4-Methoxy-phenyl)- | (2-Chloro-4-fluoro-phenyl)- | 485.1 |
| 201 | (4-Chloro-phenyl)- | (4-Methoxy-phenyl)- | (2-Chloro-phenyl)- | 467.1 |
| 202 | (4-Chloro-phenyl)- | (4-Methoxy-phenyl)- | (2,6-Dichloro-phenyl)- | 501.1 |
| 203 | (4-Chloro-phenyl)- | (4-Methoxy-phenyl)- | (2-Methoxy-phenyl)- | 463.1 |
| 204 | (4-Chloro-phenyl)- | (4-Methoxy-phenyl)- | Phenyl- | 433.1 |
| 205 | (4-Chloro-phenyl)- | (4-Methoxy-phenyl)- | (2-Methyl-phenyl)- | 447.1 |
| 206 | (4-Chloro-phenyl)- | (4-Methoxy-phenyl)- | (2-Fluoro-phenyl)- | 451.1 |
| 207 | (4-Chloro-phenyl)- | (4-Methoxy-phenyl)- | Naphthalen-1-yl- | 483.1 |
| 208 | (4-Chloro-phenyl)- | (4-Methoxy-phenyl)- | Pyridin-3-yl- | 434.1 |
| 209 | (3,4-Dichloro-phenyl)- | (4-Methoxy-phenyl)- | (3-Chloro-phenyl)- | 501.0 |
| 210 | (3,4-Dichloro-phenyl)- | (4-Methoxy-phenyl)- | Naphthalen-1-yl- | 517.1 |
| 211 | (3,4-Dichloro-phenyl)- | (4-Methoxy-phenyl)- | (3-Methoxy-phenyl)- | 497.1 |
| 212 | (3,4-Dichloro-phenyl)- | (4-Methoxy-phenyl)- | Naphthalen-2-yl- | 517.1 |
| 213 | (3,4-Dichloro-phenyl)- | (4-Methoxy-phenyl)- | (3-Nitro-phenyl)- | 512.1 |
| 214 | (3,4-Dichloro-phenyl)- | (4-Methoxy-phenyl)- | Benzo[1,3]dioxol-5-yl- | 511.1 |
| 215 | (3,4-Dichloro-phenyl)- | (4-Methoxy-phenyl)- | (2-Fluoro-3-trifluoromethyl-phenyl)- | 553.1 |
| 216 | (3,4-Dichloro-phenyl)- | (4-Methoxy-phenyl)- | (4-Trifluoromethoxy-phenyl)- | 551.1 |
| 217 | (3,4-Dichloro-phenyl)- | (4-Methoxy-phenyl)- | (3-Iodo-phenyl)- | 593.0 |
| 218 | (3,4-Dichloro-phenyl)- | (4-Methoxy-phenyl)- | (3,5-Dimethyl-phenyl)- | 495.1 |
| 219 | (3,4-Dichloro-phenyl)- | (4-Methoxy-phenyl)- | (2,3-Dichloro-phenyl)- | 535.0 |
| 220 | Benzo[1,3]dioxol-5-yl- | (4-Methoxy-phenyl)- | (3-Methyl-phenyl)- | 457.1 |
| 221 | Benzo[1,3]dioxol-5-yl- | (4-Methoxy-phenyl)- | (3-Chloro-phenyl)- | 477.1 |
| 222 | Benzo[1,3]dioxol-5-yl- | (4-Methoxy-phenyl)- | Phenyl- | 443.1 |
| 223 | Benzo[1,3]dioxol-5-yl- | (4-Methoxy-phenyl)- | Naphthalen-2-yl- | 493.1 |
| 224 | Benzo[1,3]dioxol-5-yl- | (4-Methoxy-phenyl)- | (3-Nitro-phenyl)- | 488.1 |
| 225 | Benzo[1,3]dioxol-5-yl- | (4-Methoxy-phenyl)- | (2,3-Difluoro-phenyl)- | 479.1 |

TABLE 1a-continued

| EX | R² | R¹ | Ar | [M + H]⁺ |
|---|---|---|---|---|
| 226 | Benzo[1,3]dioxol-5-yl- | (4-Methoxy-phenyl)- | (2-Trifluoromethyl-phenyl)- | 511.1 |
| 227 | Benzo[1,3]dioxol-5-yl- | (4-Methoxy-phenyl)- | (3-Ethoxy-phenyl)- | 487.2 |
| 228 | Benzo[1,3]dioxol-5-yl- | (4-Methoxy-phenyl)- | (2-Fluoro-3-trifluoromethyl-phenyl)- | 529.1 |
| 229 | Benzo[1,3]dioxol-5-yl- | (4-Methoxy-phenyl)- | (4-Trifluoromethoxy-phenyl)- | 527.1 |
| 230 | Benzo[1,3]dioxol-5-yl- | (4-Methoxy-phenyl)- | (3-Trifluoromethyl-sulfanyl-phenyl)- | 543.1 |
| 231 | Benzo[1,3]dioxol-5-yl- | (4-Methoxy-phenyl)- | (3-Iodo-phenyl)- | 569.1 |
| 232 | Benzo[1,3]dioxol-5-yl- | (4-Methoxy-phenyl)- | (3,5-Dimethyl-phenyl)- | 471.2 |
| 233 | Benzo[1,3]dioxol-5-yl- | (4-Methoxy-phenyl)- | (2,3-Dichloro-phenyl)- | 511.1 |
| 234 | (4-Methoxy-phenyl)- | (4-Methoxy-phenyl)- | (3-Methyl-phenyl)- | 443.2 |
| 235 | (4-Methoxy-phenyl)- | (4-Methoxy-phenyl)- | (3-Chloro-phenyl)- | 463.1 |
| 236 | (4-Methoxy-phenyl)- | (4-Methoxy-phenyl)- | Naphthalen-1-yl- | 479.2 |
| 237 | (4-Methoxy-phenyl)- | (4-Methoxy-phenyl)- | Naphthalen-2-yl- | 479.2 |
| 238 | Phenyl- | (4-Methoxy-phenyl)- | (3-Chloro-phenyl)- | 433.1 |
| 239 | Phenyl- | (4-Methoxy-phenyl)- | Naphthalen-1-yl- | 449.2 |
| 240 | Phenyl- | (4-Methoxy-phenyl)- | (3-Methoxy-phenyl)- | 429.2 |
| 241 | Phenyl- | (4-Methoxy-phenyl)- | Phenyl- | 399.2 |
| 242 | (2-Chloro-phenyl)- | (4-Methoxy-phenyl)- | (3-Methoxy-phenyl)- | 463.1 |
| 243 | (2-Chloro-phenyl)- | (4-Methoxy-phenyl)- | Phenyl- | 433.1 |
| 244 | (2-Chloro-phenyl)- | (4-Methoxy-phenyl)- | Naphthalen-2-yl- | 483.1 |
| 245 | (4-Phenoxy-phenyl)- | (4-Methoxy-phenyl)- | (3-Methyl-phenyl)- | 505.2 |
| 246 | (4-Phenoxy-phenyl)- | (4-Methoxy-phenyl)- | (3-Chloro-phenyl)- | 525.2 |
| 247 | (4-Phenoxy-phenyl)- | (4-Methoxy-phenyl)- | Naphthalen-1-yl- | 541.2 |
| 248 | (4-Phenoxy-phenyl)- | (4-Methoxy-phenyl)- | (3-Methoxy-phenyl)- | 521.2 |
| 249 | (4-Phenoxy-phenyl)- | (4-Methoxy-phenyl)- | Phenyl- | 491.2 |
| 250 | (4-Phenoxy-phenyl)- | (4-Methoxy-phenyl)- | Naphthalen-2-yl- | 541.2 |
| 251 | (4-Phenoxy-phenyl)- | (4-Methoxy-phenyl)- | Benzo[1,3]dioxol-5-yl- | 535.2 |
| 252 | (4-Phenoxy-phenyl)- | (4-Methoxy-phenyl)- | (2,3-Difluoro-phenyl)- | 527.2 |
| 253 | (4-Phenoxy-phenyl)- | (4-Methoxy-phenyl)- | (2-Trifluoromethyl-phenyl)- | 559.2 |
| 254 | (4-Phenoxy-phenyl)- | (4-Methoxy-phenyl)- | (3-Ethoxy-phenyl)- | 535.2 |
| 255 | (4-Phenoxy-phenyl)- | (4-Methoxy-phenyl)- | (2-Fluoro-3-trifluoromethyl-phenyl)- | 577.2 |
| 256 | (4-Phenoxy-phenyl)- | (4-Methoxy-phenyl)- | (3-Trifluoromethoxy-phenyl)- | 575.2 |
| 257 | (4-Phenoxy-phenyl)- | (4-Methoxy-phenyl)- | (3-Trifluoromethyl-sulfanyl-phenyl)- | 591.2 |
| 258 | (4-Phenoxy-phenyl)- | (4-Methoxy-phenyl)- | (3-Iodo-phenyl)- | 617.1 |
| 259 | (4-Phenoxy-phenyl)- | (4-Methoxy-phenyl)- | (3,5-Dimethyl-phenyl)- | 519.2 |
| 260 | (4-Phenoxy-phenyl)- | (4-Methoxy-phenyl)- | (2,3-Dichloro-phenyl)- | 559.1 |

Preferred compounds of Table 1b, which were made according to the synthetic methods outlined in Schemes A, H, J and L, are given by the formula:

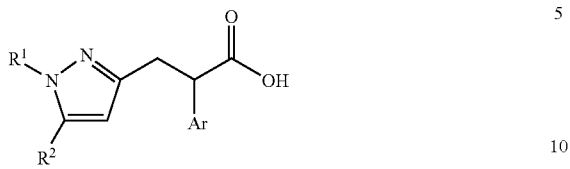

where $R^2$, $R^1$ and Ar are selected concurrently from the groups consisting of:

TABLE 1b

| EX | $R^2$ | $R^1$ | Ar | $[M + H]^+$ *$[M - H]^-$ |
|---|---|---|---|---|
| 77 | (4-Bromo-phenyl)- | (4-Methyl-phenyl)- | (3-Methyl-phenyl)- | 475/477 |
| 85 | (4-Bromo-2-chloro-phenyl)- | (4-Methyl-phenyl)- | (3-Methyl-phenyl)- | 509/511 |
| 106 | Quinolin-6-yl- | (4-Methyl-phenyl)- | (3-Methyl-phenyl)- | 448.2 |
| 126 | (3,4-Dichloro-phenyl)- | (4-Ethoxy-phenyl)- | (3-Chloro-phenyl)- | *513 |
| 127 | Naphthalen-2-yl- | (2,5-Dichloro-phenyl)- | (3-Chloro-phenyl)- | 521/523 |
| 128 | Naphthalen-2-yl- | (4-Ethoxy-phenyl)- | (3-Chloro-phenyl)- | 497.1 |
| 319 | Benzo[1,3]dioxol-5-yl- | (4-Methyl-phenyl)- | (3-Methyl-phenyl)- | |
| 320 | (4-Chloro-phenyl)- | (4-Methoxy-phenyl)- | 3-Isopropoxy- | |
| 321 | Naphthalen-2-yl- | Benzyl- | (3-Methyl-phenyl)- | |
| 322 | Benzo[1,3]dioxol-5-yl- | Benzyl | (3-Methyl-phenyl)- | |
| 323 | (3,4-Dichloro-phenyl)- | (2,4-Dichloro-phenyl)- | (2,5-Dimethyl-phenyl)- | |
| 324 | (3,4-Dichloro-phenyl)- | (2,4-Dichloro-phenyl)- | (3-Chloro-phenyl)- | |
| 325 | (3,4-Dichloro-phenyl)- | (2,4-Dichloro-phenyl)- | (3-Isoproxy-phenyl)- | |
| 326 | (3,4-Dichloro-phenyl)- | (2,4-Dichloro-phenyl)- | (2-Fluoro-5-methyl-phenyl)- | |
| 327 | (3,4-Dichloro-phenyl)- | (2,4-Dichloro-phenyl)- | (2-Methyl-3-trifluoromethyl-phenyl)- | |
| 328 | (3,4-Dichloro-phenyl)- | (4-Hydroxy-phenyl)- | (3-Methyl-phenyl)- [(S) enantiomer] | |
| 329 | (3,4-Dichloro-phenyl)- | (4-Ethoxy-phenyl)- | (3-Methyl-phenyl)- | |
| 330 | Naphthalen-2-yl- | (4-Ethoxy-phenyl)- | (3-Chloro-phenyl)- | |
| 331 | (3,4-Dichloro-phenyl)- | (4-Ethoxy-phenyl)- | (3-Chloro-phenyl)- | |
| 332 | (3,4-Dichloro-phenyl)- | (2,5-Dichloro-phenyl)- | (3-Chloro-phenyl)- | |
| 333 | (4-Chloro-phenyl)- | (4-Methoxy-phenyl)- | (4-Chloro-phenyl)- | |
| 334 | (3,4-Dichloro-phenyl)- | (4-Methoxy-phenyl)- | (3-Trifluoromethylsulfanyl-phenyl)- | |

Compound 328 was made by demethylation of Compound 1.

Preferred compounds of Table 2, which were made according to the synthetic methods outlined in Scheme A and as described in Method 2 or Example 71, are given by the formula:

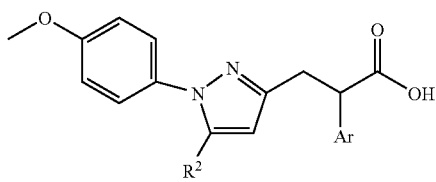

where $R^2$ and Ar are selected concurrently from the groups consisting of:

TABLE 2

| EX | $R^2$ | Ar | $[M + H]^+$ |
| --- | --- | --- | --- |
| 14 | (4-Methoxy-phenyl)- | Benzofuran-3-yl- | 469.2 |
| 71 | (4-Methyl-phenyl)- | (1H-indol-3-yl)- | 452.2 |
| 72 | (4-Methyl-phenyl)- | (1-Methyl-1H-indol-3-yl)- | 466.2 |
| 261 | (3,4-Dichloro-phenyl)- | Benzofuran-3-yl- | 507.1 |
| 262 | Benzo[1,3]dioxol-5-yl- | Benzofuran-3-yl- | 483.2 |
| 263 | Phenyl- | Benzofuran-3-yl- | 439.1 |
| 264 | (2-Chloro-phenyl)- | Benzofuran-3-yl- | 473.1 |
| 265 | (4-Phenoxy-phenyl)- | Benzofuran-3-yl- | 531.2 |

Preferred compounds of Table 3a, which were made according to the synthetic methods outlined in Schemes A, B, C, D and H, and as described in Examples 64-68, 73 and 74, are given by the formula:

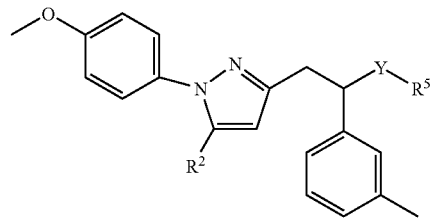

where $R^2$ and $R^5$—Y— are selected concurrently from the groups consisting of:

TABLE 3a

| EX | $R^2$ | $R^5$—Y— | $[M + H]^+$ |
| --- | --- | --- | --- |
| 64 | (4-Methyl-phenyl)- | (2-Hydroxy-cyclohexyl-carbamoyl)- | 524.2 |
| 65 | (4-Methyl-phenyl)- | Carbamoyl- | 426.2 |
| 66 | (4-Methyl-phenyl)- | (Dimethyl-carbamoyl)- | 454.2 |
| 67 | (4-Methyl-phenyl)- | (Methyl-carbamoyl)- | 440.2 |
| 68 | (4-Methyl-phenyl)- | (4-Methyl-piperazine-1-carbonyl)- | 509.2 |

Preferred compounds of Table 3b, which were made according to the synthetic methods outlined in Schemes D and I, are given by the formula:

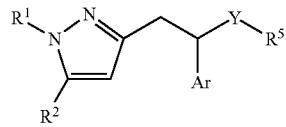

where $R^2$ and $R^5$-Y-are selected concurrently from the groups consisting of:

TABLE 3b

| EX | $R^2$ | $R^1$ | Ar | $R^5$—Y— | $[M + H]^+$ |
| --- | --- | --- | --- | --- | --- |
| 74 | (4-Methyl-phenyl)- | (4-Methoxy-phenyl)- | (3-Methyl-phenyl)- | (1H-Tetrazol-5-yl)- | 451.2 |
| 129 | (3,4-Dichloro-phenyl)- | (4-Methoxy-phenyl)- | (3-Methyl-phenyl)- | (1H-Tetrazol-5-yl)- [(S) enantiomer] | 505.3 |
| 130 | (3,4-Dichloro-phenyl)- | (4-Methoxy-phenyl)- | (3-Methyl-phenyl)- | (1H-Tetrazol-5-yl)- [racemic] | 505.1 |
| 131 | (3,4-Dichloro-phenyl)- | (4-Methoxy-phenyl)- | (3-Methyl-phenyl)- | (1H-Tetrazol-5-yl)- [(R) enantiomer] | 505.3 |
| 132 | Benzo[1,3]dioxol-5-yl- | (2,5-Dichloro-phenyl)- | (3-chloro-phenyl)- | (1H-Tetrazol-5-yl)- | 539.0 |
| 135 | 3,4-Dichloro-phenyl- | (4-Methoxy-phenyl)- | (3-Methyl-phenyl)- | (2H-[1,2,4]Triazol-3-ylsulfanylmethyl)- | 550.1 |
| 136 | (4-Methyl-phenyl)- | (4-Methyl-phenyl)- | (3-Methyl-phenyl)- | (2H-[1,2,4]Triazole-3-sulfinylmethyl)- | 496.2 |
| 137 | (4-Methyl-phenyl)- | (4-Methyl-phenyl)- | (3-Methyl-phenyl)- | (2H-[1,2,4]Triazole-3-sulfonylmethyl)- | 512.2 |
| 138 | 3,4-Dichloro-phenyl- | (4-Methoxy-phenyl)- | (3-Methyl-phenyl)- | (2H-[1,2,4]Triazole-3-sulfonylmethyl)- [(S) enantiomer] | 582.3 |

TABLE 3b-continued

| EX | R² | R¹ | Ar | R⁵—Y— | [M + H]⁺ |
|---|---|---|---|---|---|
| 335 | (4-Methyl-phenyl)- | (4-Methyl-phenyl)- | (3-Methyl-phenyl)- | (2H-[1,2,4]Triazol-3-ylsulfanylmethyl)- | |

Preferred compounds of Table 4, which were made according to the synthetic methods outlined in Schemes E and F, and as described in Methods 4 and 6, are given by the formula:

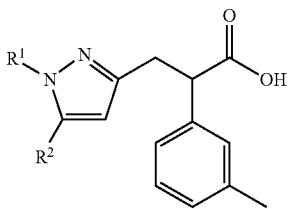

where R² and R¹ are selected concurrently from the groups consisting of:

TABLE 4

| EX | R² | R¹ | [M + H]⁺ |
|---|---|---|---|
| 53 | (4-Phenoxy-phenyl)- | (4-tert-Butyl-phenyl)- | 531.2 |
| 54 | (3,4-Dichloro-phenyl)- | (4-Methanesulfonyl-phenyl)- | 529.1 |
| 55 | Benzo[1,3]dioxol-5-yl- | (2-Chloro-phenyl)- | 461.0 |
| 57 | (3-Chloro-phenyl)- | (2,4-Dichloro-phenyl)- | 485.1 |
| 58 | (4-Benzyloxy-phenyl)- | (4-Trifluoromethoxy-phenyl)- | 573.5 |
| 59 | (4-Dimethylamino-phenyl)- | (4-Methyl-phenyl)- | 440.3 |
| 60 | (3-Methoxy-4-methyl-phenyl)- | (4-Methyl-phenyl)- | 441.3 |
| 61 | (3-Cyclopentyloxy-4-methoxy-phenyl)- | (4-Methyl-phenyl)- | 511.4 |
| 62 | (4-Bromo-3-methyl-phenyl)- | (4-Phenoxy-phenyl)- | 567.4 |
| 266 | Naphthalen-2-yl- | (2,4-Dichloro-phenyl)- | 501.0 |
| 267 | Naphthalen-2-yl- | (2-Chloro-phenyl)- | 467.1 |
| 268 | Naphthalen-2-yl- | (4-Methanesulfonyl-phenyl)- | 511.1 |
| 269 | Naphthalen-2-yl- | (4-tert-Butyl-phenyl)- | 489.2 |
| 270 | Naphthalen-2-yl- | (4-Trifluoromethoxy-phenyl)- | 517.5 |
| 271 | Naphthalen-2-yl- | (4-Methyl-phenyl)- | 447.3 |
| 272 | Naphthalen-2-yl- | (4-Phenoxy-phenyl)- | 525.4 |
| 273 | (3,4-Dichloro-phenyl)- | (2,4-Dichloro-phenyl)- | 519.0 |
| 274 | (3,4-Dichloro-phenyl)- | (2-Chloro-phenyl)- | 485.0 |
| 275 | (3,4-Dichloro-phenyl)- | (4-tert-Butyl-phenyl)- | 507.1 |
| 276 | Benzo[1,3]dioxol-5-yl- | (2,4-Dichloro-phenyl)- | 495.0 |
| 277 | Benzo[1,3]dioxol-5-yl- | (4-Methanesulfonyl-phenyl)- | 505.1 |
| 278 | Benzo[1,3]dioxol-5-yl- | (4-tert-Butyl-phenyl)- | 483.2 |
| 279 | (3-Chloro-phenyl)- | (2-Chloro-phenyl)- | 451.0 |
| 280 | (3-Chloro-phenyl)- | (4-Methanesulfonyl-phenyl)- | 495.1 |
| 281 | (3-Chloro-phenyl)- | (4-tert-Butyl-phenyl)- | 473.2 |
| 282 | (4-Phenoxy-phenyl)- | (2,4-Dichloro-phenyl)- | 543.1 |
| 283 | (4-Phenoxy-phenyl)- | (2-Chloro-phenyl)- | 509.1 |
| 284 | (4-Phenoxy-phenyl)- | (4-Methanesulfonyl-phenyl)- | 553.1 |
| 285 | (4-Benzyloxy-phenyl)- | (4-Methyl-phenyl)- | 503.4 |
| 286 | (4-Benzyloxy-phenyl)- | (4-Phenoxy-phenyl)- | 581.5 |
| 287 | (4-Dimethylamino-phenyl)- | (4-Trifluoromethoxy-phenyl) | 510.1 |
| 288 | (4-Dimethylamino-phenyl)- | (4-Phenoxy-phenyl)- | 518.4 |
| 289 | (4-Bromo-3-methyl-phenyl)- | (4-Methyl-phenyl)- | 489.3 |
| 290 | (3-Methoxy-4-methyl-phenyl)- | (4-Trifluoromethoxy-phenyl)- | 511.1 |
| 291 | (3-Methoxy-4-methyl-phenyl)- | (4-Phenoxy-phenyl)- | 519.4 |
| 292 | (3-Cyclopentyloxy-4-methoxy-phenyl)- | (4-Trifluoromethoxy-phenyl)- | 581.4 |
| 293 | (3-Cyclopentyloxy-4-methoxy-phenyl)- | (4-Phenoxy-phenyl)- | 589.5 |
| 294 | (4-Chloro-3-methyl-phenyl)- | (4-Isopropyl-phenyl)- | 473.2 |

Preferred compounds of Table 5a, which were made according to the synthetic methods outlined in Schemes E and F, and as described in Methods 4 and 6, are given by the formula:

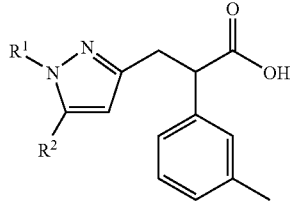

where R² and R¹ are selected concurrently from the groups consisting of:

TABLE 5a

| EX | R² | R¹ | [M + H]⁺ |
|---|---|---|---|
| 52 | Naphthalen-2-yl- | Pyridin-2-yl- | 434.2 |
| 56 | Pyridin-3-yl- | (2,4-Dichloro-phenyl)- | 452.0 |
| 295 | (3,4-Dichloro-phenyl)- | Pyridin-2-yl- | 452.1 |
| 296 | Benzo[1,3]dioxol-5-yl- | Pyridin-2-yl- | 428.1 |
| 297 | (3-Chloro-phenyl)- | Pyridin-2-yl- | 418.1 |
| 298 | (4-Phenoxy-phenyl)- | Pyridin-2-yl- | 476.2 |
| 299 | Pyridin-3-yl- | (4-tert-Butyl-phenyl)- | 440.2 |

Preferred compounds of Table 5b, which were made according to the synthetic methods outlined in Scheme L, and as described in Example 105, are Methods given by the formula:

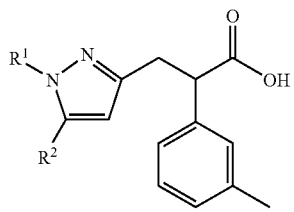

where $R^2$ and $R^1$ are selected concurrently from the groups consisting of:

TABLE 5b

| EX | $R^2$ | $R^1$ | $[M + H]^+$ |
| --- | --- | --- | --- |
| 78 | (4-Dimethylamino-phenyl)- | Pyridin-2-yl- | 427.2 |
| 80 | Naphthalen-2-yl- | (5-Trifluoromethyl-pyridin-2-yl)- | |
| 81 | (2-Chloro-pyridin-3-yl)- | (2,4-Dichloro-phenyl)- | 486/488 |
| 89 | Naphthalen-2-yl- | Pyridin-4-ylmethyl- | 448.3 |
| 92 | Naphthalen-2-yl- | Pyridin-2-yl- [(S) enantiomer] | 434.1 |
| 93 | Naphthalen-2-yl- | Pyridin-2-yl- [(R) enantiomer] | 434.1 |
| 105 | Naphthalen-2-yl- | (1-Oxy-pyridin-2-yl)- | 450.1 |
| 337 | (3,4-Dichloro-phenyl)- | (5-Trifluoromethyl-pyridin-2-yl)- | |

Preferred compounds of Table 6, which were made according to the synthetic methods outlined in Schemes E, F and L, and as described in Methods 4 and 6, are given by the formula:

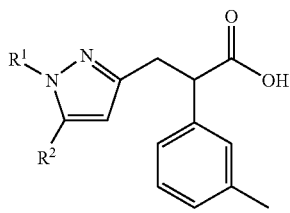

where $R^2$ and $R^1$ are selected concurrently from the groups consisting of:

TABLE 6

| EX | $R^2$ | $R^1$ | $[M + H]^+$ |
| --- | --- | --- | --- |
| 47 | Naphthalen-2-yl- | H— | 357.2 |
| 49 | (3,4-Dichloro-phenyl)- | Methyl | 388.9 |
| 51 | Naphthalen-2-yl- | Cyclohexyl- | 439.2 |
| 300 | (3,4-Dichloro-phenyl)- | Cyclohexyl- | 457.0 |
| 301 | Benzo[1,3]dioxol-5-yl- | Cyclohexyl- | 433.3 |
| 302 | (3-Chloro-phenyl)- | H— | 341.1 |
| 303 | (3-Chloro-phenyl)- | Methyl | 355.0 |
| 304 | (3-Chloro-phenyl)- | Cyclohexyl- | 423.2 |
| 305 | (4-Phenoxy-phenyl)- | H— | 399.1 |
| 306 | (4-Phenoxy-phenyl)- | Cyclohexyl- | 481.1 |
| 307 | (4-Dimethylamino-phenyl)- | Cyclohexyl- | 432.4 |
| 308 | (4-Bromo-3-methyl-phenyl)- | Cyclohexyl- | 481.4 |
| 309 | (3-Cyclopentyloxy-4-methoxy-phenyl)- | Cyclohexyl- | 503.5 |
| 338 | (3,4-Dichloro-phenyl)- | H— | |

Preferred compounds of Table 7, which were made according to the synthetic methods outlined in Schemes E and F, and as described in Methods 4 and 6, are given by the formula:

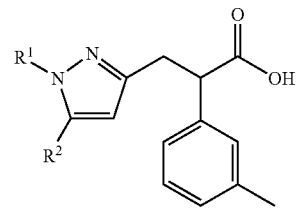

where $R^2$ and $R^1$ are selected concurrently from the groups consisting of:

TABLE 7

| EX | $R^2$ | $R^1$ | $[M + H]^+$ |
| --- | --- | --- | --- |
| 63 | (7-Methoxy-benzofuran-2-yl)- | (4-Phenoxy-phenyl)- | 545.4 |
| 310 | (7-Methoxy-benzofuran-2-yl)- | (4-Trifluoromethoxy-phenyl)- | 537.3 |
| 311 | (7-Methoxy-benzofuran-2-yl)- | (4-Methyl-phenyl)- | 467.4 |
| 312 | (7-Methoxy-benzofuran-2-yl)- | Cyclohexyl- | 459.4 |

Preferred compounds of Table 8a, which were made according to the synthetic methods outlined in Schemes E and F, and as described in Methods 4 and 6, are given by the formula:

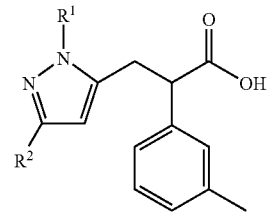

where $R^2$ and $R^1$ are selected concurrently from the groups consisting of:

TABLE 8a

| EX | $R^2$ | $R^1$ | $[M + H]^+$ |
| --- | --- | --- | --- |
| 48 | (3,4-Dichloro-phenyl)- | Methyl | 388.9 |
| 50 | Naphthalen-2-yl- | Cyclohexyl- | 439.2 |
| 313 | (4-Bromo-3-methyl-phenyl)- | Cyclohexyl- | 481.4 |
| 314 | (3,4-Dichloro-phenyl)- | Cyclohexyl- | 457.0 |
| 315 | Benzo[1,3]dioxol-5-yl- | Cyclohexyl- | 433.2 |
| 316 | (3-Chloro-phenyl)- | Methyl | 355.0 |
| 317 | (3-Chloro-phenyl)- | Cyclohexyl- | 423.1 |
| 318 | (4-Phenoxy-phenyl)- | Cyclohexyl- | 481.1 |

Preferred compounds of Table 8b, which were made according to the synthetic methods outlined in Scheme L, are given by the formula:

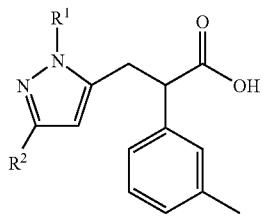

where R² and R¹ are selected concurrently from the groups consisting of:

TABLE 8b

| EX | R² | R¹ | [M + H]⁺ |
|---|---|---|---|
| 79 | Naphthalen-1-yl | Pyridin-2-yl | 434.2 |
| 82 | Benzo[1,3]dioxol-5-yl- | Cyclohexylmethyl- | 447.2 |
| 83 | Naphthalen-2-yl- | Benzyl- | |
| 84 | (4-Dimethylamino-phenyl)- | Benzyl- | |
| 88 | Naphthalen-2-yl- | Pyridin-4-ylmethyl- | 448.3 |
| 90 | (3-Dimethylamino-phenyl)- | (4-Methyl-phenyl)- | 440.3 |
| 339 | (4-Dimethylamino-phenyl)- | (4-Methanesulfonyl-phenyl)- | |
| 340 | Benzo[1,3]dioxol-5-yl- | Benzyl- | |
| 341 | (3-Dimethylamino-phenyl)- | (2,5-Dimethyl-phenyl)- | |
| 342 | (3-Dimethylamino-phenyl)- | (4-Methoxy-phenyl)- | |

Preferred compounds of Table 9, which were made according to the synthetic methods outlined in Scheme L, are given by the formula:

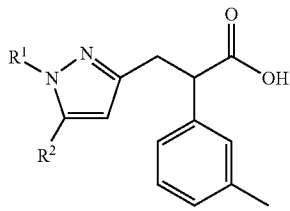

where R² and R¹ are selected concurrently from the groups consisting of:

TABLE 9

| EX | R² | R¹ | [M + H]⁺ |
|---|---|---|---|
| 86 | (4-Dimethylamino-phenyl)- | (4-Methyl-phenyl)- | 440.2 |
| 87 | (1-Methyl-2,3-dihydro-1H-indol-5-yl)- | (4-Methyl-phenyl)- | 452.3 |
| 91 | (3-Dimethylamino-phenyl)- | (4-Methyl-phenyl)- | 440.4 |
| 94 | (4-Allylamino-phenyl)- | (4-Methyl-phenyl)- | 452.6 |
| 95 | (2-Chloro-4-pyrrolidin-1-yl-phenyl)- | (4-Methyl-phenyl)- | 500.1 |
| 96 | (4-Diethylamino-phenyl)- | (4-Methyl-phenyl)- | 468.3 |
| 97 | (4-Isobutylamino-phenyl)- | (4-Methyl-phenyl)- | 468.3 |

TABLE 9-continued

| EX | R² | R¹ | [M + H]⁺ |
|---|---|---|---|
| 98 | (4-Morpholin-4-yl-phenyl)- | (4-Methyl-phenyl)- | 482.2 |
| 99 | [2-Chloro-4-(ethyl-methyl-amino)-phenyl]- | (4-Methyl-phenyl)- | 488.1 |
| 100 | [4-(Ethyl-methyl-amino)-phenyl]- | (4-Methyl-phenyl)- | 454.3 |
| 101 | [4-(Isopropyl-methyl-amino)-phenyl]- | (4-Methyl-phenyl)- | 468.3 |
| 102 | (4-Acetylamino-phenyl)- | (4-Methyl-phenyl)- | 454.3 |
| 103 | [4-(Formyl-methyl-amino)-phenyl]- | (4-Methyl-phenyl)- | 454.3 |
| 104 | [4-(2-Oxo-pyrrolidin-1-yl)-phenyl]- | (4-Methyl-phenyl)- | 480.3 |
| 107 | (4-Amino-phenyl)- | (4-Methyl-phenyl)- | 412.2 |
| 344 | (4-Dimethylamino-phenyl)- | Cyclohexylmethyl- | |
| 345 | (4-Dimethylamino-phenyl)- | Pyridin-4-ylmethyl- | |
| 346 | (4-Dimethylamino-phenyl)- | Benzyl- | |
| 347 | (3-Dimethylamino-phenyl)- | (2,5-Dimethyl-phenyl)- | |
| 348 | (3-Dimethylamino-phenyl)- | (4-Methoxy-phenyl)- | |
| 349 | (4-Piperidin-1-yl-phenyl)- | (4-Methyl-phenyl)- | |
| 350 | [4-(Methyl-propyl-amino)-phenyl]- | (4-Methyl-phenyl)- | |
| 351 | (4-Isopropylamino-phenyl)- | (4-Methyl-phenyl)- | |
| 352 | (4-Pyrrolidin-1-yl-phenyl)- | (4-Methyl-phenyl)- | |
| 353 | (4-Propylamino-phenyl)- | (4-Methyl-phenyl)- | |
| 354 | [2-Chloro-4-(methyl-propyl-amino)-phenyl]- | (4-Methyl-phenyl)- | |
| 355 | (4-Azetidin-1-yl-phenyl)- | (4-Methyl-phenyl)- | |
| 356 | [4-(Acetyl-methyl-amino)-phenyl]- | (4-Methyl-phenyl)- | |

Preferred compounds of Table 10, which were made according to the synthetic methods outlined in Scheme H, are given by the formula:

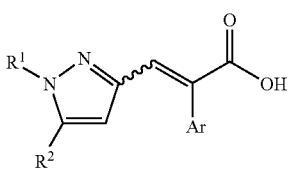

where R², R¹ and Ar are selected concurrently from the groups consisting of:

TABLE 10

| EX | R² | R¹ | Ar | [M + H]⁺ *[M − H]⁻ |
|---|---|---|---|---|
| 75 | (3,4-Dichloro-phenyl)- | (4-Methoxy-phenyl)- | (3-Methyl-phenyl)-[(E) stereoisomer] | 479.0 |
| 108 | (3,4-Dichloro-phenyl)- | (4-Ethoxy-phenyl)- | (3-Chloro-phenyl)-[(Z) stereoisomer] | *511/513 |
| 109 | (3,4-Dichloro-phenyl)- | (4-Ethoxy-phenyl)- | (3-Chloro-phenyl)-[(E) stereoisomer] | 513 |
| 110 | (3,4-Dichloro-phenyl)- | Pyridin-2-yl- | (3-Chloro-phenyl)-[(Z) stereoisomer] | *468 |
| 111 | (3,4-Dichloro-phenyl)- | (2,5-Dichloro-phenyl)- | (3-Chloro-phenyl)-[(Z) stereoisomer] | *535/537 |
| 112 | Naphthalen-2-yl- | (2,5-Dichloro-phenyl)- | (3-Chloro-phenyl)-[(Z) stereoisomer] | 519/521 |
| 113 | Naphthalen-2-yl- | (4-ethoxy-phenyl)- | (3-Chloro-phenyl)-[(Z) stereoisomer] | 495.1 |
| 114 | (3,4-Dichloro-phenyl)- | (4-Methoxy-phenyl)- | Phenyl-[(Z) stereoisomer] | 465.1 |
| 115 | (3,4-Dichloro-phenyl)- | (4-Methoxy-phenyl)- | (3-Chloro-phenyl)-[(Z) stereoisomer] | 499.0 |
| 116 | (3,4-Dichloro-phenyl)- | (4-Methoxy-phenyl)- | (4-Chloro-phenyl)-[(Z) stereoisomer] | 499.0 |
| 117 | (3,4-Dichloro-phenyl)- | (4-Methoxy-phenyl)- | (4-Methoxy-phenyl)-[(Z) stereoisomer] | 495.0 |
| 118 | (3,4-Dichloro-phenyl)- | (4-Methoxy-phenyl)- | (3,4-Dichloro-phenyl)-[(Z) stereoisomer] | 533.0 |
| 119 | (3,4-Dichloro-phenyl)- | (4-Methoxy-phenyl)- | (4-Methyl-phenyl)-[(Z) stereoisomer] | 479.1 |
| 120 | (3,4-Dichloro-phenyl)- | (4-Methoxy-phenyl)- | (3-Methyl-phenyl)-[(Z) stereoisomer] | 479.1 |
| 121 | Benzo[1,3]dioxol-5-yl- | (4-Ethoxy-phenyl)- | (3-Chloro-phenyl)-[(Z) stereoisomer] | 489.1 |
| 122 | Benzo[1,3]dioxol-5-yl- | (2,5-Dichloro-phenyl)- | (3-Chloro-phenyl)-[(Z) stereoisomer] | 513.0 |
| 123 | Benzo[1,3]dioxol-5-yl- | (2,5-Dichloro-phenyl)- | (3-Chloro-phenyl)-[(E) stereoisomer] | 513 |
| 124 | (3,4-Dichloro-phenyl)- | (4-Methoxy-phenyl)- | (3,4-Dichloro-phenyl)-[(E) stereoisomer] | 532.9 |
| 125 | Benzo[1,3]dioxol-5-yl- | (4-Ethoxy-phenyl)- | (3-Chloro-phenyl)-[(E) stereoisomer] | 489.1 |
| 357 | (3,4-Dichloro-phenyl)- | (4-Methoxy-phenyl)- | Phenyl-[(E) stereoisomer] | |
| 358 | (3,4-Dichloro-phenyl)- | (4-Methoxy-phenyl)- | (3-Chloro-phenyl)-[(E) stereoisomer] | |
| 359 | (3,4-Dichloro-phenyl)- | (4-Methoxy-phenyl)- | (4-Chloro-phenyl)-[(E) stereoisomer] | |
| 360 | (3,4-Dichloro-phenyl)- | (4-Methoxy-phenyl)- | (4-Methoxy-phenyl)-[(E) stereoisomer] | |
| 361 | (3,4-Dichloro-phenyl)- | (4-Methoxy-phenyl)- | (3,4-Dichloro-phenyl)-[(E) stereoisomer] | |
| 362 | (3,4-Dichloro-phenyl)- | (4-Methoxy-phenyl)- | (3-Methyl-phenyl)-[(E) stereoisomer] | |
| 363 | (3,4-Dichloro-phenyl)- | (4-Methoxy-phenyl)- | (4-Methyl-phenyl)-[(E) stereoisomer] | |
| 364 | Benzo[1,3]dioxol-5-yl- | (4-Ethoxy-phenyl)- | (3-Chloro-phenyl)-[(E) stereoisomer] | |

The preferred compounds that follow were made according to the synthetic methods outlined in Schemes A, B, C, D and J and as described in Examples 76, 139, 133, 134, 140, 141, 336 and 343:

3-[5-(3,4-Dichloro-phenyl)-1-(4-methoxy-phenyl)-1H-pyrazol-3-yl]-2-methyl-2-m-tolyl-propionic acid (Example 76);

3-[5-(3,4-Dichloro-phenyl)-1-(4-methoxy-phenyl-1H-pyrazol-3-yl]-2-fluoro-2-m-tolyl-propionic acid (Example 139);

3-[5-(3,4-Dichloro-phenyl)-1-(2,4-dichloro-phenyl)-1H-pyrazol-3-yl]-2-(3-dimethylamino-phenyl)-propionic acid (Example 133);

3-[5-(3,4-Dichloro-phenyl)-1-(2,4-dichloro-phenyl)-1H-pyrazol-3-yl]-2-quinolin-8-yl-propionic acid (Example 134);

4-(15-Di-p-tolyl-1H-pyrazol-3-yl)-3-m-tolyl-butyric acid (Example 140);

5-[5-(3,4-Dichloro-phenyl)-1-(4-methoxy-phenyl)-1H-pyrazol-3-yl]-4-m-tolyl-pentanoic acid (Example 141);

5-{2-[5-(3,4-Dichloro-phenyl)-2-(4-methoxy-phenyl)-2H-pyrazol-3-yl]-1-m-tolyl-ethyl}-1H-tetrazole (Example 336); and 3-[2-(4-Methoxy-phenyl)-5-p-tolyl-2H-pyrazol-3-yl]-2-naphthalen-1-yl-propionic (Example 343).

Preferred compounds of Table 11, which are made according to the synthetic methods outlined in Schemes A, E and F, are given by the formula:

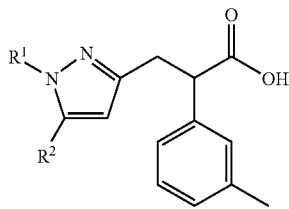

where $R^2$ and $R^1$ are selected concurrently from the groups consisting of:

TABLE 11

| EX | $R^2$ | $R^1$ |
|---|---|---|
| 365 | Naphthalen-2-yl- | Pyridin-3-yl- |
| 366 | Naphthalen-2-yl- | Pyridin-4-yl- |
| 367 | Naphthalen-2-yl- | (6-Methyl-pyridin-2-yl)- |
| 368 | Naphthalen-2-yl- | (3-Methoxy-pyridin-2-yl)- |
| 369 | Naphthalen-2-yl- | (5-Methoxy-pyridin-2-yl)- |
| 370 | Naphthalen-2-yl- | (6-Methoxy-pyridin-3-yl)- |
| 371 | Naphthalen-2-yl- | (4-Ethoxy-pyridin-2-yl)- |
| 372 | Naphthalen-2-yl- | (4-Dimethylamino-phenyl)- |
| 373 | Naphthalen-2-yl- | (5-Dimethylamino-2-methoxy-phenyl)- |
| 374 | (3,5-Bis-dimethylamino-phenyl) | (4-Methyl-phenyl)- |
| 375 | (3-Dimethylamino-4-methoxy-phenyl)- | (4-Methyl-phenyl)- |

Preferred compounds of Table 12, which may be made according to the synthetic methods outlined in Schemes A, B, C, D, H and J, are given by the formula:

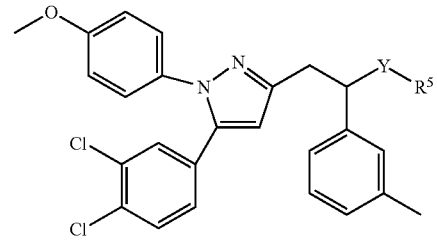

where $R^5$—Y— is selected from the groups consisting of:

TABLE 12

| EX | $R^5$—Y— |
|---|---|
| 376 | (5-Oxo-4,5-dihydro-1H-[1,2,4]triazol-3-ylsulfanyl)-methyl- |
| 377 | (3H-[1,2,3]Triazol-4-ylsulfanyl)-methyl- |
| 378 | (2H-[1,2,4]Triazole-3-sulfinyl)-methyl- |

Preferred compounds of Table 13, which may be made according to the synthetic methods outlined in Scheme H, are given by the formula:

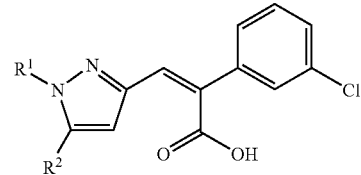

where $R^2$ and $R^1$ of such (Z) stereoisomeric compounds are selected concurrently from the groups consisting of:

TABLE 13

| EX | $R^2$ | $R^1$ |
|---|---|---|
| 379 | (4-Dimethylamino-phenyl)- | (4-Dimethylamino-phenyl)- |
| 380 | (4-Dimethylamino-phenyl)- | Naphthalen-2-yl- |
| 381 | (4-Dimethylamino-phenyl)- | (4-chloro-phenyl)- |
| 382 | (4-Dimethylamino-phenyl)- | Phenyl- |
| 383 | (4-Dimethylamino-phenyl)- | Benzo[1,3]dioxol-5-yl- |
| 384 | Naphthalen-2-yl- | (4-Dimethylamino-phenyl)- |
| 385 | Naphthalen-2-yl- | Naphthalen-2-yl- |
| 386 | Naphthalen-2-yl- | (4-Chloro-phenyl)- |
| 387 | Naphthalen-2-yl- | Phenyl- |
| 388 | Naphthalen-2-yl- | Benzol[1,3]dioxol-5-yl- |
| 389 | (4-Chloro-phenyl)- | (4-Dimethylamino-phenyl)- |
| 390 | (4-Chloro-phenyl)- | Naphthalen-2-yl- |
| 391 | (4-Chloro-phenyl)- | (4-chloro-phenyl)- |
| 392 | (4-Chloro-phenyl)- | Phenyl- |
| 393 | (4-Chloro-phenyl)- | Benzo[1,3]dioxol-5-yl- |
| 394 | Phenyl- | (4-Dimethylamino-phenyl)- |
| 395 | Phenyl- | Naphthalen-2-yl- |
| 396 | Phenyl- | (4-chloro-phenyl)- |
| 397 | Phenyl- | Phenyl |
| 398 | Phenyl- | Benzo[1,3]dioxol-5-yl- |
| 399 | Benzo[1,3]dioxol-5-yl- | (4-Dimethylamino-phenyl)- |
| 400 | Benzo[1,3]dioxol-5-yl- | Naphthalen-2-yl- |
| 401 | Benzo[1,3]dioxol-5-yl- | (4-Chloro-phenyl)- |
| 402 | Benzo[1,3]dioxol-5-yl- | Phenyl- |
| 403 | Benzo[1,3]dioxol-5-yl- | Benzo[1,3]dioxol-5-yl- |

The preferred compounds that follow are made according to Scheme A and as described in Method 2:

2-Benzofuran-3-yl-3-[1-(4-methoxy-phenyl)-5-p-tolyl-1H-pyrazol-3-yl]-propionic acid; and 2-Benzofuran-3-yl-3-[5-(4-chloro-phenyl)-1-(4-methoxy-phenyl)-1H-pyrazol-3-yl]-propionic acid.

The compounds as described above may be made according to processes within the skill of the art and/or which are described in the schemes and examples that follow. To obtain the various compounds herein, starting materials may be employed which carry the ultimately desired substituents though the reaction scheme with or without protection as appropriate. Starting materials maybe obtained from commercial sources or synthesized by methods known to one skilled in the art. Alternatively, it may be necessary to employ, in the place of the ultimately desired substituent, a suitable group, which may be carried through the reaction scheme and replaced as appropriate with the desired substituent. In the Schemes, the pyrazole is depicted with broken lines indicating that the conventional position of the unsaturation is dependent upon the position of the $R^1$ substituent. Any product containing a chiral center may be separated into its enantiomers by HPLC using a chiral stationary phase.

SCHEME A

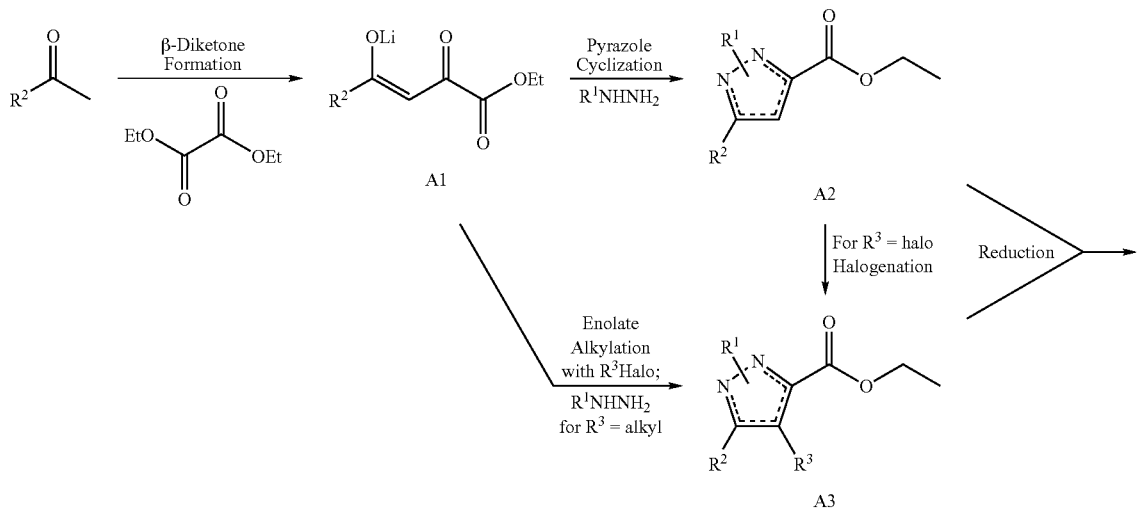

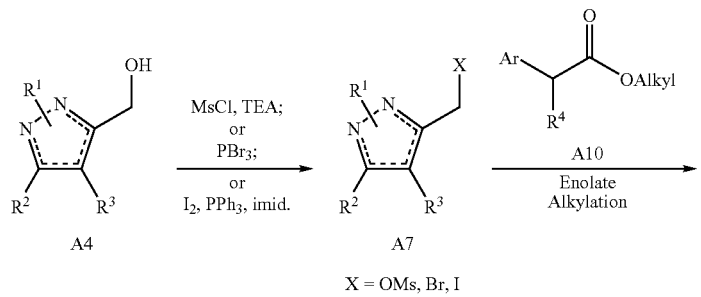

X = OMs, Br, I

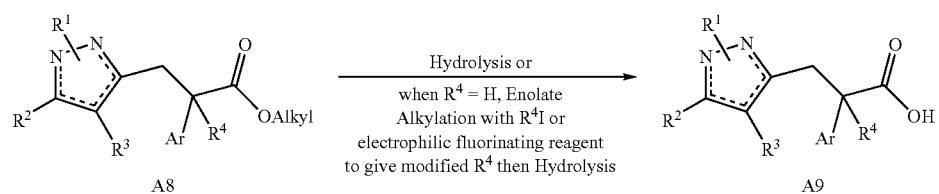

Referring to Scheme A, there are disclosed the following notes and additions. A1 is preferably isolated as an enol salt. In addition to the lithium, the sodium and potassium salts may also be used. A2 is formed as a mixture of regioisomers with either the 1,5- or 1,3-isomer predominating. A2 regioisomers may be separated and carried forward individually. The reduction to A4 may be effected with a number of reducing agents including DIBAL-H and LiAlH$_4$. The conversion of alcohol A4 to bromide, iodide or mesylate A7 may be carried out with various agents including PBr$_3$, CBr$_4$/PPh$_3$, I$_2$/imidazole, or MsCl/TEA. The enolate alkylation to A8 may be carried out with R$^4$ as hydrogen or alkyl. When R$^4$ is hydrogen in A8, R$^4$ as alkyl or halogen may be obtained in A9 by enolate alkylation or electrophilic fluorination. Various starting materials A10 may be purchased or certain such starting materials may be synthesized by homologation of aryl aldehydes using chemistry described by Wang (Synthetic Communications 29, (1999), 2321), or Mikolajczyk (J. Am. Chem. Soc. 120, (1998) 11633.

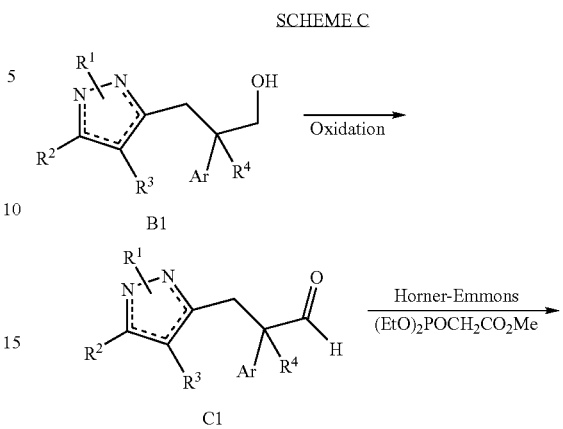

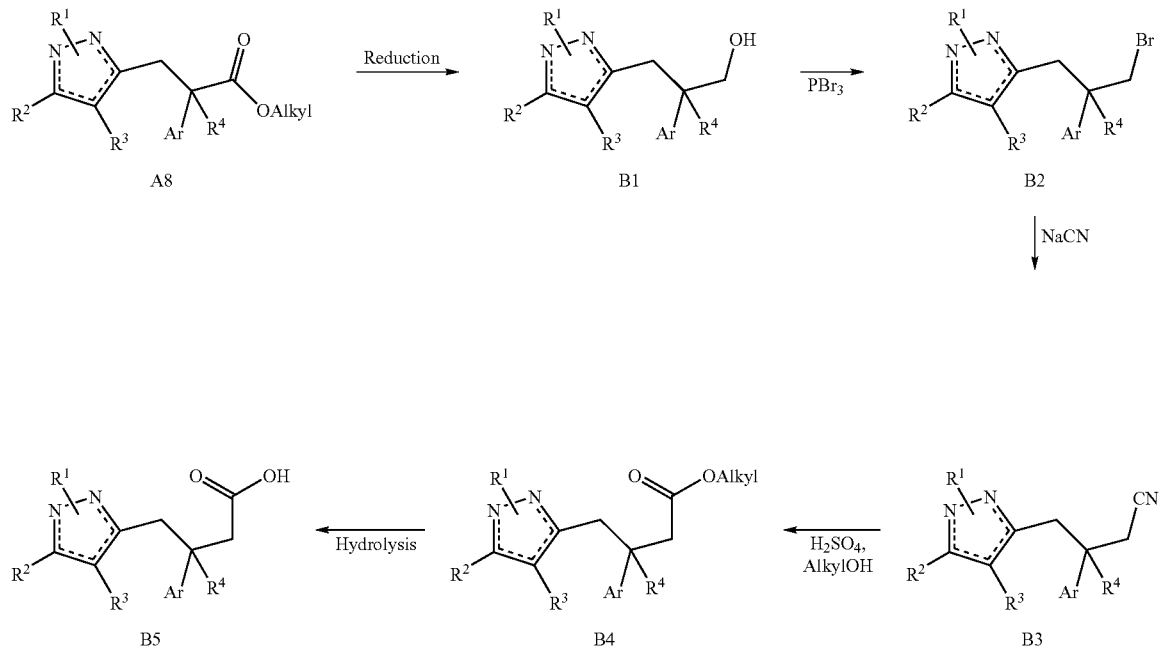

Referring to Scheme B, there are disclosed the following notes and additions. The reduction to B$_1$ may be effected with a number of reducing agents including DIBAL-H and LiAlH$_4$. Displacement of the hydroxy to form bromide B2 can be carried out using a variety of reagents including PBr$_3$, or CBr$_4$/PPh$_3$. Hydrolysis of the nitrile B3 to the ester B4 can be carried out with a variety of acids including HCl, TsOH, or H$_2$SO$_4$. Hydrolysis of the ester B4 to the acid B5 can be performed under basic conditions generally using LiOH. As with the reduction of ester A8 to B1, ester B4 may be reduced to a n+1 analogue of B1, which will produce according to the teachings in Scheme B, a n=2 analogue of B5. Thus, according to Scheme B, both a n=1 and n=2 acid B5 is produced.

-continued

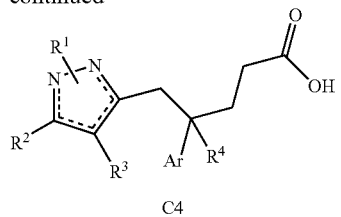

C4

Referring to Scheme C, there are disclosed the following notes and additions. Oxidation of B1 to C1 can be performed using procedures such as the Dess-Martin or Swern oxidations. Hydrogenation to form C3 can be done with a variety of catalytic hydrogenation conditions such as Raney Nickel, Pd/C, $CoCl_2/NaBH_4$, $RhCl(PPh_3)_3$. Hydrolysis of ester C3 is generally done under basic conditions with LiOH, but other bases could be used.

SCHEME D

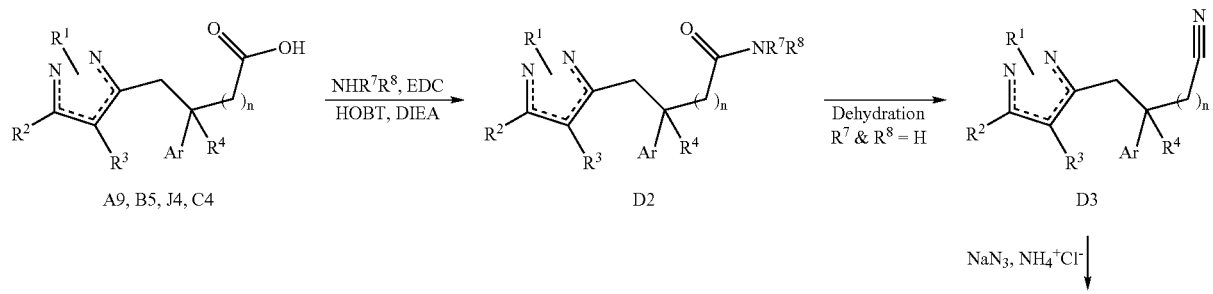

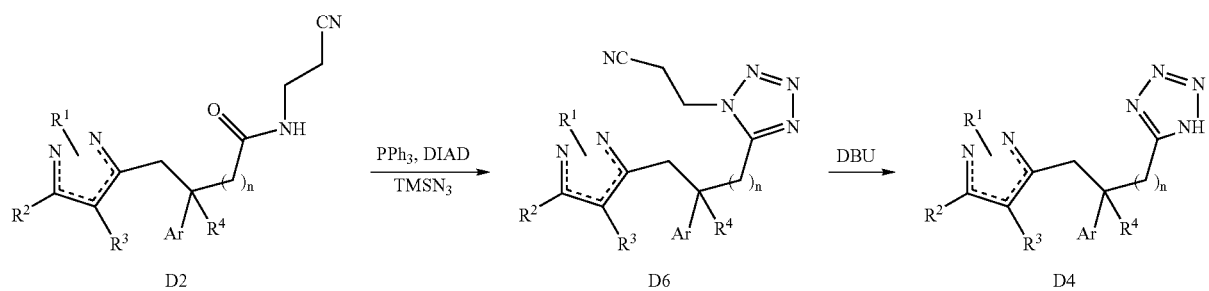

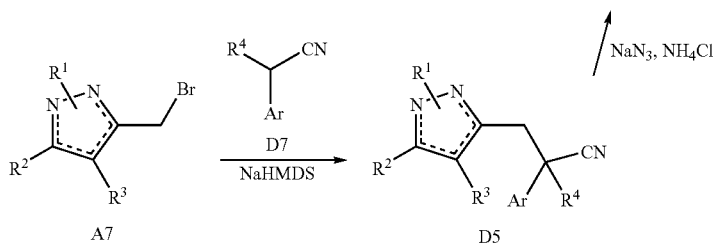

Referring to Scheme D, there are disclosed the following notes and additions. As shown, any of the acids, A9, B5, J4, or C4 can be employed as a starting material. Formation of amide D2 can be performed using a variety of amide bond forming conditions (see: Synthesis, (1974) 549). Dehydration with TFAA followed by cyclization of the cyano with NaN$_3$ gave the desired tetrazole D4. Additionally D5 can be synthesized by addition of bromide A7 to the anion of nitrile D7. Compound D5 can then be converted to the tetrazole D4 using NaN$_3$. Alternatively the specific amide D2 can be converted to the protected tetrazole D6 using TMSN$_3$ under Mitsunobu conditions, deprotection with DBU then provides D4.

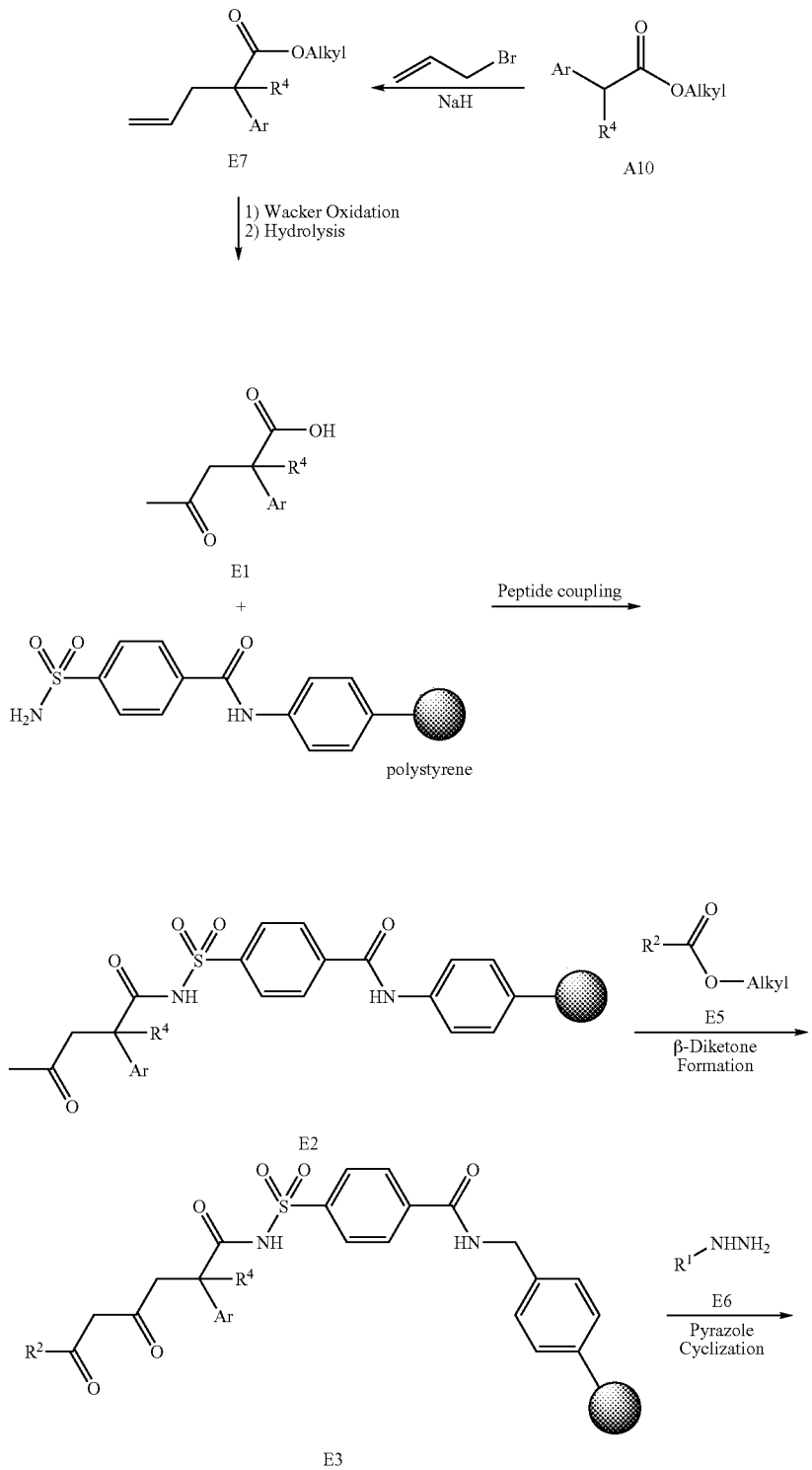

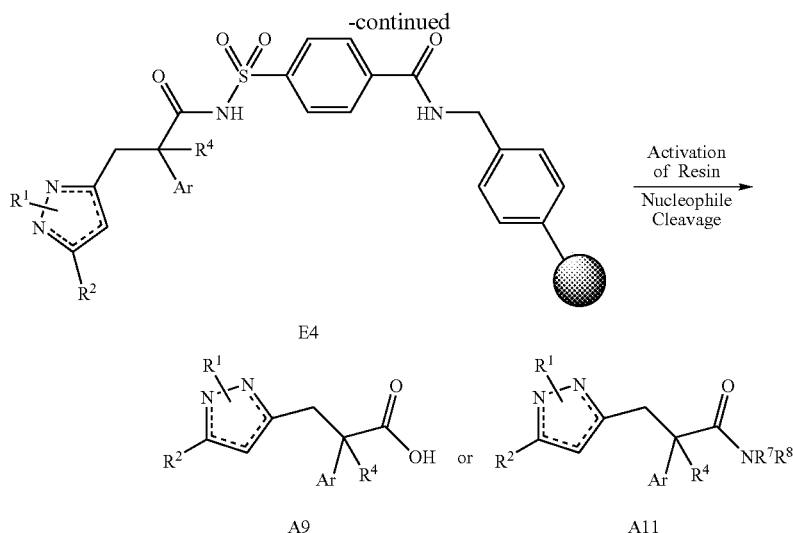

E4

A9 or A11

Referring to Scheme E, there are disclosed the following notes and additions. In the manufacture of starting material E1, an aryl acetic acid ester such as A10 is condensed with appropriate terminal olefinic alkyl halide followed by Wacker oxidation to give the ester E7. Hydrolysis of the ester will give the methyl ketone E1. Coupling of acid E1 is to Kenner's safety-catch resin can be accomplished with a variety of peptide coupling reagent including CDI, PyBOP, HOBt. Condensation with E5 gives E3, which is then cyclized with the appropriate hydrazine to give the desired pyrazole E4 as a mixture of regioisomers. Activation of the resin with $TMSCH_2N_2$ followed by cleavage with hydroxide gives acids A9 as a mixture of regioisomers, which can be separated by HPLC. Alternatively, the activated sulfonamide resin can be cleaved with amine nucleophiles to provide amides A11. Scheme E follows a process similar to that disclosed in Organic Letters, Vol. 2, 2000, pages 2789 to 2792.

SCHEME E

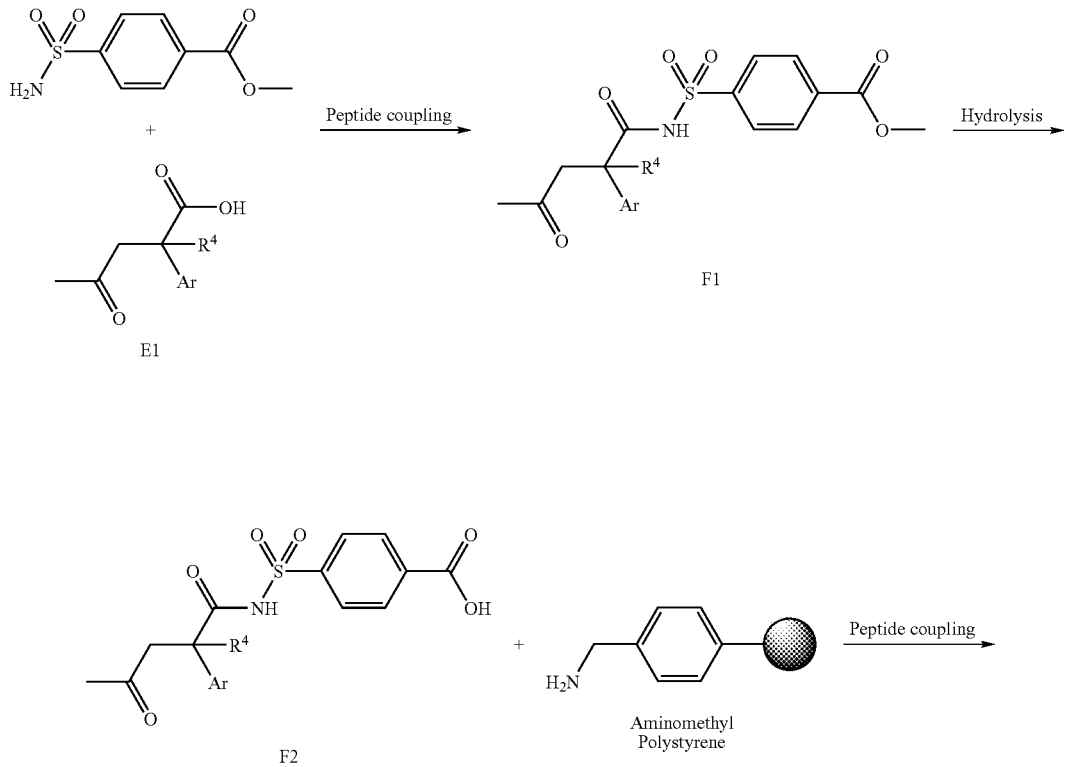

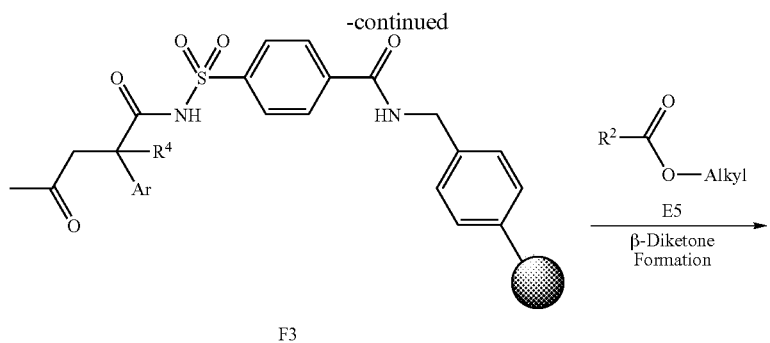
F3
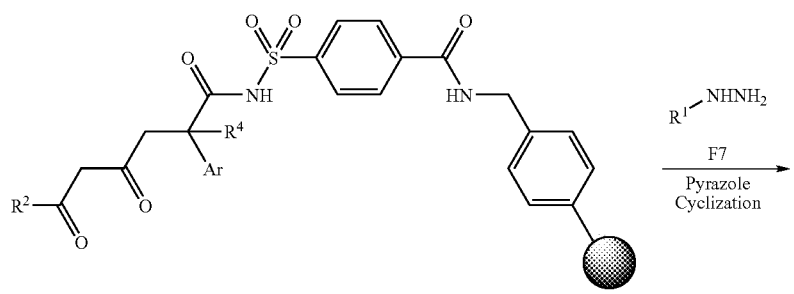
F4
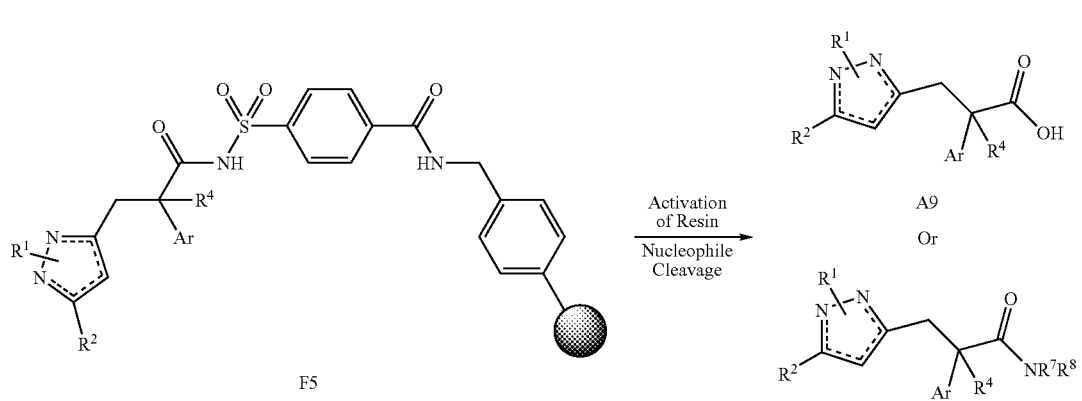
F5

Referring to Scheme F, there are disclosed the following notes and additions. Compounds of type A9 and A11 can be synthesized in a manner similar to scheme E, this approach is outlined in scheme F. In this case a sulfonamide linker is coupled to E1 prior to attachment to resin, to facilitate quantitation of resin loading. Acid F2 is then coupled to macroporous aminomethyl polystyrene support to provide F3, which is similar to E2. Scheme F proceeds from F3 to A9 or A11 in an analogous fashion to Scheme E. Use of macroporous resin provides higher yields of product and easier handling of reactions than the resin used in scheme E.

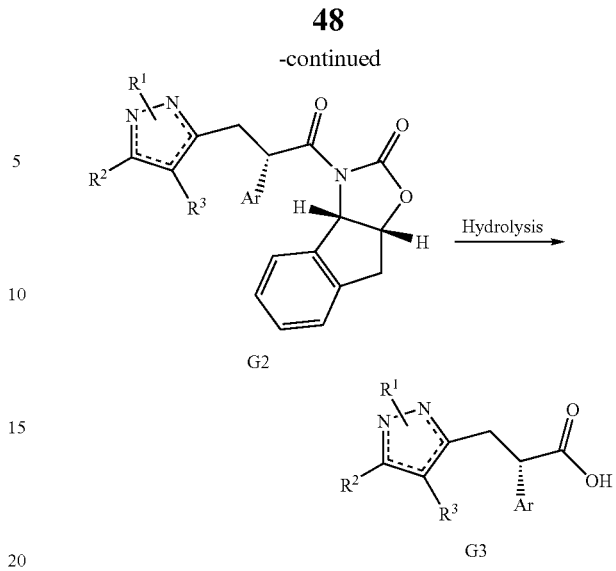

SCHEME G

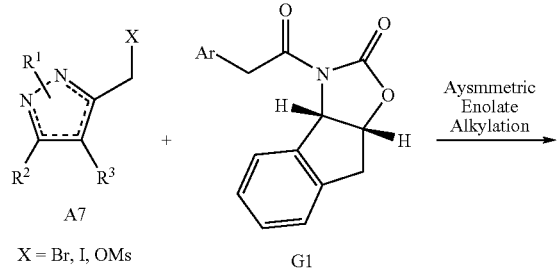

Referring to Scheme G, there are disclosed the following notes and additions. Using the appropriate chiral auxiliary attached to the Ar-acetic acid derivative G1, enolate alkylation by pyrrole A7 affords the desired stereochemistry about the new stereocenter in G2. In addition, other chiral auxiliaries such as the valine and phenylalanine derived oxazolidinones of Evans can also be used. Alternatively, the opposite enantiomer of the chiral auxiliary depicted can be used to synthesize the opposite absolute stereochemistry of G3. As depicted, G3 is the (S) configuration when $R^4$ is H and the depicted chiral auxiliary is used. For $R^4$ other than H and for other chiral auxiliaries, the absolute configuration G3 may be either the one shown or the opposite configuration depending upon the conditions used.

SCHEME H

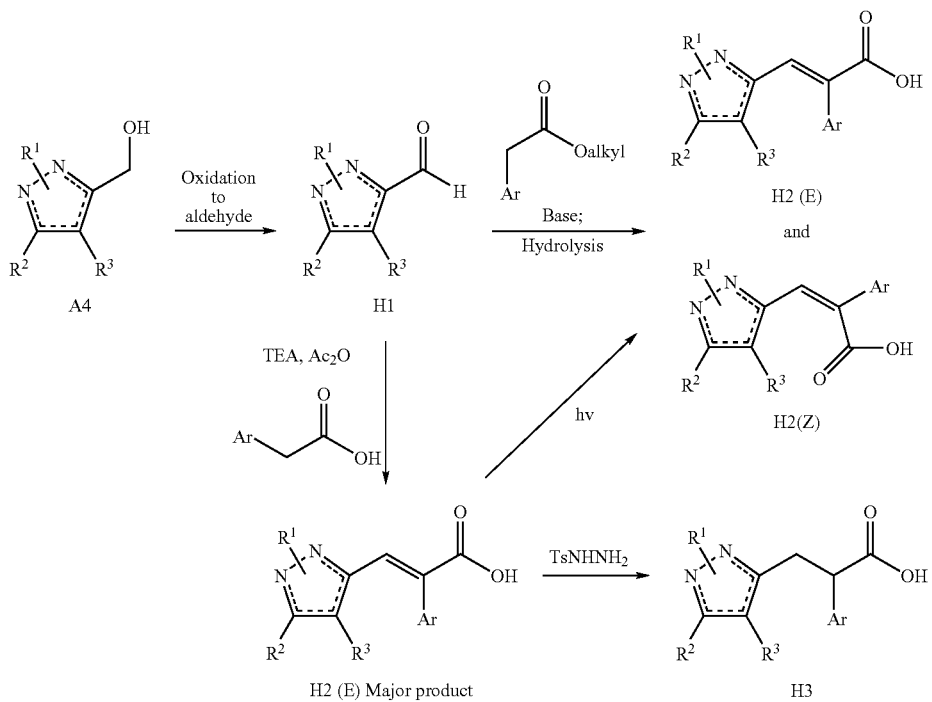

Referring to Scheme H, there are disclosed the following notes and additions. Oxidation of the alcohol A4 can be performed using Dess-Martin or Swern oxidation conditions to provide aldehyde H1. H1 can be condensed with an Ar-acetic acid ester using standard aldol condensation conditions to give the olefin-ester as a mixture of the E- and Z-isomers, which upon hydrolysis affords acids H2 (E) and H2 (2). The E- and Z-isomers maybe separated by chromatography. Alternatively the acid H2 (E) can be obtained directly via a Perkin condensation using an arylacetic acid and $Ac_2O$. In this case, only acid H2 (E) is formed. Furthermore, photoisomerization of the isolated E- or Z-isomer results in the creation of a mixture of E- and Z-isomers. Additionally reduction of the olefin with $TsNHNH_2$, or other reducing agent can provide the saturated analogs H3.

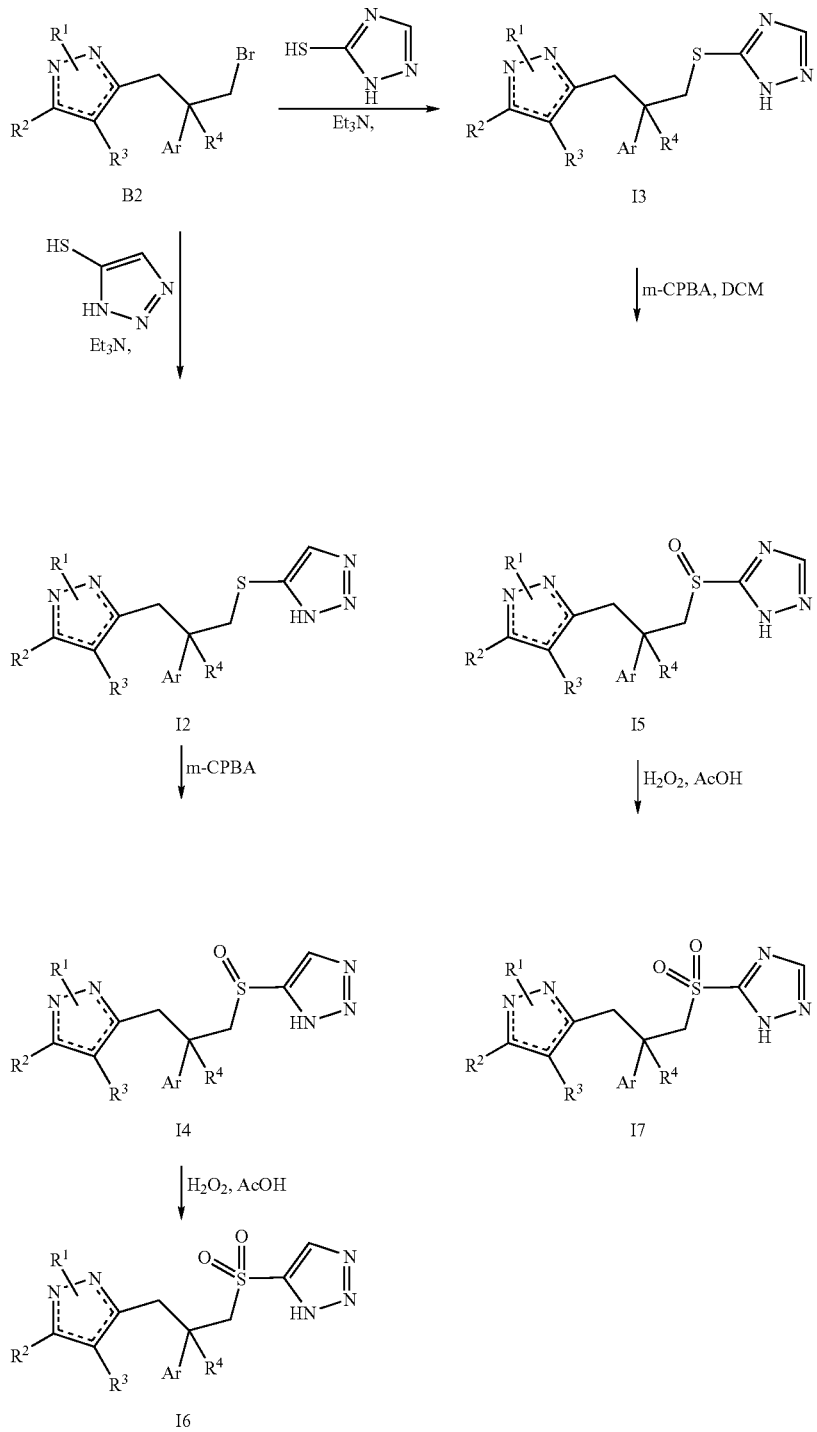

SCHEME I

Referring to Scheme I, there are disclosed the following notes and additions. The alkyl bromide B2 can be displaced with several thiol linked heterocycles to give compounds such as I2 or I3. Additionally, the sulfur can be selectively oxidized to the sulfinyl compounds with an oxidant such as mCPBA to afford I4 and I5. Additionally these compounds can be further oxidized to the sulfonyl linked heterocycles by oxidation with such agents as $H_2O_2$. To obtain analogues of I2 through I7 in which n=2, an n+1 bromide B2 may be used as the starting material. The n+1 bromide B2 may be obtained as described in the paragraph following Scheme B.

rated by standard chromatographic methods. Esterification can be performed with a variety of alkyl groups to form esters J3, the preferred Alkyl group being t-Butyl. Coupling of an aryl bromide with the enolate of J3 using the conditions described by Buchwald (J. Am. Chem. Soc. 123, (2001) 7996) then provide the ester of J4, which can be hydrolyzed to J4.

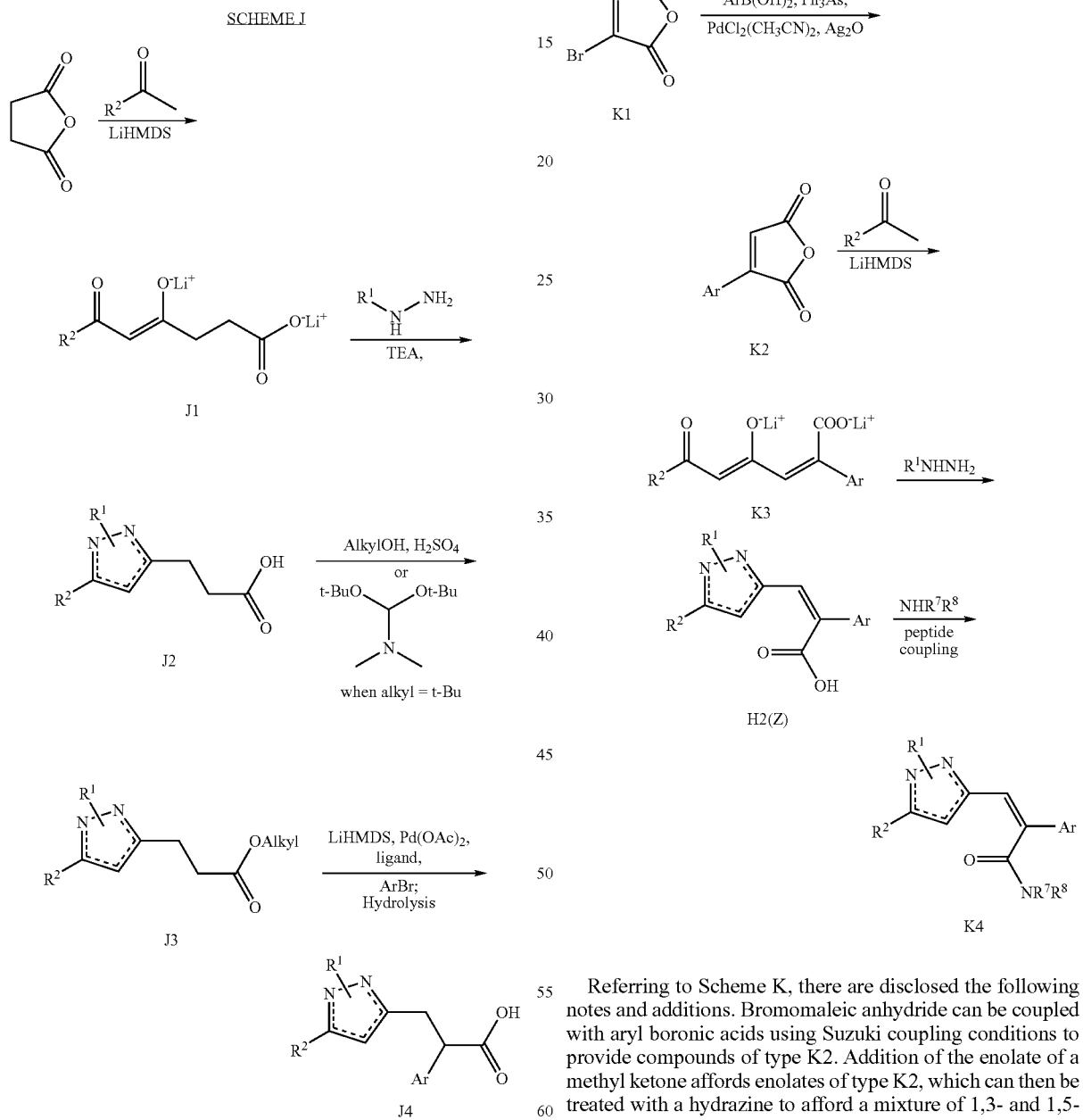

Referring to Scheme J, there are disclosed the following notes and additions. Succinic anhydride can be reacted with the enolate of a methyl ketone to provide enolates of type J1. Additions of hydrazines provide pyrazoles J2 as a mixture of 1,3- and 1,5 regioisomers, these isomers can be readily sepa- Referring to Scheme K, there are disclosed the following notes and additions. Bromomaleic anhydride can be coupled with aryl boronic acids using Suzuki coupling conditions to provide compounds of type K2. Addition of the enolate of a methyl ketone affords enolates of type K2, which can then be treated with a hydrazine to afford a mixture of 1,3- and 1,5-substituted pyrazoles H2 with exclusively to (Z) olefin geometry shown. These pyrazole regioisomers can be readily separated by chromatography. Pyrazoles H2 may be converted to amides K4 through peptide coupling. Pyrazole H2 may be esterified to produce an alkene equivalent compound A8, which can be used, as disclosed in Scheme B, to produce the n=1 and n=2 analogues.

SCHEME L

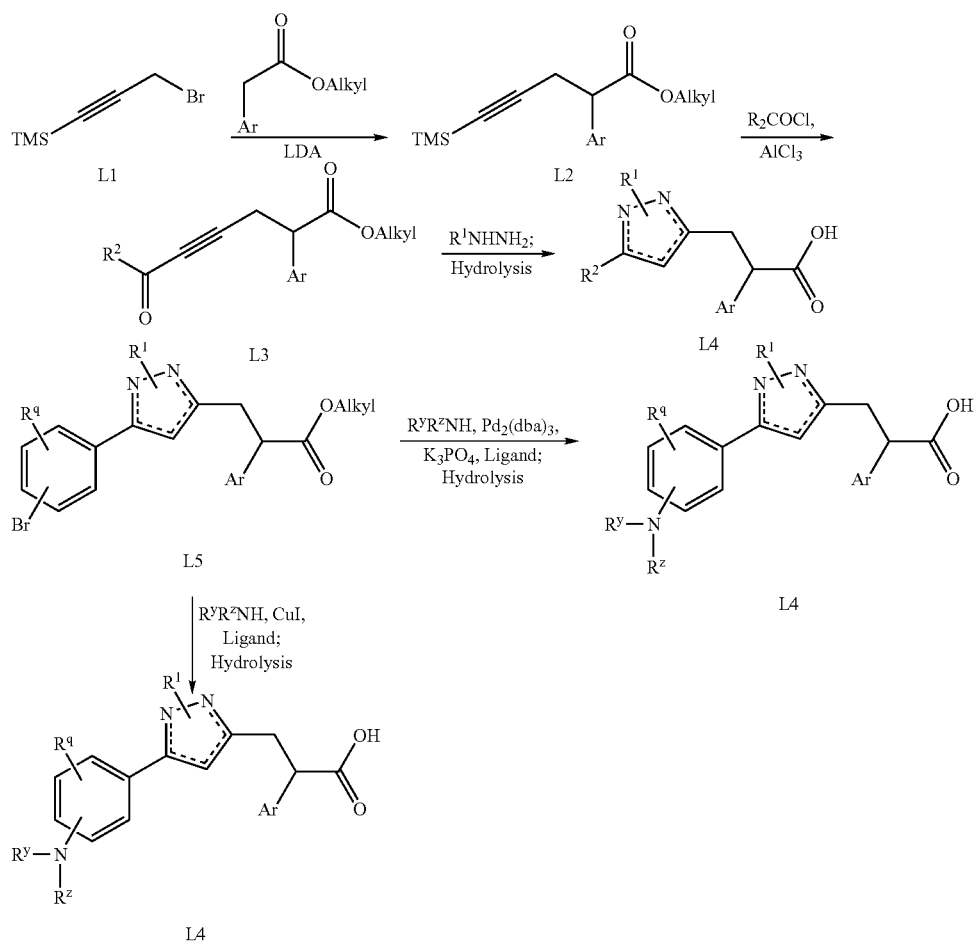

Referring to Scheme L, there are disclosed the following notes and additions. Arylacetic acid esters can be alkylated with propargyl bromides of type L1 to form alkynes of type L2. If the alkyl group is a chiral auxiliary such as depicted in scheme G this transformation can be performed to produce enatiomerically pure compounds of type L2. Friedel-Crafts type coupling of the alkyne L2 with and acid chloride then provides alkynyl ketone L3. Addition of a hydrazine followed by hydrolysis of the ester provides pyrazoles of type L4 as a mixture of 1,3- and 1,5-regioisomers. In addition if the esters L5 contain a halogen on any of the aromatic rings (chemistry is specifically indicated for $R^2$ in the scheme) the compound can be coupled with an amine or amide using either the copper or palladium coupling conditions described by Buchwald (J. Am. Chem. Soc. 123, (2001) 7727; J. Org. Chem. 65, (2000) 1158) to obtain nitrogen substituted compounds L4 upon hydrolysis. Additionally if any of the aromatic rings in L4 are a pyridine they can be oxidized to the N-oxide using mCPBA. The racemic mixtures of compounds L4 and L5 can optionally be separated into their individual pure enantiomers through chiral chromatography.

SCHEME M

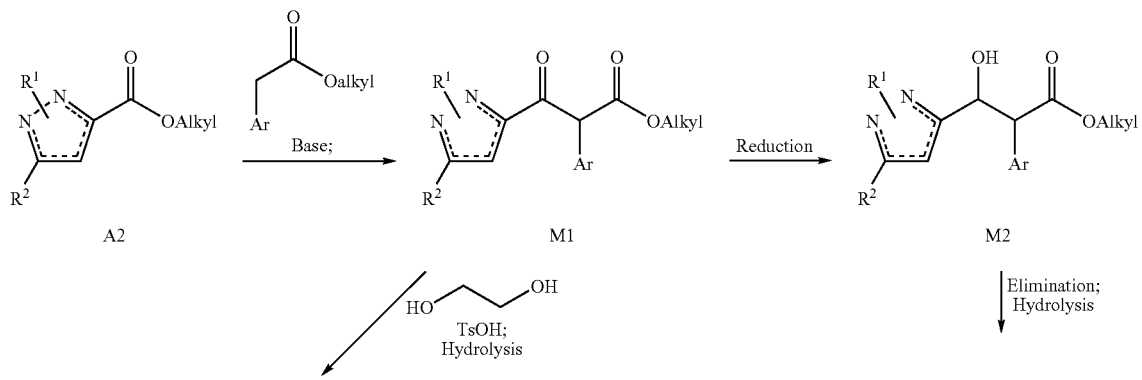

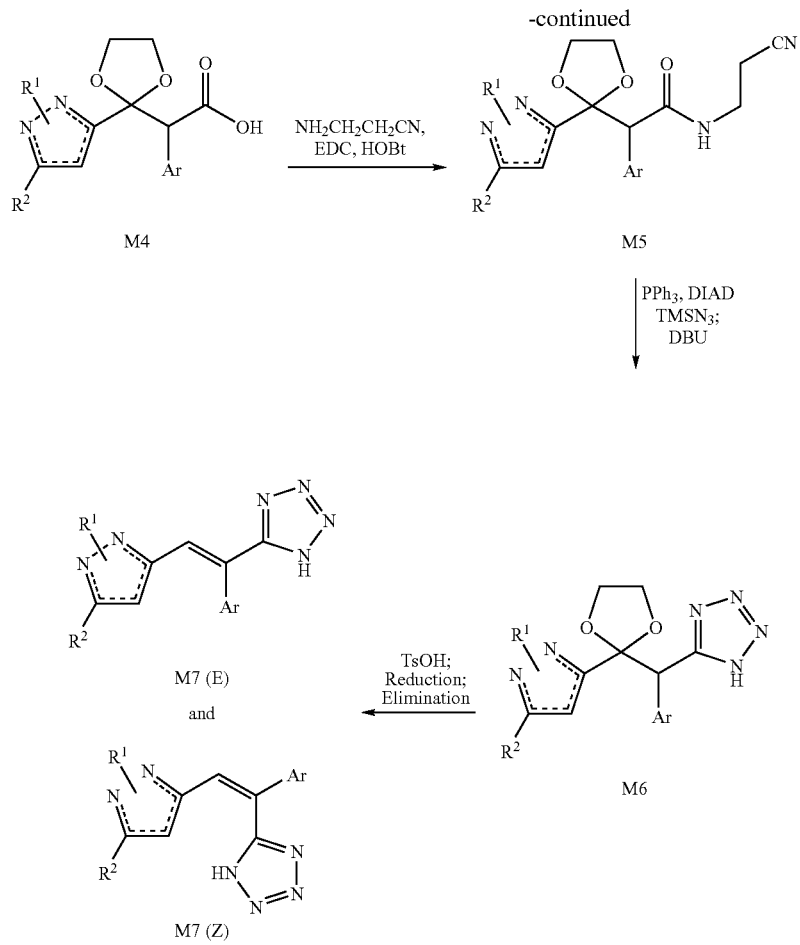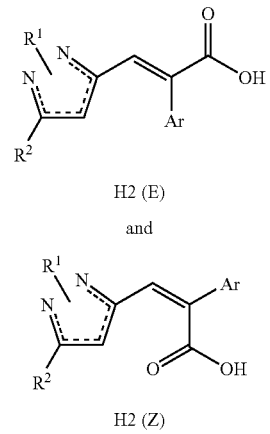

Referring to Scheme M, there are disclosed the following notes and additions. Pyrazole esters of type A2 of either regioisomeric form can be condensed with the enolate of a phenylacetic acid ester to form ketoester M1. Reduction of M1 to the alcohol followed by elimination of the β-hydroxy ester in the presence of base results in the ester of H2, which can then be hydrolyzed to form acid H2 as a mixture of (E) and (Z) isomers. These isomers can be separated by chromatographic methods. Alternatively the ketone M1 can be protected as the ketal, and the ester hydrolyzed to form M4. Amide coupling and tetrazole formation can then be performed using the procedures outlined in scheme D to provide M6. Deprotection, reduction, and elimination as previously described then afford olefinic tetrazoles of the type M7.

In addition to the teachings provided by foregoing Schemes, there are disclosed the following notes and additions regarding the making compounds of formula (I) by processes that are stereoselective and/or regioselective.

It is understood that the teachings provided by foregoing Schemes are not meant to be mutually exclusive with the teachings provided by the following Schemes in their application to chemically meaningful combinations of process steps.

Furthermore, scheme labeling is provided herein only for the convenience of scheme designation, but it is not meant to imply any limitation to the schemes themselves. In addition, scheme labeling provided herein is not meant to imply any limitation to and/or exclusion of any chemically meaningful combination made in light of the ordinary skill in the art, and/or in light of the present disclosure, of the teachings in one or several of the schemes provided herein.

Terms such as "stereoselective", "stereoselectivity", and morphologic variations thereof refer to the production of stereoisomeric products in unequal amounts. As conventionally used, enantiomeric excess (often abbreviated as "ee") means herein $|F_{(+)}-F_{(-)}|$, where $F_{(+)}$ denotes mole fraction (or mass fraction) of enantiomer (+), $F_{(-)}$ denotes mole fraction (or mass fraction) of enantiomer (−), and $F_{(+)}+F_{(-)}=1$. When given as a percentage, enantiomeric excess is $100 \cdot |F_{(+)}-F_{(-)}|$. Terms such as "enantiomerically pure", "optically pure", and morphologic variations thereof refer to products that satisfy ee >99%.

Terms such as "racemic", "racemate", and morphologic variations thereof apply as used herein to mixtures in which the enantiomers are present in equimolar amounts (ee=0) and such mixtures do not exhibit optical activity.

Terms such as "regioselectivity", "regioselective", and morphologic variations thereof refer to the existence of a preferential direction of bond making or breaking over other possible directions. Regioselectivity extent is given in terms of a percentage (which is also referred to as regioisomeric excess) of a desired product with certain bonding pattern that is formed in excess of other product or products with some other bonding pattern.

Embodiments of processes illustrated herein include, when chemically meaningful, one or more steps such as hydrolysis, halogenation, protection, and deprotection. These steps can be implemented in light of the teachings provided herein and the ordinary skill in the art.

Embodiments of this invention provide compounds with a desired bonding pattern and/or with a desired chirality by processes that have a small number of synthetic steps. Such small number of steps makes embodiments of this invention particularly suitable for synthetic processes where significant quantities of the desired compound are to be obtained. Scale-up processes are examples of such embodiments.

According to embodiments of this invention, compounds with a desired chirality are synthesized with no need to resort to column chromatographic separation. Furthermore, the compounds with a desired chirality are synthesized in embodiments of this invention with no need to resort to process steps that involve expensive chiral auxiliary compounds.

reomeric excess with respect to the chirality of a stereogenic center for any pair of diaestereomers is defined analogously as enantiomeric excess is defined above.

The chiral ester was added to a cooled medium. The medium was obtained by mixing an organic base with an acid halide in an organic solvent. Acid chlorides are examples of such acid halides, tertiary amines are examples of such bases, and low polarity solvents are examples of such solvents. Trialkyl amines are preferred tertiary amines, and dimethylethyl amine is a more preferred embodiment. Other amines such as triethyl amine, diethylmethyl amine, and mixtures thereof can be used in embodiments of this invention, preferably tertiary amines whose molecular volume is comparable to that of dimethylethyl amine. An estimate of molecular volumes for such comparison can be performed by resorting to consultation of standard tables of atomic and molecular

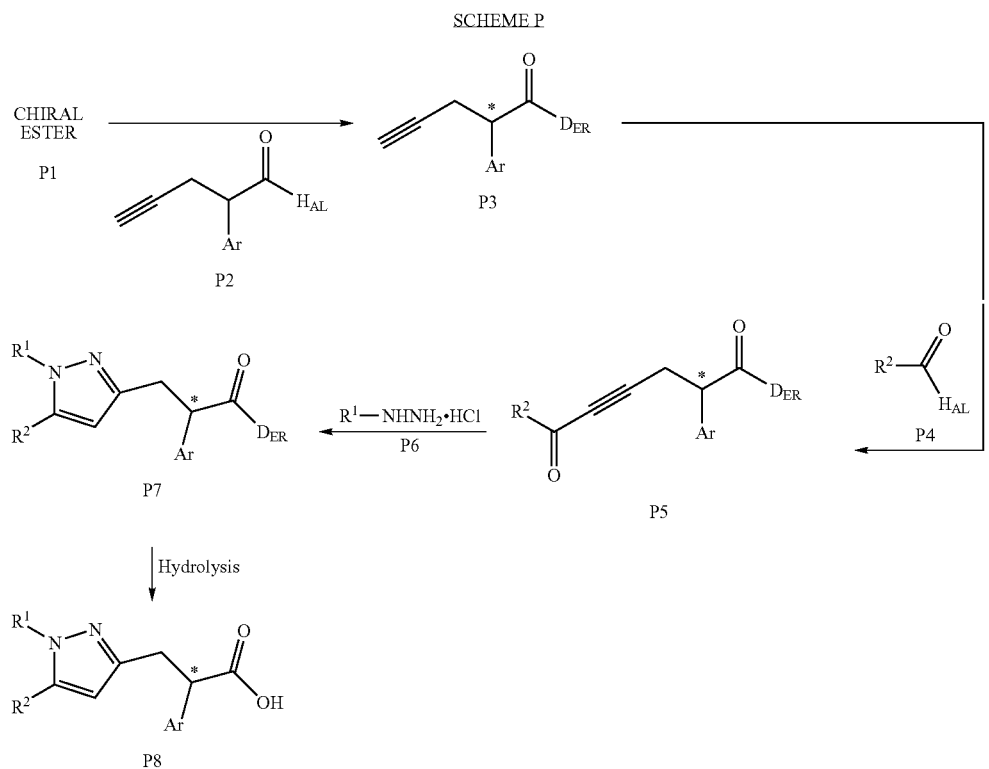

SCHEME P

Referring to Scheme P, there are disclosed the following notes and additions. Stereoselectivity is introduced through an acetylenic ketone, such as P5, obtained from a coupling of chiral acetylenic addition product P3 and an acid halide P4. Product P3 is obtained by a stereoselective addition of a chiral ester, such as P1, with an acetylenic acid halide, such as P2. Substituent H$_{AL}$ in P2 and P4 is an appropriate leaving group.

The addition reaction with a chiral ester and an acetylenic acid halide was developed in the context of this invention. It was found in the context of this invention that compounds P3 can be produced by this reaction with high enantiomeric excess regarding the stereogenic center-shown in Scheme P with an asterisk. This enantiomeric excess was in embodiments of this invention at least 80%. Referring to diastereomeric excess (de), embodiments of this invention yield P3 with a high diastereomeric excess. Embodiments of this invention produced P3 with de of at least about 80%. Diasteparameters, including radii, bond lengths, volumes, and molecular properties that lead to an indirect estimate of molecular volumes.

Toluene is a preferred organic solvent. Other solvents such as hexane and mixtures thereof can be used in embodiments of this invention. Preferred solvents are those that are not significantly more polar than toluene, so that the solvent medium preferably has a dielectric constant not greater than about 6, and more preferably not greater than about 3. Organic solvents whose dielectric constant is not greater than about 6 are referred herein as "low polarity organic solvents". The cooled medium is preferably at a temperature in the range from about −70° C. to about −85° C.

Compound P2 is more preferably an acid halide, in which case the substituent HAL is a halo group, more preferably Cl or Br, and most preferably Cl. Substituent Ar is defined above.

Substituent D_ER is determined by the choice of ester P1. In some embodiments of this invention, ester P1 is ethyl lactate, in which case -D_ER is

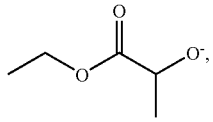

where "o-" denotes the attachment member. In general, -D_ER is —O-D_ER' where D_ER' is the moiety of the chiral ester that attaches through the O member to form a compound P3.

Compound P2 is either available or it can be prepared by an acid halide formation reaction. In embodiments of this invention in which H_AL is Cl, and Ar is m-tolyl, compound P2 was obtained from 2-m-tolyl-pent-4-ynoic acid and oxalyl chloride under suitable acid chloride formation conditions.

The acid that is used in the formation of the acetylenic compound from which an acetylenic acid halide is subsequently formed is either available or it can be obtained by an alkylation reaction. In some embodiments, 2-m-tolyl-pent-4-ynoic acid was obtained by alkylating m-tolyl acetic acid with propargyl bromide under suitable alkylation conditions.

The alkylation and acid halide formation steps are not displayed in Scheme P for brevity, but they can be implemented in light of the teachings provided herein. Starting reagents for the alkylation and acid halide formation reactions are readily available or can be prepared according to methodology within the ordinary skill in the art.

An asterisk (*) next to a C center in the schemes provided herein denotes a single stereogenic center. The chirality of the stereogenic center of compound P3 is determined by the chirality in chiral ester P1. In some embodiments, P1 was chosen to be (S)-(–)-ethyl lactate, so that each stereogenic center denoted by an asterisk in scheme P was in such case an S-center. Accordingly, the local stereospecific environment of the center

in Scheme P was the S-center

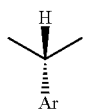

in such embodiments. This choice is illustrative, and another election is possible. For example, the stereogenic center can be R, in which case a chiral ester with R chirality is suitably chosen. A desired chirality can also be introduced by using a hydroxy ester, such as an α-hydroxycarboxylic ester

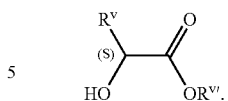

When such α-hydroxycarboxylic ester is used, D_ER is

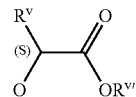

and D_ER' is

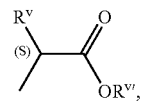

that the α-hydroxycarboxylic ester is D_ER'-OH. $R^v$ and $R^{v'}$ are groups such that compound P7 can be hydrolyzed to P8. $R^v$ and $R^{v'}$ are independently chosen preferably from the group of linear and branched $C_{1-4}$alkyl.

In some embodiments, compound P3 is a chiral 2-arylpentynoic acid derivative. An example of such P3 is 2-m-tolyl-pent-4-ynoic acid 1-ethoxycarbonyl-ethyl ester.

Chiral acetylenic ketone P5 is obtained by coupling suitably substituted acid halide P4 with the addition product P3. H_AL in compound P4 is defined as with respect to P2. This coupling is performed in some embodiments of this invention by a Sonogashira reaction.

Sonogashira reaction conditions include the presence of a palladium-containing catalyst, such as palladium on carbon, $Pd(PPh_3)_2Cl_2$, $Pd_2(dba)_3$, $Pd_2(dba)_3 \cdot CHCl_3$, $Pd(P^tBu_3)_2$, $Pd_2(dba)_3 \cdot CHCl_3/Pd(P^tBu_3)_2$, $Pd(OAc)_2$, $Pd(PhCN)_2Cl_2$, and $PdCl_2$, and a base, such as N-methylmorpholine (NMM), triethyl amine, 1,4-dimethylpiperazine, diisopropylethyl amine, and mixtures thereof in a solvent such as THF, DME, dioxane, DCE, DCM, toluene, acetonitrile, and mixtures thereof at a temperature from 0° C. to 100° C. Preferred bases are not significantly stronger than NMM and they are compatible with the presence of Cu(I) species in the medium.

A copper compound is used as a catalyst in this reaction, such as Cu(I) compound. Such Cu(I) catalyst is preferably incorporated in the reaction medium as substoichiometric quantities of a copper salt, such as CuI or $CuBrMe_2S$. The use of phosphine ligands, such as $PPh_3$ or $P(^tBu)_3$, is part of the methodology of some embodiments of the present invention.

As in other process steps in the context of embodiments of this invention, the use of a high polarity solvent may increase the rate and reduce by-product formation in these reactions. Such high polarity solvent is provided in some embodiments as a mixture of a first solvent with a cosolvent that increases the dielectric constant of the mixture with respect to the dielectric constant of such first solvent. For example, one of ordinary skill in the art will recognize in light of this disclosure that the use of water as such cosolvent may increase the rate and reduce by-product formation in these reactions.

In a preferred embodiment, the palladium source is $Pd_2(dba)_3 \cdot CHCl_3/Pd(P^tBu_3)_2$, $Pd(PPh_3)_2Cl_2$, or palladium on carbon, the base is NMM, the solvent is THF, toluene, THF with toluene, or a mixture of 1,2-dimethoxyethane (DME) and water, and the temperature is between room temperature and 80° C. In a particularly preferred embodiment, the palladium source is $Pd(PPh_3)_2Cl_2$, the base is NMM, the solvent is THF with toluene, a catalytic quantity of CuI or $CuBrMe_2S$ is used, and the reaction temperature is room temperature to reflux temperature, most preferably room temperature.

$R^2$ and HAL are defined above. In some embodiments, compound P5 is 6-(3,4-dichloro-phenyl)-6-oxo2-m-tolyl-hex-4-ynoic acid 1-ethoxycarbonyl-ethyl ester.

Regioselectivity with respect to the pyrazole framework in P7 is achieved by a condensation reaction involving compound P5 and a suitably substituted hydrazine P6. In some embodiments P6 is a suitably substituted hydrazine in other than free base form, referred to herein as non-free base form, in which the hydrazine is in the presence of an acid, thus forming the combinations that these two components form when they are present in the same medium. An example of such embodiments is a suitably substituted hydrazine hydrochloride. In other embodiments, P6 is a suitably substituted hydrazine in free base form. P6 is preferably a suitably substituted hydrazine in non-free base form in embodiments of the process shown in Scheme P. Substituent $R^1$ in P6 is defined above, and it is chosen according to the type of substitution desired in product P8.

Compound P7 is a pyrazole derivative wherein n=1 and $R^3$ is H. Other embodiments of this pyrazole derivative, and also of P8 and other pyrazole derivatives referred to herein, such as Q3, Q8, R5.1, R5-R8, and S8 in the following Schemes, can have other assignments of n and $R^3$ in light of the definitions of n and $R^3$ given above, and they can be prepared according to teachings given herein, such as the teachings provided in the context of Scheme A.

The term "substituted" as applied to the hydrazines referred to in condensations described herein is to be read in light of the generic form of compounds P6, where $R^1$ is defined herein, and it can be, inter alia, H. Therefore, "substituted hydrazine" in this context includes "substituted" (wherein $R^1$ is a substituent other than H) and "unsubstituted" (wherein $R^1$ is H) hydrazine as exemplified by P6 together with the definition of $R^1$ given herein.

The regioselective condensation reaction with an acetylenic ketone and a suitably substituted hydrazine to produce a preferred bonding pattern in compound P7 was developed in the context of this invention. It was found that compounds with a nitrogen substitution pattern in the pyrazole framework as shown in P7 in the surrounding chemical environment of compounds of this invention can be produced by this reaction with high regioselectivity, which reached in embodiments of this invention at least about 80%, or a molar ratio of 1:4, with the isomer in excess being the isomer with the pyrazole framework substituted as shown in Scheme P.

An inorganic base and a suitably substituted hydrazine were added in embodiments of this invention to a solution of acetylenic ketone P5 and later quenched with an acidic solution to obtain a medium with an acidic pH.

Examples of acidic solutions are aqueous acidic solutions, such that their acidity is suitable to bring the medium pH to a sufficiently low pH value. Quenching to an acidic pH was performed in some embodiments with $HCl_{(aq)}$ until the medium pH was in the range from about 2 to about 3. The hydrazine in embodiments of this invention is preferably incorporated as a hydrochloride, and one example of suitably substituted hydrazines used in the context of this invention is 4-methoxyphenyl hydrazine.HCl.

Compound P7 in Scheme P shows a pyrazole framework

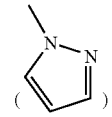

with one of the nitrogen members in the pyrazole framework substituted. This substitution is illustrated in P7 by substituent $R^1$. It is understood that the other regioisomer is also produced in the same step of formation of P7; and that such other regioisomer has substituent $R^1$ in the nitrogen member of the pyrazole framework that is shown unsubstituted in Scheme P, whereas the substituted nitrogen member in the same framework is unsubstituted in such other regioisomer.

The solvent in the solution of P5 is preferably an organic solvent, such as benzene, DCM, DCE, THF, DMF, acetonitrile, hexamethylphosphoramide (HMPA), hexane, pentane, alcohol, and mixtures thereof. Regioselectivity for the nitrogen substitution pattern in the pyrazole framework shown in Scheme P (1-($R^1$)-1H-pyrazol substitution) was achieved in embodiments of this invention with a non-protic solvent (a solvent that does not readily release a proton), such as THF, TMF, and combinations thereof, preferably THF. Other illustrative non-protic solvents include ether, toluene, and dichloromethane. The other nitrogen substitution pattern, 2-($R^1$)-2H-pyrazol, was preferentially obtained with a protic solvent (a solvent that more readily releases a proton), such as a carboxylic acid, water, an alcohol and alcohol mixtures, mixtures thereof, and preferably methanol, ethanol, and mixtures thereof.

Examples of inorganic bases that can be used in this condensation are alkali metal hydroxides, such as KOH, NaOH, and mixtures thereof, and alkali metal carbonates, such as $Na_2CO_3$, $K_2CO_3$, $Cs_2CO_3$, and mixtures thereof. Other bases that would perform in this reaction medium as the bases exemplified herein can also be used. A carbonate is preferred, such as $Cs_2CO_3$.

Embodiments of this invention achieved regioselectivity referred to the nitrogen substitution in the pyrazole framework of at least 1:4, wherein the more abundant isomer conforms to the nitrogen substitution pattern exhibited by compound P7 where the condensation is performed under suitable conditions described herein. In some embodiments, P5 was 6-(3,4-dichloro-phenyl)-6-oxo-2-m-tolyl-hex-4-ynoic acid 1-ethoxycarbonyl-ethyl ester, and P6 was 4-methoxyphenyl hydrazine.HCl, in which case P7 was embodied by 3-[5-(3,4-dichloro-phenyl)-1-(4-methoxy-phenyl)-1H-pyrazol-3-yl]-2-m-tolyl-propionic acid 1-ethoxycarbonyl-ethyl ester. A smaller amount of isomer 3-[5-(3,4-dichloro-phenyl)-2-(4-methoxy-phenyl)-2H-pyrazol-3-yl]-2-m-tolyl-propionic acid 1-ethoxycarbonyl-ethyl ester (P7') was also formed (nitrogen substitution pattern "2-( . . . )-2H-pyrazol", a pattern that is not shown in Scheme P), and the molar ratio of this two products was 1:4 referred to relative amounts of P7' and P7, or 20% and 80%, respectively.

Removal of substituent D$_{ER}$ by a suitable process leads to the formation of the final product. Scheme P illustrates an embodiment of P7 wherein D$_{ER}$ is such that P7 is an ester, such as a lactate ester. In such embodiments, substituent D$_{ER}$ is preferably removed by hydrolysis. Removal of D$_{ER}$ leads to product P8. Acetic and hydrochloric acids were used in some embodiments of this invention in the ester hydrolysis.

In some embodiments, compound P7 was 3-[5-(3,4-dichloro-phenyl)-1-(4-methoxy-phenyl)-1H-pyrazol-3-yl]-2-m-tolyl-propionic acid 1-ethoxycarbonyl-ethyl ester, in which case P8 was (S)-3-[5-(3,4-dichloro-phenyl)-1-(4-methoxy-phenyl)-1H-pyrazol-3-yl]-2-m-tolyl-propionic acid. This embodiment of P8 was obtained with an S-enantiomeric excess ee(S) of at least about 80%, which corresponds to a molar enantiomeric ratio R/S of at least about 1:9.

The enantiomeric excess of a product obtained according to the present invention can be increased by crystallization, whether the product is obtained by a synthesis as in Scheme P or by resolution of a racemate. An enantiomeric excess of 80% may be acceptable for some applications of compounds P8. Embodiments of P8 that are to be eventually obtained in enantiomerically pure form are further purified by crystallization.

Embodiments of acids include herein any one of the acid forms such as the acid itself and derivatives thereof such as salts, whether any such salt is isolated or in solution. For example, embodiments of P8 accordingly include P8 salts.

Enantiomeric purification of compounds P8 (not displayed in Scheme P as an additional step) was developed in the context of this invention. It was found in the context of this invention that compounds P8 crystallize under suitable conditions. A salt of P8 is formed to this effect. Such salt is preferably an inorganic salt, such as an alkali metal salt. Other salts are amine salts.

For example an aqueous solution of an inorganic base, preferably a hydroxide, was added to a solution of P8 in an organic solvent, such as THF. Examples of such hydroxides are sodium and potassium hydroxides, but other bases can also be used. Evaporation in a rarefied environment of some of the mixture components is performed until a small amount of water is left in the medium. This residue with a small amount of water is dissolved in a suitable solvent and subsequently crystallized out of a suitable crystallization medium.

It was found in the context of this invention that a suitable crystallization medium is provided by a medium with at least one solvent component, "first component", and at least another component, "second component". The first component is such that the residue is soluble therein, and the second component is such that the residue is less soluble than in the first component. For example the residue can be insoluble in the second component; in other embodiments the residue is relatively less soluble in such second component. THF is a preferred embodiment of the first component, and $CH_3CN$ is a preferred embodiment of the second component.

In a preferred crystallization process, the residue with a small amount of water is dissolved in the first component, and then the second component is added, from which medium the P8 salt separates. The term "crystallization" is generically used herein for this process, but it is understood that the salt separates in some embodiments as a crystalline product, in other embodiments it separates as a semicrystalline product, and it can separate in other embodiments as an amorphous product.

In addition to the preferred THF —$CH_3CN$ medium as first-second component medium, other illustrative first-second component media include MeOH—$CH_3CN$, $CH_2Cl_2$-toluene, $CH_2Cl_2$-hexane, and $CH_2Cl_2$-(toluene-hexane) media, wherein "(toluene-hexane)" refers to mixtures of toluene and hexane. THF, MeOH and $CH_2Cl_2$ are examples of first component, and $CH_3CN$, toluene, hexane, and (toluene-hexane) are examples of second component.

In preferred embodiments, this amount of water left in the medium does not differ by more than about 20% from an equimolar amount of water with respect to the amount of P8 salt. For example, in some embodiments this amount of water did not exceed about 1.2 times the amount of water that would be equimolar to the amount of P8 salt. In other embodiments, this amount of water was not less than about 0.8 times the amount of water that would be equimolar to the amount of P8 salt. In these embodiments, the amount of water left in the medium is within about 20% of the water amount that would be equimolar with the amount of P8 salt. In more preferred embodiments, this amount of water left in the medium does not differ by more than about 10% from an equimolar amount of water with respect to the amount of P8 salt, in still more preferred embodiments, this amount of water left in the medium does not differ by more than about 5% from an equimolar amount of water with respect to the amount of P8 salt, and in most preferred embodiments this amount of water left in the medium is about equimolar with respect to the amount of P8 salt.

Crystallization in the context of this invention permits not only enantiomeric enrichment, but also the enrichment of a desired regioisomer. Products with a desired enantiomeric excess and/or a desired degree of regioisomeric enrichment are obtained by crystallization as described herein.

It was found in the context of this invention that inorganic and organic salts are obtained by this crystallization method. Examples of inorganic salts are sodium and potassium salts. Examples of organic salts are amine salts, such as meglumine, tromethamine, tributylamine, and ethylene diamine salts.

The terms "compound (I)" in the context of this invention refer to any of the forms of compound (I), such as the solvent free compound, a solvate thereof, including a hydrate thereof, the compound as in solution, and any crystalline, semicrystalline (semicrystalline referring to a mixture of crystalline and amorphous material), or amorphous form thereof, and mixtures thereof. For example, the terms "a salt of P8" include any one of the forms of such salt, whether anhydrous, or in the form of a solvate, such as any form of hydrate. The same illustration applies to Q8, R8, and S8. Furthermore, the crystallization described herein also applies to the final products obtained according to this invention, such as the final products referred to in Schemes Q, R, and S.

Enantiomeric excess achieved by crystallization according to this invention can readily reach and exceed 90%, and also enantiomeric purity. Regioisomeric enrichment achieved by crystallization according to this invention converts a product with about 80% (regioisomeric excess of at least 80%) of one regioisomer to a product with at least 90% (regioisomeric excess of at least 90%) of the same regioisomer, and embodiments of this invention achieved a regioisomeric enrichment such that the crystallization product was at least 99% (regioisomeric excess of at least 99%) in one of the regioisomers.

When P8 was embodied by (S)-3-[5-(3,4-dichloro-phenyl)-1-(4-methoxy-phenyl)-1H-pyrazol-3-yl]-2-m-tolyl-propionic acid, purification by crystallization led to the isolation of an enantiomerically pure salt, such as (S)-sodium 3-[5-(3,4-dichloro-phenyl)-1-(4-methoxy-phenyl)-1H-pyrazol-3-yl]-2-m-tolyl-propionate, with embodiments of this invention reaching ee(S) >99.9%.

Embodiments of processes schematically illustrated in Scheme P comprise a 6-step synthesis (these steps referring in some embodiments to alkylation, acid halide formation, stereoselective addition, regioselective condensation, and hydrolysis) in which a chosen chirality at a specific stereogenic center is generated at an early synthetic stage by a stereoselective addition between a chiral ester, such as P1, and an acid halide, such as P2. Chiral acetylenic ketone P3 is thus generated. Such embodiments also comprise regioselective condensation and recrystallization enantioenrichment to an optically pure final product. A stereoselective addition in some embodiments of this invention was implemented by using an inexpensive chiral reagent such as (S)—(−)-ethyl lactate.

In contrast with embodiments of the present invention, synthetic processes that rely on other approaches, such as processes that require column chromatographic separation, comprise at least eight steps. Also in contrast with embodiments of the present invention, other processes rely on expensive chiral auxiliary reagents.

Some embodiments include methods of making a compound of formula (I), enantiomers, diastereomers, racemics, pharmaceutically acceptable salts, esters, and amides thereof, comprising: an addition reaction of a chiral ester and an acetylenic acid halide to form a chiral acetylenic addition product. More specifically, additional embodiments include those methods wherein any one of the following features applies:

said chiral acetylenic addition product is produced with an enatiomeric excess of at least about 80%;

said chiral acetylenic addition product is produced by mixing an acetylenic acid halide, an organic base, and said chiral ester in an organic solvent;

said acid halide is an acid chloride;

said organic base is a tertiary amine;

said organic base is a trialkyl amine;

said organic base is dimethylethyl amine;

said organic base is a tertiary amine whose molecular volume is about the molecular volume of dimethylamine;

said organic solvent is a low polarity organic solvent;

said organic solvent is an organic solvent having a dielectric constant and said dielectric constant is not greater than about 6;

said organic solvent is an organic solvent having a dielectric constant and said dielectric constant is not greater than about 3;

said organic solvent is an organic solvent having a dielectric constant and said dielectric constant is not greater than the dielectric constant of toluene;

said chiral acetylenic addition product is produced by mixing an acetylenic acid halide and an organic base to form an organic mixture, cooling said organic mixture to a temperature in the range from about −70° C. and −85° C., and adding said chiral ester;

said chiral ester is a chiral hydroxy ester;

said chiral ester is an a-hydroxycarboxylic ester;

said chiral acetylenic addition product is a chiral 2-arylpentynoic acid derivative;

said chiral acetylenic addition product is 2-m-tolyl-pent-4-ynoic acid 1-thoxycarbonyl-ethyl ester;

said chiral ester is ethyl lactate;

said acetylenic acid halide is 2-m-tolyl-pent-4-ynoyl chloride;

wherein the Ar attached carbon is saturated and has the configuration

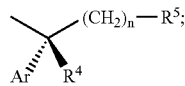

said $R^1$, optionally substituted with $R^p$ as described above, is selected from the group $GR^1$, said group $GR^1$ consisting of hydrogen:

a) phenyl, 5-, 6-, 7-, 8-benzo-1,4-dioxanyl, 4-, 5-, 6-, 7-benzo-1,3-dioxolyl, 4-, 5-, 6-, 7-indolinyl, 4-, 5-, 6-, 7-isoindolinyl, 1,2,3,4-tetrahydro-quinolin-4, 5, 6 or 7-yl, 1,2,3,4-tetrahydro-isoquinolin-4, 5, 6 or 7-yl, b) 4-, 5-, 6- or 7-benzoxazolyl, 4-, 5-, 6- or 7-benzothiophenyl, 4-, 5-, 6- or 7-benzofuranyl, 4-, 5-, 6- or 7-indolyl, 4-, 5-, 6- or 7-benzthiazolyl, 4-, 5-, 6- or 7-benzimidazolyl, 4-, 5-, 6- or 7-indazolyl, imidazo[1,2-a]pyridin-5, 6, 7 or 8-yl, pyrazolo[1,5-a]pyridin-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4, 5 or 7-yl, 1H-pyrrolo[3,2-b]pyridin-5, 6 or 7-yl, c) 5-, 6-, 7- or 8-isoquinolinyl, 5-, 6-, 7- or 8-quinolinyl, 5-, 6-, 7- or 8-quinoxalinyl, 5-, 6-, 7- or 8-quinazolinyl, d) naphthyl, e) furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, 3-indoxazinyl, 2-benzoxazolyl, 2- or 3-benzothiophenyl, 2- or 3-benzofuranyl, 2- or 3-indolyl, 2-benzthiazolyl, 2-benzimidazolyl, 3-indazolyl, f) pyridinyl, pyridinyl-N-oxide, pyrazinyl, pyrimidinyl, pyridazinyl, 1-,3- or 4-isoquinolinyl, 2-, 3- or 4-quinolinyl, 2- or 3-quinoxalinyl, 2- or 4-quinazolinyl, 1-oxy-pyridin-2, 3, or 4-yl, g) cyclopentyl, cyclohexyl, cycloheptyl, piperidin-2,3 or 4-yl, 2-pyrrolin-2, 3, 4 or 5-yl, 3-pyrrolin-2 or 3-yl, 2-pyrazolin-3, 4 or 5-yl, morpholin-2, 3, 5 or 6-yl, thiomorpholin-2, 3, 5 or 6-yl, piperazin-2, 3, 5 or 6-yl, pyrrolidin-2 or 3-yl, homopiperidinyl, adamantanyl, h) methyl, ethyl, n-propyl, i-propyl, n-butyl, i-butyl, t-butyl, n-pentyl, pent-2-yl, hexyl, hex-2-yl, and i) —$C_{1-2}$alkyl mono-substituted with any one of the preferred substituents of a) to g), in more specific embodiments $R^1$, optionally substituted with $R^p$ as described above, is selected from the group $PGR^1$, said group $PGR^1$ consisting of H, methyl, phenyl, benzyl, cyclohexyl, cyclohexylmethyl, pyridinyl, pyridinylmethyl and pyridinyl-N-oxide, and specific $R^1$ are selected from the group SGR1, said group $SGR^1$ consisting of phenyl, 2-methoxy-phenyl, 3-methoxy-phenyl, 4-methoxy-phenyl, 2,3-dimethoxy-phenyl, 3,4-dimethyoxy-phenyl, 2-chloro-phenyl, 3-chloro-phenyl, 4-chloro-phenyl, 2,4-dicloro-phenyl, 3,4-dichlorophenyl, 2,4-dichlorophenyl, 2,5-dichlorophenyl, 2-methyl-phenyl, 3-methyl-phenyl, 4-methyl-phenyl, 2,5-dimethyl-phenyl, 2-trifluoromethyl-phenyl, 3-trifluoromethyl-phenyl, 4-trifluoromethyl-phenyl, 3-trifluoromethoxy-phenyl, 4-trifluoromethoxy-phenyl, 4-t-butyl-phenyl, benzyl, cyclohexyl, pyridin-2-yl, pyridin-3-yl, pyridin-4-yl, 4-triflouromethyl-2-pyridyl, 2-pyridyl-N-oxide, 4-methanesulfonyl-phenyl, 4-phenoxy-phenyl, 4-isopropyl-phenyl, 4-ethoxy-phenyl, 4-hydroxy-phenyl, 4-pyridinyl-methyl, benzo[1,3]diox-5-yl, 2,3-diydro benzo[1,4]dioxin-6-yl and cyclohexylmethyl;

said $R^p$ is selected from the group $GR^p$, said group $GR^p$ consisting of —OH, —$CH_3$, —$CH_2CH_3$, i-propyl, t-butyl, —OCH₃, —OCH₂CH₃, —OCH(CH₃)₂, cyclopropyl, cyclobutyl, cyclopentyl, cyclohexyl, —Ocyclopentyl, —Ocyclohexyl, phenyl, —Ophenyl, benzyl, —Obenzyl, —CN, —NO₂, —C(O)NH₂, —C(O)N(CH₃)₂, —C(O)NH(CH₃), —NH(CO)H, —NH-COCH₃, —NCH₃(CO)H, —NCH₃COCH₃, —NHSO₂CH₃, —NCH₃SO₂CH₃, —C(O)CH₃, —SOCH₃, —SO₂CH₃, —SO₂NH₂, —SO₂NHCH₃, —SO₂N(CH₃)₂, —SCF₃—F, —Cl, —Br, I, —CF₃, —OCF₃, —COOH, —COOCH₃, —COOCH₂CH₃, —NH₂, —NHCH₃, —NHCH₂CH₃, —NH(CH₂CH₂CH₃), —NH(CH(CH₃)CH₂CH₃), —NH(allyl), —NH(CH₂(CH₃)₂), —N(CH₃)₂, —N(CH₂CH₃)₂, —NCH₃(CH₂CH₂CH₃), —NCH₃(CH₂CH₃), —NCH₃(CH(CH₃)₂), pyrrolidin-2-one-1-yl, azetidinyl, piperidin-1-yl, 2- or 3-pyrrolin-1-yl, morpholin-4-yl, thiomorpholin-4-yl, piperazin-1-yl, pyrrolidin-1-yl, homopiperidin-1-yl, and in more specific embodiments $R^p$ is selected from the group $PGR^p$, said group $PGR^p$ consisting of hydrogen, methyl, methoxy, ethoxy, chloro, fluoro, trifluoromethyl, trifluoromethoxy, t-butyl, methanesulfonyl, phenoxy, isopropyl and hydroxy;

said $R^2$, optionally substituted with $R^q$ as described above, is selected from the group $GR^2$, said group $GR^2$ consisting of:
  i) phenyl, 5-, 6-, 7-, 8-benzo-1,4-dioxanyl, 4-, 5-, 6-, 7-benzo-1,3-dioxolyl, 4-, 5-, 6-, 7-indolinyl, 4-, 5-, 6-, 7-isoindolinyl, 1,2,3,4-tetrahydro-quinolin-4, 5, 6 or 7-yl, 1,2,3,4-tetrahydro-isoquinolin-4, 5, 6 or 7-yl,
  ii) 4-, 5-, 6- or 7-benzoxazolyl, 4-, 5-, 6- or 7-benzothiophenyl, 4-, 5-, 6- or 7-benzofuranyl, 4-, 5-, 6- or 7-indolyl, 4-, 5-, 6- or 7-benzthiazolyl, 4-, 5-, 6- or 7-benzimidazolyl, 4-, 5-, 6- or 7-indazolyl, imidazo[1,2-a]pyridin-5, 6, 7 or 8-yl, pyrazolo[1,5-a]pyridin-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4, 5 or 7-yl, 1H-pyrrolo[3,2-b]pyridin-5, 6 or 7-yl,
  iii) 5-, 6-, 7- or 8-isoquinolinyl, 5-, 6-, 7- or 8-quinolinyl, 5-, 6-, 7- or 8-quinoxalinyl, 5-, 6-, 7- or 8-quinazolinyl,
  iv) naphthyl,
  v) furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, 3-indoxazinyl, 2-benzoxazolyl, 2- or 3-benzothiophenyl, 2- or 3-benzofuranyl, 2- or 3-indolyl, 2-benzthiazolyl, 2-benzimidazolyl, 3-indazolyl, and
  vi) pyridinyl, pyridinyl-N-oxide, pyrazinyl, pyrimidinyl, pyridazinyl, 1-, 3- or 4-isoquinolinyl, 2-, 3- or 4-quinolinyl, 2- or 3-quinoxalinyl, 2- or 4-quinazolinyl,
    in more specific embodiments $R^2$, optionally substituted with $R^q$ as described above, is selected from the group $PGR^2$, said group $PGR^2$ consisting of phenyl, naphthalenyl, pyridinyl, thiophenyl, benzothiophenyl, furanyl, benzofuranyl, indolyl, indolinyl, isoquinolinyl and quinolinyl,
    and specific $R^2$ are selected from the group $SGR^2$, said group $SGR^2$ consisting of 4-methyl-phenyl, 2-chloro-phenyl, 3-chloro-phenyl, 4-chloro-phenyl, 3,4-dichloro-phenyl, benzo[1,3]dioxol-5-yl, 2,3-diydro benzo[1,4]dioxin-6-yl, 4-methoxy-phenyl, phenyl, 4-phenoxy-phenyl, naphthalen-2-yl, pyridin-3-yl, 2-chloro-pyridin-3-yl, pyridin-4-yl-methyl, 4-benzyloxy-phenyl, 4-dimethylamino-phenyl, 4-bromo-3-methyl-phenyl, 3-methoxy-4-methyl-phenyl, 3-cyclopentyloxy-4-methoxy-phenyl, 4-bromo-2-chloro-phenyl, 4-bromo-phenyl, 3-dimethylamino-phenyl, 4-morpholin-1-yl-phenyl, 4-pyrrolidin-1-yl-phenyl, 4-(N-propylamino)-phenyl, 4-(N-isobutylamino)-phenyl, 4-diethylamino-phenyl, 4-(N-allylamino)-phenyl, 4-(N-isopropylamino)-phenyl, 4-(N-methyl-N-propylamino)-phenyl, 4-(N-methyl-N-isopropylamino)-phenyl, 4-(N-methyl-N-ethylamino)-phenyl, 4-amino-phenyl, 4-(N-methyl-N-propylamino)-2-chloro-phenyl, 4-(N-ethyl-N-methylamino)-2-chloro-phenyl, 4-(pyrrolidin-1-yl)-2-chloro-phenyl, 4-azetidinyl-phenyl, 4-(pyrrolidin-2-one-1-yl)-phenyl, 4-bromo-3-methyl-phenyl, 4-chloro-3-methyl-phenyl, 1-methyl-5-indolinyl, 5-indolinyl, 5-isoquinolinyl, 6-quinolinyl, benzo[1,3]diox-5-yl and 7-methoxy-benzofuran-2-yl;

said $R^q$ is selected from the group $GR^q$, said group $GR^q$ consisting of —OH, —CH₃, —CH₂CH₃, i-propyl, t-butyl, —OCH₃, —OCH₂CH₃, —OCH(CH₃)₂, cyclopropyl, cyclobutyl, cyclopentyl, cyclohexyl, —Ocyclopentyl, —Ocyclohexyl, phenyl, —Ophenyl, benzyl, —Obenzyl, —CN, —NO₂, —C(O)NH₂, —C(O)N(CH₃)₂, —C(O)NH(CH₃), —NH(CO)H, —NH-COCH₃, —NCH₃(CO)H, —NCH₃COCH₃, —NHSO₂CH₃, —NCH₃SO₂CH₃, —C(O)CH₃, —SOCH₃, —SO₂CH₃, —SO₂NH₂, —SO₂NHCH₃, —SO₂N(CH₃)₂, —SCF₃—F, —Cl, —Br, I, —CF₃, —OCF₃, —COOH, —COOCH₃, —COOCH₂CH₃, —NH₂, —NHCH₃, —NHCH₂CH₃, —NH(CH₂CH₂CH₃), —NH(CH(CH₃)CH₂CH₃), —NH(allyl), —NH(CH₂(CH₃)₂), —N(CH₃)₂, —N(CH₂CH₃)₂, —NCH₃(CH₂CH₂CH₃), —NCH₃(CH₂CH₃), —NCH₃(CH(CH₃)₂), pyrrolidin-2-one-1-yl, azetidinyl, piperidin-1-yl, 2- or 3-pyrrolin-1-yl, morpholin-4-yl, thiomorpholin-4-yl, piperazin-1-yl, pyrrolidin-1-yl, homopiperidin-1-yl;

and in more specific embodiments $R^q$ is selected from the group $PGR^q$ said group $PGR^q$ consisting of methyl, bromo, chloro, methoxy, cyclopentyloxy, phenoxy, benzyloxy, pyrrolidinyl, N-methyl-N-ethylamino and dimethylamino;

there are 0, 1 or 2 $R^q$ substituents;

said $R^3$ is selected from the group consisting of —H, —F, Cl, Br and —CH₃, most preferably $R^3$ is H;

said n is 0, or 1.

said $R^4$ is selected from the group consisting of —H, —F and —CH₃, most preferably $R^4$ is H;

said Ar, optionally substituted with $R^r$ as described above, is selected from the group $GA^r$, said group $GA^r$ consisting of:
  A) phenyl, 5-, 6-, 7-, 8-benzo-1,4-dioxanyl, 4-, 5-, 6-, 7-benzo-1,3-dioxolyl, 4-, 5-, 6-, 7-indolinyl, 4-, 5-, 6-, 7-isoindolinyl, 1,2,3,4-tetrahydro-quinolin-4, 5, 6 or 7-yl, 1,2,3,4-tetrahydro-isoquinolin-4, 5, 6 or 7-yl,
  B) 4-, 5-, 6- or 7-benzoxazolyl, 4-, 5-, 6- or 7-benzothiophenyl, 4-, 5-, 6- or 7-benzofuranyl, 4-, 5-, 6- or 7-indolyl, 4-, 5-, 6- or 7-benzthiazolyl, 4-, 5-, 6- or 7-benzimidazolyl, 4-, 5-, 6- or 7-indazolyl, imidazo[1,2-a]pyridin-5, 6, 7 or 8-yl, pyrazolo[1,5-a]pyridin-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4, 5 or 7-yl, 1H-pyrrolo[3,2-b]pyridin-5, 6 or 7-yl, C) 5-, 6-, 7- or 8-isoquinolinyl, 5-, 6-, 7- or 8-quinolinyl, 5-, 6-, 7- or 8-quinoxalinyl, 5-, 6-, 7- or 8-quinazolinyl, D) naphthyl, E) furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, 3-indoxazinyl, 2-benzoxazolyl, 2- or 3-benzothiophenyl, 2- or 3-benzofuranyl, 2- or 3-indolyl, 2-benzthiazolyl, 2-benzimidazolyl, 3-indazolyl, and F) pyridinyl, pyridinyl-N-oxide, pyrazinyl, pyrimidinyl, pyridazinyl, 1-, 3- or 4-isoquinolinyl, 2-, 3- or 4-quinolinyl, 2- or 3-quinoxalinyl, 2- or 4-quinazolinyl, and in more specific embodiments Ar, optionally substituted with $R^r$ as described above, is selected from the group PGAr, said group PGA rconsisting of phenyl, naphthalenyl, benzofuran-3-yl, 4, 5, 6 or 7-benzothiophenyl, 4, 5, 6 or 7-benzo[1,3]dioxolyl, 8-quinolinyl, 2-indolyl, 3-indolyl and pyridinyl, and specific Ar are selected from the group SGAr, said group SGAr consisting of phenyl, 2-methyl-phenyl, 3-methyl-phenyl, 4-rethyl-phenyl, 2,5-dimethyl-phenyl, 2-trifluoromethyl-phenyl, 3-trifluoromethyl-phenyl, 2-fluoro-3-trifluoromethyl-phenyl, 2-fluoro-phenyl, 2,3-difluoro-phenyl, 2-chloro-phenyl, 3-chloro-phenyl, 4-chloro-phenyl, 2,3-dicloro-phenyl, 3,4-dichlorophenyl, 2,6-dichlorophenyl, 3-iodo-phenyl, 2-chloro-4-fluoro-phenyl, benzofuran-3-yl, 2-methoxy-phenyl, 3-methoxy-phenyl, 4-methoxy-phenyl, 2,3-dimethoxy-phenyl, 3-trifluoromethoxy-phenyl, 4-trifluoromethoxy-phenyl, 3-ethoxy-phenyl, 3-trifluoromethylsulfanyl-phenyl, naphthalen-1-yl, naphthalen-2-yl, benzo[b]thiophen-4-yl, 3-nitro-phenyl, benzo[1,3]dioxol-5-yl, pyridin-3-yl and pyridin-4-yl, 3-indolyl, 1-methyl-indol-3-yl, 4-biphenyl, 3,5-dimethyl-phenyl, 3-isopropoxy-phenyl, 3-dimethylamino-phenyl, 2-flouro-5-methyl-phenyl, 2-methyl-3-triflouromethyl-phenyl;

there are 0, 1 or 2 $R^r$ substituents;

wherein $R^r$ is selected from the group $GR^r$, said group $GR^r$ consisting of —OH, —CH$_3$, —CH$_2$CH$_3$, -propyl, -t-butyl, —OCH$_3$, —OCH$_2$CH$_3$, —OCH(CH$_3$)$_2$, cyclopropyl, cyclobutyl, cyclopentyl, cyclohexyl, —Ocyclopentyl, —Ocyclohexyl, phenyl, —Ophenyl, benzyl, —Obenzyl, —CN, —NO$_2$, —C(O)NH$_2$, —C(O)N(CH$_3$)$_2$, —C(O)NH(CH$_3$), —NH(CO)H, —NHCOCH$_3$, —NCH$_3$(CO)H, —NCH$_3$COCH$_3$, —NHSO$_2$CH$_3$, —NCH$_3$SO$_2$CH$_3$, —C(O)CH$_3$, —SOCH$_3$, —SO$_2$CH$_3$, —SO$_2$NH$_2$, —SO$_2$NHCH$_3$, —SO$_2$N(CH$_3$)$_2$, —SCF$_3$, —F, —Cl, —Br, I, —CF$_3$, —OCF$_3$, —COOH, —COOCH$_3$, —COOCH$_2$CH$_3$, —NH$_2$, —NHCH$_3$, —NHCH$_2$CH$_3$, —NH(CH$_2$CH$_2$CH$_3$), —NH(CH(CH$_3$)CH$_2$CH$_3$), —NH(allyl), —NH(CH$_2$(CH$_3$)$_2$), —N(CH$_3$)$_2$, —N(CH$_2$CH$_3$)$_2$, —NCH$_3$(CH$_2$CH$_2$CH$_3$), —NCH$_3$(CH$_2$CH$_3$), —NCH$_3$(CH(CH$_3$)$_2$), pyrrolin-2-one-1-yl, azetidinyl, piperidin-1-yl, 2- or 3-pyrrolin-1-yl, morpholin-4-yl, thiomorpholin-4-yl, piperazin-1-yl, pyrrolidin-1-yl, homopiperidin-1-yl;

and in more specific embodiments said $R^r$ is selected from the group $PGR^r$, said group $PGR^r$ consisting of methyl, methoxy, ethoxy, isopropoxy, dimethylamino, fluoro, chloro, iodo, trifluoromethyl, trifluoromethoxy, nitro, phenyl and trifluoromethylsulfanyl;

said $R^5$ is selected from the group $GR^5$, said group $GR^5$ consisting of:

I) —COOH, —COOCH$_3$, —COOCH$_2$CH$_3$,

II) —CONH(CH$_3$), —CONH(CH$_2$CH$_3$), —CONH(CH$_2$CH$_2$CH$_3$), —CONH(CH(CH$_3$)$_2$), —CONH(CH$_2$CH$_2$CH$_2$CH$_3$), —CONH(CH(CH$_3$)CH$_2$CH$_3$), —CONH(C(CH$_3$)$_3$), —CONH(cyclohexyl), —CONH(2-hydroxy-cyclohexyl), —CON(CH$_3$)$_2$, —CONCH$_3$(CH$_2$CH$_3$), —CONCH$_3$(CH$_2$CH$_2$CH$_3$), —CONCH$_3$(CH(CH$_3$)$_2$), —CONCH$_3$(CH$_2$CH$_2$CH$_2$CH$_3$), —CONCH$_3$(CH(CH$_3$)CH$_2$CH$_3$), —CONCH$_3$(C(CH$_3$)$_3$), —CON(CH$_2$CH$_3$)$_2$, —CO-piperidin-1-yl, —CO-morpholin-4-yl, —CO-piperazin-1-yl, —CO-imidazolidin-1-yl, —CO-pyrrolidin-1-yl, —CO-2-pyrrolin-1-yl, —CO-3-pyrrolin-1-yl, —CO-2-imidazolin-1-yl, —CO-piperidin-1-yl, and III) -tetrazolyl, 1H-[1,2,4]triazol-5-ylsulfinyl, 1H-[1,2,4]triazol-5-ylsulfonyl, 1H-[1,2,4]triazol-5-ylsulfanyl, and in more specific embodiments $R^5$ is selected from the group $PGR^5$, said group $PGR^5$ consisting of —COOH and tetrazol-5-yl.

wherein the compound of formula (I) is (S)-3-[5-(3,4-dichloro-phenyl)-1-(4-methoxy-phenyl)-1H-pyrazol-3-yl]-2-m-tolyl-propionic acid;

wherein the compound of formula (I) is (S)-sodium 3-[5-(3,4-dichloro-phenyl)-1-(4-methoxy-phenyl)-1H-pyrazol-3-yl]-2-m-tolyl-propionate;

further comprising reacting said chiral acetylenic addition product with an acid halide in a reaction medium to form a chiral acetylenic ketone, wherein at least one of these additional features applies:

a1) said reacting said chiral acetylenic addition product with an acid halide is made in the presence of a palladium-containing catalyst and Cu(I) catalyst;

a2) a base is added to said reaction medium;

a3) a base selected from the group consisting of N-methylmorpholine, triethyl amine, 1,4-dimethylpiperazine, diisopropylethyl amine, and mixtures thereof, is added to said reaction medium;

a4) N-methylmorpholine is added to said reaction medium;

a5) N-methylmorpholine, a palladium-containing catalyst, and a Cu(I) catalyst are added to said reaction medium;

a6) said acid halide is 3,4-dichlorobenzoyl chloride;

a7) said chiral acetylenic addition product is 2-m-tolyl-pent-4-ynoic acid 1-ethoxycarbonyl-ethyl ester;

a8) said chiral acetylenic ketone is 6-(3,4-dichloro-phenyl)-6-oxo-2-m-tolyl-hex-4-ynoic acid 1-ethoxycarbonyl-ethyl ester;

a9) said compound of formula (I) is (S)-3-[5-(3,4-dichloro-phenyl)-1-(4-methoxy-phenyl)-1H-pyrazol-3-yl]-2-m-tolyl-propionic acid;

a10) said compound of formula (I) is (S)-sodium 3-[5-(3,4-dichloro-phenyl)-1-(4-methoxy-phenyl)-1H-pyrazol-3-yl]-2-m-tolyl-propionate.

Some embodiments include methods of making a compound of formula (I), enantiomers, diastereomers, racemics, pharmaceutically acceptable salts, esters, and amides thereof, comprising a condensation of a substituted hydrazine and an acetylenic ketone to form a pyrazole derivative, said pyrazole derivative having a pyrazole framework with one of the nitrogen members in said pyrazole framework substituted. In some embodiments, said condensation is a regioselective condensation. More specifically, additional embodiments include those methods wherein any one of the following features applies:

said pyrazole derivative is formed with a regioisomeric excess of at least about 80%;

said acetylenic ketone is a chiral acetylenic ketone and said pyrazole derivative is a chiral pyrazole derivative;

said pyrazole derivative is a compound of formula P7'

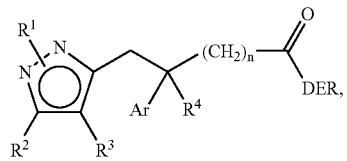

(P7')

wherein the substituent DER in P7' is such that the group C(=O)DER in P7' is an ester group, in even more specific embodiments wherein the Ar-attached carbon member is a stereogenic center with two enantiomeric forms and one of said two enantiomeric forms is in excess with respect to the other of said enantiomeric forms, and in even more specific embodiments wherein said enantiomer that is in excess is the (S) enantiomer;

said condensation is a regioselective condensation that comprises mixing an inorganic base and said substituted hydrazine with an acetylenic ketone in a reaction medium, and in even more specific embodiments further comprising quenching said reaction medium with an acidic solution to bring the pH of said reaction medium to an acidic pH;

said condensation is a regioselective condensation that comprises mixing an inorganic base and said substituted hydrazine with an acetylenic ketone that is a chiral acetylenic ketone in a reaction medium, and in even more specific embodiments further comprising quenching said reaction medium with an acidic solution to bring the pH of said reaction medium to an acidic pH;

said condensation is a regioselective condensation that is performed in a non-protic solvent;

said condensation is a regioselective condensation that is performed in a non-protic solvent selected form the group consisting of THF, TMF, ether, toluene, dichloromethane, and mixtures thereof;

said condensation is a regioselective condensation that is performed in THF;

said condensation is a regioselective condensation that comprises mixing an inorganic base and said substituted hydrazine with an acetylenic ketone in a reaction medium comprising a non-protic solvent, and more specific embodiments further comprising quenching said reaction medium with an acidic solution to bring the pH of said reaction medium to an acidic pH, in even more specific embodiments said pyrazole derivative is an ester and further comprising hydrolyzing said ester to form a pyrazole acid derivative, and in even more specific embodiments further comprising forming a salt of said pyrazole acid derivative, and in even more specific embodiments further comprising crystallizing said salt of said pyrazole acid derivative;

said condensation is a regioselective condensation that comprises mixing an inorganic base and said substituted hydrazine with an acetylenic ketone that is a chiral acetylenic ketone in a reaction medium comprising a non-protic solvent, and in more specific embodiments further comprising quenching said reaction medium with an acidic solution to bring the pH of said reaction medium to an acidic pH, in even more specific embodiments said pyrazole derivative is a chiral pyrazole ester derivative and further comprising hydrolyzing said ester to form a chiral pyrazole acid derivative, and in even more specific embodiments further comprising forming a chiral salt of said chiral pyrazole acid derivative, and in even more specific embodiments further comprising crystallizing said chiral salt of said chiral pyrazole acid derivative;

said condensation is a regioselective condensation that is performed in a protic solvent;

said condensation is a regioselective condensation that is performed in a protic solvent selected from the group consisting of water, alcohol, alcohol mixtures, carboxylic acid, and mixtures thereof;

said condensation is a regioselective condensation that is performed in a protic solvent selected from the group consisting of methanol, ethanol, and mixtures thereof;

said condensation is a regioselective condensation that comprises mixing an inorganic base and said substituted hydrazine with an acetylenic ketone in a reaction medium comprising a protic solvent, and in more specific embodiments further comprising quenching said reaction medium with an acidic solution to bring the pH of said reaction medium to an acidic pH, in even more specific embodiments said pyrazole derivative is an ester and further comprising hydrolyzing said ester, to form a pyrazole acid derivative, and in even more specific embodiments further comprising forming a salt of said pyrazole acid derivative, and in even more specific embodiments further comprising crystallizing said salt of said pyrazole acid derivative;

said condensation is a regioselective condensation that comprises mixing an inorganic base and said substituted hydrazine with an acetylenic ketone that is a chiral acetylenic ketone in a reaction medium comprising a protic solvent, in more specific embodiments further comprising quenching said reaction medium with an acidic solution to bring the pH of said reaction medium to an acidic pH, in even more specific embodiments said pyrazole derivative is a chiral pyrazole ester derivative, and further comprising hydrolyzing said ester, to form a chiral pyrazole acid derivative, and in even more specific embodiments further comprising forming a chiral salt of said chiral pyrazole acid derivative, and in even more specific embodiments further comprising crystallizing said chiral salt of said chiral pyrazole acid derivative;

said acetylenic ketone is 6-(3,4-dichloro-phenyl)-6-oxo-2-m-tolyl-hex-4-ynoic acid 1-ethoxycarbonyl-ethyl ester;

said substituted hydrazine is a non-free base hydrazine, and in more specific embodiments said non-free base hydrazine is 4-methoxyphenyl hydrazine.HCl;

said substituted hydrazine is a free base hydrazine, and in more specific embodiments said free base hydrazine is 4-methoxyphenyl hydrazine;

said pyrazole derivative is a mixture of a first pyrazole derivative and a second pyrazole derivative, wherein said first pyrazole derivative has the nitrogen-member substitution pattern in the pyrazole framework specified by 1-($R^1$)-1H-pyrazol, said second pyrazole derivative has the nitrogen-member substitution pattern in the pyrazole framework specified by 2-($R^1$)-2H-pyrazol, and said first pyrazole derivative is obtained in an amount that is greater than the amount of said second pyrazole derivative;

said pyrazole derivative is a mixture of a first pyrazole derivative and a second pyrazole derivative, wherein said first pyrazole derivative has the nitrogen-member substitution pattern in the pyrazole framework specified by 1-($R^1$)-1H-pyrazol, said second pyrazole derivative has the nitrogen-member substitution pattern in the pyrazole framework specified by 2-($R^1$)-2H-pyrazol, and said second pyrazole derivative is obtained in an amount that is greater than the amount of said first pyrazole derivative;

said pyrazole derivative is a mixture of a first pyrazole derivative and a second pyrazole derivative, wherein said first pyrazole derivative is 3-[5-(3,4-dichloro-phenyl)-1-(4-methoxy-phenyl)-1H-pyrazol-3-yl]-2-m-tolyl-propionic acid 1-ethoxycarbonyl-ethyl ester, said second pyrazole derivative is 3-[5-(3,4-dichloro-phenyl)-2-(4-methoxy-phenyl)-2H-pyrazol-3-yl]-2-m-tolyl-propionic acid 1-ethoxycarbonyl-ethyl ester, and said first pyrazole derivative is obtained in an amount that is greater than the amount of said second pyrazole derivative;

said pyrazole derivative is a mixture of a first pyrazole derivative and a second pyrazole derivative, wherein said first pyrazole derivative is 3-[5-(3,4-dichloro-phenyl)-1-(4-methoxy-phenyl)-1H-pyrazol-3-yl]-2-m-tolyl-propionic acid 1-ethoxycarbonyl-ethyl ester, said second pyrazole derivative is 3-[5-(3,4-dichloro-phenyl)-2-(4-methoxy-phenyl)-2H-pyrazol-3-yl]-2-m-tolyl-propionic acid 1-ethoxycarbonyl-ethyl ester, and said second pyrazole derivative is obtained in an amount that is greater than the amount of said first pyrazole derivative;

said pyrazole derivative is 3-[5-(3,4-dichloro-phenyl)-1-(4-methoxy-phenyl)-1H-pyrazol-3-yl]-2-m-tolyl-propionic acid 1-ethoxycarbonyl-ethyl ester, in more specific embodiments further comprising hydrolyzing said ester to form the chiral pyrazole acid derivative (S)-3-[5-(3,4-dichloro-phenyl)-1-(4-methoxy-phenyl)-1H-pyrazol-3-yl]-2-m-tolyl-propionic acid, in more specific embodiments further-comprising forming the chiral salt (S)-CAT 3-[5-(3,4-dichlorophenyl)-1-(4-methoxy-phenyl)-1H-pyrazol-3-yl]-2-m-tolyl-propionate, wherein CAT is one of alkali metal and amine, in even more specific embodiments further comprising crystallizing said chiral salt to obtain a chiral product; in even more specific embodiments said chiral pyrazol acid derivative is formed with an S-enantiomeric excess ee(S) of at least about 80%, and in even more specific embodiments said chiral product is obtained with an S-enantiomeric excess ee(S) of at least about 99%;

the Ar attached carbon is saturated and has the configuration

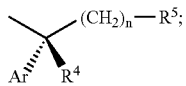

the Ar attached carbon is unsaturated and has the configuration

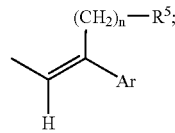

Ar, optionally substituted with $R^r$ as described above, is selected from the group GAr as described above, in more specific embodiments Ar, optionally substituted with $R^r$ as described above, is selected from the group PGAr as described above, and specific Ar are selected from the group SGAr as described above;

there are 0, 1, or 2 $R^r$ substituents;

$R^r$ is selected from the group $GR^r$ as described above, and in more specific embodiments $R^r$ is selected from the group $PGR^r$ as described above;

$R^5$ is selected from the group $GR^5$ as described above, and in more specific embodiments $R^5$ is selected from the group $PGR^5$ as described above;

$R^4$ is selected from the group consisting of —H, —F and —$CH_3$, and in more specific embodiments $R^4$ is H;

n is 0 or 1;

$R^1$, optionally substituted with $R^p$ as described above, is selected from the group $GR^1$ as described above, in more specific embodiments $R^1$, optionally substituted with $R^p$ as described above, is selected from the group $PGR^1$ as described above, and in even more specific embodiments $R^1$ is selected from the group $SGR^1$ as described above;

$R^p$ is selected from the group $GR^p$ as described above, and in more specific embodiments $R^p$ is selected from the group $PGR^p$ as described above;

$R^2$, optionally substituted with $R^q$ as described above, is selected from the group $GR^2$ as described above, in more specific embodiments $R^2$, optionally substituted with $R^q$ as described above, is selected from the group $PGR^2$ as described above, and in even more specific embodiments $R^2$ is selected from the group $SGR^2$ as described above;

$R^q$ is selected from the group $GR^q$ as described above, and in more specific embodiments $R^q$ is selected from the group $PGR^q$ as described above;

there are 0, 1, or 2 $R^q$ substituents;

$R^3$ is selected from the group consisting of —H, —F, Cl, Br and —$CH_3$, and in more specific embodiments $R^3$ is H;

the compound of formula (I) is (S)-3-[5-(3,4-dichloro-phenyl)-1-(4-methoxy-phenyl)-1H-pyrazol-3-yl]-2-m-tolyl-propionic acid;

the compound of formula (I) is (S)-sodium 3-[5-(3,4-dichloro-phenyl)-1-(4-methoxy-phenyl)-1H-pyrazol-3-yl]-2-m-tolyl-propionate.

Some embodiments include methods of making a compound of formula (I), enantiomers, diastereomers, racemics, pharmaceutically acceptable salts, esters, and amides thereof, comprising: crystallizing a salt of the pyrazole acid derivative of formula (I-A)

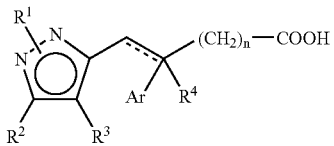

(I-A)

out of a medium to form a crystallization product, wherein said medium before said crystallizing contains an amount of said salt of said pyrazole acid derivative, said medium contains a water amount, and wherein said water amount is within about 20% of the water amount equimolar with said amount of said salt. More specifically additional embodiments include those methods wherein any one of the following features applies:

said pyrazole acid derivative (I-A) is a compound of formula (P8')

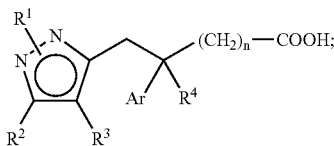

(P8')

said salt before said crystallizing has an enantiomeric excess of at least 80% and said crystallization product has an enatiomeric excess of at least 90%, and in even more specific embodiments, said crystallization product is enantiomerically pure;

said salt before crystallizing has a regioisomeric excess of at least 80% and said crystallization product has a regioisomeric excess of at least 90%, and in even more specific embodiments, said crystallization product has a regioisomeric excess of at least 90%;

said salt before said crystallizing has an enantiomeric excess of at least 80% and a regioisomeric excess of at least 80%, and said crystallization product has an enatiomeric excess of at least 90% and a regiosisomeric excess of at least 90%, and in even more specific embodiments, said crystallization product is enantiomerically pure and has a regioisomeric excess of at least 99%;

the Ar attached carbon is saturated and has the configuration

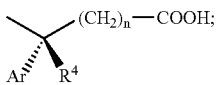

the Ar attached carbon is unsaturated and has the configuration

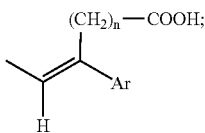

Ar, optionally substituted with $R^r$ as described above, is selected from the group GAr as described above, in more specific embodiments Ar, optionally substituted with $R^r$ as described above, is selected from the group PGAr as described above, and specific Ar are selected from the group SGAr as described above;

there are 0, 1, or 2 $R^r$ substituents;

$R^r$ is selected from the group $GR^r$ as described above, and in more specific embodiments $R^r$ is selected from the group $PGR^r$ as described above;

$R^4$ is selected from the group consisting of —H, —F and —$CH_3$, and in more specific embodiments $R^4$ is H;

n is 0 or 1;

$R^1$, optionally substituted with $R^p$ as described above, is selected from the group $GR^1$ as described above, in more specific embodiments $R^1$, optionally substituted with $R^p$ as described above, is selected from the group $PGR^1$ as described above, and in even more specific embodiments $R^1$ is selected from the group $SGR^1$ as described above;

$R^p$ is selected from the group $GR^p$ as described above, and in more specific embodiments $R^p$ is selected from the group $PGR^p$ as described above;

$R^2$, optionally substituted with $R^q$ as described above, is selected from the group $GR^2$ as described above, in more specific embodiments $R^2$, optionally substituted with $R^q$ as described above, is selected from the group $PGR^2$ as described above, and in even more specific embodiments $R^2$ is selected from the group $SGR^2$ as described above;

$R^q$ is selected from the group $GR^q$ as described above, and in more specific embodiments $R^q$ is selected from the group $PGR^q$ as described above;

there are 0, 1, or 2 $R^q$ substituents;

$R^3$ is selected from the group consisting of —H, —F, Cl, Br and —$CH_3$, and in more specific embodiments $R^3$ is H;

the compound of formula (I) is (S)-3-[5-(3,4-dichloro-phenyl)-1-(4-methoxy-phenyl)-1H-pyrazol-3-yl]-2-m-tolyl-propionic acid;

the compound of formula (I) is (S)-sodium 3-[5-(3,4-dichloro-phenyl)-1-(4-methoxy-phenyl)-1H-pyrazol-3-yl]-2-m-tolyl-propionate;

said pyrazole acid derivative and said salt are chiral;

said pyrazole acid derivative comprises a mixture of regioisomers with respect to the substitution of the nitrogen members in the pyrazole framework of said pyrazole acid derivative, and in more specific embodiments said mixture of regioisomers comprises two regioisomers that are chiral;

said pyrazole acid derivative comprises (S)-3-[5-(3,4-dichloro-phenyl)-1-(4-methoxy-phenyl)-1H-pyrazol-3-yl]-2-m-tolyl-propionic acid;

said water amount is within about 10% of the water amount equimolar with said salt;

said water amount is within 5% of the water amount equimolar with said salt;

said water amount is about equimolar with said salt;

said medium comprises a solvent component in which said salt is soluble and another component in which said salt is less soluble than in said solvent component;

said medium comprises a solvent component in which said salt is soluble, said solvent component comprising a solvent being selected form the group consisting of THF, MeOH, CH$_2$Cl$_2$, and mixtures thereof, and another component in which said salt is less soluble than in said solvent component, said another component being selected from the group consisting of CH$_3$CN, toluene, hexane, and mixtures thereof;

said medium comprises a solvent component in which said salt is soluble, said solvent component comprising THF, and another component in which said salt is less soluble than in said solvent component, said another component comprising CH$_3$CN;

said salt is chiral, said crystallizing leads to a chiral separated product, and the enantiomeric excess of said separated product is at least 90%;

said salt is chiral, said crystallizing leads to a chiral separated product, and said chiral separated product is enantiomerically pure;

said water amount is within 5% of the water amount equimolar with said salt, said medium comprises a solvent component in which said salt is soluble, said solvent component comprising THF, and another component comprising CH$_3$CN;

said salt is an alkali metal salt, and in more specific embodiments said salt is one of sodium salt and potassium salt;

said salt is an amine salt, and in more specific embodiments said salt is one of meglumine salt, tromethamine salt, tributylamine salt, S-alpha-methylbenzyl amine, and ethylene diamine salt;

said water amount is within 5% of the water amount equimolar with said salt, said medium comprises a solvent component in which said salt is soluble, said solvent component comprising THF, said another component comprising CH$_3$CN, and said salt being (S)-sodium 3-[5-(3,4-dichloro-phenyl)-1-(4-methoxy-phenyl)-1H-pyrazol-3-yl]-2-m-tolyl-propionate.

Some embodiments include products, enantiomers, diastereomers, racemics, pharmaceutically acceptable salts, esters, and amides thereof, obtained by a method comprising: crystallizing a salt of the pyrazole acid derivative of formula (I-A)

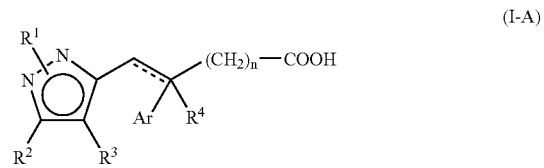

out of a medium, wherein said medium contains an amount of said salt of said pyrazole acid derivative, said medium contains a water amount, and wherein said water amount is within about 20% of the water amount equimolar with said amount of said salt. More specifically additional embodiments include those products obtained by crystallization methods wherein any one of the features referred to herein for the crystallization of a salt of the pyrazole acid derivative of formula (I-A) applies.

SCHEME Q

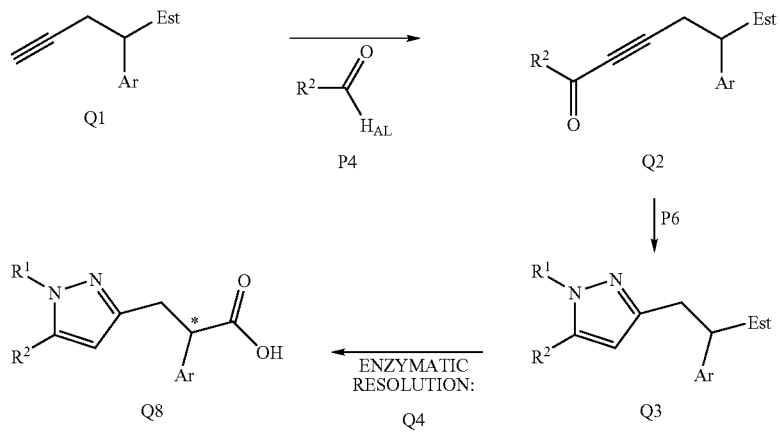

Referring to Scheme Q, there are disclosed the following notes and additions. Acetylenic ketone Q2 is obtained by coupling suitably substituted acid halide P4 with Q1 as described in Scheme Q. This coupling is performed in some embodiments of this invention by a Sonogashira reaction as described in Scheme P.

"Est" is an ester group, such as C(O)(Rox), where Rox is preferably a C$_{1-4}$alkoxy, wherein "C$_{1-4}$" denotes herein a linear or branched chain for said alkoxy, such as ethoxy. Compound Q1 is either available or it can be prepared by alkylation as described in Scheme P.

Condensation with a suitably substituted hydrazine P6 is performed as indicated in Scheme P to obtain racemic product Q3. As indicated in the context of Scheme P, compounds with a nitrogen substitution pattern in the pyrazole frameowrk as shown in Q3 in the surrounding chemical environment of compounds of this invention can be produced by this reaction with high regioselectivity, which reached in embodiments of this invention at least about 80%, or a molar ratio of 1:4, with the isomer in excess being the isomer with the pyrazole framework substituted as shown in Scheme Q. Chiral product Q8 is obtained from Q3, preferably by enzymatic resolution Q4.

Enzymatic resolution of compounds Q3 was developed in the context of this invention. It was found in the context of this invention that compounds Q3 could be enzymatically resolved to achieve an enantiomeric excess of at least 90% with an enzyme suitable for hydrolyzing one enantiomer (for example enantiomer (S)) while leaving the other enantiomer (for example enantiomer (F)) esterified. Embodiments of this enzymatic resolution utilized an enzyme comprising a lipase. Examples of lipases include *Mucor miehei*, lyo; *Rhizomucor miehei*; and *Candida cyclindracea*, of which *Mucor miehei*, lyo, is the preferred lipase. Commercial lipase products used in embodiments of this invention are known as Altus catalyst #8. The enzyme was used in a buffered medium mixed with solutions of compound Q3 in a suitable solvent, such as isopropyl alcohol/toluene. Enzymatic resolution quenching and separation of resolution products lead to product Q8.

When one enantiomer in a mixture of enantiomers is to be enriched, for example when the S-enantiomer is the desired stereospecific form of Q8, the other enantiomer-rich fraction, for example the R-enantiomer enriched fraction, is preferably racemized and incorporated into the process as product Q3 that is subject to enzymatic resolution Q4. Racemization is accomplished, for example, by adding a base, such as KHMDS (potassium bis(trimethylsilyl)amide, also known as potassium hexamethyldisilazide), to a solution of the ester to be racemized (the R-enantiomer enriched ester in some embodiments of this invention).

Preferred bases include bases whose $pK_a$ is greater than about 23, and more preferably greater than about 25. One of ordinary skill in the art will recognize in light of this disclosure that the use of a base whose $pK_a$ is chosen according to the direction provided herein will cause the removal of a proton from the stereogenic center and that subsequent reprotonation at the same center will result in racemization of the ester.

Racemization quenching and product separation lead to racemates that can be incorporated in the enzymatic resolution through a recycling process. This recycling process comprises at least one cycle of racemization and enzymatic resolution. The implementation of this recycling step (not displayed in Scheme Q) leads to a quantitatively improved recovery of the desired enantiomer.

As indicated in Scheme P with respect to P8, product Q8 can be further purified by crystallization. Embodiments of this invention lead to the production of the a salt form of Q8 with ee(S)≧99.9%. In some embodiments of this invention, Q1 was 2-m-tolyl-pent-4-ynoic acid ethyl ester, Q2 was 6-(3,4-dichloro-phenyl)-6-oxo-2-m-tolyl-hex-4-ynoic acid ethyl ester, Q3 was 3-[5-(3,4-dichloro-phenyl)-1-(4-methoxy-phenyl)-1H-pyrazol-3-yl]-2-m-tolyl-propionic acid ethyl ester, and Q8 was (S)-3-[5-(3,4-dichloro-phenyl)-1-(4-methoxy-phenyl)-1H-pyrazol-3-yl]-2-m-tolyl-propionic acid, or a salt thereof, such as (S)-sodium 3-[5-(3,4-dichloro-phenyl)-1-(4-methoxy-phenyl)-1H-pyrazol-3-yl]-2-m-tolyl-propionate.

Embodiments of processes schematically illustrated in Scheme Q comprise a 3-step convergent synthesis of a pyrazole framework from acetylenic ketone Q2 by a regioselective condensation. An additional step of enzymatic resolution Q4 comprises kinetic resolution through enzyme-catalyzed hydrolysis of a racemic ester with the pyrazole framework incorporated therein. Optical purity following enzymatic resolution Q4 in embodiments of this invention was at least 92% (ee >92%). Embodiments of such 4-step synthesis according to the present invention contrast with other synthetic approaches that rely on at least eight synthetic steps.

Some embodiments include methods of making a compound of formula (I), enantiomers, diastereomers, racemics, pharmaceutically acceptable salts, esters, and amides thereof, comprising: enzymatically resolving with a lipase a esterified pyrazole derivative of formula (Q3')

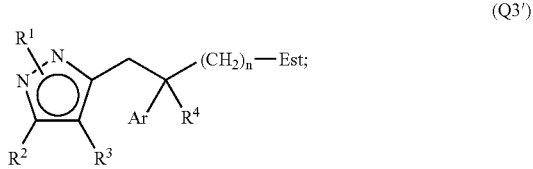

(Q3')

wherein the Ar attached carbon forms a stereogenic center, Est is a substituent chosen from the definition of $R^5$ such that Est is a carboxylic acid ester group. More specifically, additional embodiments include those methods wherein any one of the following features applies:

the Ar attached carbon in one of the enantiomers of compound (Q3') has the configuration

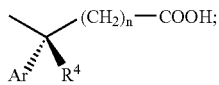

Ar, optionally substituted with $R^r$ as described above, is selected from the group GAr as described above, in more specific embodiments Ar, optionally substituted with $R^r$ as described above, is selected from the group PGAr as described above, and specific Ar are selected from the group SGAr as described above;

there are 0, 1, or 2 $R^r$ substituents;

$R^r$ is selected from the group $GR^r$ as described above, and in more specific embodiments $R^r$ is selected from the group $PGR^r$ as described above;

$R^4$ is selected from the group consisting of —H, —F and —$CH_3$, and in more specific embodiments $R^4$ is H;

n is 0 or 1;

$R^1$, optionally substituted with $R^p$ as described above, is selected from the group $GR^1$ as described above, in more specific embodiments $R^1$, optionally substituted with $R^p$ as described above, is selected from the group $PGR^1$ as described above, and in even more specific embodiments $R^1$ is selected from the group $SGR^1$ as described above;

$R^p$ is selected from the group $GR^p$ as described above, and in more specific embodiments $R^p$ is selected from the group $PGR^p$ as described above;

$R^2$, optionally substituted with $R^q$ as described above, is selected from the group $GR^2$ as described above, in more specific embodiments $R^2$, optionally substituted with $R^q$ as described above, is selected from the group $PGR^2$ as described above, and in even more specific embodiments $R^2$ is selected from the group $SGR^2$ as described above;

$R^q$ is selected from the group $GR^q$ as described above, and in more specific embodiments $R^q$ is selected from the group $PGR^q$ as described above;

there are 0, 1, or 2 $R^q$ substituents;

$R^3$ is selected from the group consisting of —H, —F, Cl, Br and —$CH_3$, and in more specific embodiments $R^3$ is H;

the compound of formula (I) is (S)-3-[5-(3,4-dichloro-phenyl)-1-(4-methoxy-phenyl)-1H-pyrazol-3-yl]-2-m-tolyl-propionic acid;

the compound of formula (I) is (S)-sodium 3-[5-(3,4-dichloro-phenyl)-1-(4-methoxy-phenyl)-1H-pyrazol-3-yl]-2-m-tolyl-propionate;

said compound (Q3') comprises a mixture of regioisomers with respect to the substitution of the nitrogen members in the pyrazole framework of said compound (Q3');

said enzymatically resolving leads to a chiral resolution product, and the enantiomeric excess of said resolution product is at least 90%;

said enzymatically resolving is performed with an enzyme comprising a lipase that preferentially hydrolyzes enantiomer S of said compound of formula (Q3');

said enzymatically resolving is performed with an enzyme comprising a lipase selected form the group consisting of *Mucor miehei*, lyo; *Rhizomucor miehei*; *Candida cyclindracea*; and mixtures thereof;

said enzymatically resolving is performed with lipase *Mucor miehei*, lyo;

said enzymatically resolving is performed with Altus catalyst #8;

further comprising enzymatic resolution quenching and separation of a resolution product to form at least two fractions, a first fraction comprising said resolution product with an excess of a first enantiomer with respect to a second enantiomer, and a second fraction comprising a product with an excess of said second enantiomer with respect to said first enantiomer, and in more specific embodiments said first enantiomer is the S enantiomer and said second enantiomer is the R enantiomer;

further comprising enzymatic resolution quenching and separation of a resolution product to form at least two fractions, a first fraction comprising said resolution product with an excess of a first enantiomer with respect to a second enantiomer, and a second fraction comprising a product with an excess of said second enantiomer with respect to said first enantiomer, and racemazing said second fraction to form a recycle fraction, in more specific embodiments further comprising enzymatically resolving said recycle fraction, wherein said racemazing and said enzymatically resolving define a recycling, in more specific embodiments said recycling is peformed at least once, in more specific embodiments said racemazing is performed by mixing said second fraction with a base, in still more specific embodiments, said base is a base with a $pK_a$ greater than 23, and in still more specific embodiments, said base comprises potassium bis(trimethylsilyl)amide;

further comprising enzymatic resolution quenching and separation of a resolution product to form at least two fractions, a first fraction comprising said resolution product with an excess of a first enantiomer with respect to a second enantiomer, said first enantiomer being in the form of a pyrazole acid derivative and said second enantiomer being in the form of a pyrazole ester derivative, in more specific embodiments further comprising forming a salt of said pyrazole acid derivative enantiomer, and in still more specific embodiments further comprising crystallizing said salt;

further comprising enzymatic resolution quenching and separation of a resolution product to form at least two fractions, a first fraction comprising said resolution product with an excess of a first enantiomer with respect to a second enantiomer, said first enantiomer being (S)-3-[5-(3,4-dichloro-phenyl)-1-(4-methoxy-phenyl)-1H-pyrazol-3-yl]-2-m-tolyl-propionic acid;

further comprising enzymatic resolution quenching and separation of a resolution product to form at least two fractions, a first fraction comprising said resolution product with an excess of a first enantiomer with respect to a second enantiomer, said first enantiomer being (S)-3-[5-(3,4-dichloro-phenyl)-1-(4-methoxy-phenyl)-1H-pyrazol-3-yl]-2-m-tolyl-propionic acid, in more specific embodiments further comprising forming the salt (S)-sodium 3-[5-(3,4-dichloro-phenyl)-1-(4-methoxy-phenyl)-1H-pyrazol-3-yl]-2-m-tolyl-propionate, and in still more specific embodiments further comprising crystallizing said salt.

SCHEME R

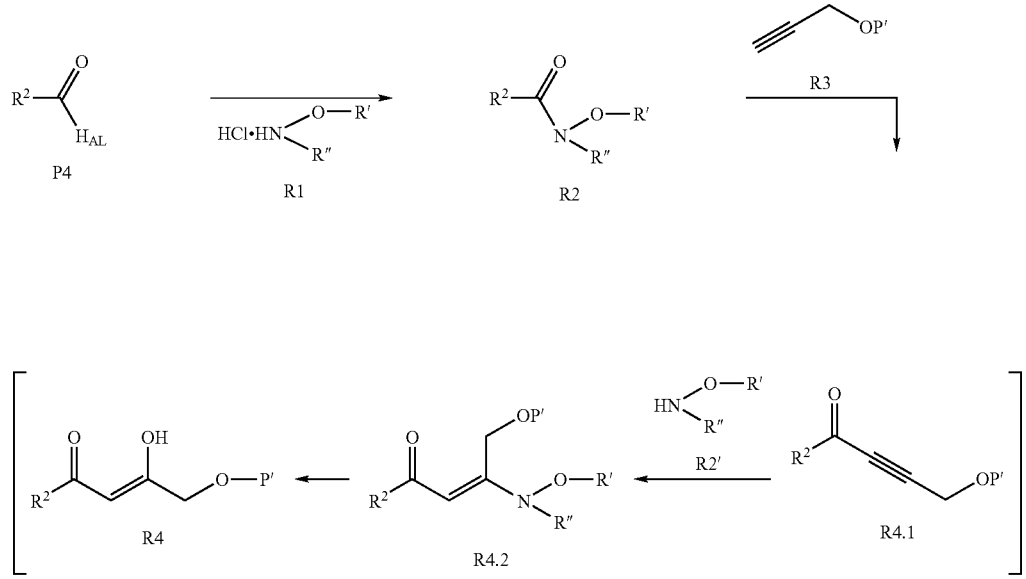

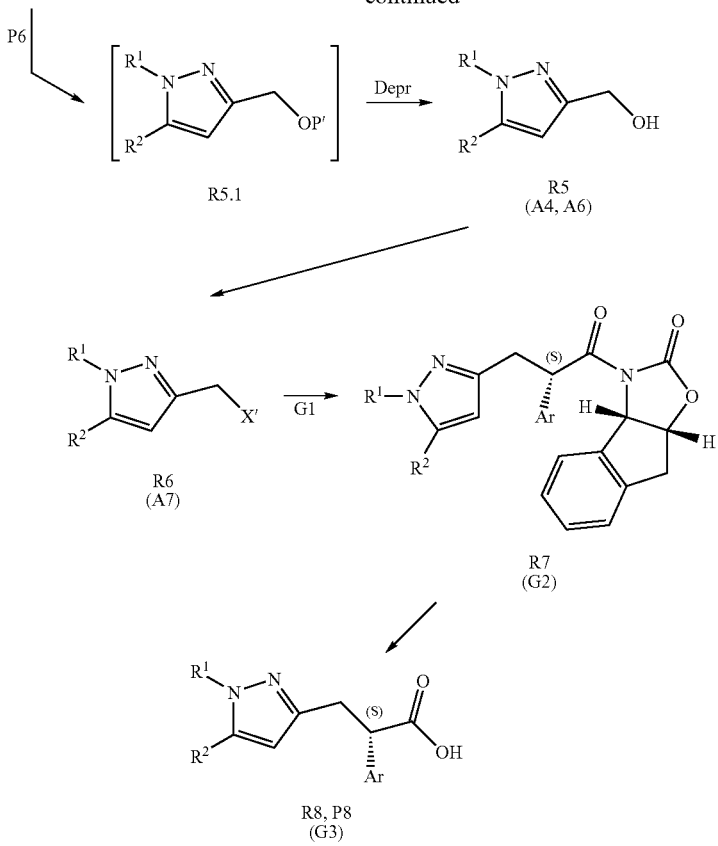

Referring to Scheme R, there are disclosed the following notes and additions. In some embodiments of this invention, a specific stereoisomer was obtained by stereoselective enolate alkylation of a product of condensation with a substituted hydrazine. Regioselective condensation was performed in some embodiments between a substituted hydrazine and a β-diketone, such as R4 that shows a β-diketone in its enol form. Reference herein to one tautomer of any compound that can exist in more than one tautomeric form includes a reference to any other tautomeric form that is not explicitly referred to. For example, reference to structure R4 in an enol form (as shown in Scheme R) also refers to the same structure in its keto form.

Amide R2 is obtained from acid halide P4 and amine R1. Substituents R' and R" are independently chosen, preferably as $C_{1-4}$alkyl, and most preferably R' is $CH_3$ and R" is $CH_3$.

Amide R2 reacts with acetylenic ether R3 to form acetylenic ketone R4.1, which reacts with amine R2' to form β-enaminoketone R4.2 which, under acidic conditions hydrolyzes in situ to β-diketone R4, shown in Scheme R in its enol form. Regioselective condensation produces R5.1 which can be deprotected as in Depr in Scheme R, to form pyrazole alcohol R5.

Amide R2 is preferably prepared through a controlled temperature quench that generates, in addition to R2, amine R2'. Acetylenic ketone R4.1 is preferably obtained by propargylating R2 and subsequently quenching the raction mixture with an acidic substance at about 0° C. The acidic substance is chosen so that it preferably comprises a chemically compatible acid capable of regulating the medium pH to a moderately acidic value, such as to an aqueous layer pH of about 5.

In other embodiments of this invention, quenching is performed with a saturated aqueous solution of ammonium chloride. In these embodiments, R2 converts to an amine, such as β-aminoketone R4.3:

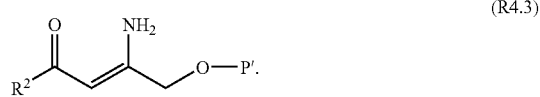

(R4.3)

This amine, and also β-enaminoketone R4.2, also participate in the condensation reaction with suitably substituted hydrazine P6 as described herein to form R5.1 in a high regioselectivity process.

Substituent P' in R3 is preferably a heterocyclic ring attached by a C that is next to a heteroatom, more preferably the heterocyclic ring has only one heteroatom, most preferably this heteroatom is O and P' is tetrahydropyranyl (THP). Any other suitable protecting group that can subsequently be removed in a deprotection step can be used as P'. Groups P' that form ethers OP' are preferred groups.

β-Enaminoketone R4.2 is formed in situ in the addition of amine R2' to acetylenic ketone R4.1. The enamino group in R4.2 undergoes in situ hydrolysis under aqueous acidic conditions to form β-diketone R4, shown in Scheme R in its enol form. Analysis of the reaction layer (organic layer) reveals that R4 predominates over R4.1. In embodiments of this invention the molar ratio of the amount of R4.1 to the amount of R4 in the mixture was about 5:95, respectively. The species in this mixture do not need isolation for further processing. Suitably substituted hydrazine P6 in other than a free base form and an inorganic base are added to this mixture to form pyrazole derivative R5.1. An example of P6 in non-free base form is a suitably substituted hydrazine hydrochloride. As indicated herein for this condensation, a carbonate is a preferred inorganic base. It was found in the context of this invention that this pyrazole derivative formation achieves high regioselectivity of, in some embodiments, at least 90%, and in some embodiments at least 95%, with R5.1 (one regioisomer, with nitrogen substitution pattern 1-($R^1$)-1H-pyrazol) being formed preferentially with respect to the pyrazole derivative that has $R^1$ as a substituent in the nitrogen member of the pyrazole framework shown unsusbstituted in Scheme R (the other regioisomer, with nitrogen substitution pattern 2-($R^1$)-2H-pyrazol). The molar ratio in embodiments of this invention referring to the ratio of the amount of R5.1 to the amount of the other regioisomer (not shown in Scheme R) was about 98:2. The condensation reaction with hydrazine P6 is thought to take place with R4 and also with R4.2, and furthermore with R4.3 when this substance is present.

Suitably substituted hydrazine P6 is used in some embodiments of this invention in a free base form. When the suitably substituted hydrazine P6 is in free base form, the isomer with the nitrogen substitution pattern in the pyrazole framework that corresponds to the 2-($R^1$)-2H-pyrazol substitution (not shown in Scheme R) is preferentially formed. No inorganic base is preferably used in such embodiments with a hydrazine in free base form.

Pyrazole derivative R5.1 undergoes deprotection to generate pyrazole alcohol R5. When P' is THP, this deprotection is preferably performed by using tosic acid in an alcoholic medium, such as methanol.

Pyrazole alcohol R5 can be isolated or it can be maintained in solution and converted to R6, where substituent X' is a suitable substituent for the stereoselective alkylation with G1 to form R7 as described in Scheme G. X' is preferably halo, more preferably Br or I, and most preferably I, in which case R5 is halogenated to R6.

In embodiments in which pyrazole alcohol R5 is isolated, such isolation is preferentially performed by precipitation from a low polarity medium, such as heptane. Halogenation of R5 can be achieved by converting the hydroxyl group with a suitable reagent to a leaving group in a halogenation step, such as by mesylation of the alcohol and subsequent reaction with iodide or bromide.

Halogenated pyrazole derivative R6 can be isolated as shown in Scheme R. Such isolation is not needed in some embodiments, in which R6 is kept in the organic medium for stereoselective alkylation. Halogenated pyrazole derivative R6 is the alkylating agent that reacts with derivative G1 to form chiral R7. This chiral compound R7 does not require its isolation for further processing, and it is subject in embodiments of this invention to an oxidative hydrolysis and acidification to yield pyrazole acid R8.

G1 is obtained in embodiments of this invention from an acid, such as

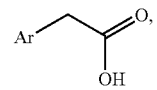

and a chiral tetrahydro-indeno-oxazole in the presence of an organic base, such as triethylamine, and an activating agent. A preferred activating agent is pivaloyl chloride. A preferred organic solvent for this reaction is a low polarity solvent, such as toluene.

As indicated in Scheme R by the symbols within parenthesis, R7 is converted to R8 analogously as G2 is converted to G3 according to Scheme G. Product R8 can further be purified as described above. Also as indicated in Scheme R by the symbols within parenthesis, R6 is in some embodiments obtained from R5 by halogenation, and A7 is obtained from A4 or A6 by halogenation as shown in Scheme A.

As described herein, R8 salts can be prepared (not shown in Scheme R). Inorganic and organic salts of R8, such as alkali metal salts and amine salts, were prepared in embodiments of this invention. Also as described herein, it was found in the context of this invention that these salts can be isolated by crystallization, and that embodiments of such crystallization are crystalline material, and other embodiments comprise a mixture of crystalline and amorphous material, the latter embodiments being referred to as being semicrystalline.

Some embodiments include methods of making a compound of formula (I), enantiomers, diastereomers, racemics, pharmaceutically acceptable salts, esters, and amides thereof, comprising: a condensation of a substituted hydrazine and at least one of a β-diketone, a β-enaminoketone, and a β-aminoketone to form a pyrazole derivative, said pyrazole derivative having a pyrazole framework with one of the nitrogen members in said pyrazole framework substituted. In some embodiments said condensation is a regioselective condensation. More specifically, additional embodiments include those methods wherein any one of the following features applies:

said β-diketone comprises a compound of formula R4:

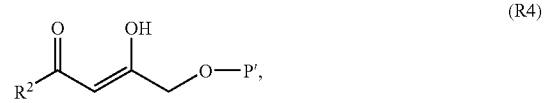

(R4)

wherein $R^2$ is defined above and P' is a protecting group that can be removed to form a hydroxyl group, in more specific embodiments P' is a group such that OP' is an ether group, and in even more specific embodiments P' is THP;

said β-enaminoketone comprises a compound of formula R4.2:

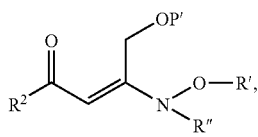

(R4.2)

wherein R² is defined above, P' is a protecting group that can be removed to form a hydroxyl group, and R' and R" are independently chosen from the group of $C_{1-4}$alkyl groups, in more specific embodiments P' is a group such that OP' is an ether group, in even more specific embodiments P' is THP, and in other more specific embodiments each one of R' and R" is methyl;

said β-aminoketone comprises a compound of formula R4.3:

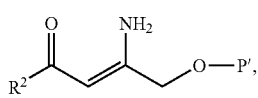

(R4.3)

wherein R² is defined above and P' is a protecting group that can be removed to form a hydroxyl group, in more specific embodiments P' is a group such that OP' is an ether group, and in even more specific embodiments P' is THP;

said substituted hydrazine is a non-free base hydrazine, and in more specific embodiments said non-free base hydrazine is 4-methoxyphenyl hydrazine·HCl;

said substituted hydrazine is a free base hydrazine, and in more specific embodiments said free base hydrazine is 4-methoxyphenyl hydrazine;

said pyrazole derivative is formed with a regioisomeric excess of at least about 90%, and in more specific embodiments said pyrazole derivative is formed with a regioisomeric excess of at least about 95%;

said pyrazole derivative is a mixture of a first pyrazole derivative and a second pyrazole derivative, wherein said first pyrazole derivative has the nitrogen-member substitution pattern in the pyrazole framework specified by 1-(R¹)-1H-pyrazol, said second pyrazole derivative has the nitrogen-member substitution pattern in the pyrazole framework specified by 2-(R¹)-2H-pyrazol, and said first pyrazole derivative is obtained in an amount that is greater than the amount of said second pyrazole derivative;

said pyrazole derivative is a mixture of a first pyrazole derivative and a second pyrazole derivative, wherein said first pyrazole derivative has the nitrogen-member substitution pattern in the pyrazole framework specified by 1-(R¹)-1H-pyrazol, said second pyrazole derivative has the nitrogen-member substitution pattern in the pyrazole framework specified by 2-(R¹)-2H-pyrazol, and said second pyrazole derivative is obtained in an amount that is greater than the amount of said first pyrazole derivative;

said pyrazole derivative is a mixture of a first pyrazole derivative and a second pyrazole derivative, wherein said first pyrazole derivative is [5-(3,4-dichloro-phenyl)-1-(4-methoxy-phenyl)-1H-pyrazol-3-yl]-methanol, said second pyrazole derivative is [5-(3,4-dichloro-phenyl)-2-(4-methoxy-phenyl)-2H-pyrazol-3-yl]-methanol, and said first pyrazole derivative is obtained in an amount that is greater than the amount of said second pyrazole derivative;

said pyrazole derivative is a mixture of a first pyrazole derivative and a second pyrazole derivative, wherein said first pyrazole derivative is [5-(3,4-dichloro-phenyl)-1-(4-methoxy-phenyl)-1H-pyrazol-3-yl]-methanol, said second pyrazole derivative is 3-[5-(3,4-dichloro-phenyl)-2-(4-methoxy-phenyl)-2H-pyrazol-3-yl]-methanol, and said second pyrazole derivative is obtained in an amount that is greater than the amount of said first pyrazole derivative;

said pyrazole derivative is a pyrazole alcohol derivative of formula (R5')

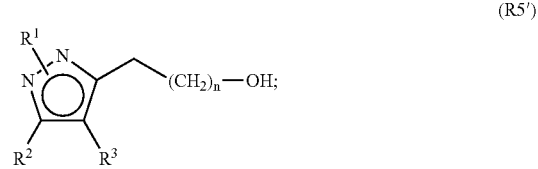

(R5')

said pyrazole derivative is a pyrazole alcohol derivative of formula (R5')

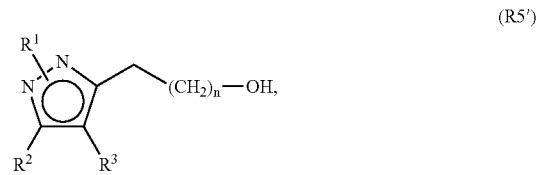

(R5')

and further comprising halogenating said pyrazole alcohol derivative to replace the hydroxyl group in said pyrazole alcohol derivative by a halo group to form a compound of formula (R6')

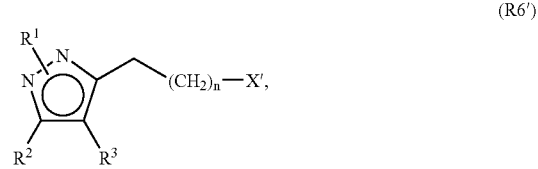

(R6')

wherein substituent X' is said halo group, and in more specific embodiments said halo group is one in the group of bromo and iodo;

said pyrazole derivative is a pyrazole alcohol derivative of formula (R5')

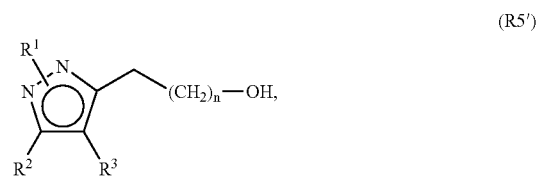

(R5')

further comprising halogenating said pyrazole alcohol derivative to replace the hydroxyl group in said pyrazole alcohol derivative by a halo group to form a compound of formula (R6')

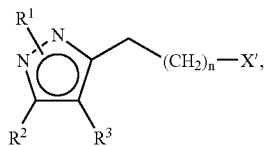

(R6')

wherein substituent X' is said halo group, and further comprising alkylating a chiral agent with said compound of formula (R6') as an alkylating agent, in more specific embodiments said chiral agent being a chiral tetrahydro-indeno-oxazole derivative, in even more specific embodiments said chiral tetrahydro-indeno-oxazole derivative being formed from an acid

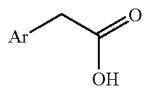

and a chiral tetrahydro-indeno-oxazole in the presence of an organic base and an activating agent, in even more specific embodiments said activating agent being pivaloyl chloride, and in even more specific embodiments said chiral tetrahydro-indeno-oxazole derivative is formed in a medium that comprises a low polarity solvent, and in even more specific embodiments said R5' is [5-(3,4-dichlorophenyl)-1-(4-methoxyphenyl)-1H-pyrazol-3-yl]-methanol, said R6' is [5-(3,4-dichlorophenyl)-1-(4-methoxyphenyl)-1H-pyrazole, said acid is m-tolylacetic acid, said chiral tetrahydro-indeno-oxazole derivative is 3-(2-m-tolyl-acetyl)-3,3a,8,8a-tetrahydro-indeno[1,2-d]oxazol-2-one, said chiral tetrahydro-indeno-oxazole is (3aS-cis)-(–)-3,3a,8,8a-tetrahydro-2H-indeno[1,2-d]-oxazol-2-one;

said pyrazole derivative is a pyrazole alcohol derivative of formula (R5')

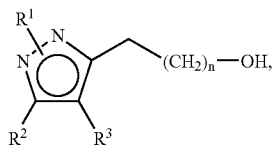

(R5')

further comprising halogenating said pyrazole alcohol derivative to replace the hydroxyl group in said pyrazole alcohol derivative by a halo group to form a compound of formula (R6')

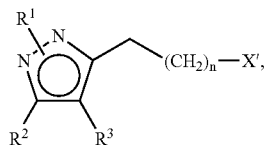

(R6')

wherein substituent X' is said halo group, and further comprising alkylating a chiral agent with said compound of formula (R6') as an alkylating agent to form a chiral pyrazole derivative, in more specific embodiments said chiral agent being a chiral tetrahydro-indeno-oxazole derivative, in even more specific embodiments further comprising an oxidative hydrolysis and acidification of said chiral pyrazole derivative to form a chiral pyrazole acid derivative of formula (R8')

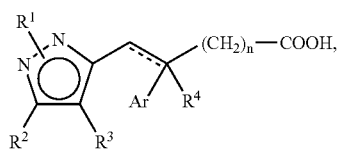

(R8')

wherein the Ar-attached carbon member in (R8') is a saturated stereogenic center, in even more specific embodiments forming a salt of said pyrazole acid derivative (R8'), and in even more specific embodiments crystallizing said salt, and in even more specific embodiments said R5' is [5-(3,4-dichlorophenyl)-1-(4-methoxyphenyl)-1H-pyrazol-3-yl]-methanol, said R6' is [5-(3,4-dichlorophenyl)-3-iodomethyl-1-(4-methoxyphenyl)-1H-pyrazole, said acid is m-tolylacetic acid, said chiral tetrahydro-indeno-oxazole derivative is 3-(2-m-tolyl-acetyl)-3,3a,8,8a-tetrahydro-indeno[1,2-d]oxazol-2-one, said chiral tetrahydro-indeno-oxazole is (3aS-is)-(–)-3,3a,8,8a-tetrahydro-2H-indeno[1,2-d]-oxazol-2-one, said R8' is (S)-3-[5-(3,4-dichloro-phenyl)-1-(4-methoxy-phenyl)-1H-pyrazol-3-yl]-2-m-tolyl-propionic acid, and said salt of said pyrazole acid derivative is (S)-sodium 3-[5-(3,4-dichloro-phenyl)-1-(4-methoxy-phenyl)-1H-pyrazol-3-yl]-2-m-tolyl-propionate;

wherein said β-diketone is obtained from an acidic hydrolysis of a β-enaminoketone;

wherein said β-diketone is obtained from an acidic hydrolysis of a β-enaminoketone, said β-enaminoketone is obtained form an addition of an amine and an acetylenic ketone;

wherein said β-diketone is obtained from an acidic hydrolysis of a β-enaminoketone, said β-enaminoketone is obtained form an addition of an amine and an acetylenic ketone, and said acetylenic ketone is obtained from a propargylation of an amide and acidic quenching of said propargylation, in even more specific embodiments, said β-diketone is (Z)-1-(3,4-dichlorophenyl)-3-hydroxy-4-[(tetrahydro-2H-pyran-2-yl)oxy]-2-buten-1-one, said β-enaminoketone is (E)-1-(3,4-dichlorophenyl)-3-methoxymethylamino-4-[(tetrahydro-2H-pyran-2-yl)oxy]-2-buten-1-one, said amide is 3,4-dichloro-N-methoxy-N-methyl-benzamide, said amine is N-methoxymethylamine, said acetylenic ketone is 1-(3,4-dichlorophenyl)-4-[(tetrahydro-2H-pyran-2-yl)oxy]-2-butyn-1-one, and said propargylation is performed with tetrahydro-2-(2-propynyloxy)-2H-pyran;

wherein said β-aminoketone is obtained from a propargylation of an amide and quenching of said propargylation with a saturated aqueous solution of ammonium chloride;

wherein said β-diketone is obtained from an acidic hydrolysis of a β-enaminoketone, said β-enaminoketone is obtained form an addition of an amine and an acetylenic ketone, said acetylenic ketone is obtained from a propargylation of an amide and acidic quenching of said propargylation, and said amide is obtained in an amide formation reaction of a first amine and an acid chloride, and in even more specific embodiments, said first amine is N,O-dimethylhydroxylamine hydrochloride, and said acid chloride is 3,4-dichlorobenzoyl-chloride;

wherein said β-aminoketone is obtained from a propargylation of an amide and quenching of said propargylation with a saturated aqueous solution of ammonium chloride, and said amide is obtained in an amide formation reaction of an amine and an acid chloride;

the Ar attached carbon is saturated and has the configuration

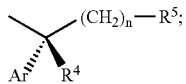

the Ar attached carbon is unsaturated and has the configuration

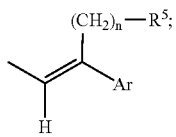

Ar, optionally substituted with $R^r$ as described above, is selected from the group GAr as described above, in more specific embodiments Ar, optionally substituted with $R^r$ as described above, is selected from the group PGAr as described above, and specific Ar are selected from the group SGAr as described above;

there are 0, 1, or 2 $R^r$ substituents;

$R^r$ is selected from the group $GR^r$ as described above, and in more specific embodiments $R^r$ is selected from the group $PGR^r$ as described above;

$R^5$ is selected from the group $GR^5$ as described above, and in more specific embodiments $R^5$ is selected from the group $PGR^5$ as described above;

$R^4$ is selected from the group consisting of —H, —F and —CH$_3$, and in more specific embodiments $R^4$ is H;

n is 0 or 1;

$R^1$, optionally substituted with $R^p$ as described above, is selected from the group $GR^1$ as described above, in more specific embodiments $R^1$, optionally substituted with $R^p$ as described above, is selected from the group $PGR^1$ as described above, and in even more specific embodiments $R^1$ is selected from the group $SGR^1$ as described above;

$R^p$ is selected from the group $GR^p$ as described above, and in more specific embodiments $R^p$ is selected from the group $PGR^p$ as described above;

$R^2$, optionally substituted with $R^q$ as described above, is selected from the group $GR^2$ as described above, in more specific embodiments $R^2$, optionally substituted with $R^q$ as described above, is selected from the group $PGR^2$ as described above, and in even more specific embodiments $R^2$ is selected from the group $SGR^2$ as described above;

$R^q$ is selected from the group $GR^q$ as described above, and in more specific embodiments $R^q$ is selected from the group $PGR^q$ as described above;

there are 0, 1, or 2 $R^q$ substituents;

$R^3$ is selected from the group consisting of —H, —F, Cl, Br and —CH$_3$, and in more specific embodiments $R^3$ is H;

the compound of formula (I) is (S)-3-[5-(3,4-dichloro-phenyl)-1-(4-methoxy-phenyl)-1H-pyrazol-3-yl]-2-m-tolyl-propionic acid;

the compound of formula (I) is (S)-sodium 3-[5-(3,4-dichloro-phenyl)-1-(4-methoxy-phenyl)-1H-pyrazol-3-yl]-2-m-tolyl-propionate.

SCHEME S

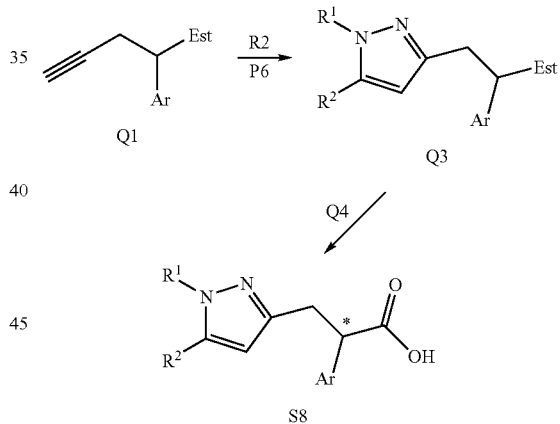

Referring to Scheme S, there are disclosed the following notes and additions. A product of the addition of acetylenic ester Q1 to amide R2 is regioselectively condensed with suitably substituted hydrazine P6 to form racemic Q3.

Q1 can be obtained by propargylation of the corresponding ester Ar—CH$_2$-Est. In some embodiments, the reaction of Q1 with R2 is quenched with a saturated aqueous solution of ammonium chloride and then the organic layer is treated with P6 to regioselectively form racemic Q3.

Scheme S shows another strategy for forming species that will condense with a suitably substituted hydrazine in a high regioselective process. The nitrogen substitution in the pyrazole framework as shown in Q3 in Scheme S was in embodiments of this invention in a molar ratio of about 98:2 referring to the amount of the isomer shown in Q3 with respect to the isomer that would have the substituent $R^1$ in the nitrogen member that is shown unsubstituted in Q3.

Substituent Est is defined above. Regioselective condensation with suitably substituted hydrazine P6 according to Schemes R and S is performed under conditions similar to those described in Schemes P and Q. Compound S8 is obtained by enzymatic resolution Q4 as described in Scheme Q.

Some embodiments include methods of making a compound of formula (I), enantiomers, diastereomers, racemics, pharmaceutically acceptable salts, esters, and amides thereof, comprising: an addition of an acetylenic ester to an amide to form an addition product, and a condensation of said addition product with a substituted hydrazine to form a pyrazole ester derivative of formula Q3'

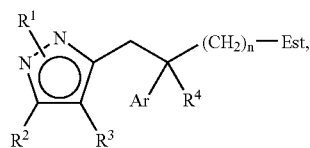

(Q3')

wherein the group Est in Q3' is a substituent chosen from the definition of $R^5$ such that Est is a carboxylic acid ester group. In some embodiments said condensation is a regioselective condensation. More specifically, additional embodiments include those methods wherein any one of the following features applies:

said pyrazole derivative is formed with a regioisomeric excess of at least about 90%;

said pyrazole ester derivative is a racemic;

further comprising quenching said addition with a saturated aqueous solution of ammonium chloride;

wherein said pyrazole ester derivative is a racemic and further comprising enzymatically resolving said racemic, in more specific embodiments, said enzymatically resolving is performed with a lipase to form a chiral pyrazole acid derivative of formula (P8'),

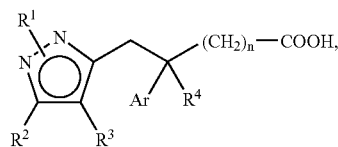

(P8')

wherein the Ar-attached carbon member in P8' is a stereogenic center and one of the enantiomers of said stereogenic center is in excess with respect to the other enantiomer, in even more specific embodiments further comprising forming a salt of said pyrazole acid derivative, in even more specific embodiments further comprising crystallizing said salt of said pyrazole acid derivative, in even more specific embodiments, said enzymatically resolving is performed so that at least one of the features given above for an enzymatic resolution with a lipase applies, and in even more specific embodiments, said crystallizing is performed so that at least one of the features given above for crystallizing a salt of a pyrazole acid derivative applies;

further comprising obtaining said acetylenic ester by propargylating an ester

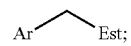

said amide is 3,4-dichloro-N-methoxy-N-methyl-benzamide;

said substituted hydrazine is a non-free base hydrazine, and in more specific embodiments said non-free base hydrazine is 4-methoxyphenyl hydrazine·HCl;

said substituted hydrazine is a free base hydrazine, and in more specific embodiments said free base hydrazine is 4-methoxyphenyl hydrazine;

said pyrazole derivative is a mixture of a first pyrazole derivative and a second pyrazole derivative, wherein said first pyrazole derivative has the nitrogen-member substitution pattern in the pyrazole framework specified by 1-($R^1$)-1H-pyrazol, said second pyrazole derivative has the nitrogen-member substitution pattern in the pyrazole framework specified by 2-($R^1$)-2H-pyrazol, and said first pyrazole derivative is obtained in an amount that is greater than the amount of said second pyrazole derivative;

said pyrazole derivative is a mixture of a first pyrazole derivative and a second pyrazole derivative, wherein said first pyrazole derivative has the nitrogen-member substitution pattern in the pyrazole framework specified by 1-($R^1$)-1H-pyrazol, said second pyrazole derivative has the nitrogen-member substitution pattern in the pyrazole framework specified by 2-($R^1$)-2H-pyrazol, and said second pyrazole derivative is obtained in an amount that is greater than the amount of said first pyrazole derivative;

said pyrazole derivative is a mixture of a first pyrazole derivative and a second pyrazole derivative, wherein said first pyrazole derivative is 3-[5-(3,4-dichloro-phenyl)-1-(4-methoxy-phenyl)-1H-pyrazol-3-yl]-2-m-tolyl-propionic acid, said second pyrazole derivative is 3-[5-(3,4-dichloro-phenyl)-2-(4-methoxy-phenyl)-2H-pyrazol-3-yl]-2-m-tolyl-propionic acid, and said first pyrazole derivative is obtained in an amount that is greater than the amount of said second pyrazole derivative;

said pyrazole derivative is a mixture of a first pyrazole derivative and a second pyrazole derivative, wherein said first pyrazole derivative is 3-[5-(3,4-dichloro-phenyl)-1-(4-methoxy-phenyl)-1H-pyrazol-3-yl]-2-m-tolyl-propionic acid, said second pyrazole derivative is 3-[5-(3,4-dichloro-phenyl)-2-(4-methoxy-phenyl)-2H-pyrazol-3-yl]-2-m-tolyl-propionic acid, and said second pyrazole derivative is obtained in an amount that is greater than the amount of said first pyrazole derivative;

the Ar attached carbon is saturated and has the configuration

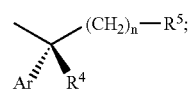

the Ar attached carbon is unsaturated and has the configuration

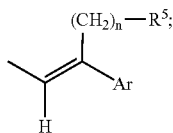

Ar, optionally substituted with $R^r$ as described above, is selected from the group GAr as described above, in more specific embodiments Ar, optionally substituted with $R^r$ as described above, is selected from the group PGAr as described above, and specific Ar are selected from the group SGAr as described above;

there are 0, 1, or 2 $R^r$ substituents;

$R^r$ is selected from the group $GR^r$ as described above, and in more specific embodiments $R^r$ is selected from the group $PGR^r$ as described above;

$R^5$ is selected from the group $GR^5$ as described above, and in more specific embodiments $R^5$ is selected from the group $PGR^5$ as described above;

$R^4$ is selected from the group consisting of —H, —F and —$CH_3$, and in more specific embodiments $R^4$ is H;

n is 0 or 1;

$R^1$, optionally substituted with $R^p$ as described above, is selected from the group $GR^1$ as described above, in more specific embodiments $R^1$, optionally substituted with $R^p$ as described above, is selected from the group $PGR^1$ as described above, and in even more specific embodiments $R^1$ is selected from the group $SGR^1$ as described above;

$R^p$ is selected from the group $GR^p$ as described above, and in more specific embodiments $R^p$ is selected from the group $PGR^p$ as described above;

$R^2$, optionally substituted with $R^q$ as described above, is selected from the group $GR^2$ as described above, in more specific embodiments $R^2$, optionally substituted with $R^q$ as described above, is selected from the group $PGR^2$ as described above, and in even more specific embodiments $R^2$ is selected from the group $SGR^2$ as described above;

$R^q$ is selected from the group $GR^q$ as described above, and in more specific embodiments $R^q$ is selected from the group $PGR^q$ as described above;

there are 0, 1, or 2 $R^q$ substituents;

$R^3$ is selected from the group consisting of —H, —F, Cl, Br and —$CH_3$, and in more specific embodiments $R^3$ is H;

the compound of formula (I) is (S)-3-[5-(3,4-dichloro-phenyl)-1-(4-methoxy-phenyl)-1H-pyrazol-3-yl]-2-m-tolyl-propionic acid;

the compound of formula (I) is (S)-sodium 3-[5-(3,4-dichloro-phenyl)-1-(4-methoxy-phenyl)-1H-pyrazol-3-yl]-2-m-tolyl-propionate.

The assignments $R^3$=H and n=1 in the structures displayed in Schemes P-S are used as illustrations and they are not meant as limitations of the processes illustrated in Schemes P-S. As indicated above, it is understood that the teachings provided herein can be used together to apply the processes illustrated in Schemes P-S to the general range of assignments for $R^3$ and n as defined herein. Accordingly to this description, P7 is one embodiment of P7' and P8 is an embodiment of P8', wherein P7' and P8' are also within the scope of the present invention, and they are represented by the following structures:

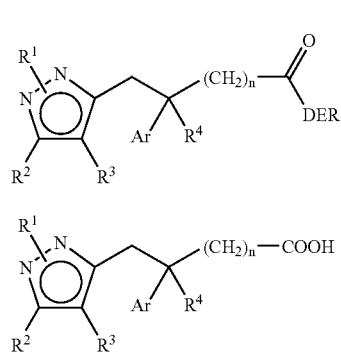

Furthermore, Q3 is one embodiment of Q3', Q8 is one embodiment of Q8' (with the same structural representation as P8'), and S8 is an embodiment of S8' (with the same structural representation as P8'), wherein Q3', Q8' and S8' are also within the scope of the present invention, and they are represented by the following structures (structures for Q8' and S8' not given because they have the same structural representation as P8'):

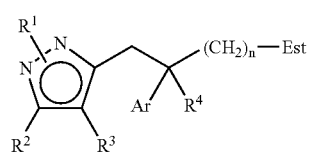

In addition, R5 is an embodiment of R5', R6 is an embodiment of R6', and R8 is an embodiment of R8', wherein R5', R6', and R8' are also within the scope of the present invention, and they are represented by the following structures:

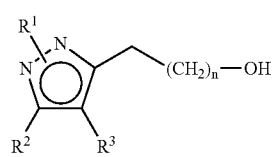

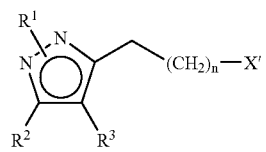

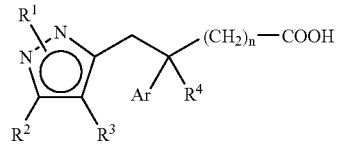

Choice of the more suitable of the Schemes disclosed herein, or of any combination thereof, can be made in light of the teachings provided herein and the form of the desired final product (I). For example, embodiments of Scheme P are preferred for a compound with Ar and H substituents at the stereogenic center, such as the title compound in Example 4.

As an additional illustration, embodiments of Scheme Q are more suitable for compounds with Ar and another substituent other than H at the stereogenic center, such as the title compound in Example 76.

Processes according to the present invention include embodiments in which the regioselective and/or the stereoselective constraints are removed. For example, regioselective reactions involving an inorganic base, a substituted hydrazine, and an acetylenic ketone in a reaction medium that are referred to above as involving a chiral acetylenic ketone to form a chiral pyrazole derivative can also be performed in some embodiments with an acetylenic ketone that has no chirality to form a pyrazole derivative that has no chirality. For example, the title compound in Example 75 illustrates an embodiment of compound (I) in which chirality concerning a single sterogenic center is not relevant because it has no single stereogenic center. Furthermore, when a final chiral compound is desired with no regioselectivity concerns, stereoselective synthetic steps taught herein can be combined with non- or low-regioselective synthetic steps, also taught herein.

During any of the processes for preparation of the compounds of the present invention, it may be necessary and/or desirable to protect sensitive or reactive groups on any of the molecules concerned. In addition, compounds of the invention may be modified by using protecting groups; such compounds, precursors, or prodrugs are also within the scope of the invention. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", $3^{rd}$ ed., John Wiley & Sons, 1999. The protecting groups may be removed at a convenient subsequent stage using methods known from the art.

Hydroxyl Protecting Groups

Protection for the hydroxyl group includes methyl ethers, substituted methyl ethers, substituted ethyl ethers, substituted benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(Imidazol-1-ylmethyl)bis(4',4''-dimethoxyphenyl)methyl, 1,1-bis(4-methoxyphenyl)-1'-pyrenylmethyl, 9-anthryl, 9-(9-phenyl)xanthenyl, 9,9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate).

Carbonates

Examples of carbonates include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethylbenzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate(tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate.

Sulfonates

Examples of sulfonates include sulfate, methanesulfonate (mesylate), benzylsulfonate, and tosylate.

Protection for 1,2- and 1,3-Diols

Cyclic Acetals and Ketals

Examples of cyclic acetals and ketals include methylene, ethylidene, 1-t-butylethylidene, 1-phenylethylidene, (4-methoxyphenyl)ethylidene, 2,2,2-trichloroethylidene, acetonide (isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Examples of cyclic ortho esters include methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino)benzylidene derivative, and 2-oxacyclopentylidene.

Silyl Derivatives

Examples of silyl derivatives include di-t-butylsilylene group, and 1,3-(1,1,3,3-tetraisopropyldisiloxanylidene) derivative.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of amides include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special —NH Protective Groups

Examples of special NH protective groups include:

N-Alkyl and N-Aryl Amines

N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-4-methoxybenzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl)mesityl]methylene, and N-(N',N'-dimethylaminomethylene).

Protection for the Carbonyl Group

Acyclic Acetals and Ketals

Examples of acyclic acetals and ketals include dimethyl, bis(2,2,2-trichloroethyl), dibenzyl, bis(2-nitrobenzyl) and diacetyl.

Cyclic Acetals and Ketals

Examples of cyclic acetals and ketals include 1,3-dioxanes, 5-methylene-1,3-dioxane, 5,5-dibromo-1,3-dioxane, 5-(2-pyridyl)-1,3-dioxane, 1,3-dioxolanes, 4-bromomethyl-1,3-dioxolane, 4-(3-butenyl)-1,3-dioxolane, 4-phenyl-1,3-dioxolane, 4i2-nitrophenyl)-1,3-dioxolane, 4,5-dimethoxymethyl-1,3-dioxolane, O,O-phenylenedioxy and 1,5-dihydro-3H-2,4-benzodioxepin.

Acyclic Dithio Acetals and Ketals

Examples of acyclic dithio acetals and ketals include S,S'-dimethyl, S,S'-diethyl, S,S'-dipropyl, S,S'-dibutyl, S,S'-dipentyl, S,S'-diphenyl, S,S'-dibenzyl and S,S'-diacetyl.

Cyclic Dithio Acetals and Ketals

Examples of cyclic dithio acetals and ketals include 1,3-dithiane, 1,3-dithiolane and 1,5-dihydro-3H-2,4-benzodithiepin.

Acyclic Monothio Acetals and Ketals

Examples of acyclic monothio acetals and ketals include O-trimethylsilyl-S-alkyl, O-methyl-S-alkyl or -S-phenyl and O-methyl-S-2-(methylthio)ethyl.

Cyclic Monothio Acetals and Ketals

Examples of cyclic monothio acetals and ketals include 1,3-oxathiolanes.

Miscellaneous Derivatives

O-Substituted Cyanohydrins

Examples of O-substituted cyanohydrins include O-acetyl, O-trimethylsilyl, O-1-ethoxyethyl and O-tetrahydropyranyl.

Substituted Hydrazones

Examples of substituted hydrazones include N,N-dimethyl and 2,4-dinitrophenyl.

Oxime Derivatives

Examples of oxime derivatives include O-methyl, O-benzyl and O-phenylthiomethyl.

Imines

Substituted Methylene Derivatives, Cyclic Derivatives

Examples of substituted methylene and cyclic derivatives include oxazolidines, 1-methyl-2-(1'-hydroxyalkyl)imidazoles, N,N'-dimethylimidazolidines, 2,3-dihydro-1,3-benzothiazoles, diethylamine adducts, and methylaluminum bis (2,6-di-t-butyl-4-methylphenoxide)(MAD)complex.

Monoprotection of Dicarbonyl Compounds

Selective Protection of α-and β-Diketones

Examples of selective protection of α- and β-diketones include enamines, enol acetates, enol ethers, methyl, ethyl, i-butyl, piperidinyl, morpholinyl, 4-methyl-1,3-dioxolanyl, pyrrolidinyl, benzyl, S-butyl, and trimethylsilyl.

Cyclic Ketals, Monothio and Dithio Ketals

Examples of cyclic ketals, monothio and dithio ketals include bismethylenedioxy derivatives and tetramethylbismethylenedioxy derivatives.

Protection for the Carboxyl Group

Esters

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt(III) complex.

Stannyl Esters

Examples of stannyl esters include triethylstannyl and tri-n-butylstannyl.

Amides and Hydrazides

Amides

Examples of amides include N,N-dimethyl, pyrrolidinyl, piperidinyl, 5,6-dihydrophenanthridinyl, o-nitroanilides, N-7-nitroindolyl, N-8-Nitro-1,2,3,4-tetrahydroquinolyl, and p-P-benzenesulfonamides.

Hydrazides

Examples of hydrazides include N-phenyl and N,N'-diisopropyl.

Compounds of the present invention may be used in pharmaceutical compositions to treat patients (humans and other mammals) with disorders involving the action of the CCK-1 receptor. As CCK-1 receptor modulators the compounds may be divided into compounds, which are pure or partial agonists and compounds that are antagonists. Where the compound is a CCK-1 receptor antagonist, it may be used in the treatment of pain, drug dependence, anxiety, panic attack, schizophrenia, pancreatic disorder, secretory disorder, motility disorders, functional bowel disease, biliary colic, anorexia and cancer. Where the compound is a CCK-1 receptor agonist, it may be used in the treatment of obesity, hypervigilance and gallstones.

The preferred route is oral administration, however compounds maybe administered by intravenous infusion or topical administration. Oral doses range from about 0.05 to 100 mg/kg, daily, taken in 1-4 separate doses. Some compounds of the invention may be orally dosed in the range of about 0.05 to about 50 mg/kg daily, while others may be dosed at 0.05 to about 20 mg/kg daily. Infusion doses can range from about 1.0 to $1.0 \times 10^4$ µg/kg/min of inhibitor, admixed with a pharmaceutical carrier over a period ranging from several minutes to several days. For topical administration compounds of the present invention I may be mixed with a pharmaceutical carrier at a concentration of about 0.1 to about 10% of drug to vehicle.

The pharmaceutical compositions can be prepared using conventional pharmaceutical excipients and compounding techniques. Oral dosage forms may be elixers, syrups, capsules tablets and the like. Where the typical solid carrier is an inert substance such as lactose, starch, glucose, methylcellulose, magnesium sterate, dicalcium phosphate, mannitol and the like; and typical liquid oral excipients include ethanol, glycerol, water and the like. All excipients may be mixed as needed with disintegrants, diluents, granulating agents, lubricants, binders and the like using conventional techniques known to those skilled in the art of preparing dosage forms. Parenteral dosage forms may be prepared using water or another sterile carrier.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions.

EXAMPLES

NMR spectra were obtained on either a Bruker model DPX400 (400 MHz) or DPX500 (500 MHz) spectrometer. The format of the $^1$H NMR data below is: chemical shift in ppm down field of the tetramethylsilane reference (multiplicity, coupling constant J in Hz, integration).

Mass spectra were obtained on an Agilent series 1100 MSD using electrospray ionization (ESI) in either positive or negative mode as indicated. The "mass calculated" for a molecular formula is the monoisotopic mass of the compound.

Protocol for Reversed-Phase HPLC (Method A):
Manufactured by Agilent HPLC 1100;
Column: Zorbax Eclipse XDB-C8, 5 μm, 4.6×150 mm;
Flow rate: 0.75 mL/min; λ=220 & 254 nm;
Gradient (Acetonitrile/Water):
1) 0.0 min 1% Acetonitrile
2) 8.0 min 99% Acetonitrile
3) 12.0 min 99% Acetonitrile Protocol for Reversed-Phase HPLC (Method B):
Manufactured by Agilent HPLC 1100;
Column: Xterra™, RP18, 3.5 μm, 4.6×50 mm;
Flow rate: 1.5 mL/min; λ=220 & 254 nm;
Gradient (Acetonitrile/Water):
1) 0.0 min 85% Acetonitrile
2) 3.5 min 1.0% Acetonitrile
3) 5 min 1.0% AcetonitrHe Protocol for Chiral HPLC (Method C):
Manufactured by Agilent HPLC 1100;
Chiral Column: Chiralpak AD, 4.6×250 mm;
Column Manufacturer: Chiral Technologies Inc.;
Mobile Phase: 85:15 Ethanol/Hexane with 0.1% TFA;
Flow Rate: 0.75 mL/min; λ=220 & 254 nm Protocol for Semi-Preparation. Chiral HPLC (Method D):
Manufactured by Agilent HPLC 1100;
Chiral Column: Chiralpak AD, 20×250 mm;
Column Manufacturer: Chiral Technologies Inc.;
Mobile Phase: 85:15 Ethanol/Hexane with 0.1% TFA;
Flow Rate: 7 mL/min; λ=220 & 254 nm Reversed-Phase HPLC (Method E):
Column: Zorbax Eclipse XDB-C8, 5 μm, 4.6×150 mm;
Flow rate: 0.75 mL/min; λ=220 & 254 nm;
Gradient (Acetonitrile/Water):
1) 8.0 min 1%-99% Acetonitrile
2) 10.0 min 99% Acetonitrile Chiral HPLC (Method F):
Column: Chiralcel AD 0.46×25 cm;
Mobile Phase: 85:15 Ethanol/Hexane with 0.07% TFA;
Flow rate: 1 mL/min; λ=220 & 254 nm Reversed-Phase HPLC (Method G):
Column: XTerra Prep MS C18, 5 μm, 19×50 mm;
Mobile Phase: Acetonitrile/Water with 0.1% TFA;
Flow rate: 25 mL/min; λ=220 & 254 nm;
Gradient:
1) 0.0 min 15% Acetonitrile
2) 13.0 min 99% Acetonitrile
3) 15.0 min 99% Acetonitrile Protocol for Reversed-Phase HPLC (Method H):
Manufactured by Agilent HPLC 1100;
Column: Chromolith SpeedROD, 4.6×50 mm;
Mobile Phase: Acetonitrile/Water with 0.1% TFA;
Flow rate: 5 mL/min; λ=220 & 254 nm;
Gradient (Acetonitrile/Water):
1) 0.0 min 85% Acetonitrile
2) 2.0 min 1.0% Acetonitrile
3) 2.5 min 1.0% Acetonitrile Protocol for Reversed-Phase HPLC (Method I):
Manufactured by Agilent HPLC 1100;
Column: Xterra™, RP18, 3.5 μm, 4.6×50 mm;
Mobile Phase: Acetonitrile/Water with 10 mM NH$_4$OH;
Flow rate: 1 mL/min; λ=220 & 254 nm;
Gradient (Acetonitrile/Water):
1) 0.0 min 1% Acetonitrile
2) 7.0 min 99% Acetonitrile
3) 10.0 min 99% Acetonitrile HPLC Method J; (Chiral)
Chiralcel AD 0.46 cm×25 cm column
Flow rate: 1 mL/min; λ=220 nm & 254 nm
Solvent: 60/40 EtOH/Hexane
Gradient conditions: Isocratic Reported retention times (R$_t$) are in minutes.

Example 1

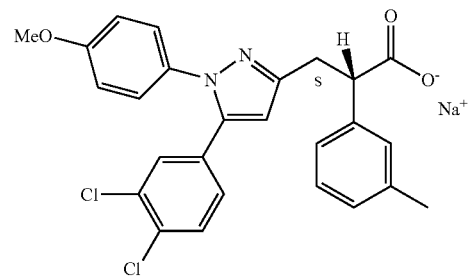

(S)-Sodium; 3-[5-(3,4-dichloro-phenyl)-1-(4-methoxy-phenyl)-1H-pyrazol-3-yl]-2-m-tolyl-propionate

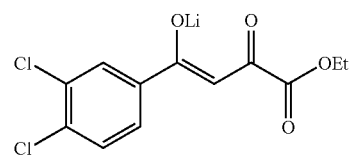

A. Lithium 4-(3,4-dichlorophenyl)-4-hydroxy-2-oxo-but-3-enoic acid ethyl ester

In a dried 1-L round-bottomed flask, lithium bis(trimethylsilyl)amide in tetrahydrofuran (THF) (265 mL, 0.265 mol) was concentrated under reduced pressure to a solid using a rotary evaporator at 25-30° C. Anhydrous diethyl ether (200 mL) was added and this stirred suspension of LHMDS in diethyl ether was cooled to −78° C. under N$_2$. 3,4-Dichloracetophenone (50.0 g, 0.265 mol) in diethyl ether (200 mL) was slowly added to the reaction mixture over 15 min. The mixture was allowed to stir for 60 min, and diethyl oxalate (36.0 mL, 0.265 mol) in diethyl ether (75 mL) was then added over 20 min. After 90 min, the mixture was allowed to warm to room temperature (rt) and stirred overnight. The light yellow solids were filtered, washed with diethyl ether and dried in vacuum to afford 78.4 g of lithium 4-(3,4-dichlorophenyl)-4-hydroxy-2-oxo-but-3-enoic acid ethyl ester as a white solid. This material was used in the next step without further purification.

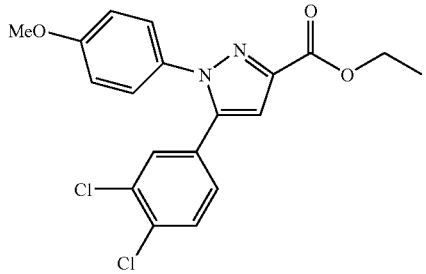

B. 5-(3,4-Dichloro-phenyl)-1-(4-methoxy-phenyl)-1H-pyrazole-3-carboxylic acid ethyl ester.

A stirred suspension of lithium 4-(3,4-dichlorophenyl)-4-hydroxy-2-oxo-but-3-enoic acid ethyl ester (90.7 g, 0.307 mol) and 4-methoxyphenyl hydrazine hydrochloride (54.0 g, 0.309 mol) in EtOH (600 mL) was heated to 55° C. for 5 h then stirred at rt overnight. HPLC analysis showed a 4:1 mixture of 5-(3,4-dichloro-phenyl)-1-(4-methoxy-phenyl)-1H-pyrazole-3-carboxylic acid ethyl ester and 5-(3,4-dichloro-phenyl)-2-(4-methoxy-phenyl)-2H-pyrazole-3-carboxylic acid ethyl ester. The precipitated solids were filtered and washed with EtOH. The solids were recrystallized with 1:1 CH$_3$CN/MeOH to recover 9.0 g of minor product 5-(3,4-dichloro-phenyl)-2-(4-methoxy-phenyl)-2H-pyrazole-3-carboxylic acid ethyl ester. Crystallization was repeated several times to recover 71.0 9 of major product 5-(3,4-dichloro-phenyl)-1-(4-methoxy-phenyl)-1H-pyrazole-3-carboxylic acid ethyl ester. The crude filtrate was purified by column chromatography (silica gel, 4:1 hexane/ethyl acetate (EtOAc)) to recover another 17.6 g of 5-(3,4-dichloro-phenyl)-1-(4-methoxy-phenyl)-1H-pyrazole-3-carboxylic acid ethyl ester for a total combined yield of 74%. HPLC: R$_t$=10.57 (Method E). MS (ES+): mass calculated for C$_{19}$H$_{16}$Cl$_2$N$_2$O$_3$, 391.25; m/z found 392.3 [M+H]$^+$. $^1$H NMR (400 MHz, CDCl$_3$): 7.37 (d, J=2.0 Hz,1H), 7.35 (d, J=8.4 Hz, 1H), 7.26-7.22 (m, 2H), 7.04 (s, 1H), 6.97 (dd, J=8.0, 1.0 Hz, 1H), 6.95-6.88 (m, 2H), 4.45 (q, J=7.1 Hz, 2H), 3.84 (s, 3H), 1.42 (q, J=7.1 Hz, 3H).

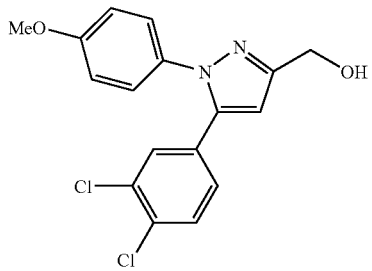

C. [5-(3,4-Dichlorophenyl)-1-(4-methoxyphenyl)-1H-pyrazol-3-yl]-methanol

To a stirred solution of 5-(3,4-dichloro-phenyl)-1-(4-methoxy-phenyl)-1H-pyrazole-3-carboxylic acid ethyl ester (55.7 g, 0.140 mol) in THF (150 mL) at −78° C. under N$_2$ was slowly added a 1.0 M solution of diisobutylaluminum hydride (DIBAL-H) (350 mL, 0.35 mol) over 45 min. The solution was allowed to stir for 20 min then warmed to rt over 90 min. The mixture was then cooled to 0° C., and a saturated solution of potassium sodium tartrate (300 mL) and EtOAc (400 mL) was added. The slurry mixture was stirred overnight whereupon both layers became clear. The organic layer was extracted with EtOAc (2×75 mL), dried with Na$_2$SO$_4$, filtered and concentrated. The crude product was dried under vacuum to recover 46.8 g (96%) of the title compound. This was used in the next step without further purification. HPLC: R$_t$=9.16 (Method E). MS (ES+): mass calculated for C$_{17}$H$_{14}$Cl$_2$N$_2$O$_2$, 349.21; m/z found 371.1 [M+Na]$^+$. $^1$H NMR (400 MHz, CDCl$_3$): 7.39 (d, J=2.1 Hz, 1H), 7.34 (d, J=3.6 Hz, 1H), 7.20-7.09 (m, 2H), 6.97 (dd, J=8.36, 2.1 Hz,1H), 6.91-6.79 (m, 2H), 6.43 (s, 1H), 4.69 (s, 2H), 3.74 (s, 3H).

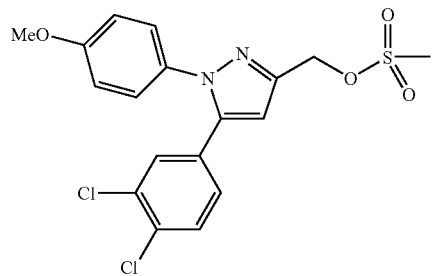

D. Methanesulfonic acid 5-(3,4-dichlorophenyl)-1-(4-methoxyphenyl)-1H-pyrazol-3-ylmethyl ester To a stirred solution of [5-(3,4-dichlorophenyl)-1-(4-methoxyphenyl)-1H-pyrazol-3-yl]-methanol (7.2 g, 0.021 mol) in THF (125 mL) and triethylamine (TEA) (4.6 mL, 0.033 mol) was added methanesulfonyl chloride (2.5 mL, 0.031 mol). The reaction mixture was stirred at 45° C. for 4 h. The reaction mixture was cooled to rt, quenched with H$_2$O (75 mL) then washed with EtOAc (3×50 mL). The organic layer was dried over Na$_2$SO$_4$, filtered and concentrated to oil. This crude pyrazole mesylate was used in the next step without further purification. HPLC: R$_t$=10.03 (Method E). MS (ES+): mass calculated for C$_{18}$H$_{18}$Cl$_2$N$_2$O$_4$S, 427.30; m/z found 428.1 [M+H]$^+$.

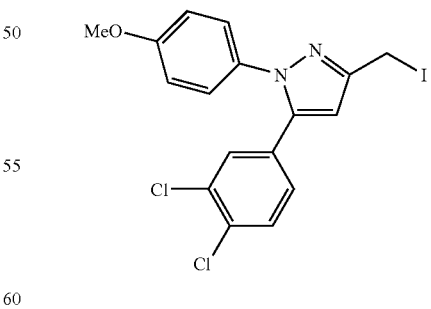

E. 5-(3,4-Dichloro-phenyl)-3-iodomethyl-1-(4-methoxyphenyl)-1H-pyrazole

A stirred solution of methanesulfonic acid 5-(3,4-dichlorophenyl)-1-(4-methoxyphenyl)-1H-pyrazol-3-ylmethyl ester (8.80 g, 0.0206 mol) and NaI (4.64 g, 0.0309 mol) in acetone (175 mL) was refluxed for 90 min. The thick reaction slurry was cooled to rt, quenched with H$_2$O (200 mL) and extracted with EtOAc (3×75 mL). The organic layer was dried with Na$_2$SO$_4$, filtered and concentrated to a dark oil. The crude oil was purified by column chromatography (silica gel, 85:15 hexane/EtOAc) to obtain 9.15 g (97%) of the title compound after two steps. HPLC: R$_t$=11.03 (Method E). MS (ES+): mass calculated for C$_{17}$H$_{13}$Cl$_2$IN$_2$O, 459.10; m/z found 460.9 [M+H]$^+$. $^1$H NMR (400 MHz, CDCl$_3$): 7.37 (d, J=2.0 Hz, 1H), 7.34 (d, J=8.3 Hz, 1H), 7.18 (d, J=8.8 Hz, 2H), 6.95 (dd, J=6.3, 2.0 Hz, 1H), 6.88 (d, J=9.1 Hz, 2H), 6.55 (s, 1H), 4.47 (s, 2H), 3.83 (s, 3H).

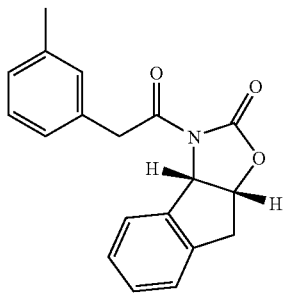

F. (3aS,8aR)-3-(2-m-Tolyl-acetyl)-3,3a,8,8a-tetrahydro-indeno[1,2-d]oxazol-2-one To a stirred solution of m-tolylacetic acid (8.57 g, 0.0571 mol), 2-chloro-1-methylpyridinium iodide (19.0 g, 0.0744 mol) and (3aS-cis)-(–)-3,3a,8,8a-tetrahydro-2H-indeno[1,2-d]-oxazol-2-one (10.0 g, 0.0571 mol) in CH$_2$Cl$_2$ (130 mL) were added TEA (18.0 mL, 0.129 mol) and 4-dimethylaminopyridine (DMAP, 1.39 g, 0.0114 mol) at 0° C. The reaction mixture was stirred at rt for 3 h then treated with hexane (130 mL). The resulting slurry was passed through a pad of silica gel, eluting with 3:2 EtOAc/hexane. The filtrate was concentrated to an oil and recrystallized in hot hexane to recover 13 g (74%) of the title compound as a white solid. HPLC: R$_t$=9.85 (Method E). MS (ES+): mass calculated for C$_{19}$H$_{17}$NO$_3$, 307.36; m/z found 330.2 [M+Na]$^+$. $^1$H NMR (400 MHz, CDCl$_3$): 7.65 (d, J=7.6 Hz, 1H), 7.08-7.37 (m, 7H), 5.95 (d, J=6.8 Hz, 1H), 5.27-5.31 (m, 1H), 4.26 (dd, J=15.9, 39.1 Hz, 2H), 3.40 (d, J=3.5 Hz, 2H), 2.34 (s, 3H).

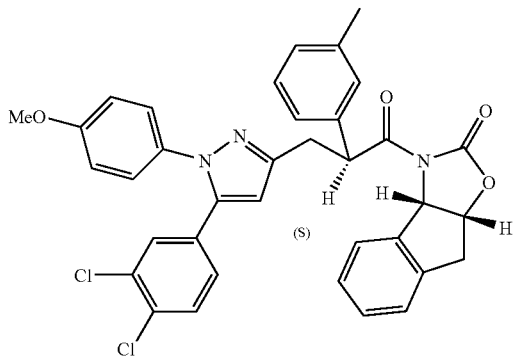

G. (2S,3aS,8aR)-3-{3-[5-(3,4-Dichlorophenyl)-1-(4-methoxyphenyl)-1H-pyrazol-3-yl]-2-m-tolyl-propionyl}-3,3a,8,8a-tetrahydro-indeno[1,2-d]oxazol-2-one To a stirred solution of (3aS,8aR)-3-(2-m-tolyl-acetyl)-3, 3a,8,8a-tetrahydro-indeno[1,2-d]oxazol-2-one (product of Step F., 12 g, 0.039 mol) in THF (100 mL) was added 1.0 M sodium 1,1,1,3,3,3-hexamethyldisilazane (NaHMDS) (41 mL, 0.041 mol) in THF at –78° C. The mixture was stirred for 45 min at –78° C. then treated with 5-(3,4-dichloro-phenyl)-3-iodomethyl-1-(4-methoxy-phenyl)-1l-H-pyrazole (product of Step E., 18.4 g, 0.0405 mol) in THF (100 mL). The reaction mixture was allowed to warm to rt overnight and then was quenched with H$_2$O (100 mL) and concentrated to half the volume. The aqueous layer was washed with EtOAc (3×75 mL). The extracted organic layer was washed with saturated NaCl, dried over Na$_2$SO$_4$, filtered and concentrated to an oil. The crude oil was purified by flash column chromatography (silica gel, 7:3 hexane/EtOAc) to obtain 20.7 g of the title compound (83%) as white foam. HPLC: R$_t$=11.38 (Method E). MS (ES+): mass calculated for C$_{36}$H$_{29}$Cl$_2$N$_3$O$_4$, 638.55; m/z found 660.3 [M+Na]$^+$. $^1$H NMR (400 MHz, CDCl$_3$): 7.52 (d, J=7.6 Hz, 1H), 7.11-7.35 (m, 8H), 6.93-6.99 (m, 3H), 6.74-6.82 (m, 3H), 6.20 (s, 1H), 5.89 (d, J=6.8 Hz, 1H), 5.58 (q, J=6.1, 4.5 Hz, 1H), 5.11-5.15 (m, 1H), 3.8 (s, 3H), 3.72 (dd, J=10.6, 4.1 Hz, 1H), 3.33 (br, s, 2H), 3.07 (dd, J=9.8, 4.8 Hz, 1H), 2.37 (s, 3H).

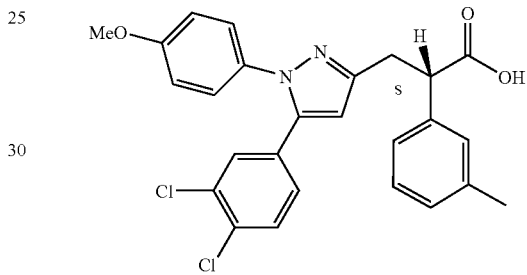

H. (S)-3-[5-(3,4-Dichloro-phenyl)-1-(4-methoxyphenyl)-1H-pyrazol-3-yl]-2-m-tolyl-propionic acid To a stirred solution of (2S,3aS,8aR)-3-{3-[5-(3,4-dichlorophenyl)-1-(4-methoxyphenyl)-1H-pyrazol-3-yl]-2-m-tolyl-propionyl}-3,3a,8,8a-tetrahydro-indeno[1,2-d]oxazol-2-one (20.7 g, 0.0323 mol) in THF (230 mL) and H$_2$O (45 mL) at 0° C. was added 30% H$_2$O$_2$ (15.0 mL, 0.147 mol) followed by LiOH hydrate (2.75 g, 0.0655 mol) in H$_2$O (15 mL). The reaction mixture was allowed to warm to rt and was stirred for 90 min. The mixture was cooled to 0° C. and then quenched with 1.5 N Na$_2$SO$_3$ (20 mL) maintaining pH 9-10. The mixture was concentrated to ¼ volume, then treated with H$_2$O (200 mL) and acidified to pH 1-2 using 3 N HCl. The aqueous layer was washed with EtOAc (3×100 mL). The combined organic layers were dried with Na$_2$SO$_4$, filtered and concentrated to ¼ volume. Solid crystals that developed overnight were filtered and washed with cold 1:1 hexane/EtOAc. The chiral auxiliary was recovered in 66% yield (3.72 g). The filtrate was purified by flash chromatography (7:3 hexane/EtOAc with 0.3% MeOH) to afford 12.7 g (81.5%) of (S)-3-[5-(3,4-dichloro-phenyl)-1-(4-methoxy-phenyl)-1H-pyrazol-3-yl]-2-m-tolyl-propionic acid as orange oil. HPLC: R$_t$=10.44 (Method E). MS (ES+): mass calculated for C$_{26}$H$_{22}$Cl$_2$N$_3$, 481.37; m/z found 503.2 [M+Na]$^+$. $^1$H NMR (400 MHz, CDCl$_3$): 7.12-7.31 (m, 9H), 6.90 (dd, J=6.3, 2.0 Hz, 1H), 6.86 (d, J=9.1 Hz, 2H), 6.21 (s, 1H), 4.07-4.15 (m, 1H), 3.82 (s, 3H), 3.53 (dd, J=9.3, 5.3 Hz, 1H), 3.10 (dd, J=9.1, 5.8 Hz, 1H), 2.35 (s, 3H).

I. (S)-Sodium; 3-[5-(3,4-dichloro-phenyl)-1-(4-methoxy-phenyl)-1H-pyrazol-3-yl]-2-m-tolyl-propionate To a stirred solution of (S)-3-[5-(3,4-dichloro-phenyl)-1-(4-methoxy-phenyl)-1H-pyrazol-3-yl]-2-m-tolyl-propionic acid (12.7 g, 0.0264 mol) in THF (125 mL) was added aqueous NaOH (1.05 g, 0.0264 mol in H$_2$O, 10 mL) at 0° C. The mixture was stirred for 30 min at 0° C. then concentrated to an oil under reduced pressure using a rotary evaporator (25-30 ° C.). The oil was diluted in THF (150 mL), chilled in an ice bath and CH$_3$CN (50 mL) was added whereupon a precipitate developed. The suspension was stirred for 2 h, filtered and then washed with CH$_3$CN to afford 10.9 g (67%) of the title compound as a white solid. HPLC: R$_t$=7.10 (Method F). HRMS: exact mass of [M+H]$^+$ calculated for C$_{26}$H$_{22}$Cl$_2$N$_2$O$_3$, 481.1086; m/z found, 481.1079. M.P. 295.5-297.5 ° C. Anal. Calcd for C$_{25}$H$_{18}$Cl$_2$N$_2$NaO$_3$: C, 61.49; H, 3.72; N, 5.74 Found: C, 61.98; H, 4.14; N, 5.43. Optical rotation [α]$^{20}_{589}$+58.8° (c=0.1, EtOH). $^1$H NMR (400 MHz, D$_2$O); 6.90-6.93 (m, 2H), 6.77 (t, J=7.3 Hz, 1H), 6.61 (d, J=9.1 Hz, 2H), 6.53 (d, J=7.3 Hz, 1H), 6.38 (t, J=8.6 Hz, 4H), 6.12 (d, J=8.1 Hz, 1H), 5.46 (s, 1H), 3.55-3.63 (m, 1H), 3.22 (s, 3H), 3.06-3.18 (m, 2H), 1.81 (s, 3H). $^{13}$C NMR (100 MHz. DMSO-d$_6$): 175.3, 157.9, 152.5, 143.6, 139.2, 135.7, 132.1, 130.7, 130.5, 130.1, 130.0, 129.2, 128.0, 127.7, 126.9, 126.1, 125.4, 124.5, 113.7, 107.0,.54.9, 54.5, 32.6, 20.6 ppm.

Method 1

Synthesis of 3-Bromomethyl-1,5-diaryl-1H-pyrazoles (Pyrazole Bromides)

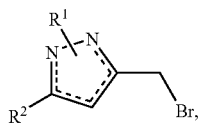

such as:

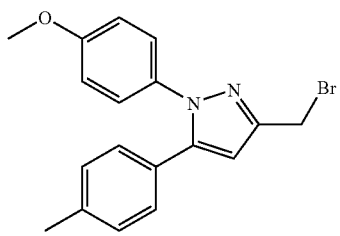

3-Bromomethyl-1-(4-methoxyphenyl)-5-p-tolyl-1H-pyrazole

A solution of phosphorus tribromide (9.31 g, 34.5 mmol) in CH$_2$Cl$_2$ (186 mL) was added drop-wise to a stirred solution of [1-(4-methoxy-phenyl)-5-p-tolyl-1H-pyrazol-3-yl]-methanol (7.80 g, 26.5 mmol; prepared analogously to the procedure described in Step C of Example 1) in 50 mL CH$_2$Cl$_2$ at 0° C. The reaction mixture was stirred for an additional 18 h at rt, and then the mixture was neutralized by addition of 40% NaOH with cooling in an ice bath. The organic layer was separated and dried over Na$_2$SO$_4$, and solvent was removed under reduced pressure. The residue was purified by silica gel chromatography (CH$_2$Cl$_2$) yielding 8.09 g (86%) of 3-bromomethyl-1-(4-methoxy-phenyl)-5-p-tolyl-1H-pyrazole. HPLC: R$_t$=10.38. (Method A). MS (ES+): mass calculated for C$_{18}$H$_{17}$BrN$_2$O, 356.05; m/z found 357.5 [M+H]$^+$. $^1$H NMR (400 MHz, CDCl$_3$): 7.42 (s, 4H), 7.39-7.34 (m, 2H), 7.02-6.98 (m, 2H), 6.69 (s, 2H), 4.73 (s, 2H), 3.97 (s, 1H), 2.49 (s, 3H).

Method 2

General Method for the Synthesis of 3-(1,5-Diaryl-1H-pyrazol-3-yl)-2-aryl-propionic Acids (A9)

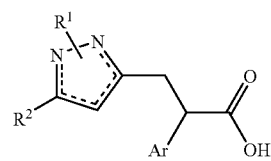

Scheme A. In each of eight 10-mL test tubes, 60% NaH in mineral oil (18 mg, 0.45 mmol) was suspended in 5 mL of N,N-dimethylformamide (DMF) at 0° C. under N$_2$. Then, to each test tube, a unique phenyl-acetic acid ester (A10) was added, and the reaction mixtures were stirred for 1 h. Equal portions of the first such mixture were then loaded into the six wells of the first row of a 48-well Robbins block under N$_2$, and equal portions of the next mixture were loaded into the six wells of the second row, and so on, until all eight reaction mixtures had been apportioned, and all forty-eight wells had been loaded. Then, 0.15 mmol of one of six different pyrazole bromides (A7, prepared analogously to the procedure described in Method 1) in 0.5 mL DMF was loaded into each of eight wells of the first of six orthogonal columns of the block, and 0.15 mmol of a second pyrazole bromide in 0.5 mL DMF was loaded into each of eight wells of the second column of the block, and so on, yielding a matrix of forty-eight unique reaction mixtures. After the block was shaken for 18 h at rt, 0.3 mL of 2 M aqueous LiOH was added to each well, and the block was shaken an additional 18 h at rt. The solutions were drained into the 48 wells of a Beckman microtiter collection plate, and the solvent was removed under reduced pressure. Each residue was dissolved in 1.5 mL of DMF and purified on a Gilson 215 prep-HPLC system (Method G; recoveries of 12-34 mg for the products, 16-44% yield, isolated as TFA salts).

Example 2

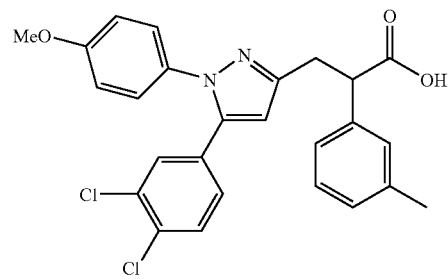

3-[5-(3,4-Dichloro-phenyl)-1-(4-methoxy-phenyl)-1H-pyrazol-3-yl]-2-m-tolyl-propionic acid The title compound was prepared by Method 2: HPLC: $R_t$=10.46 (Method A), $R_f$=4.81, 7.95 (Method C). MS (ES+): mass calculated for $C_{26}H_{22}Cl_2N_2O_3$, 480.10; m/z found 481.1 [M+H]+. 1H NMR (400 MHz, CDCl3): 7.31-7.28 (m, 2H), 7.22 (d, J=7.6 Hz, 1H), 7.21-7.18 (m, 2H), 7.14-7.08 (m, 3H), 6.89 (dd, J=5.3, 2.0 Hz, 1H), 6.85 (d, J=8.5 Hz, 2H), 6.22 (s, 1H), 4.13-4.07 (m, 1H), 3.82 (s, 3H), 3.52 (dd, J=14.4, 9.1, Hz, 1H), 3.12 (dd, J=10.1, 5.3 Hz, 1H), 2.01 (s, 3H).

Example 3

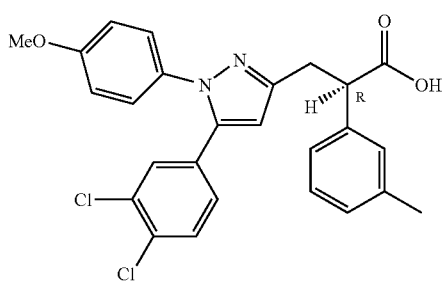

(R)-3-[5-(3,4-Dichloro-phenyl)-1-(4-methoxy-phenyl)-1H-pyrazol-3-yl]-2-m-tolyl-propionic acid The racemate (Example 2) was prepared by Method 2, and the title compound was separated by semi-preparative HPLC (Method D). HPLC: $R_t$=10.44 (Method A), $R_f$=4.81 (Method C). MS (ES+): mass calculated for $C_{26}H_{22}Cl_2N_2O_3$, 480.10; m/z found 481.1 [M+H]+. Optical rotation $[\alpha]^{20}_{589}$ −91.0 (c=0.1, EtOH). 1H NMR (400 MHz, CDCl3): 7.31 (t, J=2.2 1H), 7.29 (s, 1H), 7.22 (d, J=7.4 Hz, 1H), 7.20-7.16 (m, 2H), 7.16-7.09 (m, 3H), 6.89 (dd, J=8.4, 2.1 Hz, 1H), 6.87-6.84 (m, 2H), 6.22 (s, 1H), 4.10 (dd, J=9.2, 6.1 Hz, 1H), 3.83 (s, 3H), 3.51 (dd, J=15.0, 9.7 Hz, 1H), 3.11 (dd, J=15.2, 5.2 Hz, 1H), 2.34 (s, 3H).

Example 4

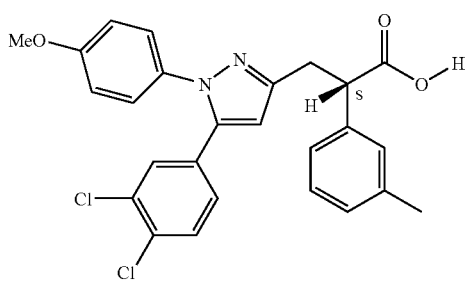

(S)-3-[5-(3,4-dichloro-phenyl)-1-(4-methoxy-phenyl)-1H-pyrazol-3-yl]-2-m-tolyl-propionic acid The racemate (Example 2) was prepared by Method 2, and the title compound was separated by semi-preparative HPLC (Method D). HPLC: $R_t$=10.44 (Method A), $R_f$=7.95 (Method C). MS (ES+): mass calculated for $C_{26}H_{22}Cl_2N_2O_3$, 480.10; m/z found 481.1 [M+H]+. 1H NMR (400 MHz, CDCl3): 7.31 (t, J=2.2 1H), 7.29 (s, 1H), 7.22 (d, J=7.4 Hz, 1H), 7.20-7.16 (m, 2H), 7.16-7.09 (m, 3H), 6.89 (dd, J=8.4, 2.1 Hz, 1H), 6.87-6.84 (m, 2H), 6.22 (s, 1H), 4.10 (dd, J=9.2, 6.1 Hz, 1H), 3.83 (s, 3H), 3.51 (dd, J=15.0, 9.7 Hz, 1H), 3.11 (dd, J=15.2, 5.2 Hz, 1H), 2.34 (s, 3H).

Example 5

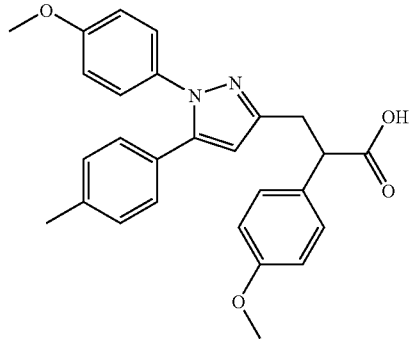

2-(4-Methoxy-phenyl)-3-[-1-(4-methoxyl-phenyl)-5-p-tolyl-1H-pyrazol-3-yl]-propionic acid The title compound was prepared by Method 2: HPLC: $R_t$=9.51 (Method A). MS (ES+): mass calculated for $C_{27}H_{26}N_2O_4$, 442.21; m/z found 443.2 [M+H]+. 1H NMR (400 MHz, CDCl3): 7.30 (d, J=8.5 Hz, 2H), 7.14 (d, J=8.5 Hz, 2H), 7.07-7.04 (m, 4H), 6.86 (d, J=8.5 Hz, 2H), 6.81 (d, J=8.5 Hz, 2H), 6.17 (s, 1H), 4.01 (dd, J=9.4, 5.3 Hz, 1H), 3.79 (s, 6H), 3.50 (dd, J=15.0, 9.1 Hz, 1H), 3.10 (dd, J=15.0, 6.0 Hz, 1H), 2.32 (s, 3H).

Example 6

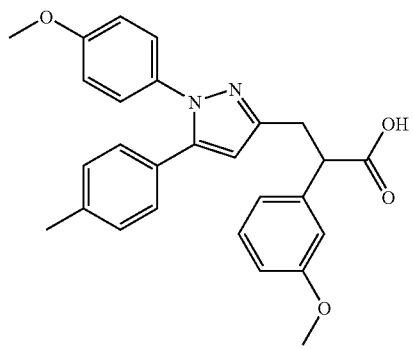

2-(3-Methoxy-phenyl)-3-[1-(4-methoxy-phenyl)-5-p-toly-1H-pyrazol-3-yl]-propionic acid The title compound was prepared by Method 2: HPLC: $R_t$=9.58 (Method A). MS (ES+): mass calculated for $C_{27}H_{26}N_2O_4$, 442.19; m/z found 443.2 [M+H]+. 1H NMR (400 MHz, CDCl3): 7.27-7.22 (m, 2H), 7.17-7.12 (m, 2H), 7.08-7.02 (m, 3H), 6.99-6.92 (m, 2H), 6.84-6.79 (m, 2H), 6.18 (s, 1H), 4.01 (dd, J=9.4, 5.3 Hz, 1H), 3.80 (s, 6H), 3.50 (dd, J=15.0, 9.1 Hz, 1H), 3.10 (dd, J=15.0, 6.0 Hz, 1H), 2.32 (s, 3H).

Example 7

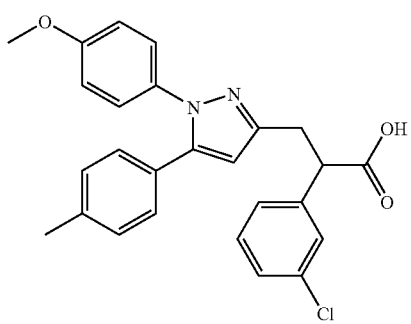

2-(3-Chloro-phenyl)-3-[1-(4-methoxy-phenyl)-5-p-toly-1H-pyrazol-3-yl]-propionic acid The title compound was prepared by Method 2: HPLC: $R_t$=9.99 (Method A). MS (ES+): mass calculated for $C_{27}H_{25}ClN_2O_3$, 446.16; m/z found 447.2 [M+H]+. 1H NMR (400 MHz, CDCl$_3$): 7.38-7.36 (m, 2H), 7.27-7.25 (m, 2H), 7.16-7.11 (m, 2H), 7.08-7.02 (m, 4H), 6.84-6.78 (m, 2H), 6.18 (s, 1H), 4.13-4.07 (m, 1H), 3.08 (s, 3H), 3.51 (dd, J=14.9, 9.0 Hz, 1H), 3.10 (dd, J=15.0, 6.0 Hz, 1H), 2.32 (s, 3H).

Example 8

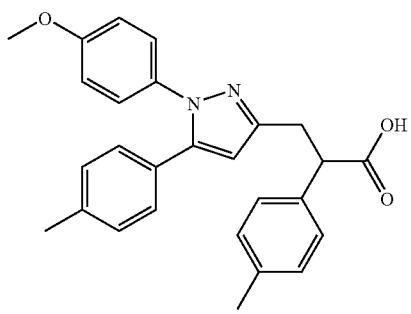

3-[1-(4-Methoxy-phenyl)-5-p-toly-1H-pyrazol-3-yl]-2-p-tolyl-propionic acid

The title compound was prepared by Method 2: HPLC: $R_t$=9.89 (Method A). MS (ES+): mass calculated for $C_{27}H_{26}N_2O_3$, 426.19; m/z found 427.2 [M+H]+. 1H NMR (400 MHz, CDCl$_3$): 7.28-7.25 (m, 2H), 7.18-7.12 (m, 4H), 7.08-7.02 (m, 4H), 6.83-6.79 (m, 2H), 6.19 (s, 1H), 4.13-4.05 (m, 1H), 3.80 (s, 3H), 3.50 (dd, J=15.0, 9.1 Hz, 1H), 3.10 (dd, J=15.0, 6.0 Hz, 1H), 2.32 (s, 6H).

Example 9

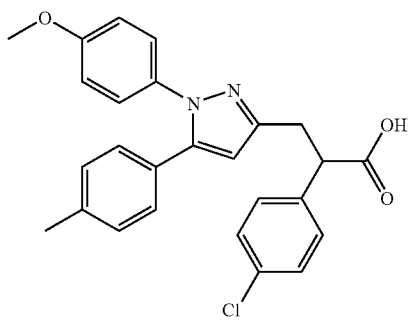

2-(4-Chloro-phenyl)-3-[1-(4-methoxy-phenyl)-5-p-toly-1H-pyrazol-3-yl]-propionic acid The title compound was prepared by Method 2: HPLC: $R_t$=10.00 (Method A). MS (ES+): mass calculated for $C_{27}H_{23}ClN_2O_3$, 446.14; m/z found 447.2 [M+H]+. 1H NMR (400 MHz, CDCl$_3$): 7.37 (br, s, 4H), 7.14-7.11 (m, 2H), 7.09-7.01 (m, 4H), 6.83-6.80 (m, 2H), 6.16 (s, 1H), 4.15-4.11 (m, 1H), 3.80 (s, 3H), 3.50 (dd, J=15.0, 9.1 Hz, 1H), 3.10 (dd, J=15.0, 6.0 Hz, 1H), 2.32 (s, 3H).

Example 10

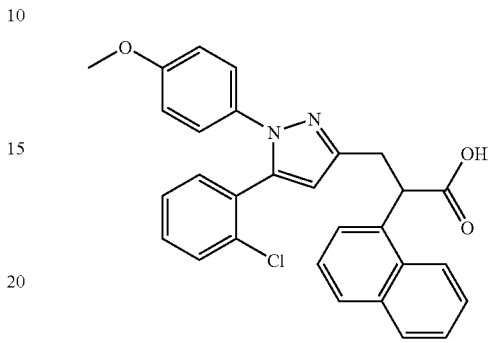

3-[5-(2-Chloro-phenyl)-1-(4-methoxy-phenyl)-1H-pyrazol-3-yl]-2-naphthalen-1-yl-propionic acid The title compound was prepared by Method 2: HPLC: $R_t$=9.87 (Method A). MS (ES+): mass calculated for $C_{29}H_{23}ClN_2O_3$, 482.14; m/z found 483.1 [M+H]+. 1H NMR (400 MHz, CDCl$_3$): 8.14 (d, J=8.3 Hz, 1H), 7.80 (d, J=7.8 Hz, 2H), 7.62-7.59 (m, 1H), 7.52-7.44 (m, 3H), 7.33-7.29 (m, 1H), 7.26-7.22 (m, 1H), 7.16-7.12 (m, 1H), 7.05-7.01 (m, 2H), 7.00-6.97 (m, 1H), 6.75-6.71 (m, 2H), 6.08 (s, 1H), 4.98 (dd, J=8.6, 6.6 Hz, 1H), 3.77 (dd, J=19.2, 4.2 Hz, 1H), 3.75 (s, 3H), 3.34 (dd, J=14.6, 6.57 Hz, 1H).

Example 11

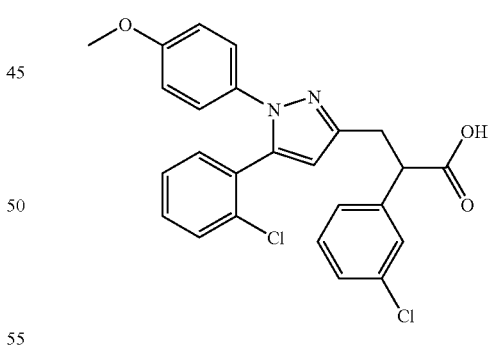

2-(3-Chloro-phenyl)-3-[5-(2-chloro-phenyl)-1-(4-methoxy-phenyl)-1H-pyrazol-3-yl]-propionic acid The title compound was prepared by Method 2: HPLC: $R_t$=9.78 (Method A). MS (ES+): mass calculated for $C_{25}H_{20}Cl_2N_2O_3$, 466.09; m/z found 467.1 [M+H]+. 1H NMR (400 MHz, CDCl$_3$): 7.37-7.34 (m, 2H), 7.29-7.24 (m, 4H), 7.19-7.07 (m, 2H), 7.14 (dd, J=8.0, 2.0 Hz, 2H), 6.77-6.73 (m, 2H), 6.16 (s, 1H), 4.14 (dd, J=8.3, 1.7 Hz, 1H), 3.76 (s, 3H), 3.53 (dd, J=14.7, 8.0 Hz, 1H), 3.17 (dd, J=15.2, 8.0 Hz, 1H).

Example 12

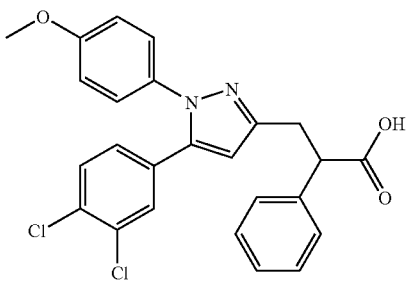

3-[5-(3,4-Dichloro-phenyl)-1-(4-methoxy-phenyl)-1H-pyrazol-3-yl]-2-phenyl-propionic acid The title compound was prepared by Method 2: HPLC: $R_t$=9.78 (Method A). MS (ES+): mass calculated for $C_{25}H_{20}Cl_2N_2O_3$, 466.09; m/z found 467.1 [M+H]⁺. ¹H NMR (400 MHz, CDCl₃): 7.37-7.34 (m, 2H), 7.29-7.24 (m, 4H), 7.19-7.07 (m, 2H), 7.14 (dd, J=8.0, 2.0 Hz, 2H), 6.77-6.73 (m, 2H), 6.16 (s, 1H), 4.14 (dd, J=8.3, 1.7 Hz, 1H), 3.76 (s, 3H), 3.53 (dd, J=14.7, 8.0 Hz, 1H), 3.17 (dd, J=15.2, 8.0 Hz, 1H).

Example 13

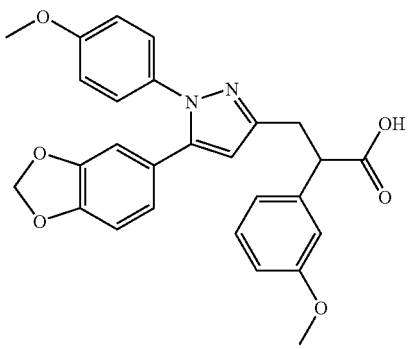

3-[5-Benzo[1,3]dioxol-5-yl-1-(4-methoxy-phenyl)-1H-pyrazol-3-yl]-2-(3-methoxy-phenyl)-propionic acid The title compound was prepared by Method 2: HPLC: $R_t$=9.03 (Method A). MS (ES+): mass calculated for $C_{27}H_{24}N_2O_6$, 472.16; m/z found 473.2 [M+H]⁺. ¹H NMR (400 MHz, CDCl₃): 7.10-7.01 (m, 2H), 6.97-6.93 (m, 2H), 6.77 (d, J=8.3 Hz, 1H), 6.73 (t, J=2.2 Hz, 1H), 6.62 (d, J=8.5 Hz, 2H), 6.51 (d, J=8.8 Hz, 1H), 6.44 (dd, J=8.0 Hz, 1.7 Hz, 1H), 6.39 (d, J=1.2 Hz, 1H), 5.94 (s, 1H), 5.75 (s, 2H), 3.91 (dd, J=9.3, 5.8 Hz, 1H), 3.60 (s, 3H), 3.59 (s, 3H), 3.31 (dd, J=14.6, 9.3 Hz, 1H), 2.93 (dd, J=13.6, 6.5 Hz, 1H).

Example 14

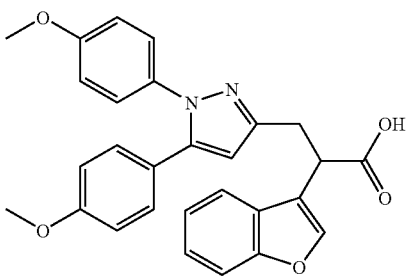

2-Benzofuran-3-yl-3-[1,5-bis-(4-methoxy-phenyl)-1H-pyrazol-3-yl]-propionic acid The title compound was prepared by Method 2: HPLC: $R_t$=9.28 (Method A). MS (ES+): mass calculated for $C_{28}H_{24}N_2O_5$, 468.17; m/z found 469.2 [M+H]⁺. ¹H NMR (400 MHz, CDCl₃): 7.45 (d, J=2.0 Hz, 1H), 7.29-7.25 (m, 1H), 7.12-7.09 (m, 3H), 6.96-6.93 (m, 2H), 6.86-6.82 (m, 2H), 6.77-6.75 (m, 1H), 6.64-6.58 (m, 4H), 5.88 (s, 1H), 4.29 (dd, J=8.8, 6.0 Hz, 1H), 3.63 (s, 3H), 3.62 (s, 3H), 3.50 (dd, J=14.4, 9.3 Hz, 1H), 3.05 (dd, J=14.9, 6.2 Hz, 1H).

Example 15

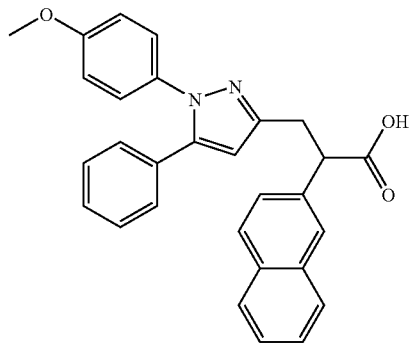

3-[1-(4-Methoxy-phenyl)-5-phenyl-1H-pyrazol-3-yl]-2-naphthalen-2-yl-propionic acid The title compound was prepared by Method 2: HPLC: $R_t$=9.79 (Method A). MS (ES+): mass calculated for $C_{29}H_{24}N_2O_3$, 448.18; m/z found 449.2 [M+H]⁺. ¹H NMR (400 MHz, CDCl₃): 7.86-7.79 (m, 4H), 7.55-7.51 (m, 1H), 7.50-7.46 (m, 2H), 7.29-7.22 (m, 2H), 7.14-7.16 (m, 4H), 6.86-6.77 (m, 2H), 6.26 (s, 1H), 4.33 (dd, J=8.8, 6.3 Hz, 1H), 3.78 (s, 3H), 3.60 (dd, J=15.0, 8.8 Hz, 1H), 3.29 (dd, J=14.6, 6.0 Hz, 1H).

Example 16

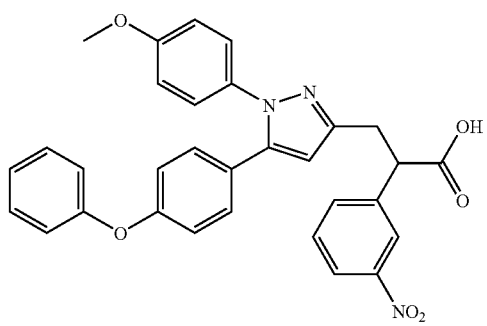

3-[1-(4-Methoxy-phenyl)-5-(4-phenoxy-phenyl)-1H-pyrazol-3-yl]-2-(3-nitro-phenyl)-propionic acid The title compound was prepared by Method 2: HPLC: $R_t$=3.47 (Method B). MS (ES+): mass calculated for $C_{31}H_{25}N_3O_6$, 535.17; m/z found 536.2[M+H]⁺. ¹H NMR (400 MHz, CDCl₃): 8.23 (t, J=1.5 Hz, 1H), 8.18-8.15 (m, 1H), 7.74 (d, J=7.5 Hz, 1H), 7.35 (t, J=7.5 Hz, 1H), 7.39-7.34 (m, 2H), 7.17-7.13 (m, 3H), 7.10-7.06 (m, 2H), 7.04-7.00 (m, 2H), 6.90-6.84 (m, 4H), 6.23 (s, 1H), 4.32 (dd, J=8.3, 6.5 Hz, 1H), 3.82 (s, 3H), 3.61 (dd, J=15.2, 8.6 Hz, 1H), 3.24 (dd, J=15.2, 6.3 Hz, 1H).

Example 17

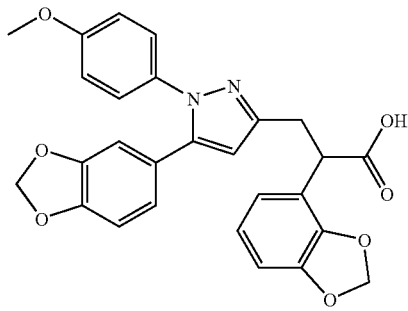

2-Benzo[1,3]dioxol-4-yl-3[5-benzo[1,3]dioxol-5-yl-1-(4-methoxy-phenyl)-1H-pyrazol-3-yl]-propionic acid The title compound was prepared by Method 2: HPLC: $R_t$=2.91 (Method B). MS (ES+): mass calculated for $C_{27}H_{22}N_2O_7$, 486.14; m/z found 487.2 [M+H]$^+$. $^1$H NMR (400 MHz, CDCl$_3$): 7.18-7.14 (m, 2H), 6.89 (d, J=1.7 Hz, 1H), 6.86-6.83 (m, 2H), 6.81 (d, J=1.5 Hz, 1H), 6.74 (dd, J=19.2, 7.8 Hz, 2H), 6.65 (dd, J=7.83, 1.7 Hz, 1H), 6.59 (d, J=1.7 Hz, 1H), 6.17 (s, 1H), 5.95 (s, 4H), 4.06 (dd, J=9.1, 6.1 Hz, 1H), 3.81 (s, 3H), 3.48 (dd, J=15.2, 8.8 Hz, 1H), 3.10 (dd, J=15.9, 7.0 Hz, 1H).

Example 18

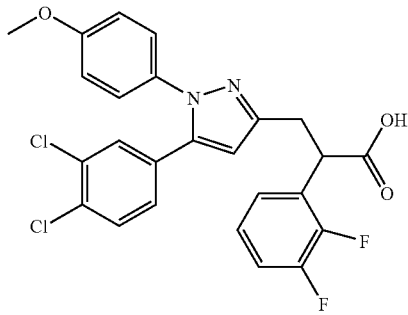

3-[5-(3,4-Dichloro-phenyl)-1-(4-methoxy-phenyl)-1H-pyrazol-3-yl]-2-(2,3-difluoro-phenyl)-propionic acid The title compound was prepared by Method 2: HPLC: $R_t$=3.62 (Method B). MS (ES+): mass calculated for $C_{25}H_{18}Cl_2F_2N_2O_3$, 502.07; m/z found 503.1 [M+H]$^+$. $^1$H NMR (400 MHz, CDCl$_3$): 7.31 (d, J=8.3 Hz, 1H), 7.29 (d, J=2.0 Hz, 1H), 7.16-7.05 (m, 5H), 6.91-6.84 (m, 3H), 6.25 (s, 1H), 4.46 (dd, J=8.0, 7.0 Hz, 1H), 3.82 (s, 3H), 3.57 (dd, J=15.1, 8.3 Hz, 1H), 3.18 (dd, J=14.6, 7.0 Hz, 1H).

Example 19

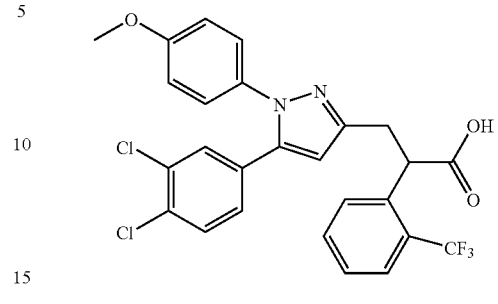

3-[5-(3,4-Dichloro-phenyl)-1-(4-methoxy-phenyl)-1H-pyrazol-3-yl]-2-(2-trifluoromethyl-phenyl)-propionic acid The title compound was prepared by Method 2: HPLC: $R_t$=3.50 (Method B). MS (ES+): mass calculated for $C_{26}H_{19}Cl_2F_3N_2O_3$, 534.07; m/z found 535.1 [M+H]$^+$. $^1$H NMR (400 MHz, CDCl$_3$): 7.71-7.66 (m, 2H), 7.57 (t, J=8.3 Hz, 1H), 7.41 (t, J=7.3 Hz, 1H), 7.31 (s, 1H), 7.29 (d, J=1.5 Hz, 1H), 7.14-7.10 (m, 2H), 6.89 (dd, J=8.34, 2.2 Hz, 1H), 6.87-6.82 (m, 2H), 6.20 (s, 1H), 4.56 (dd, J=9.3, 5.5 Hz, 1H), 3.81 (s, 3H), 3.55 (dd, J=15.6, 8.5 Hz, 1H), 3.13 (dd, J=15.16, 6.0 Hz, 1H).

Example 20

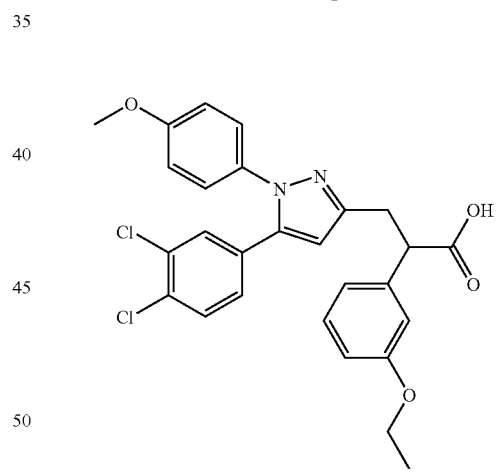

3-[5-(3,4-Dichloro-phenyl)-1-(4-methoxy-phenyl)-1H-pyrazol-3-yl]-2-(3-ethoxy-phenyl)-propionic acid The title compound was prepared by Method 2: HPLC: $R_t$=5.34 (Method B). MS (ES+): mass calculated for $C_{27}H_{24}Cl_2N_2O_4$, 510.11; m/z found 511.1 [M+H]$^+$. $^1$H NMR (400 MHz, CDCl$_3$): 7.32 (s, 1H), 7.29 (d, J=2.2 Hz, 1H), 7.27-7.23 (m, 2H), 7.15-7.12 (m, 2H), 6.95-6.82 (m, 5H), 6.24 (s, 1H), 4.08 (dd, J=9.3, 5.5 Hz, 1H), 4.07 (q, J=13.8, 7.0 Hz, 2H), 3.82 (s, 3H), 3.52 (dd, J=15.6, 9.0 Hz, 1H), 3.14 (dd, J=15.4, 5.8 Hz, 1H), 1.40 (t, J=6.8 Hz, 3H).

Example 21

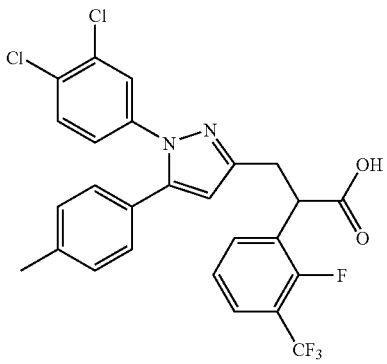

3-[1-(3,4-Dichloro-phenyl)-5-p-tolyl-1H-pyrazol-3-yl]-2-(2-fluoro-3-trifluoromethyl-phenyl)-propionic acid The title compound was prepared by Method 2: HPLC: $R_t$=3.78 (Method B). MS (ES+): mass calculated for $C_{26}H_{18}Cl_2F_4N_2O_3$, 536.07; m/z found 537.1 [M+H]$^+$. $^1$H NMR (400 MHz, CDCl$_3$): 7.62 (t, J=6.0 Hz, 1H), 7.55 (t, J=6.8 Hz, 1H), 7.39 (d, J=2.2 Hz, 1H), 7.34 (d, J=8.5 Hz, 1H), 7.28-7.22 (m, 2H), 7.13 (d, J=8.0 Hz, 2H), 7.02 (d, J=8.0, 2H), 6.96 (dd, J=8.6, 2.5 Hz, 1H), 6.20 (s, 1H), 4.54 (t, J=7.8 Hz, 1H), 3.58 (dd, J=15.2, 7.8 Hz, 1H), 3.19 (dd, J=15.2, 7.5 Hz, 1H), 2.35 (s, 3H).

Example 22

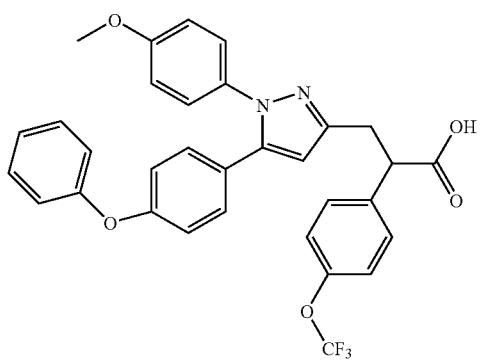

3-[1-(4-Methoxy-phenyl)-5-(4-phenoxy-phenyl)-1H-pyrazol-3-yl]-2-(4-trifluoromethoxyl-phenyl)-propionic acid The title compound was prepared by Method 2: HPLC: $R_t$=3.60 (Method B). MS (ES+): mass calculated for $C_{32}H_{25}F_3N_2O_5$, 574.17; m/z found 575.2 [M+H]$^+$. $^1$H NMR (400 MHz, CDCl$_3$): 7.42-7.38 (m, 2H), 7.36-7.31 (m, 2H), 7.21-7.12 (m, 5H), 7.11-7.07 (m, 2H), 7.03-6.99 (m, 1H), 6.89-6.81 (m, 4H), 6.18 (s, 1H), 4.18 (dd, J=9.6, 5.3 Hz, 1H), 3.80 (s, 3H), 3.52 (dd, J=14.9, 9.4 Hz, 1H), 3.12 (dd, J=15.2, 5.6 Hz, 1H).

Example 23

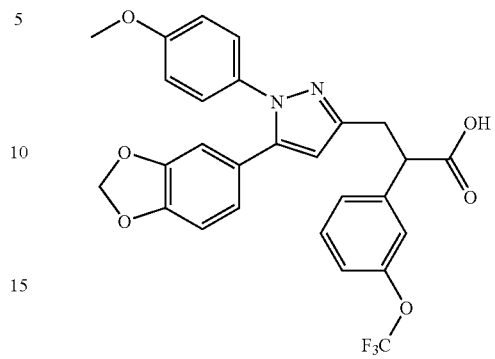

3-[5-Benzo[1,3]dioxo-5-yl-1-(4-methoxy-phenyl)-1H-pyrazol-3-yl]-2-(3-trifluoromethoxyl-phenyl)-propionic acid The title compound was prepared by Method 2: HPLC: $R_t$=3.28 (Method B). MS (ES+): mass calculated for $C_{27}H_{21}F_3N_2O_6$, 526.14; m/z found 527.1 [M+H]$^+$. $^1$H NMR (400 MHz, CDCl$_3$): 7.38-7.29 (m, 2H), 7.22-7.20 (m, 1H), 7.15-7.11 (m, 3H), 6.86-6.82 (m, 2H), 6.70 (d, J=7.8 Hz, 1H), 6.60 (dd, J=8.34, 1.5 Hz, 1H), 6.54 (d, J=1.8 Hz, 1H), 6.13 (s, 1H), 5.94 (s, 2H), 4.13 (dd, J=8.6, 6.3 Hz, 1H), 3.81 (s, 3H), 3.52 (dd, J=14.9, 8.6 Hz, 1H), 3.16 (dd, J=15.2, 6.8 Hz, 1H).

Example 24

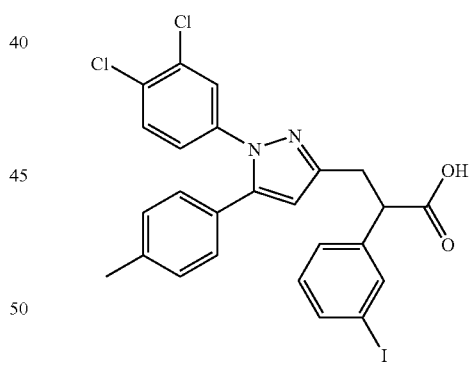

3-[1-(3,4-Dichloro-phenyl)-5-p-tolyl-1H-pyrazol-3-yl]-2-(3-iodo-phenyl)-propionic acid The title compound was prepared by Method 2: HPLC: $R_t$=3.89 (Method B). MS (ES+): mass calculated for $C_{25}H_{19}Cl_2IN_2O_2$, 575.99; m/z found 577.0 [M+H]$^+$. $^1$H NMR (400 MHz, CDCl$_3$): 7.73 (t, J=2.0 Hz, 1H), 7.64-7.62 (m, 1H), 7.48 (d, J=2.5 Hz, 1H), 7.38-7.35 (m, 1H), 7.32 (d, J=8.6 Hz, 2H), 7.15-7.07 (m, 4H), 6.98 (dd, J=8.8, 2.3 Hz, 1H), 6.18 (s, 1H), 4.11 (dd, J=9.0, 6.3 Hz, 1H), 3.49 (dd, J=15.4, 8.8 Hz, 1H), 3.10 (dd, J=15.4, 6.3 Hz, 1H), 2.35 (s, 3H).

Example 25

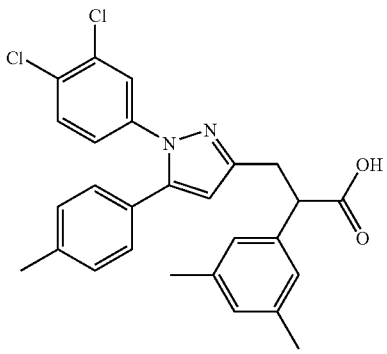

3-[1-(3,4-Dichloro-phenyl)-5-p-tolyl-1H-pyrazol-3-yl]-2-(3,5-dimethyl-phenyl)-propionic acid The title compound was prepared by Method 2: HPLC: $R_t$=3.84 (Method B). MS (ES+): mass calculated for $C_{27}H_{24}Cl_2N_2O_2$, 478.12; m/z found 479.1 [M+H]$^+$. $^1$H NMR (400 MHz, CDCl$_3$): 7.45 (d, J=2.2 Hz, 1H), 7.35 (d, J=8.6 Hz, 1H), 7.12 (d, J=7.8 Hz, 2H), 7.06-7.03 (m, 2H), 7.00-6.98 (m, 2H), 6.97 (d, J=2.3 Hz, 1H), 6.93 (br, s, 1H), 6.22 (s, 1H), 4.05 (dd, J=6.0, 5.6 Hz, 1H), 3.51 (dd, J=15.2, 9.3 Hz, 1H), 3.09 (dd, J=15.2, 5.8 Hz, 1H), 2.36 (s, 3H), 2.31 (s, 6H).

Example 26

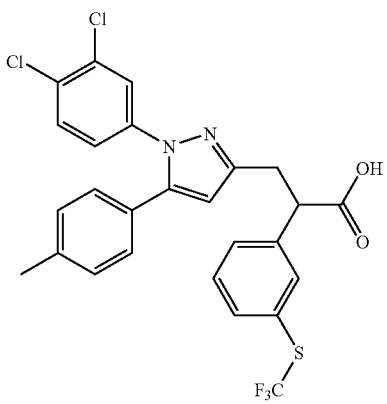

3-[1-(3,4-Dichloro-phenyl)-5-p-tolyl-1H-pyrazol-3-yl]-2-(3-trifluoromethylsulfanyl-phenyl)-propionic acid The title compound was prepared by Method 2: HPLC: $R_t$=3.91 (Method B). MS (ES+): mass calculated for $C_{26}H_{19}Cl_2F_3N_2O_2S$, 550.05; m/z found 551.0 [M+H]$^+$. $^1$H NMR (400 MHz, CDCl$_3$): 7.67-7.65 (m, 1H), 7.61-7.57 (m, 1H), 7.55-7.51 (m, 1H), 7.45 (d, J=2.5 Hz, 1H), 7.41 (t, J=7.1 Hz, 1H), 7.32 (d, J=8.3 Hz, 2H), 7.12 (d, J=8.3 Hz, 2H), 7.04-7.01 (m, 2H), 6.95 (dd, J=8.6, 2.3 Hz, 1H), 6.15 (s, 1H), 4.19 (dd, J=8.6, 6.3 Hz, 1H), 3.53 (dd, J=15.4, 8.3 Hz, 1H), 3.16 (dd, J=14.9, 6.3 Hz, 1H), 2.37 (s, 3H).

Example 27

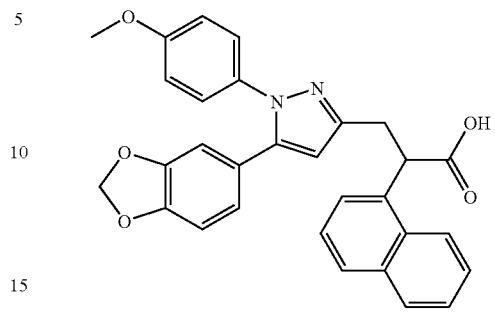

3-[5-Benzo[1,3]dioxol-5-yl-1-(4-methoxy-phenyl)-1H-pyrazol-3-yl]-2-naphthalen-1-yl-propionic acid The title compound was prepared by Method 2: HPLC: $R_t$=9.47 (Method A). MS (ES+): mass calculated for $C_{30}H_{24}N_2O_5$, 492.17; m/z found 493.2 [M+H]$^+$. $^1$H NMR (400 MHz, CDCl$_3$): 8.13 (d, J=8.6 Hz, 1H), 7.88-7.84 (m, 2H), 7.79 (d, J=7.8 Hz, 1H), 7.58 (d, J=7.3 Hz, 1H), 7.51-7.43 (m, 3H), 7.08 (d, J=8.8 Hz, 2H), 6.80 (d, J=8.6 Hz, 2H), 6.6 (d, J=8.1 Hz, 1H), 6.53 (dd, J=8.1, 1.26 Hz, 1H), 6.46 (d, J=1.8 Hz, 1H), 6.09 (s, 1H), 5.93 (s, 2H), 4.95 (dd, J=8.6, 6.3 Hz, 1H), 3.79 (s, 3H), 3.73-3.65 (m, 1H), 3.25 (dd, J=14.6, 6.3 Hz, 1H).

Example 28

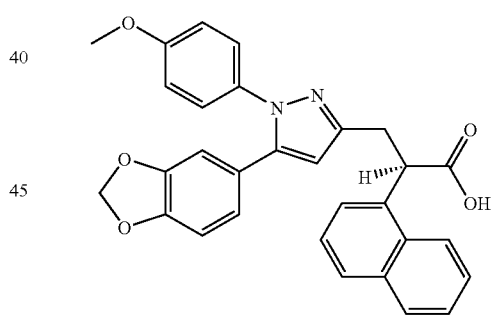

(R)-3-[5-Benzo[1,3]dioxol-5-yl-1-(4-methoxy-phenyl)-1H-pyrazol-3-yl]-2-naphthalen-1-yl-propionic acid The racemate (Example 27) was prepared by Method 2, and the title compound was isolated by semi-preparative chiral HPLC (Method D). HPLC: $R_t$=3.82 (Method C). MS (ES+): mass calculated for $C_{30}H_{24}N_2O_5$, 492.17; m/z found 493.2 [M+H]$^+$. $^1$H NMR (400 MHz, CDCl$_3$): 7.83-7.79 (m, 4H), 7.52 (dd, J=8.4, 1.6 Hz, 1H), 7.48-7.45 (m, 2H), 7.16-7.12 (m, 2H), 6.84-6.80 (m, 2H), 6.70-6.68 (m, 1H), 6.62 (dd, J=7.8, 2.0 Hz, 2H), 6.56 (d, J=1.8 Hz, 1H), 6.16 (s, 1H), 5.94 (s, 2H), 4.33 (dd, J=9.2, 5.6 Hz, 1H), 3.79 (s, 3H), 3.63 (dd, J=14.9, 9.0 Hz, 1H), 3.24 (dd, J=15.7, 5.1 Hz, 1H).

Example 29

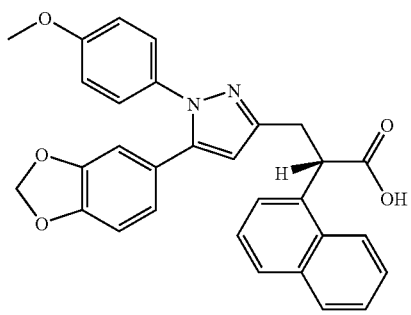

(S)-3-[5-Benzo[1,3]dioxol-5-yl-1-(4-methoxy-phenyl)-1H-pyrazol-3-yl]-2-naphthalen-1-yl-propionic acid The racemate (Example 27) was prepared by Method 2, and the title compound was isolated by semi-preparative chiral HPLC (Method D). HPLC: $R_t$=6.83 (Method C). MS (ES+): mass calculated for $C_{30}H_{24}N_2O_5$, 492.17; m/z found 493.2 [M+H]$^+$. $^1$H NMR (400 MHz, CDCl$_3$): 7.83-7.79 (m, 4H), 7.52 (dd, J=8.4, 1.6 Hz, 1H), 7.48-7.45 (m, 2H), 7.16-7.12 (m, 2H), 6.84-6.80 (m, 2H), 6.70-6.68 (m, 1H), 6.62 (dd, J=7.8, 2.0 Hz, 2H), 6.56 (d, J=1.8 Hz, 1H), 6.16 (s, 1H), 5.94 (s, 2H), 4.33 (dd, J=9.2, 5.6 Hz, 1H), 3.79 (s, 3H), 3.63 (dd, J=14.9, 9.0 Hz, 1H), 3.24 (dd, J=15.7, 5.1 Hz, 1H).

Example 30

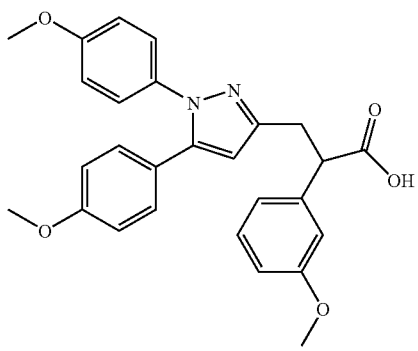

3-[1,5-Bis-(4-methoxy-phenyl)-1H-pyrazol-3-yl]-2-(3-methoxy-phenyl)-propionic acid The title compound was prepared by Method 2: HPLC: $R_t$=9.15 (Method A). MS (ES+): mass calculated for $C_{27}H_{26}N_2O_5$, 458.18; m/z found 459.2 [M+H]$^+$. $^1$H NMR (400 MHz, CDCl$_3$): 7.26-7.22 (m, 2H), 7.16-7.13 (m, 2H), 7.08-7.05 (m, 2H), 6.97 (d, J=7.3 Hz, 1H), 6.93 (t, J=2.3 Hz, 1H), 6.83-6.77 (m, 5H), 6.16 (s, 1H), 4.12 (dd, J=9.9, 5.3 Hz, 1H), 3.80 (s, 3H), 3.79 (s, 3H), 3.78 (s, 3H), 3.52 (dd, J=14.2, 9.6 Hz, 1H), 3.12 (dd, J=15.2, 6.1 Hz, 1H).

Example 31

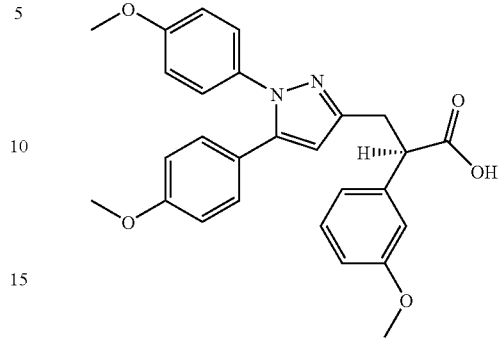

(R)-3-[1,5-Bis-(4-methoxy-phenyl)-1H-pyrazol-3-yl]-2-(3-methoxy-phenyl)-propionic acid The racemate (Example 30) was prepared by Method 2, and the title compound was isolated by semi-preparative chiral HPLC (Method D). HPLC: $R_t$=4.84 (Method C). MS (ES+): mass calculated for $C_{27}H_{26}N_2O_5$, 458.18; m/z found 459.2 [M+H]$^+$. $^1$H NMR (400 MHz, CDCl$_3$): 7.28-7.24 (m, 2H), 7.19-7.15 (m, 2H), 7.09-7.05 (m, 2H), 6.97 (d, J=7.8 Hz, 1H), 6.93 (t, J=2.0 Hz, 1H), 6.87-6.78 (m, 5H), 6.16 (s, 1H), 4.12 (dd, J=9.9, 6.2 Hz, 1H), 3.80 (s, 3H), 3.79 (s, 3H), 3.78 (s, 3H), 3.52 (dd, J=15.1, 9.5 Hz, 1H), 3.12 (dd, J=15.3, 5.5 Hz, 1H).

Example 32

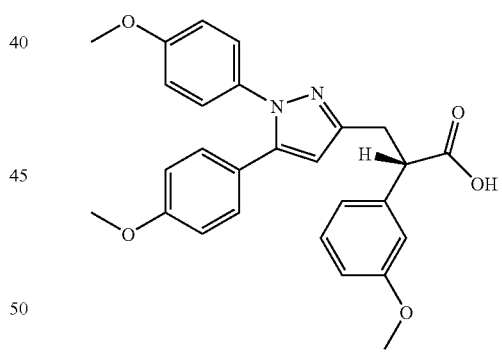

(S)-3-[1,5-Bis-(4-methoxy-phenyl)-1H-pyrazol-3-yl]-2-(3-methoxy-phenyl)-propionic acid The racemate (Example 30) was prepared by Method 2, and the title compound was isolated by semi-preparative chiral HPLC (Method D). HPLC: $R_t$=7.37 (Method C). MS (ES+): mass calculated for $C_{27}H_{26}N_2O_5$, 458.18; m/z found 459.2 [M+H]$^+$. $^1$H NMR (400 MHz, CDCl$_3$): 7.28-7.24 (m, 2H), 7.19-7.15 (m, 2H), 7.09-7.05 (m, 2H), 6.97 (d, J=7.8 Hz, 1H), 6.93 (t, J=2.0 Hz, 1H), 6.87-6.78 (m, 5H), 6.20 (s, 1H), 4.15 (dd, J=9.9, 6.2 Hz, 1H), 3.82 (s, 3H), 3.80 (s, 3H), 3.79 (s, 3H), 3.55 (dd, J=15.1, 9.5 Hz, 1H), 3.16 (dd, J=15.3, 5.5 Hz, 1H).

Example 33

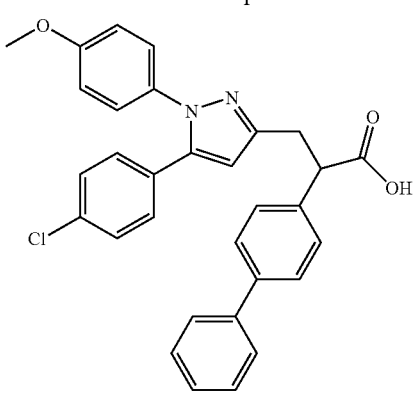

2-Biphenyl-4-yl-3-[5-(4-chloro-phenyl)-1-(4-methoxy-phenyl)-1H-pyrazol-3-yl]-propionic acid The title compound was prepared by Method 2: HPLC: $R_t$=7.21 (Method A). MS (ES+): mass calculated for $C_{31}H_{25}N_2O_3$, 508.16; m/z found 509.2 [M+H]$^+$. $^1$H NMR (400 MHz, CDCl$_3$): 7.24-7.01 (m, 7H), 6.98-6.80 (m, 4H), 6.75-6.64 (m, 2H), 6.58-6.44 (m, 2H), 5.79 (s, 1H), 3.71 (m, 1H), 3.47 (s, 3H), 3.22-3.08 (m, 3H), 2.85-2.64 (m, 3H).

Example 34

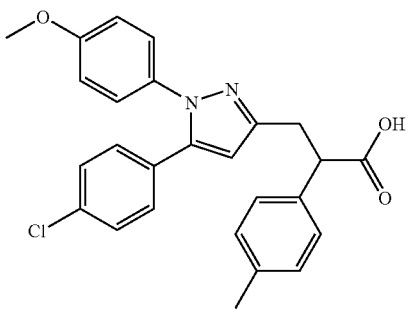

3-[5-(4-Chloro-phenyl)-1-(4-methoxy-phenyl)-1H-pyrazol-3-yl]-2-p-tolyl-propionic acid The title compound was prepared by Method 2: HPLC: $R_t$=10.11 (Method A). MS (ES+): mass calculated for $C_{26}H_{23}ClN_2O_3$, 446.14; m/z found 447.2 [M+H]$^+$. $^1$H NMR (500 MHz, DMSO-d$_6$): 12.37 (br s, 1H), 7.40 (d, J=8.6 Hz, 2H), 7.26 (d, J=8.1 Hz, 2H), 7.18-7.11 (m, 6H), 6.95 (d, J=9.0 Hz, 2H), 6.40 (s, 1H), 3.98 (dd, J=6.3, 9.1 Hz, 1H), 3.77 (s, 3H), 3.34 (dd, J=9.1, 15.1 Hz, 1H), 2.92 (dd, J=6.2, 15.0 Hz, 1H), 2.27 (s, 3H).

Example 35

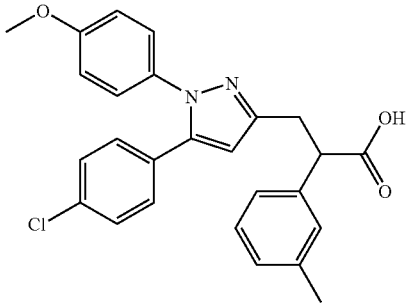

3-[5-(4-Chloro-phenyl)-1-(4-methoxy-phenyl)-1H-pyrazol-3-yl]-2-m-tolyl-propionic acid The title compound was prepared by Method 2: HPLC: $R_t$=10.11 (Method A). MS (ES+): mass calculated for $C_{26}H_{23}ClN_2O_3$, 446.14; m/z found 447.1 [M+H]$^+$. $^1$H NMR (500 MHz, DMSO-d$_6$): 12.29 (br s, 1H), 7.40 (d, J=8.6 Hz, 2H), 7.22 (t, J=7.5 Hz, 1H), 7.19-7.15 (m, 3H), 7.13 (d, J=8.9 Hz, 2H), 7.08 (d, J=7.3 Hz, 1H), 6.95 (d, J=9.0 Hz, 2H), 6.40 (s, 1H), 3.98 (dd, J=6.0, 9.3 Hz, 1H), 3.77 (s, 3H), 2.92 (dd, J=6.0, 14.9 Hz, 1H), 2.30 (s, 3H).

Example 36

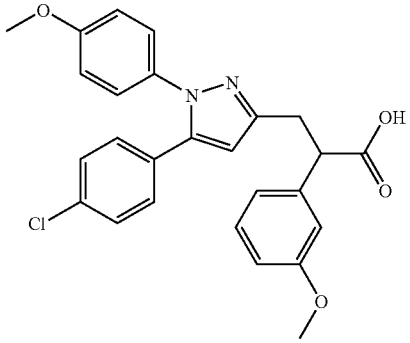

3-[5-(4-Chloro-phenyl)-1-(4-methoxy-phenyl)-1H-pyrazol-3-yl]-2-(3-methoxy-phenyl)-propionic acid The title compound was prepared by Method 2: HPLC: $R_t$=9.79 (Method A). MS (ES+): mass calculated for $C_{26}H_{23}ClN_2O_4$, 462.13; m/z found 463.1 [M+H]$^+$. $^1$H NMR (500 MHz, DMSO-d$_6$): 12.29 (br s, 1H), 7.40 (d, J=8.5 Hz, 2H), 7.26 (t, J=7.9 Hz, 1H), 7.17 (d, J=8.5 Hz 2H), 7.13 (d, J=8.9 Hz, 2H), 6.96-6.92 (m, 4H), 6.84 (d, J=8.2 Hz, 1H), 6.42 (s, 1H), 4.01 (dd, J=6.1, 9.2 Hz, 1H), 3.78 (s, 3H), 3.74 (s, 3H), 2.93 (dd, J=6.1, 14.9 Hz, 1H).

Example 37

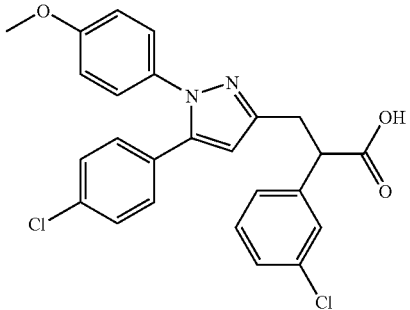

2-(3-Chloro-phenyl)-3-[5-(4-chloro-phenyl)-1-(4-methoxy-phenyl)-1H-pyrazol-3-yl]-propionic acid The title compound was prepared by Method 2: HPLC: $R_t$=10.19 (Method A). MS (ES+): mass calculated for $C_{25}H_{20}Cl_2N_2O_3$, 466.09; m/z found 467.2 [M+H]$^+$. $^1$H NMR (400 MHz, DMSO-d$_6$): 7.45 (m, 1H), 7.43 (d, J=8.6 Hz, 2H), 7.39-7.34 (m, 3H), 7.18 (d, J=8.6 Hz, 2H), 7.13 (d, J=9.0 Hz, 2H), 6.97 (d, J=9.0 Hz, 2H), 4.11 (dd, J=6.8, 8.6 Hz, 1H), 3.79 (s, 3H), 3.38 (dd, J=8.4, 14.8 Hz, 1H), 3.01 (dd, J=6.8, 14.8 Hz, 1H).

Example 38

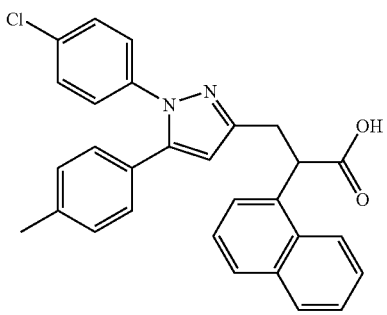

3-[1-(4-Chloro-phenyl)-5-p-tolyl-1H-pyrazol-3-yl]-2-naphthalen-1-yl-propionic acid The title compound was prepared by Method 2: HPLC: $R_t$=10.66 (Method A). MS (ES+): mass calculated for $C_{29}H_{23}ClN_2O_2$, 466.14; m/z found 467.1 [M+H]$^+$. $^1$H NMR (500 MHz, DMSO-$d_6$): 12.52 (br s, 1H), 8.22 (d, J=8.3 Hz, 1H), 7.95 (d, J=8.0 Hz, 1H), 7.86 (d, J=8.1 Hz, 1H), 7.60-7.52 (m, 4H), 7.44 (d, J=8.9 Hz, 2H), 7.17-7.15 (m, 4H), 7.02 (d, J=8.1 Hz, 2H), 6.40 (s, 1H), 4.87 (dd, J=6.3, 8.6 Hz, 1H), 3.54 (dd, J=8.6, 14.9 Hz, 1H), 3.09 (dd, J=6.2, 14.9 Hz, 1H), 2.28 (s, 3H).

Example 39

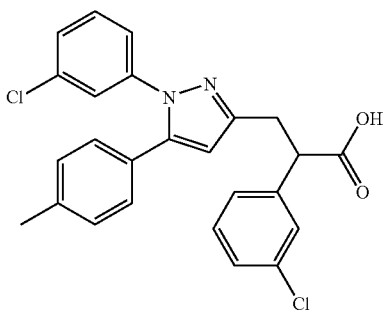

2-(3-Chloro-phenyl)-3-[1-(3-chloro-phenyl)-5-p-tolyl-1H-pyrazol-3-yl]-propionic acid The title compound was prepared by Method 2: HPLC: $R_t$=10.56 (Method A). MS (ES+): mass calculated for $C_{25}H_{20}Cl_2N_2O_2$, 450.09; m/z found 451.0 [M+H]$^+$. $^1$H NMR (500 MHz, DMSO-$d_6$): 12.59 (br s, 1H), 7.44-7.31 (m, 7H), 7.18 (d, J=8.0 Hz, 2H), 7.08 (d, J=8.1 Hz, 2H), 7.05 (d, J=7.2 Hz, 1H), 6.38 (s, 1H), 4.10 (dd, J=6.8, 8.6 Hz, 1H), 3.00 (dd, J=6.7, 14.9 Hz, 1H), 2.30 (s, 3H).

Example 40

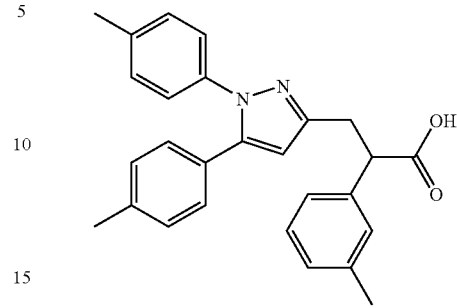

3-(1,5-Di-p-tolyl-1H-pyrazol-3-yl)-2-m-tolyl-propionic acid

The title compound was prepared by Method 2: HPLC: $R_t$=10.30 (Method A). MS (ES+): mass calculated for $C_{27}H_{26}N_2O_2$, 410.20; m/z found 411.1 [M+H]$^+$. $^1$H NMR (500 MHz, DMSO-$d_6$): 12.39 (br s, 1H), 7.24-7.17 (m, 5H), 7.13 (d, J=7.9 Hz, 2H), 7.09-7.02 (m, 5H), 6.32 (s, 1H), 3.98 (dd, J=6.0, 9.3 Hz, 1H), 2.92 (dd, J=6.0, 14.8 Hz, 1H), 2.31 (s, 3H), 2.30 (s, 3H), 2.28 (s, 3H).

Example 41

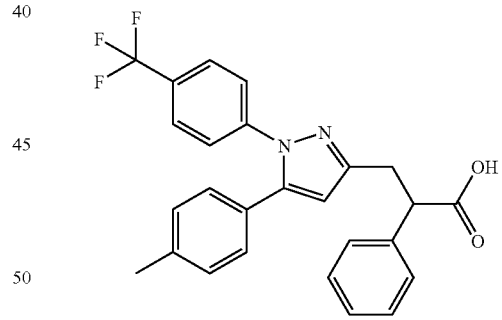

2-Phenyl-3-[5-p-tolyl-1-(4-trifluoromethyl-phenyl)-1H-pyrazol-3-yl]-propionic acid The title compound was prepared by Method 2: HPLC: $R_t$=10.41 (Method A). MS (ES+): mass calculated for $C_{26}H_{21}F_3N_2O_2$, 450.16; m/z found 451.0 [M+H]$^+$. $^1$H NMR (500 MHz, DMSO-$d_6$): 12.40 (br s, 1H), 7.76 (d, J=8.5 Hz, 2H), 7.41-7.39 (m, 4H), 735 (t, J=7.7 Hz, 2H), 7.28 (m, 1H), 7.19 (d, 7.9 Hz, 2H), 7.09 (d, J=8.1 Hz, 2H), 6.40 (s, 1H), 4.06 (dd, J=6.3, 9.1 Hz, 1H), 3.40 (dd, J=9.0, 15 Hz, 1H), 2.98 (dd, J=6.3, 15 Hz, 1H), 2.31 (s, 3H).

Example 42

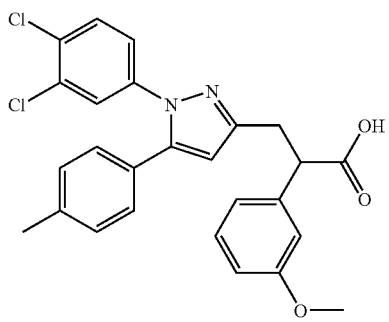

3-[1-(3,4-Dichloro-phenyl)-5-p-tolyl-1H-pyrazol-3-yl]-2-(3-methoxy-phenyl)-propionic acid The title compound was prepared by Method 2: HPLC: $R_t$=10.61 (Method A). MS (ES+): mass calculated for $C_{26}H_{22}Cl_2N_2O_3$, 480.10; m/z found 481.0 [M+H]$^+$. $^1$H NMR (500 MHz, DMSO-$d_6$): 12.40 (br s, 1H), 7.62 (d J=8.7 Hz, 1H), 7.53 (d, J=2.5 Hz, 1H), 7.26 (d, J=7.9 Hz, 1H), 7.20 (d, J=7.9 Hz, 2H), 7.11 (d, J=8.1 Hz, 2H), 7.07 (dd, J=2.5, 8.6 Hz, 1H), 6.96 (d, J=7.7 Hz, 1H), 6.94 (s, 1H), 6.85 (dd, J=2.6, 8.3 Hz, 1H), 6.40 (s, 1H), 4.03 (dd, J=6.1, 9.2 Hz, 1H), 3.74 (s, 3H), 3.36 (dd, J=9.3, 15.1 Hz, 1H), 2.95 (dd, J=6.1, 15.0 Hz, 1H), 2.31 (s, 3H).

Example 43

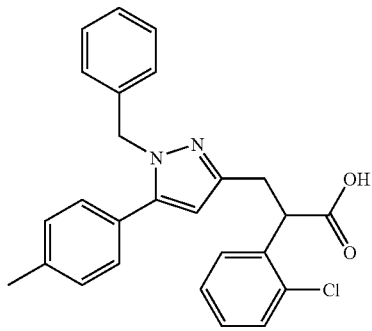

3-(1-Benzyl-5-p-tolyl-1H-pyrazol-3-yl)-2-(2-chloro-phenyl)-propionic acid

The title compound was prepared by Method 2: HPLC: $R_t$=9.95 (Method A). MS (ES+): mass calculated for $C_{26}H_{23}ClN_2O_2$, 430.14; m/z found 431.0 [M+H]$^+$. $^1$H NMR (500 MHz, DMSO-$d_6$): 12.60 (br s, 1H), 7.45-7.43 (m, 2H), 7.32-7.28 (m, 2H), 7.23-7.15 (m, 7H), 6.83 (d, J=9.0 Hz, 2H), 6.12 (s, 1H), 5.24 (s, 2H), 4.46 (t, J=7.8 Hz, 1H), 3.31 (dd, J=7.1, 14.6 Hz, 1H), 3.04 (dd, J=8.2, 14.6 Hz, 1H), 2.29 (s, 3H).

Example 44

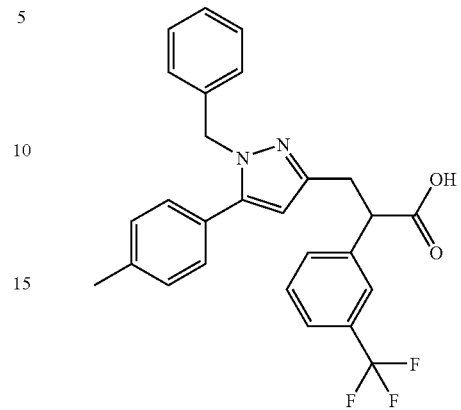

3-(1-Benzyl-5-p-tolyl-1H-pyrazol-3-yl)-2-(3-trifluoromethyl-phenyl)-propionic acid The title compound was prepared by Method 2: HPLC: $R_t$=10.19 (Method A). MS (ES+): mass calculated for $C_{27}H_{23}F_3N_2O_2$, 464.17; m/z found 465.0 [M+H]$^+$. $^1$H NMR (500 MHz, DMSO-$d_6$): 12.60 (br s, 1H), 7.65-7.63 (m, 4H), 7.56 (t, J=7.9 Hz, 1H), 7.23-7.13 (m, 7H), 6.79 (m, 2H), 6.19 (s, 1H), 5.23 (s, 2H), 4.17 (t, J=7.9 Hz, 1H), 3.32 (dd, J=7.5, 14.7 Hz, 1H), 3.03 (dd, J=8.2, 14.7 Hz, 1H), 2.30 (s, 3H).

Example 45

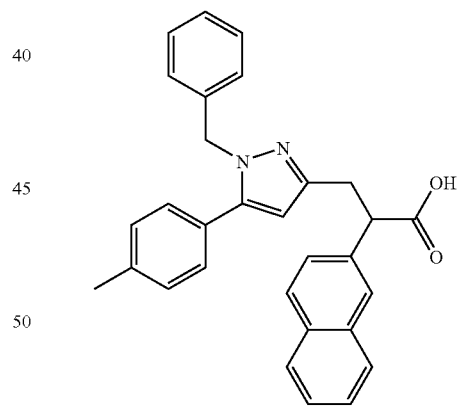

3-(1-Benzyl-5-p-tolyl-1H-pyrazol-3-yl)-2-naphthalen-2-yl-propionic acid

The title compound was prepared by Method 2: HPLC: $R_t$=10.13 (Method A). MS (ES+): mass calculated for $C_{30}H_{26}N_2O_2$, 446.20; m/z found 447.1 [M+H]$^+$. $^1$H NMR (500 MHz, DMSO-$d_6$): 12.42 (br s, 1H), 7.90-7.85 (m, 4H), 7.53-7.49 (m, 3H), 7.20-7.14 (m, 7H), 7.09 (t, J=7.6 Hz, 2H), 6.78 (d, J=7.3 Hz, 2H), 6.20 (s, 1H), 5.23 (s, 2H), 4.18 (t, J=7.8 Hz, 1H), 3.40 (dd, J=7.8, 14.8 Hz, 1H), 3.09 (dd, J=7.8, 14.7 Hz, 1H), 2.29 (s, 3H).

Example 46

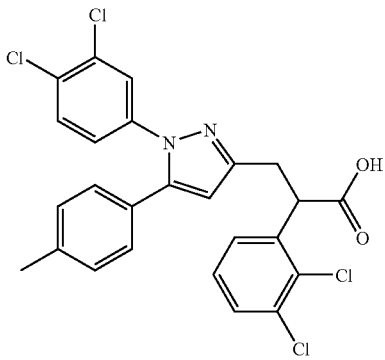

2-(2,3-Dichloro-phenyl)-3-[1-(3,4-dichloro-phenyl)-5-p-tolyl-1H-pyrazol-3-yl]-propionic acid

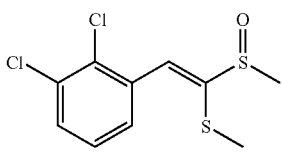

A. 1,2 Dichloro-3-(2-methanesulfinyl-2-methylsufanyl-vinyl)-benzene

To a stirred solution of methyl methylthiomethyl sulfoxide (4.97 g, 40.0 mmol) and 2,3-dichlorobenzaldehyde (5.00 g, 28.6 mmol) in 10 mL of THF was added 4 mL of triton-B (40% in MeOH). The resultant mixture was refluxed for 4 h. The solvent was removed under reduced pressure, and the residue was purified by silica gel chromatography (5:95 EtOAc/hexane) to afford 5.4 g (67.5%) of 1,2-dichloro-3-(2-methanesulfinyl-2-methylsufanyl-vinyl)-benzene. HPLC: $R_t$=8.99. (Method A). $^1$H NMR (400 MHz, CDCl$_3$): 7.86 (s, 1H), 7.73 (dd, J=8.4, 0.9 Hz, 1H), 7.47 (dd, J=9.0, 0.6 Hz, 1H), 7.38-7.23 (m, 1H), 2.83 (s, 3H), 2.24 (s, 3H).

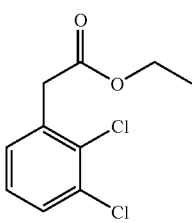

B. (2,3-Dichloro-phenyl)-acetic acid ethyl ester

A stirred solution of 1,2-dichloro-3-(2-methanesulfinyl-2-methylsufanyl-vinyl)-benzene (5.40 g, 19.3 mmol) in 30 mL of MeOH at 0° C. was bubbled with HCl gas for 10 min and then was allowed to warm to rt and stir for 0.5 h. The solvent was removed under reduced pressure, and the residue was purified by silica gel chromatography (5:95 EtOAc/hexane) to afford 3.08 g (73.4%) of (2,3-Dichloro-phenyl)-acetic acid ethyl ester. HPLC: $R_t$=9.88 (Method A). $^1$H NMR (400 MHz, CDCl$_3$): 7.40 (dd, J=7.2, 2.7 Hz, 1H), 7.20-7.15 (m, 2H), 4.18 (dd, J=14.2, 7.0 Hz, 2H), 3.79 (s, 2H), 1.26 (t, J=6.8, Hz, 2H).

C. 2-(2,3-Dichloro-phenyl)-3-[1-(3,4-dichloro-phenyl)-5-p-tolyl-1H-pyrazol-3-yl]-propionic acid The title compound was prepared by Method 2 (Scheme A) from the product of Step B and the appropriate pyrazole bromide from Method 1: HPLC: $R_t$=3.89 (Method B). MS (ES+): mass calculated for C$_{25}$H$_{18}$Cl$_4$N$_2$O$_2$, 518.01; m/z found 519.0 [M+H]$^+$. $^1$H NMR (400 MHz, CDCl$_3$): 7.43 (d, J=2.3 Hz, 1H), 7.40 (dd, J=8.6, 1.5 Hz, 1H), 7.36 (dd, J=7.8, 1.2 Hz, 1H), 7.31 (d, J=8.1 Hz, 1H), 7.21 (t, J=8.1 Hz, 2H), 7.12 (d, J=8.8 Hz, 2H), 7.05-7.02 (m, 2H), 6.96 (dd, J=8.6, 2.5 Hz, 1H), 6.18 (s, 1H), 4.76 (dd, J=8.3, 6.6 Hz, 1H), 3.52 (dd, J=15.4, 8.1 Hz, 1H), 3.16 (dd, J=14.9, 7.3 Hz, 1H), 2.35 (s, 3H).

Method 3

Synthesis of 4-Oxo-2-aryl-pentanoic Acids, Such as

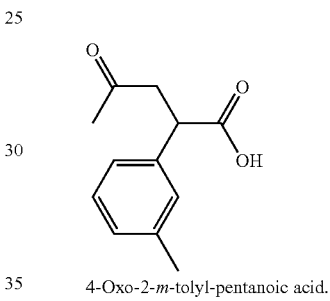

4-Oxo-2-*m*-tolyl-pentanoic acid.

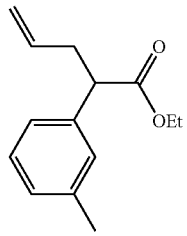

A. 2-m-Tolyl-pent-4-enoic acid ethyl ester

To a stirred solution 3-methylphenylacetic acid ethyl ester (50.0 g, 0.281 mol) in DMF (500 mL) at 0° C. under N$_2$ was added 60% NaH (12.3 g, 0.308 mol) in small portions. The mixture was allowed to warm to rt and stir for 1.5 h. In a second vessel, a stirred solution of allyl bromide (72.7 mL, 0.843 mol) in DMF (300 mL) was cooled to −42° C. (acetonitrile/CO$_2$) under N$_2$, and the enolate mixture was slowly added to this solution by cannula. After the addition was complete, the mixture was allowed to warm to rt and stir for 2 h. The mixture was then diluted with H$_2$O (100 mL) and the majority of the DMF was removed under reduced pressure. The mixture was then further diluted with H$_2$O (400 mL) and EtOAc (500 mL), and the layers were separated. The aqueous phase was extracted with EtOAc (3×150 mL) and the combined organic extracts were dried over Na$_2$SO$_4$ and filtered, and the solvent was removed under reduced pressure. Purification on silica gel (0-10% EtOAc in hexane) gave 57.4 g (93%) of desired ester as a light yellow oil. TLC (silica, 10%

EtOAc/hexane): $R_f$=0.7. $^1$H NMR (400 MHz, CDCl$_3$): 7.21 (t, J=7.8 Hz, 1H), 7.12 (s, 1H), 7.08 (t, J=7.8 Hz, 2H), 5.79-5.66 (m, 1H), 5.11-5.04 (m, 1H), 5.02-4.98 (m, 1H), 4.20-4.02 (m, 2H), 3.62-3.54 (m, 1H), 2.86-2.74 (m, 1H), 2.53-2.44 (m, 1H), 2.34 (s, 3H), 1.21 (t, J=7.1 Hz, 3H).

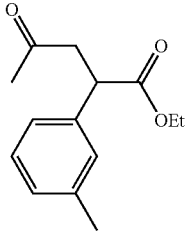

B. 4-Oxo-2-m-tolyl-pentanoic acid ethyl ester

A slow stream of O$_2$ was bubbled through a stirred suspension of 2-m-tolyl-pent-4-enoic acid ethyl ester (57.0 g, 0.261 mol), CuCl (25.7 g, 0.261 mol) and PdCl$_2$ (9.26 g, 0.052 mol) in 8:1 DMF/H$_2$O (130 mL) for 14 h. The mixture was diluted with CH$_2$Cl$_2$ (500 mL) and 9:1 saturated NH$_4$Cl/NH$_4$OH (500 mL). The mixture was stirred for 1 h and then filtered through a pad of celite. The layers were separated, and the organic phase was washed with 9:1 saturated NH$_4$Cl/NH$_4$OH (200 mL). The combined aqueous phases were extracted with CH$_2$Cl$_2$ (3×150 mL). The organics were then dried over Na$_2$SO$_4$ and filtered, and the solvent was removed under reduced pressure. Purification on silica gel (0-20% EtOAc in hexane) gave 34.4 g (56%) of desired ketone as a light yellow oil. TLC (silica, 10% EtOAc/hexane): $R_f$=0.3. $^1$H NMR (400 MHz, CDCl$_3$): 7.20 (t, J=7.6 Hz, 1H), 7.10-7.03 (m, 3H), 4.20-4.00 (m, 3H), 3.37 (dd, J=10.4, 17.9 Hz, 1H), 2.69 (dd, J=4.3, 17.9 Hz, 1H), 2.33 (s, 3H), 2.17 (s, 3H), 1.20 (t, J=7.3 Hz, 3H).

C. 4-Oxo-2-m-tolyl-pentanoic acid

To a stirred solution of 4-oxo-2-m-tolyl-pentanoic acid ethyl ester (34.0 g, 145 mmol) in 3:1:1 THF/MeOH/H$_2$O (300 mL) was added LiOH·H$_2$O (30.5 g, 0.726 mol) and the mixture was stirred overnight at rt. The mixture was then heated to 65° C. for 2 h, cooled to rt, and was diluted with H$_2$O (250 mL) and 20% diethyl ether/hexane. The layers were separated, and the aqueous layer was adjusted to pH 1 with concd HCl at 0° C. The aqueous phase was then extracted with EtOAc (3×200 mL), dried over Na$_2$SO$_4$ and filtered, and then the solvent was removed under reduced pressure to afford 28.4 g (95%) of crude acid as a light yellow solid. TLC (silica, 10% EtOAc/hexane): $R_f$=0.3. $^1$H NMR (400 MHz, CDCl$_3$): 7.21 (t, J=7.6 Hz, 1H), 7.11-7.05 (m, 3H), 4.08 (dd. J=4.0, 10.2 Hz, 1H), 3.35 (dd. J=10.2, 18.2 Hz, 1H), 2.70 (dd. J=4.0, 18.2 Hz, 1H), 2.34 (s, 3H), 2.17 (s, 3H).

Method 4

Synthesis of 3-(1,5-Disubstituted-1H-pyrazol-3-yl)-2-aryl-propionic Acids and 3-(2,5-Disubstituted-4H-pyrazol-5-yl)-2-aryl-propionic Acids, Such as

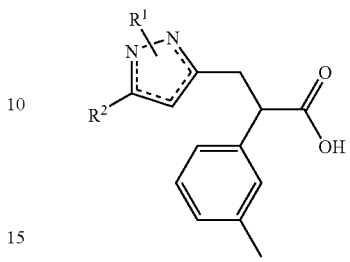

Scheme E. To a slurry of 10.0 g of 4-sulfamylbenzoyl AM resin (NovaBiochem, 1.21 mmol/g) in 1:1 THF/CH$_2$Cl$_2$ (70 mL) was added DMAP (0.201 g, 1.65 mmol), 4-oxo-2-m-tolyl-pentanoic acid (E1) (17.7 g, 86.0 mmol) prepared by Method 3, N,N-diisopropylethylamine (7.51 mL, 43.0 mmol), and diisopropylcarbodiimide (6.72 mL, 43.0 mmol). The mixture was shaken overnight, and the filtrate was drained under reduced pressure. The resin was then washed (3×5 mL) with 1:1 THF/CH$_2$Cl$_2$, MeOH, DMF, MeOH, and THF and then dried under vacuum overnight to give the coupled resin E2 (theoretical loading: 0.98 mmol/g). The resin was then loaded into a 48-position Bohdan miniblock (~200 mg/well) along with the appropriate ester E5 (3.60 mmol, 18 equiv), and the inert atmosphere manifold was added (N$_2$). To each well was then added 1.0 M NaHMDS in THF (3.63 mmol, 18 equiv), and the block was heated to 50° C. overnight. The block was cooled, the solvent was removed under reduced pressure, and each well was washed (3×5 mL) with cold 4:1 AcOH/H$_2$O, THF, DMF, and MeOH. After the resin was dried under reduced pressure, the appropriate hydrazines E6 (2.40 mmol, 12.equiv) were then loaded into the wells of the block followed by MeOH (3.0 mL), providing a unique resin in each of the 48 wells of the block, and the reaction mixtures were heated to 65° C. and shaken overnight. The block was cooled, the solvent was removed under reduced pressure, and each well was washed (3×5 mL) with THF,-MeOH, and THF. After the resin was dried under reduced pressure, THF (1.0 mL) was added to each well followed by 1.0 M (trimethylsilyl)diazomethane (TMSCHN$_2$) in hexane (1.0 mmol, 10 equiv), and the block was shaken for 1 h. The filtrates were drained under reduced pressure, and the TMSCHN$_2$ treatment was repeated. The resin was then diluted with 3:1:1 THF/MeOH/H$_2$O (2.5 mL/well), LiOH·H$_2$O (1.0 mmol, 10 equiv) was added to each well, and the block was heated to 50° C. overnight. The block was cooled and the reaction mixtures were drained into a 48-well Beckman plate. The resin was then washed with MeOH, DMF and THF (3.0 mL each), each wash being drained into a 48-well plate, and the solvent was removed under reduced pressure. The plated compounds were dissolved in DMF (1.5 mL total volume/well), and identical compounds were combined and purified on a Gilson 215 prep-HPLC system (Method G) giving the desired acids (A9) (0.5-7.0 mg, isolated as TFA salt) as well as, in some cases, the other regioisomer of the pyrazole. The 1,5-disubstituted and the 2,5-disubstituted pyrazole regioisomers were isolated and characterized, and the isomer structures were confirmed by assignment of COSY and NOESY spectra. For the 2,5-disubstituted pyrazole regioisomer, enhancement was observed between the N-aryl protons and the alkyl side-chain.

Example 47

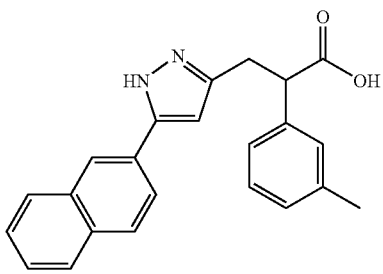

3-(5-Naphthalen-2-yl-1H-pyrazol-3-yl)-2-m-tolyl-propionic acid

The title compound was prepared by Method 4: HPLC: $R_t$=2.91 (Method B). MS (ES+): mass calculated for $C_{23}H_{20}N_2O_2$, 356.15; m/z found, 357.2 [M+H]$^+$. $^1$H NMR (400 MHz, CDCl$_3$): 8.08 (s, 1H), 7.87-7.70 (m, 4H), 7.49-7.41 (m, 2H), 7.36-7.23 (m, 4H), 7.19 (d, J=7.1 Hz, 1H), 6.58 (s, 1H), 3.95 (d, J=11.9 Hz, 1H), 3.66 (t, J=12.6 Hz, 1H), 3.05 (d, J=13.6 Hz, 1H), 2.42 (s, 3H).

Example 48

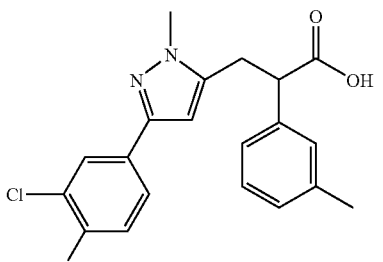

3-[5-(3,4-Dichloro-phenyl)-2-methyl-2H-pyrazol-3-yl]-2-m-tolyl-propionic acid

The title compound was prepared by Method 4: HPLC: $R_t$=3.30 (Method B). MS (ES+): mass calculated for $C_{20}H_{18}Cl_2N_2O_2$, 388.07; m/z found, 388.9 [M+H]$^+$. $^1$H NMR (400 MHz, CDCl$_3$): 7.81 (d, J=2.0 Hz, 1H), 7.54 (dd, J=8.3, 2.0 Hz, 1H) 7.42 (d, J=8.0 Hz, 1H), 7.16-7.10 (m, 4H), 6.30 (s, 1H), 3.92 (dd, J=8.9, 6.1 Hz, 1H), 3.74 (s, 3H), 3.45 (dd, J=15.4, 8.9 Hz, 1H), 3.00 (dd, J=15.4, 6.1 Hz, 1H), 2.35 (s, 3H).

Example 49

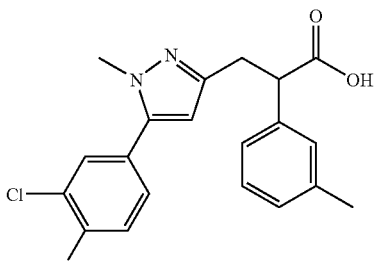

3-[5-(3,4-Dichloro-phenyl)-1-methyl-1H-pyrazol-3-yl]-2-m-tolyl-propionic acid

The title compound was prepared by Method 4: HPLC: $R_t$=3.18 (Method B). MS (ES+): mass calculated for $C_{20}H_{18}Cl_2N_2O_2$, 388.07; m/z found, 388.9 [M+H]$^+$. $^1$H NMR (400 MHz, CDCl$_3$): 7.50 (d, J=8.3 Hz, 1H), 7.45 (d, J=2.3 Hz, 1H), 7.24-7.14 (m, 4H), 7.10 (d, J=7.6 Hz, 1H), 6.03 (s, 1H), 4.03 (dd, J=9.7, 5.5 Hz, 1H), 3.79 (s, 3H), 3.46 (dd, J=14.9, 9.7 Hz, 1H), 3.03 (dd, J=14.9, 5.5 Hz, 1H), 2.34 (s, 3H).

Example 50

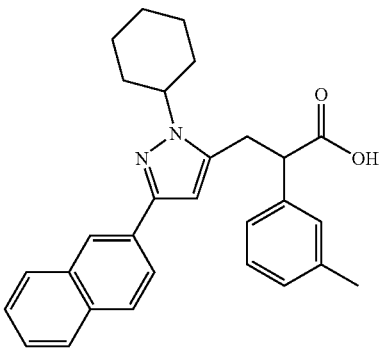

3-(2-Cyclohexyl-5-naphthalen-2-yl-2H-pyrazol-3-yl)-2-m-tolyl-propionic acid

The title compound was prepared by Method 4: HPLC: $R_t$=3.71 (Method B). MS (ES+): mass calculated for $C_{29}H_{30}N_2O_2$, 438.23; m/z found, 439.2 [M+H]$^+$. $^1$H NMR (400 MHz, CDCl$_3$): 8.20 (s, 1H), 7.88-7.78 (m, 4H), 7.51-7.44 (m, 2H), 7.28-7.22 (m, 1H), 7.18-7.11 (m, 3H), 6.48 (s, 1H), 4.08 (app tt, J=11.9, 3.5 Hz, 1H), 3.97 (dd, J=8.5, 6.8 Hz, 1H), 3.52 (dd, J=15.4, 8.5 Hz, 1H), 3.08 (dd, J=15.4, 6.8 Hz, 1H), 2.35 (s, 3H), 2.15-1.99 (m, 2H), 1.97-1.80 (m, 3H), 1.75-1.58 (m, 2H), 1.45-1.16 (m, 3H).

Example 51

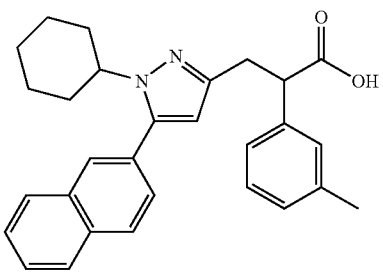

3-(1-Cyclohexyl-5-naphthalen-2-yl-1H-pyrazol-3-yl)-2-m-tolyl-propionic acid

The title compound was prepared by Method 4: HPLC: $R_t$=3.56 (Method B). MS (ES+): mass calculated for $C_{29}H_{30}N_2O_2$, 438.23; m/z found, 439.2 [M+H]$^+$. $^1$H NMR (400 MHz, CDCl$_3$): 7.95-7.85 (m, 3H), 7.79 (s, 1H), 7.60-7.55 (m, 2H), 7.38 (dd, J=8.3, 1.8 Hz, 1H), 7.24-7.12 (m, 3H), 7.08 (d, J=7.3 Hz, 1H), 6.10 (s, 1H), 4.18 (dd, J=9.5, 4.8 Hz, 1H), 4.14 (app tt, J=11.6, 3.8 Hz, 1H), 3.53 (dd, J=15.3, 9.5 Hz, 1H), 3.17 (dd, J=15.3, 4.8 Hz, 1H), 2.33 (s, 3H), 2.14-1.77 (m, 6H), 1.67-1.58 (m, 1H), 1.31-1.11 (m, 3H).

Example 52

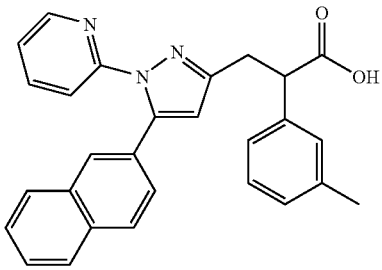

3-(5-Naphthalen-2-yl-1-pyridin-2-yl-1H-pyrazol-3-yl)-2-m-tolyl-propionic acid

The title compound was prepared by Method 4: HPLC: $R_t$=3.21 (Method B). MS (ES+): mass calculated for $C_{28}H_{23}N_3O_2$, 433.18; m/z found, 434.2 [M+H]$^+$. $^1$H NMR (400 MHz, CDCl$_3$): 8.34 (d, J=4.3 Hz, 1H), 7.83-7.62 (m, 5H), 7.52-7.45 (m, 2H), 7.33 (d, J=8.1 Hz,1H), 7.29-7.14 (m, 5H), 7.13-7.03 (m,1H), 6.34 (s, 1H), 4.17 (dd, J=9.6, 5.5 Hz, 1H), 3.60 (dd, J=14.9, 9.6 Hz, 1H), 3.16 (dd, J=14.9, 5.5 Hz, 1H), 2.35 (s, 3H).

Example 53

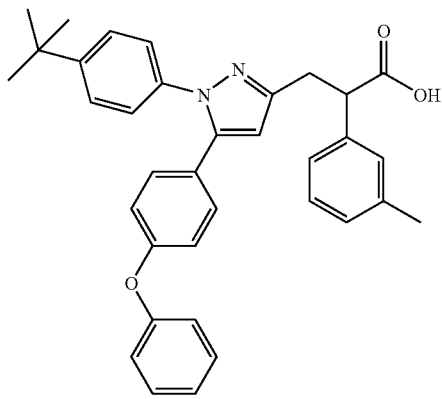

3-[1-(4- tert-Butyl-phenyl)-5-(4-phenoxy-phenyl)-1H-pyrazol-3-yl]-2-m-tolyl-propionic acid The title compound was prepared by Method 4: HPLC: $R_t$=3.87 (Method B). MS (ES+): mass calculated for $C_{35}H_{34}N_2O_3$, 530.26; m/z found, 531.2 [M+H]$^+$. $^1$H NMR (400 MHz, CDCl$_3$): 7.40-7.05 (m, 13H), 7.02 (d, J=7.9 Hz, 2H), 6.87 (d, J=8.8 Hz, 2H), 6.20 (s, 1H), 4.10 (dd, J=9.5, 5.6 Hz, 1H), 3.54 (dd, J=14.9, 9.5 Hz, 1H), 3.12 (dd, J=14.9, 5.6 Hz, 1H), 2.34 (s, 3H), 1.29 (s, 9H).

Example 54

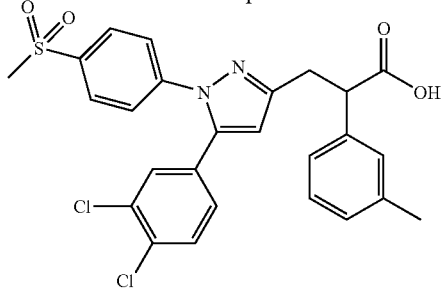

3-[5-(3,4-Dichloro-phenyl)-1-(4-methanesulfonyl-phenyl)-1H-pyrazol-3-yl]-2-m-tolyl-propionic acid The title compound was prepared by Method 4: HPLC: $R_t$=3.24 (Method B). MS (ES+): mass calculated for $C_{26}H_{22}Cl_2N_2O_4S$, 528.07; m/z found, 529.1 [M+H]$^+$. $^1$H NMR (400 MHz, CDCl$_3$): 7.90 (d, J=8.6 Hz, 2H), 7.43 (d, J=8.6 Hz, 2H), 7.39 (d, J=8.5 Hz, 1H), 7.35 (d, J=2.0 Hz, 1H), 7.28-7.17 (m, 3H), 7.13 (d, J=7.4 Hz, 1H), 6.92 (dd, J=8.4, 2.0 Hz, 1H), 6.27 (s, 1H), 4.12 (dd, J=9.5, 5.8 Hz, 1H), 3.54 (dd, J=15.2, 9.5 Hz, 1H), 3.11 (dd, J=15.2, 5.8 Hz, 1H), 3.06 (s, 3H), 2.34 (s, 3H).

Example 55

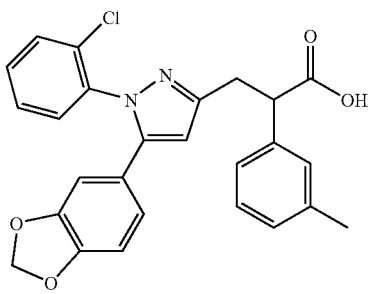

3-[5-Benzo[1,3]dioxol-5-yl-1-(2-chloro-phenyl)-1H-pyrazol-3-yl]-2-m-tolyl-propionic acid The title compound was prepared by Method 4: HPLC: $R_t$=3.12 (Method B). MS (ES+): mass calculated for $C_{26}H_{21}ClN_2O_4$, 460.12; m/z found, 461.0 [M+H]$^+$. $^1$H NMR (400 MHz, CDCl$_3$): 7.44-7.14 (m, 7H), 7.09 (d, J=7.1 Hz, 1H), 6.66 (d, J=7.8 Hz, 1H), 6.61-6.55 (m, 2H), 6.18 (s, 1H), 5.92 (s, 2H), 4.09 (dd, J=8.9, 6.3 Hz, 1H), 3.52 (dd, J=14.9, 8.9 Hz, 1H), 3.14 (dd, J=14.9, 6.3 Hz, 1H), 2.33 (s, 3H).

Example 56

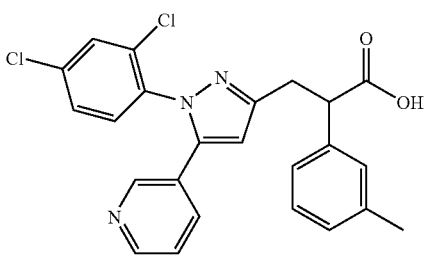

3-[1-(2,4-Dichloro-phenyl)-5-pyridin-3-yl-1H-pyrazol-3-yl]-2-m-tolyl-propionic acid The title compound was prepared by Method 4: HPLC: $R_t$=2.50 (Method B). MS (ES+): mass calculated for $C_{24}H_{19}Cl_2N_3O_2$, 451.09; m/z found, 452.0 [M+H]$^+$. $^1$H NMR (400 MHz, CDCl$_3$): 8.60 (s, 1H), 8.58 (s, 1H), 7.56 (d, J=8.1 Hz, 1H), 7.44-7.30 (m, 4H), 7.24-7.15 (m, 3H), 7.10 (d, J=7.4 Hz, 1H), 6.44 (s, 1H), 4.09 (dd, J=9.3, 6.0 Hz, 1H), 3.55 (dd, J=14.9, 9.3 Hz, 1H), 3.15 (dd, J=14.9, 6.0 Hz, 1H), 2.34 (s, 3H).

Example 57

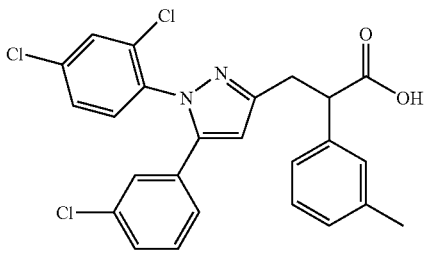

3-[5-(3-Chloro-phenyl)-1-(2,4-dichloro-phenyl)-1H-pyrazol-3-yl]-2-m-tolyl-propionic acid The title compound was prepared by Method 4: HPLC: $R_t$=3.53 (Method B).

MS (ES+): mass calculated for $C_{25}H_{19}Cl_3N_2O_2$, 484.05; m/z found, 485.1 [M+H]$^+$. $^1$H NMR (400 MHz, CDCl$_3$): 7.42 (s, 1H), 7.32-7.13 (m, 8H), 7.10 (d, J=7.1 Hz, 1H), 6.90 (d, J=7.6 Hz, 1H), 6.26 (s, 1H), 4.10 (dd, J=9.1, 6.3 Hz, 1H), 3.52 (dd, J=14.9, 9.1 Hz, 1H), 3.13 (dd, J=14.9, 6.3 Hz, 1H), 2.34 (s, 3H).

Method 5

Synthesis of
4-(4-Oxo-2-aryl-pentanoylsulfamoyl)-benzoic Acids,
such as

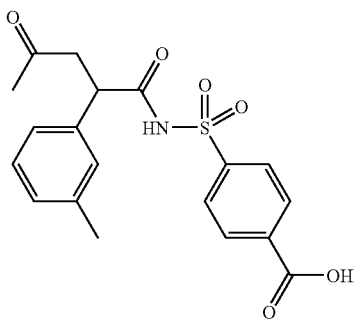

4-(4-Oxo-2-m-tolyl-pentanoylsulfamoyl)-benzoic acid

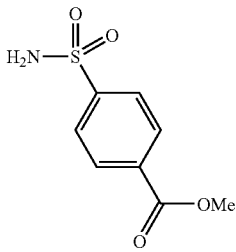

A. 4-Sulfamoyl-benzoic acid methyl ester

To a stirred suspension of 4-sulfamoyl-benzoic acid (25.0 g, 0.124 mol) in 4:1 CH$_2$Cl$_2$/MeOH at rt was added 1.0 M TMSCHN$_2$ in hexane (175 mL), and the reaction mixture was allowed to stir for 2 h. The mixture was diluted with 1N NaOH (100 mL) and CH$_2$Cl$_2$ (150 mL), and the layers were separated. The organic layer was dried over Na$_2$SO$_4$, then filtered, and the solvent was removed under reduced pressure to afford the desired ester (25.2 g, 95%), which was used without further purification. $^1$H NMR (400 MHz, DMSO-d$_6$): 8.14 (d, J=8.1 Hz, 2H), 7.96 (d, J=8.1 Hz, 2H), 7.58 (s, 2H), 3.90 (s, 3H).

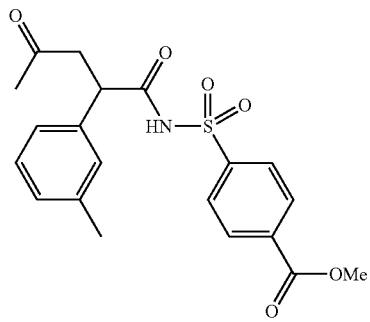

B. 4-(4-Oxo-2-m-tolyl-pentanoylsulfamoyl)-benzoic acid methyl ester

To a stirred solution of 4-sulfamoyl-benzoic acid methyl ester (6.01 g, 27.8 mmol), 4-oxo-2-m-tolyl-pentanoic acid (6.35 g, 30.7 mmol), N,N-diisopropylethylamine (12.2 mL, 69.5 mmol), and DMAP (5 mole %) in CH$_2$Cl$_2$ (275 mL) at rt under N$_2$ was added bromo-tripyrrolidino-phosphonium hexafluorophosphate (PyBroP) (18.1 g, 38.9 mmol), and the reaction mixture was allowed to stir overnight. The mixture was diluted with 1M HCl (100 mL) and CH$_2$Cl$_2$ (150 mL), and the layers were separated. The organic phase was washed with 1M HCl (1×100 mL), 1N NaOH (1×100 mL) and brine (1×100 mL). The organic layer was dried over Na$_2$SO$_4$, and then filtered, and the solvent was removed under reduced pressure. Purification on silica gel (0-15% EtOAc in hexane) gave 12.0 g (99%) of desired ester as a white solid. $^1$H NMR (400 MHz, CDCl$_3$): 8.15 (d, J=8.6 Hz, 2H), 7.99 (d, J=8.6 Hz, 2H), 7.18 (t, J=7.6 Hz, 1H), 7.10 (d, J=7.6 Hz, 1H), 6.87 (m, 2H), 3.97 (s, 3H), 3.93 (dd. J=4.3 and 9.5 Hz, 1H), 3.29 (dd. J=9.5 and 18.1 Hz, 1H), 2.60 (dd. J=4.3 and 18.1 Hz, 1H), 2.28 (s, 3H), 2.07 (s, 3H).

C. 4-(4-Oxo-2-m-tolyl-pentanoylsulfamoyl)-benzoic acid

To a stirred solution of 4-(4-oxo-2-m-tolyl-pentanoylsulfamoyl)-benzoic acid methyl ester (12.0 g, 27.7 mmol) in 3:1:1 THF/MeOH/H$_2$O (110 mL) was added LiOH·H$_2$O (5.84 g, 139 mmol), and the mixture was stirred overnight at rt. The mixture was then heated to 65° C. for 2 h, cooled to rt, and then was diluted with H$_2$O (100 mL) and 20% diethyl ether/hexane. The layers were separated, and the aqueous layer was adjusted to pH 1 with concd HCl at 0° C. The aqueous phase was then extracted with EtOAc (3×200 mL), dried over Na$_2$SO$_4$, and filtered, and the solvent was removed under reduced pressure to afford 10.6 g (96%) of crude acid as a white solid. TLC (silica, 5% MeOH—CH$_2$Cl$_2$): R$_f$=0.2. $^1$H NMR (400 MHz, DMSO-d$_6$): 8.06 (d, J=8.1 Hz, 2H), 7.96 (d, J=8.1 Hz, 2H), 7.16 (t, J=7.6 Hz, 1H), 7.05 (d, J=7.6 Hz, 1H), 6.93 (d, J=7.6 Hz, 1H), 6.82 (s, 1H), 3.89 (dd. J=3.9, 10.6 Hz, 1H), 3.14 (dd. J=10.6, 18.3 Hz, 1H), 2.70 (dd. J=3.9, 18.3 Hz, 1H), 2.19 (s, 3H), 2.00 (s, 3H).

Method 6

Synthesis of 3-(1,5-Disubstituted-1H-pyrazol-3-yl)-2-aryl-propionic Acids and 3-(2,5-Disubstituted-4H-pyrazol-5-yl)-2-aryl-propionic Acids, such as

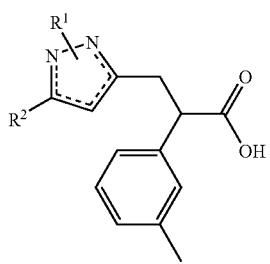

Scheme F. To a slurry of 5.0 g of 4-aminomethyl macroporous polystyrene resin (ArgoPore-NH$_2$—HL, 1.22 mmol/g) in THF (30 mL) was added HOBt (1.66 g, 12.2 mmol), 4-(4-oxo-2-m-tolyl-pentanoylsulfamoyl)-benzoic acid (E1) (4.81 g, 12.2 mmol) prepared by Method 5, and diisopropylcarbodiimide (1.91 mL, 12.2 mmol). The mixture was shaken overnight and the filtrate was drained under reduced pressure. The resin was then washed (3×5 mL) with THF, CH$_2$Cl$_2$, MeOH, DMF and THF and then dried under vacuum overnight to give the coupled resin F3 (~0.75 mmol/g based on elemental analysis of sulfur). The resin was then loaded into a 48-position Bohdan miniblock (~230 mg/well) along with the appropriate ester F6 (2.20 mmol, 12.0 equiv), and the inert atmosphere manifold was added (N$_2$). To each well was then added 1.0 M NaHMDS in THF (1.80 mmol, 12 equiv), and the block was heated to 50° C. overnight. The block was cooled, the solvent was removed under reduced pressure, and each well was washed (3×5 mL) with 5% TFA/THF, H$_2$O, THF, DMF, and MeOH. After the resin F4 was dried under reduced pressure, the appropriate hydrazines F7 (1.80 mmol, 10 equiv) were added to the wells followed by MeOH (3.0 mL) and N,N-diisopropylethylamine (0.32 mL, 1.8 mmol, for aryl hydrazines) or H$_2$SO$_4$ (2 drops, for alkyl hydrazines), creating a unique product in each well of the 48-well miniblock, and the reaction mixtures were heated to 65° C. overnight. The block was cooled, the solvent was removed under reduced pressure, and each well was washed (3×5 mL) with 5% TFA/THF, THF, MeOH, DMF and THF. After the resin F5 was dried under reduced pressure, THF (1.0 mL) was added to each well followed by 1.0 M TMSCHN$_2$ in hexane (1.0 mL, 14.0 equiv), and the block was shaken for 1 h. The filtrates were drained under reduced pressure and the TMSCHN$_2$ procedure was repeated. The resin was then diluted with 2:1 2N NaOH/THF (2.5 mL/well), and the block was heated to 50° C. overnight. The block was cooled, and the reaction mixtures were drained into a 48-well Beckman plate. The resin was then washed with MeOH, DMF and THF (3.0 mL each), each wash being drained into a 48-well plate, and the solvent was removed under reduced pressure. The plated compounds were dissolved in DMF (1.5 mL total volume/well), and identical compounds were combined and purified on a Gilson 215 prep-HPLC system (Method G) giving the desired acids (A9) (3.0-11.0 mg, isolated as TFA salt) as well as, in some cases, the other regioisomer of the pyrazole. The 1,5-disubstituted and the 2,5-disubstituted pyrazole regioisomers were isolated and characterized, and the isomer structures were confirmed by assignment of COSY and NOESY spectra. For the 2,5-disubstituted pyrazole regioisomer, enhancement was observed between the N-aryl protons and the alkyl side-chain.

Example 58

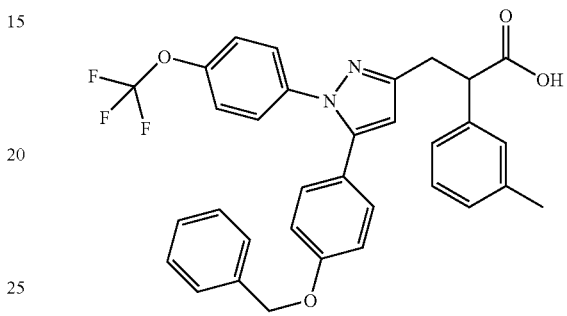

3-[5-(4-Benzyloxy-phenyl)-1-(4-trifluoromethoxy-phenyl)-1H-pyrazol-3-yl]-2-m-tolyl-propionic acid The title compound was prepared by Method 6: HPLC: R$_t$=3.58 (Method 8). MS (ES+): mass calculated for C$_{33}$H$_{27}$F$_3$N$_2$O$_4$, 572.19; m/z found, 573.5 [M+H]$^+$. $^1$H NMR (400 MHz, CDCl$_3$): 7.48-7.02 (m, 15H), 6.90 (d, J=8.6 Hz, 2H), 6.18 (s, 1H), 5.05 (s, 2H), 4.11 (dd, J=9.6, 5.6 Hz, 1H), 3.53 (dd, J=14.9, 9.6 Hz, 1H), 3.11 (dd, J=14.9, 5.6 Hz, 1H), 2.34 (s, 3H).

Example 59

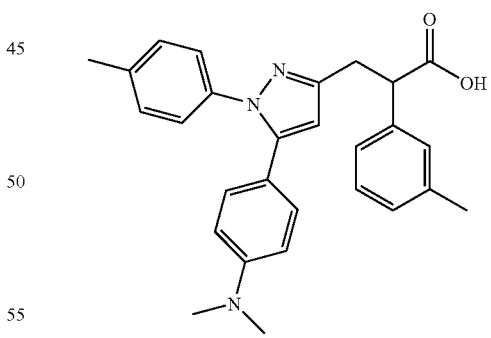

3-[5-(4-Dimethylamino-phenyl)-1-p-tolyl-1H-pyrazol-3-yl]-2-m-tolyl-propionic acid The title compound was prepared by Method 6: HPLC: R$_t$=2.65 (Method B). MS (ES+): mass calculated for C$_{28}$H$_{29}$N$_3$O$_2$, 439.23; m/z found, 440.3 [M+H]$^+$. $^1$H NMR (400 MHz, CDCl$_3$): 7.24-7.03 (m, 12H), 6.24 (s, 1H), 4.15 (dd, J=9.9, 5.6 Hz, 1H), 3.54 (dd, J=14.9, 9.9 Hz, 1H), 3.30 (s, 3H), 3.14 (dd, J=14.9, 5.6 Hz, 1H), 2.37 (s, 3H), 2.36 (s, 6H).

Example 60

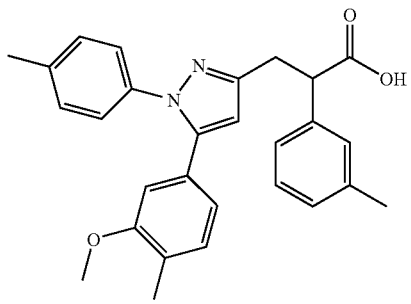

3-[5-(3-Methoxy-4-methyl-phenyl)-1-p-tolyl-1H-pyrazol-3-yl]-2-m-tolyl-propionic acid The title compound was prepared by Method 6: HPLC: $R_t$=3.30 (Method B). MS (ES+): mass calculated for $C_{28}H_{28}N_2O_3$, 440.21; m/z found, 441.3 [M+H]$^+$. $^1$H NMR (400 MHz, CDCl$_3$): 7.24-7.08 (m, 8H), 7.02 (d, J=7.6 Hz, 1H), 6.69 (dd, J=7.6, 1.0 Hz, 1H), 6.54 (s, 1H), 6.21 (s, 1H), 4.14 (dd, J=9.4, 5.3 Hz, 1H), 3.58 (s, 3H), 3.54 (dd, J=15.0, 9.6 Hz, 1H), 3.14 (dd, J=15.0, 5.3 Hz, 1H), 2.35 (s, 3H), 2.34 (s, 3H), 2.18 (s, 3H).

Example 61

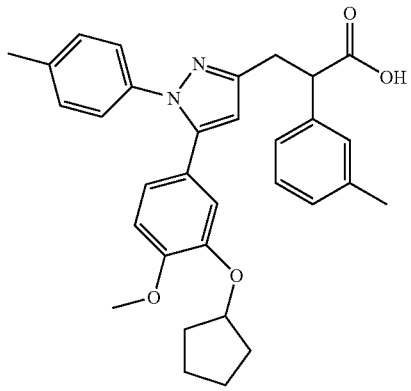

3-[5-(3-Cyclopentyloxy-4-methoxy-phenyl)-1-p-tolyl-1H-pyrazol-3-yl]-2-m-tolyl-propionic acid The title compound was prepared by Method 6: HPLC: $R_t$=3.33 (Method B). MS (ES+): mass calculated for $C_{32}H_{34}N_2O_4$, 510.25; m/z found, 511.4 [M+H]$^+$. $^1$H NMR (400 MHz, CDCl$_3$): 7.25-7.05 (m, 9H), 6.82-6.79 (m, 1H), 6.50 (d, J=2.0 Hz, 1H), 6.20 (s, 1H), 4.39 (app tt, J=4.8, 4.8 Hz, 1H), 4.15 (dd, J=9.8, 5.4 Hz, 1H), 3.83 (s, 3H), 3.55 (dd, J=15.0, 9.8 Hz, 1H), 3.14 (dd, J=15.0, 5.4 Hz, 1H), 2.35 (s, 3H), 2.34 (s, 3H), 1.76-1.68 (m, 2H), 1.67-1.59 (m, 4H), 1.55-1.45 (m, 2H).

Example 62

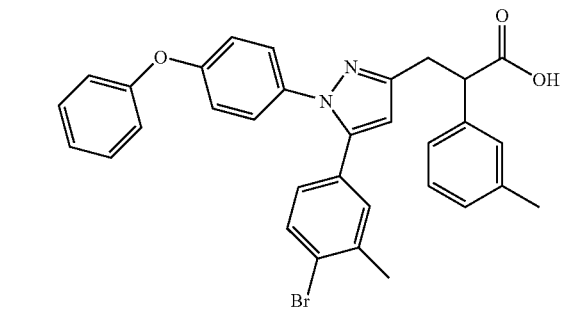

3-[5-(4-Bromo-3-methyl-phenyl)-1-(4-phenoxy-phenyl)-1H-pyrazol-3-yl]-2-m-tolyl-propionic acid The title compound was prepared by Method 6: HPLC: $R_t$=3.69 (Method B). MS (ES+): mass calculated for $C_{32}H_{27}BrN_2O_3$, 566.12; m/z found, 567.4 [M+H]$^+$. $^1$H NMR (400 MHz, CDCl$_3$): 7.47-6.91 (m, 15H), 6.80 (dd, J=8.1, 2.0 Hz, 1H), 6.23 (s, 1H), 4.13 (dd, J=9.7, 5.5 Hz, 1H), 3.54 (dd, J=14.9, 9.7 Hz, 1H), 3.13 (dd, J=14.9, 5.5 Hz, 1H), 2.35 (s, 3H), 2.33 (s, 3H).

Example 63

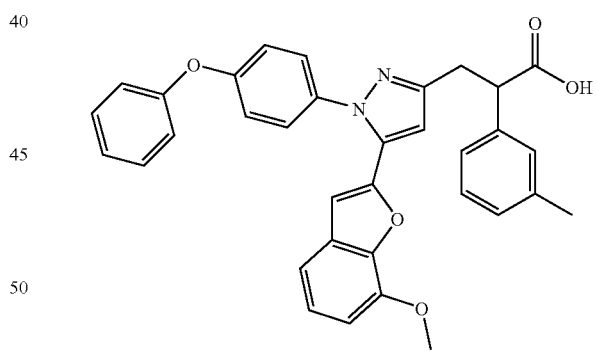

3-[5-(7-Methoxy-benzofuran-2-yl)-1-(4-phenoxy-phenyl)-1H-pyrazol-3-yl]-2-m-tolyl-propionic acid The title compound was prepared by Method 6: HPLC: $R_t$=3.53 (Method B). MS (ES+): mass calculated for $C_{34}H_{28}N_2O_5$, 544.20; m/z found, 545.4 [M+H]$^+$. $^1$H NMR (400 MHz, CDCl$_3$): 7.43-7.35 (m, 3H), 7.31-7.01 (m, 12H), 6.80 (d, J=7.8 Hz, 1H), 6.68 (s, 1H), 6.23 (s, 1H), 4.14 (dd, J=9.2, 5.8 Hz, 1H), 3.98 (s, 3H), 3.54 (dd, J=14.9, 9.2 Hz, 1H), 3.14 (dd, J=14.9, 5.8 Hz, 1H), 2.35 (s, 3H), 2.34 (s, 3H).

Example 64

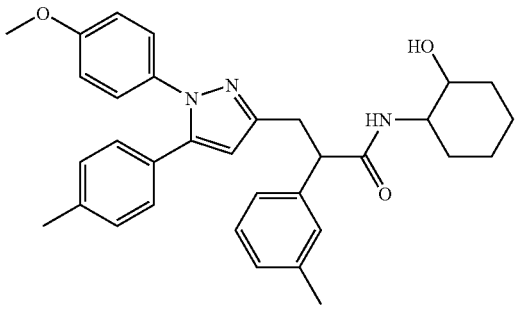

N-(2-Hydroxy-cyclohexyl)-3-[1-(4-methoxy-phenyl)-5-p-tolyl-1H-pyrazol-3-yl]-2-m-tolyl-propionamide To a solution of 3-[1-(4-methoxy-phenyl)-5-p-tolyl-1H-pyrazol-3-yl]-2-m-tolyl-propionic acid. (product of Method 2) (100 mg, 0.23 mmol), EDC (65 mg, 0.35 mmol), and HOBT (46 mg, 0.34 mmol) in DMF (4.0 mL) was added trans-2-aminocyclohexanol hydrochloride (52 mg, 0.34 mmol) and DIEA (0.20 mL, 1.2 mmol). The reaction mixture was stirred for 24 h, diluted with EtOAc, and washed with 1.0 N NaOH (2×25 mL), water (1×25 mL), 5% formic acid (2×25 mL), water (1×25 mL) and brine (1×25 mL). The organic layer was dried ($Na_2SO_4$) and the solvent was removed under reduced pressure. Reversed-phase HPLC afforded 40 mg (33%) of N-(2-hydroxy-cyclohexyl)-3-[1-(4-methoxy-phenyl)-5-p-tolyl-1H-pyrazol-3-yl]-2-m-tolyl-propionamide as a mixture of diastereomers. HPLC: $R_t$=3.17 (Method B). MS (ES+): mass calculated for $C_{33}H_{37}N_3O_3$, 523.28; m/z found 524.2 [M+H]$^+$. $^1$H NMR (400 MHz, CDCl$_3$): 7.92-7.85 (m, 1H), 7.26-7.10 (m, 6H), 7.05-7.01 (m, 3H), 6.94-6.91 (m, 2H), 6.32 (s, 0.5H), 6.29 (s, 0.5H), 4.42 (d, J=4.7 Hz, 0.5H), 4.34 (d, J=5.4 Hz, 0.5H), 3.90 (ddd, J=5.4, 9.4, 20.3 Hz, 1H), 3.76 (s, 3H), 3.24 (m, 0.5H), 3.17 (m, 0.5H), 2.85 (m, 1H), 2.30 (s, 1.5H), 2.28 (s, 1.5H), 2.27 (s, 3H), 1.75 (m, 1H), 1.55 (m, 2H), 1.13 (m, 4H), 0.97 (m, 1H).

Example 65

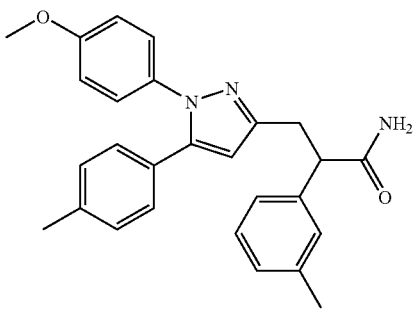

3-[1-(4-methoxy-phenyl)-5-p-tolyl-1H-pyrazol-3-yl]-2-m-tolyl-propionamide

A mixture of 3-[1-(4-methoxy-phenyl)-5-p-tolyl-1H-pyrazol-3-yl]-2-m-tolyl-propionic acid (product of Method 2) (0.10 g, 0.23 mmol) and CDI (85 mg, 0.52 mmol) in DMF (2.5 mL) was stirred at rt for 30 min. The solution was then cooled to 0° C., and ammonium carbonate (99 mg, 1.0 mmol) was added in portions. The reaction mixture was allowed to warm to rt and stirred for an additional 18 h. The reaction mixture was then diluted with water (25 mL) and extracted with EtOAc (3×25 mL). Organic layers were combined, washed with water (3×25 mL) and brine (1×25 mL) and dried with $Na_2SO_4$, and the solvent removed under reduced pressure giving 70 mg (71%) of the title compound. HPLC: $R_t$=9.38 (Method A). MS (ES+): mass calculated for $C_{27}H_{27}N_3O_2$, 425.21; m/z found 426.2 [M+H]$^+$. $^1$H NMR (400 MHz, DMSO-d$_6$): 7.50 (s, 1H), 7.22 (s, 1H), 7.20 (d, J=5.1 Hz, 2H), 7.14-7.10 (m, 3H), 7.04 (d, J=8.2 Hz, 2H), 6.93 (d, J=9.0 Hz, 2H), 6.82 (s, 1H), 6.27 (s, 1H), 3.89 (dd, J=5.5, 9.6 Hz, 1H), 3.76 (s, 3H), 3.34 (m, 1H), 2.82 (dd, J=5.5, 14.7 Hz, 1H), 2.29 (s, 3H), 2.27 (s, 3H).

Example 66

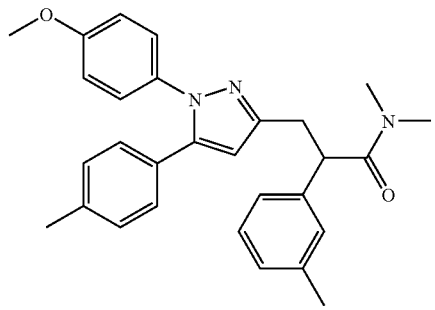

3-[1-(4-Methoxy-phenyl)-5-p-tolyl-1H-pyrazol-3-yl]-N,N-dimethyl-2-m-tolyl-propionamide The title compound was prepared analogously to Example 64, where N,N-dimethylamine hydrochloride was substituted for trans-2-aminocyclohexanol hydrochloride. HPLC: $R_t$=10.13 (Method A). MS (ES+): mass calculated for $C_{29}H_{31}N_3O_2$, 453.24; m/z found 454.2 [M+H]$^+$. $^1$H NMR (400 MHz, DMSO-d$_6$): 7.22-7.08 (m, 7H), 7.06-7.03 (m, 3H), 6.93 (d, J=9.0 Hz, 2H), 6.25 (s, 1H), 4.39 (dd, J=5.6, 9.0 Hz, 1H), 3.76 (s, 3H), 3.35 (dd, J=8.8, 14.8 Hz, 1H), 2.95 (s, 3H), 2.81 (s, 3H), 2.80 (dd, J=5.6, 14.8 Hz, 1H), 2.28 (s, 3H), 2.27 (s, 3H).

Example 67

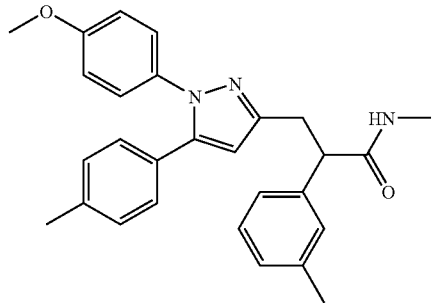

3-[1-(4-Methoxy-phenyl)-5-p-tolyl-1H-pyrazol-3-yl]-N-methyl-2-m-tolyl-propionamide The title compound was prepared analogously to Example 64, where N-methylamine hydrochloride was substituted for trans-2-aminocyclohexanol hydrochloride. HPLC: $R_t$=9.62 (Method A). MS (ES+): mass calculated for $C_{28}H_{29}N_3O_2$, 439.23; m/z found 440.2 [M+H]+. $^1$H NMR (400 MHz, DMSO-$d_6$): 7.99 (q, J=4.7 Hz, 1H), 7.20-7.18 (m, 3H), 7.14-7.09 (m, 4H), 7.04-7.01 (m, 3H), 6.93 (d, J=9.0 Hz, 2H), 6.22 (s, 1H), 3.85 (dd, J=5.8, 9.4 Hz, 1H), 3.76 (s, 3H), 3.35 (dd, J=9.4, 14.6 Hz, 1H), 2.86 (dd, J=5.7, 14.6 Hz, 1H), 2.54 (s, 1.5 H), 2.53 (s, 1.5 H), 2.329 (s, 3H), 2.27 (s, 3H).

Example 68

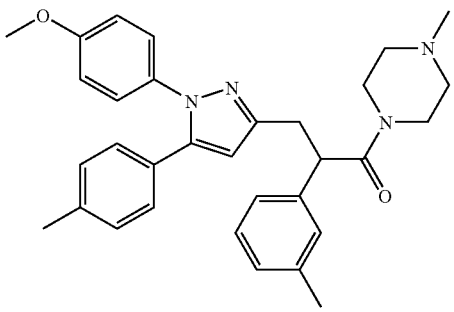

3-[1-(4-Methoxy-phenyl)-5-p-tolyl-1H-pyrazol-3-yl]-1-(4-methyl-piperazin-1-yl)-2-m-tolyl-propan-1-one The title compound was prepared analogously to Example 64, where N-methyl piperazine was substituted for trans-2-aminocyclohexanol hydrochloride. HPLC: $R_t$=8.37 (Method A). MS (ES+): mass calculated for $C_{32}H_{36}N_4O_2$, 508.28; m/z found 509.2 [M+H]+. $^1$H NMR (400 MHz, DMSO-$d_6$): 7.24-7.17 (m, 3H), 7.14-7.11 (m, 4H), 7.07 (d, J=7.6 Hz, 1H), 7.04 (d, J=8.2 Hz, 2H), 6.95 (d, J=9.0 Hz, 2H), 6.27 (s, 1H), 4.53 (dd, J=5.8, 8.8 Hz, 1H), 3.76 (s, 3H), 3.39 (dd, J=8.9, 15.0 Hz, 1H), 3.05 (br s, 4H), 2.90 (br s, 4H), 2.87 (dd, J=5.6, 15.0 Hz, 1H), 2.54 (s, 3H), 2.29 (s, 3H), 2.27 (s, 3H).

Example 69

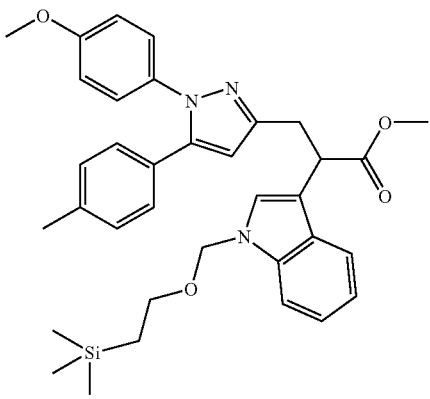

3-[1-(4-Methoxy-phenyl)-5-p-tolyl-1H-pyrazol-3-yl]-2-[1-(2-trimethylsilanyl-ethoxymethyl)-1H-indol-3-yl]-propionic acid methyl ester

A. [1-(2-Trimethylsilanyl-ethoxymethyl)-1H-indol-3yl]-acetic acid methyl ester To a suspension of sodium hydride (326 mg, 8.10 mmol) in DMF (13 mL) at 0° C. was added a solution of (1H-Indol-3-yl)-acetic acid methyl ester (1.0 g, 5.3 mmol) in DMSO (3 mL). The mixture was stirred at 0° C. for 30 min and then at rt for 1 h. The reaction mixture was cooled back down to 0° C., and SEMCl (1.35 mL, 8.41 mmol) was added neat. The reaction mixture was stirred at 0° C. for 15 min and then at rt for 1 h. The reaction mixture was then partitioned between water (200 mL) and diethyl ether (200 mL) followed by further extraction of the water layer with ether (2×200 mL) and drying of the combined organic layers with $Na_2SO_4$. After removal of the solvent under reduced pressure, the crude material was purified by flash chromatography (EtOAc/hexanes) giving 1.1 g (70%) of [1-(2-trimethylsilanyl-ethoxymethyl)-1H-indol-3yl]-acetic acid methyl ester. $^1$H NMR (400 MHz, $CDCl_3$): 7.65 (d, J=7.8 Hz, 1H), 7.46 (d, J=8.1, 1H), 7.26 (m, 1H), 7.22 (m, 2H), 5.51 (s, 2H), 3.83 (s, 2H), 3.76 (s, 3H), 3.53 (t, J=7.9 Hz, 2H), 0.94 (t, J=7.9 Hz, 2H), 0.0 (s, 9H).

B. 3-[1-(4-Methoxy-phenyl)-5-p-tolyl-1H-pyrazol-3-yl]-2-[1-(2-trimethylsilanyl-ethoxymethyl)-1H-indol-3-yl]-propionic acid methyl ester The title compound was synthesized via Method 2 from [1-(2-trimethylsilanyl-ethoxymethyl)-1H-indol-3yl]-acetic acid methyl ester (Step A, 0.17 g, 0.56 mmol), 3-bromoethyl-1-(4-methoxy-phenyl)-5-p-tolyl-1H-pyrazole (Method 1 pyrazole bromide, 0.10 g, 0.28 mmol), sodium hydride (22 mg, 0.56 mmol) and DMF (4.0 mL), yielding 140 mg (84%) of 3-[1-(4-methoxy-phenyl)-5-p-tolyl-1H-pyrazol-3-yl]-2-[1-(2-trimethylsilanyl-ethoxymethyl)-1H-indol-3-yl]-propionic acid methyl ester. HPLC: $R_t$=3.91 (Method B). MS (ES+): mass calculated for $C_{35}H_{41}N_3O_4Si$, 595.29; m/z found 596.27 [M+H]+. $^1$H NMR (400 MHz, DMSO-$d_6$): 7.76 (d, J=7.8 Hz, 1H), 7.65 (d, J=8.2 Hz, 1H), 7.61 (s, 1H), 7.30 (t, J=7.6 Hz, 1H), 7.27-7.19 (m, 5H), 7.15 (d, J=8.1 Hz, 2H), 7.05 (d, J=9.0 Hz, 2H), 6.44 (s, 1H), 5.64 (s, 2H), 4.47 (t, J=7.6 Hz, 1H), 3.89 (s, 3H), 3.71 (s, 3H), 3.62-3.52 (m, 3H), 3.25 (dd, J=6.6, 14.9 Hz, 1H), 2.40 (s, 3H), 0.87 (t, J=8.0 Hz, 2H), 0.0 (s, 9H).

Example 70

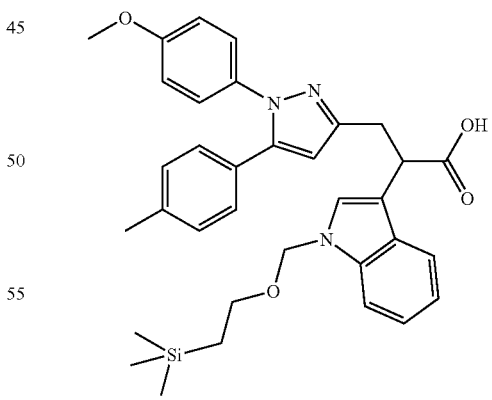

3-[1-(4-Methoxy-phenyl)-5-p-tolyl-1H-pyrazol-3-yl]-2-[1-(2-trimethylsilanyl-ethoxymethyl)-1H-indol-3-yl]-propionic acid The title compound was synthesized by Method 2 from 3-[1-(4-methoxy-phenyl)-5-p-tolyl-1H-pyrazol-3-yl]-2-[1-

(2-trimethylsilanyl-ethoxymethyl)-1H-indol-3-yl]-propionic acid methyl ester (Example 69, 0.19 g, 0.32 mmol), lithium hydroxide (40 mg, 0.96 mmol), THF (1.25 mL), water (0.43 mL) and MeOH (0.43 mL), giving 167 mg (89%) of 3-[1-(4-methoxy-phenyl)-5-p-tolyl-1H-pyrazol-3-yl]-2-[1-(2-trimethylsilanyl-ethoxymethyl)-1H-indol-3-yl]-propionic acid. HPLC: $R_t$=3.66 (Method B). MS (ES+): mass calculated for $C_{34}H_{39}N_3O_4Si$, 581.27; m/z found 582.3 $[M+H]^+$. $^1H$ NMR (400 MHz, DMSO-$d_6$): 7.64 (d, J=8.2 Hz, 1H), 7.51 (d, J=8.2 Hz, 1H), 7.45 (s, 1H), 7.19-7.04 (m, 6H), 7.01 (d, J=8.2 Hz, 2H), 6.92 (d, J=9.0 Hz, 2H), 6.33 (s, 1H), 5.52 (s, 2H), 4.21 (m, 1H), 3.76 (s, 3H), 3.41 (m, 2H), 3.07 (dd, J=6.3, 14.3 Hz, 1H), 2.27 (s, 3H), 0.75 (t, J=8.0 Hz, 2H), 0.00 (s, 9H).

Example 71

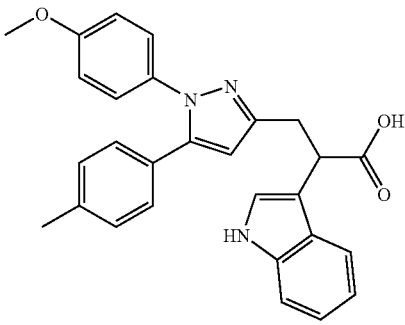

2-(1H-Indol-3-yl)-3-[1-(4-methoxy-phenyl)-5-p-tolyl-1H-pyrazol-3-yl]-propionic acid A solution of 3-[1-(4-methoxy-phenyl)-5-p-tolyl-1H-pyrazol-3-yl]-2-[1-(2-trimethylsilanyl-ethoxymethyl)-1H-indol-3-yl]-propionic acid (Example 70, 0.17 g, 0.29 mmol) and 1.0 M TBAF (2.88 mL) in THF was heated to 60° C. for 24 h. The reaction mixture was cooled to rt, diluted with EtOAc (100 mL), and washed with water (3×30 mL) and brine (1×30 mL). The organic layer was dried with $Na_2SO_4$, and the solvent was removed under reduced pressure. The crude residue was purified by reversed-phase HPLC giving 111 mg (85%) of 2-(1H-indol-3-yl)-3-[1-(4-methoxy-phenyl)-5-p-tolyl-1H-pyrazol-3-yl]-propionic acid. HPLC: $R_t$=3.0 (Method B). MS (ES+): mass calculated for $C_{28}H_{25}N_3O_3$, 451.19; m/z found 452.2 $[M+H]^+$. $^1H$ NMR (400 MHz, DMSO-$d_6$): 10.97 (s, 1H), 7.64 (d, J=6.3 Hz, 1H), 7.35 (d, J=8.1 Hz, 1H), 7.31 (d, J=2.4 Hz, 1H), 7.13-7.07 (m, 5H), 7.04 (d, J=8.1 Hz, 2H), 6.98 (t, J=8.0 Hz, 1H), 6.93 (d, J=9.0 Hz, 2H), 6.36 (s, 1H), 4.22 (dd, J=6.1, 9.0 Hz, 1H), 3.77 (s, 3H), 3.45 (dd, J=9.0, 14.7 Hz, 1H), 3.06 (dd, J=6.2, 14.7 Hz, 1H), 2.27 (s, 3H).

Example 72

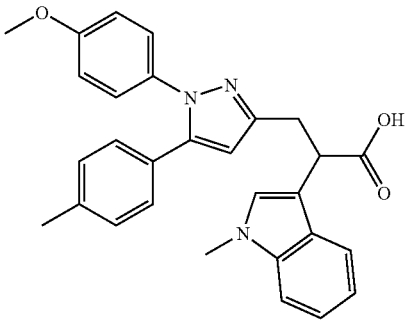

3-[1-(4-Methoxy-phenyl)-5-p-tolyl-1H-pyrazol-3-yl]-2-(1-methyl-1H-indol-3-yl)-propionic acid A. (1-Methyl-1H-indol-3-yl)-acetic acid methyl ester To a suspension of sodium hydride (104 mg, 7.61 mmol) in DMF (11 mL) was added a solution of 1H-indol-3-yl-acetic acid methyl ester (0.50 g, 2.6 mmol) in DMF (5.0 mL). The mixture was stirred for 1 h followed by addition of methyl iodide (1.1 g, 7.8 mmol). The reaction mixture was stirred for an additional 18 h, quenched, diluted with saturated ammonium chloride (200 mL), and then extracted with diethyl ether (3×100 mL). The combined organic layers were dried with $Na_2SO_4$, and the solvent was removed under reduced pressure. The crude residue was purified by flash chromatography (EtOAc/hexanes) giving 100 mg (19%) of (1-methyl-1H-indol-3-yl)-acetic acid methyl ester after purification. HPLC: $R_t$=8.91 (Method A). MS (ES+): mass calculated for $C_{12}H_{13}NO_2$, 203.09; m/z found 204.09 $[M+H]^+$. $^1H$ NMR (400 MHz, CDCl$_3$): 7.60 (d, J=7.9 Hz, 1H), 7.30 (d, J=8.2 Hz, 1H), 7.23 (t, J=8.2 Hz, 1H), 7.13 (t, 7.4 Hz, 1H), 7.04 (s, 1H), 3.77 (s, 2H), 3.76 (s, 3H), 3.69 (s, 3H).

B. 3-[1-(4-Methoxy-phenyl)-5-p-tolyl-1H-pyrazol-3-yl]-2-(1-methyl-1H-indol-3-yl)-propionic acid The title compound was prepared by Method 2 from (1-methyl-1H-indol-3-yl)-acetic acid methyl ester (0.10 g, 0.49 mmol), 3-bromoethyl-1-(4-methoxy-phenyl)-5-p-tolyl-1H-pyrazole (89 mg, 0.25 mmol), sodium hydride (19 mg, 0.49 mmol) and DMF (4.0 mL), giving 3-[1-(4-methoxy-phenyl)-5-p-tolyl-1H-pyrazol-3-yl]-2-(1-methyl-1H-indol-3-yl)-propionic acid methyl ester, which was not isolated. The ester was converted to the acid in situ by adding 2.5 mL (4.9 mmol) LiOH solution giving 57 mg (49%) of 3-[1-(4-methoxy-phenyl)-5-p-tolyl-1H-pyrazol-3-yl]-2-(1-methyl-1H-indol-3-yl)-propionic acid. HPLC: $R_t$=3.23 (Method B). MS (ES+): mass calculated for $C_{29}H_{27}N_3O_3$, 465.21; m/z found 466.2 $[M+H]^+$. $^1H$ NMR (400 MHz, DMSO-$d_6$): 12.15 (br s, 1H), 7.64 (d, J=7.9 Hz, 1H), 7.40 (d, J=8.2 Hz, 1H), 7.32 (s, 1H), 7.17-7.10 (m, 5H), 7.05-7.03 (m, 3H), 6.93 (d, J=8.9 Hz, 2H), 6.38 (s, 1H), 4.22 (dd, J=9.1, 5.9 Hz, 1H), 3.76 (s, 6H), 3.44 dd, J=14.7, 9.2 Hz, 1H), 3.04 (dd, J=5.9, 14.7 Hz, 1H), 2.27 (s, 3H).

Example 73

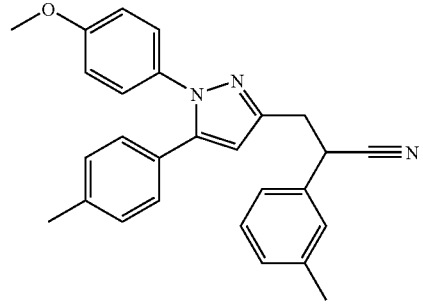

3-[1-(4-Methoxy-phenyl)-p-tolyl-1H-pyrazol-3-yl]-2-m-tolyl-propionitrile

To a solution of 3-[1-(4-methoxy-phenyl)-5-p-tolyl-1H-pyrazol-3-yl]-2-m-tolyl-propionamide (Example 65, 0.31 g, 0.73 mmol) in pyridine (0.115 mL, 1.46 mmol) and dioxane (2.0 mL) at 0° C. was added TFAA (0.11 mL, 0.80 mmol). The solution was stirred at 0° C. for 30 min, allowed to warm to rt and stirred for an additional 3 h. The solvent was removed under reduced pressure, and the residue was re-dissolved in EtOAc (100 mL). This solution was washed with water (1×50 mL) and brine (1×50 mL) and dried with $Na_2SO_4$, and then solvent was removed under reduced pressure giving 295 mg (>99%) of 3-[1-(4-methoxy-phenyl)-p-tolyl-1H-pyrazol-3-yl]-2-m-tolyl-propionitrile. HPLC: $R_t$=3.53 (Method B). MS (ES+): mass calculated for $C_{27}H_{25}N_3O$, 407.20; m/z found 408.2 [M+H]$^+$. $^1$H NMR (400 MHz, DMSO-$d_6$): 7.33-7.26 (m, 3H), 7.18-7.12 (m, 5H), 7.08 (d, J=8.2 Hz, 2H), 6.95 (d, J=8.9 Hz, 2H), 6.48 (s, 1H), 4.58 (dd, J=5.9, 9.6 Hz, 1H), 3.77 (s, 3H), 3.27 (dd, J=9.6, 14.6 Hz, 1H), 3.15 (dd, J=5.9, 14.6 Hz, 1H), 2.33 (s, 3H), 2.28 (s, 3H).

Example 74

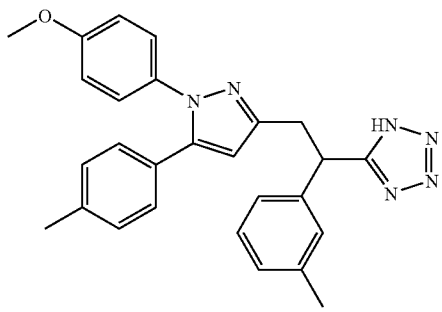

5-{2-[1-(4-Methoxy-phenyl)-5-p-tolyl-1H-pyrazol-3-yl]-1-m-tolyl-ethyl}-1H-tetrazole 3-[1-(4-Methoxy-phenyl)-p-tolyl-1H-pyrazol-3-yl]-2-m-tolyl-propionitrile (Example 73, 0.10 g, 0.24 mmol), sodium azide (32 mg, 0.50 mmol) and ammonium chloride (26 mg, 0.50 mmol) were mixed in DMF (3.0 mL) and heated at 100° C. for 4 days. The reaction mixture was cooled, diluted with water (25 mL) and extracted with EtOAc (3×25 mL). The combined organic layers were washed with brine (1×25 mL) and dried with $Na_2SO_4$, and the solvent was removed under reduced pressure yielding 21 mg (20%) of 5-{2-[1-(4-methoxy-phenyl)-5-p-tolyl-1H-pyrazol-3-yl]-1-m-tolyl-ethyl}-1H-tetrazole. HPLC: $R_t$=3.16 (Method B). MS (ES+): mass calculated for $C_{27}H_{26}N_6O$, 450.22; m/z found 451.2 [M+H]$^+$. $^1$H NMR (400 MHz, DMSO-$d_6$): 7.25-7.17 (m, 3H), 7.12 (d, J=7.9 Hz, 2H), 7.07 (d, J=7.4 Hz, 1H), 7.04 (d, J=9.0 Hz, 2H), 6.99 (d, J=8.1 Hz, 2H), 6.92 (d, J=9.0 Hz, 2H), 6.23 (s, 1H), 4.85 (dd, J=6.7, 9.2 Hz, 1H), 3.75 (s, 3H), 3.60 (dd, J=9.3, 14.8 Hz, 1H), 3.34 (dd, J=6.4, 14.4 Hz, 1H), 2.28 (s, 3H), 2.26 (s, 3H).

Example 75

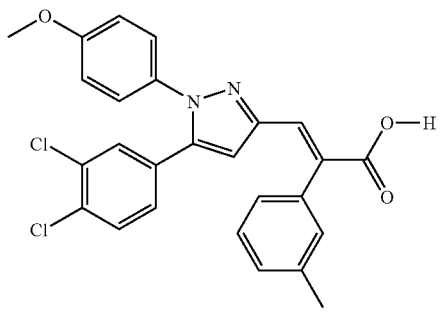

(E)-3-[5-(3,4-Dichloro-phenyl)-1-(4-methoxy-phenyl)-1H-pyrazol-3-yl]-2-m-tolyl-acrylic acid

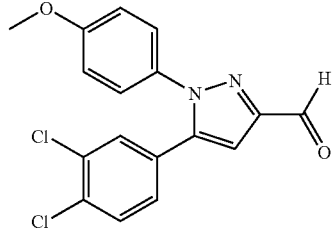

A. 5-(3,4-Dichloro-phenyl)-1-(4-methoxy-phenyl)-1H-pyrazole-3-carbaldehyde

To a stirred solution of [5-(3,4-dichlorophenyl)-1-(4-methoxyphenyl)-1H-pyrazol-3-yl]-methanol (Example 1 Step C, 1.0 g, 2.9 mmol) in $CH_2Cl_2$ (13 mL) under $N_2$ was added Dess-Martin periodinane (2.1 g, 4.9 mmol) at rt. After 3 h, $Na_2S_2O_3$ (5.0 g, 20 mmol) dissolved in saturated $NaHCO_3$ (25 mL) and EtOAc (25 mL) were added, and the mixture was stirred until the layers were clear. The layers were separated, and the aqueous phase was extracted with EtOAc (3×15 mL). The combined organic extracts were dried over $Na_2SO_4$ and filtered, and the solvent was removed under reduced pressure to afford 0.95 g (96%) of the crude aldehyde, which was used without further purification. HPLC: $R_t$=10.3 (Method A). $^1$H NMR (400 MHz, CDCl$_3$): 9.98 (s, 1H), 7.32 (s, 1H), 7.30 (d, J=2.3 Hz, 1H), 7.19-7.16 (m, 2H), 6.95 (s, 1H), 6.91 (dd, J=8.1, 2.3 Hz, 1H), 6.88-6.84 (m, 2H), 3.78 (s, 3H).

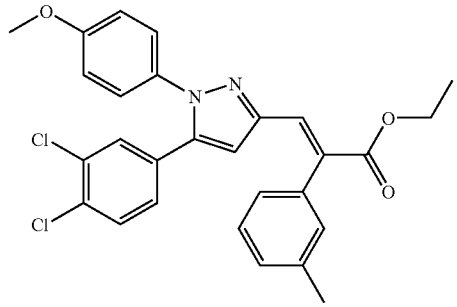

B. 3-[5-(3,4-Dichloro-phenyl)-1-(4-methoxy-phenyl)-1H-pyrazol-3-yl]-2-m-tolyl-acrylic acid ethyl ester To a stirred solution containing sodium hydride (0.20 mg, 60% in mineral oil, 4.8 mmol) suspended in EtOH (5 mL) was added ethyl-m-tolyacetate (0.87 g, 4.9 mmol) at rt. After 30 min, 5-(3,4-dichloro-phenyl)-1-(4-methoxy-phenyl)-1H-pyrazole-3-carbaldehyde (Step A, 0.562 g, 1.63 mmol) in 2 mL DMF was added. The reaction mixture was stirred for 18 h at 70° C. The solvent was removed under reduced pressure, and the residue was purified by silica gel chromatography with 7:93 MeOH/$CH_2Cl_2$ to afford 220 mg (27.2%) of 3-[5-(3,4-dichloro-phenyl)-1-(4-methoxy-phenyl)-1H-pyrazol-3- yl]-2-m-tolyl-acrylic acid ethyl ester. HPLC: $R_t$=11.76 (Method A). MS (ES+): mass calculated for $C_{28}H_{24}Cl_2N_2O_3$, 506.12; m/z found 507.0 [M+H]+. $^1$H NMR (400 MHz, CDCl$_3$): 7.83-7.80 (m, 1H), 7.74-7.71 (m, 2H), 7.37-7.35 (m, 1H), 7.33-7.29 (m, 4H), 7.19 (d, J=4.5 Hz, 2H), 6.92-6.88 (m, 2H), 4.19 (dd, J=13.9, 7.2 Hz, 2H), 3.78 (s, 3H), 2.51 (s, 3H), 1.21 (t, J=6.8, Hz, 3H).

C. 3-[5-(3,4-Dichloro-phenyl)-1-(4-methoxy-phenyl)-1H-pyrazol-3-yl]-2-m-tolyl-acrylic acid To a stirred solution containing 3-[5-(3,4-dichloro-phenyl)-1-(4-methoxy-phenyl)-1-H-pyrazol-3-yl]-2-m-tolyl-acrylic acid ethyl ester (Step B, 50 mg, 0.10 mmol) was added 2 mL LiOH (2 M). After 4 h at 50° C., the solvent was removed under reduced pressure and the residue was purified by silica gel chromatography with 5:95 MeOH/CH$_2$Cl$_2$ to afford 34 mg (72.3%) of the title compound. HPLC: $R_t$=10.65 (Method A). MS (ES+): mass calculated for $C_{26}H_{20}Cl_2N_2O_3$, 478.09; m/z found 479.0 [M+H]+. $^1$H NMR (400 MHz, CDCl$_3$): 7.35 (t, J=8.0 Hz, 1H), 7.28-7.23 (m, 3H), 7.15-7.11 (m, 3H), 7.09 (d, J=2.0 Hz, 1H), 6.88-6.86 (m, 2H), 6.77 (dd, J=8.3, 2.0 Hz, 1H), 5.45 (s, 1H), 3.82 (s, 3H), 2.39 (s, 3H).

Example 76

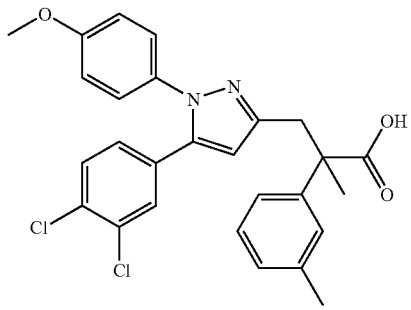

3-[5-(3,4-Dichloro-phenyl)-1-(4-methoxy-phenyl)-1H-pyrazol-3-yl]-2-methyl-2-m-tolyl-propionic acid A. 3-[5-(3,4-Dichloro-phenyl)-1-(4-methoxy-phenyl)-1H-pyrazol-3-yl]-2-methyl-2-m-tolyl-propionic acid ethyl ester To a solution of 3-[5-(3,4-dichloro-phenyl)-1-(4-methoxy-phenyl)-1H-pyrazol-3-yl]-2-m-tolyl-propionic acid ethyl ester (Method 2, product from alkylation step before hydrolysis) (50 mg, 0.10 mmol) in THF (1.0 mL) at 0° C. was added a 1.0 M solution of NaHMDS (0.15 mL, 0.15 mmol). The solution was stirred at 0° C. for 2 h, then iodomethane (41 mg, 0.29 mmol) was added neat. After stirring for 1 h the reaction was quenched with saturated ammonium chloride (50 mL), and the reaction mixture was extracted with EtOAc (3×50 mL). The combined organic layers were washed with brine (1×50 mL) and dried with Na$_2$SO$_4$, and the solvent was removed under reduced pressure. The crude material was purified by flash chromatography (EtOAc/hexanes) giving 31 mg (60%) of 3-[5-(3,4-dichloro-phenyl)-1-(4-methoxy-phenyl)-1H-pyrazol-3-yl]-2-methyl-2-m-tolyl-propionic acid ethyl ester. HPLC: $R_t$=3.79 (Method B). MS (ES+): mass calculated for $C_{29}H_{28}Cl_2N_2O_3$, 522.15; m/z found 523.1 [M+H]+. $^1$H NMR (400 MHz, DMSO-d$_6$): 7.58 (d, J=8.4 Hz, 1H), 7.42 (d, J=2.0 Hz, 1H), 7.25 (t, J=7.6 Hz, 1H), 77.17-7.14 (m, 4H), 7.08 (d, J=7.4 Hz, 1H), 7.05 (dd, J=2.0 Hz, 8.3 Hz, 1H), 6.97 (d, J=8.9 Hz, 2H), 6.22 (s, 1H), 4.10 (m, 2H), 3.77 (s, 3H), 3.40 (d, J=13.9 Hz, 1H), 3.17 (d, J=13.9 Hz, 1H), 2.13 (s, 3H), 1.49 (s, 3H), 1.12 (t, J=7.1 Hz, 3H).

B. 3-[5-(3,4-Dichloro-phenyl)-1-(4-methoxy-phenyl)-1H-pyrazol-3-yl]-2-methyl-2-m-tolyl-propionic acid The title compound was prepared by Method 2 from 3-[5-(3,4-dichloro-phenyl)-1-(4-methoxy-phenyl)-1H-pyrazol-3-yl]-2-methyl-2-m-tolyl-propionic acid ethyl ester (0.11 g, 0.21 mmol), lithium hydroxide (88 mg, 2.1 mmol), THF (2.3 mL), MeOH (0.87 mL) and water (0.87 mL) giving 93 mg (90%) of 3-[5-(3,4-dichloro-phenyl)-1-(4-methoxy-phenyl)-1H-pyrazol-3-yl]-2-methyl-2-m-tolyl-propionic acid. HPLC: $R_t$=3.42 (Method B). MS (ES+): mass calculated for $C_{27}H_{24}Cl_2N_2O_3$, 494.12; m/z found 495.0 [M+H]+. $^1$H NMR (400 MHz, DMSO-d$_6$): 12.50 (s, 1H), 7.58 (d, J=8.4 Hz, 1H), 7.41 (d, J=2.0 Hz, 1H), 7.26-7.19 (m, 3H), 7.16 (d, J=9.0 Hz, 2H), 7.08 (d, J=7.1 Hz, 1H), 7.03 (dd, J=2.0 Hz, 8.4 Hz, 1H), 6.97 (d, J=9.0 Hz, 2H), 6.20 (s, 1H), 3.78 (s, 3H), 3.37 (d, J=14.0 Hz, 1H), 3.14 (d, J=14.0 Hz, 1H), 2.31 (s, 3H), 1.46 (s, 3H).

Example 77

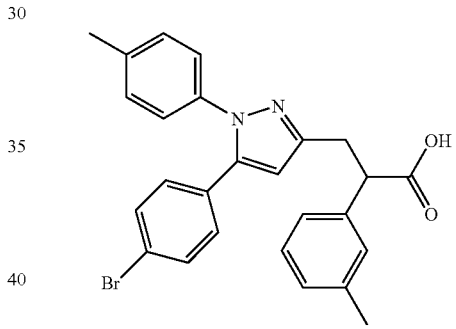

3-[5-(4-Bromo-phenyl)-1-p-tolyl-1H-pyrazol-3-yl]-2-m-tolyl-propionic acid

A. 2-m-Tolyl-5-trimethylsilanyl-pent-4-ynoic acid ethyl ester

To a −78° C. solution of m-tolyl-acetic acid ethyl ester (2.0 g, 11 mmol) in THF (37 mL), a 2.0 M solution of lithium diisopropylamine in THF (5.6 mL, 11 mmol) was added dropwise. The mixture was stirred at −78° C. for 1 h and then added to a −78° C. solution of propargyl bromide (5.6 mL, 11 mmol, 1 equiv) in THF (30 mL). The reaction mixture was allowed to warm to room temperature and stirred for 12 h. Diethyl ether (40 mL) and satd aq NH$_4$Cl (50 mL) were added, and the resulting aqueous layer was back-extracted with Et$_2$O (2×50 mL). The combined organic layers were washed with 1N HCl (50 mL) then brine (50 mL), and dried (MgSO$_4$). The solvent was evaporated under reduced pressure, and the residue was purified by chromatography (silica gel, 20% ethyl acetate/hexanes) to afford the desired silanyl-pentynoic acid ester (2.90 g, 90% yield). TLC (silica gel, 1:9 EtOAc/hexanes): $R_f$=0.54. MS (ESI): mass calculated for $C_{17}H_{24}O_2Si$, 288.15; m/z found, 289.1 [M+H]+. $^1$H NMR (400 MHz, CDCl$_3$): 7.17-6.96 (m, 4H), 4-13-3.99 (m, 2H), 3.65-3.62 (m, 1H), 2.82 (dd, J=16.8, 8.4 Hz, 1H), 2.54 (d, J=16.8, 7.0 Hz, 1H), 2.23 (s, 3H), 1.13 (t, J=10.0 Hz, 3H), 0.00 (s, 9H).

B. 6-(4-Bromo-phenyl)-6-oxo-2-m-tolyl-hex-4-ynoic acid ethyl ester

To a 0° C. solution of 2-m-tolyl-5-trimethylsilanyl-pent-4-ynoic acid ethylester (9.5 g, 33 mmol) and 4-bromobenzoyl chloride (9.4 g, 43 mmol, 1.3 equiv) in CH$_2$Cl$_2$ (550 mL) was added aluminum chloride (9.5 g, 50 mmol, 1.5 equiv) portionwise. The mixture was stirred at 0° C. for 2 h, then the reaction was quenched with satd aq potassium sodium tartrate (200 mL). The resulting mixture was stirred at room temperature for 2 h. The layers were separated, and the aqueous layer was back-extracted with CH$_2$Cl$_2$ (3×150 mL). The combined organic layers were washed with 1N NaOH (70 mL) then brine (70 mL), and dried (MgSO$_4$). The solvent was evaporated under reduced pressure, and the residue was purified by chromatography (silica gel, 25% ethyl acetate/hexanes) to afford the desired benzoyl-pentynoic acid ester (9.2 g, 70%). TLC (silica gel, 1:9 EtOAc/hexanes): R$_f$=0.28. MS (ESI): mass calculated for C$_{21}$H$_{19}$BrO$_3$, 398.05; m/z found, 399/400 [M+H]$^+$. $^1$H NMR (500 MHz, CDCl$_3$): 7.14 (d, J=8.9 Hz, 2H), 7.14 (d, J=8.9 Hz, 2H), 7.29-7.14 (m, 3H), 4.23-4.12 (m, 2H), 3.88 (t, J=7.8 Hz, 1H), 3.09 (dAB syst., J=17.3, 7.8 Hz, 2H), 2.38 (s, 3H), 1.24 (t, J=9.2 Hz, 3H).

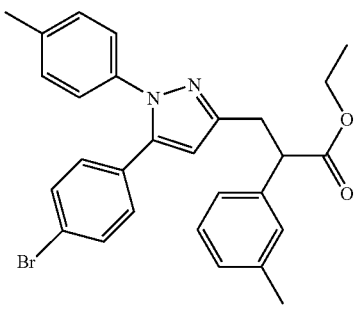

C. 3-[5-(4-Bromo-phenyl)-1-p-tolyl-1H-pyrazol-3-yl]-2-m-tolyl-propionic acid ethyl ester To a solution of 6-(4-bromo-phenyl)-6-oxo-2-m-tolyl-hex-4-ynoic acid ethyl ester (7.5 g, 19 mmol) in THF (40 mL) was added hydrazine (4.5 g, 28 mmol, 1.5 equiv) and Cs$_2$CO$_3$ (9.0 g, 28 mmol, 1.5 equiv). The reaction mixture was stirred at room temperature for 12 h. The resulting mixture was diluted with ethyl acetate (30 mL), and a satd aq solution of cesium carbonate (50 mL) was added. The resulting aqueous layer was back-extracted with ethyl acetate (2×30 mL). The combined organic layers were washed with satd aq NaHCO$_3$ (50 mL) then brine (50 mL), and dried (MgSO$_4$). The solvent was evaporated under reduced pressure, and the residue was purified by chromatography (silica gel, 25% ethyl acetate/hexanes) to afford the desired compound (5.5 g, 58%). TLC (silica gel, 3:7 EtOAc/hexanes): R$_f$=0.35. MS (ESI): mass calculated for C$_{28}$H$_{27}$BrN$_2$O$_2$, 502.13; m/z found, 503/505 [M+H]$^+$. $^1$H NMR (400 MHz, CDCl$_3$): 7.39 (d, J=10.7 Hz, 2H), 7.25-7.01 (m, 10H), 6.17 (s, 1H), 4.19-4.03 (m, 3H), 3.52 (dd, J=14.7, 9.6 Hz, 1H), 3.09 (dd, J=14.7, 6.0 Hz, 1H), 2.35 (s, 6H), 1.19 (t, J=7.1 Hz, 3H).

D. 3-[5-(4-Bromo-phenyl)-1-p-tolyl-1H-pyrazol-3-yl]-2-m-tolyl-propionic acid To a solution of 3-[5-(4-bromo-phenyl)-1-p-tolyl-1H-pyrazol-3-yl]-2-m-tolyl-propionic acid ethyl ester (100 mg, 0.2 mmol) was added LiOH (14 mg, 0.6 mmol, 3 equiv) in 2:1 THF/H$_2$O (1 mL). After 3 h at 45° C., the mixture was purified by preparative reversed-phase HPLC (acetonitrile/water) to afford the title compound (66 mg, 79 %). HPLC: R$_t$=4.25 (Method A). MS (ESI): mass calculated for C$_{26}$H$_{23}$BrN$_2$O$_2$, 474.09; m/z found, 475/477 [M+H]$^+$. $^1$H NMR (500 MHz, CDCl$_3$): 7.40 (d, J=8.5 Hz, 2H), 7.22 (d, J=7.6 Hz, 2H), 7.19-7.05 (m, 7H), 7.01 (d, J=8.5 Hz, 2H), 6.23 (s, 1H), 4.10 (dd, J=9.6, 5.5 Hz, 1H), 3.53 (dd, J=14.8, 9.6 Hz, 1H), 3.13 (dd, J=14.8, 5.5 Hz, 1H), 2.36 (s, 3H), 2.34 (s, 3H).

The compounds of Examples 78-93 were made according to the synthetic methods outlined in Example 77 and Scheme L.

Example 78

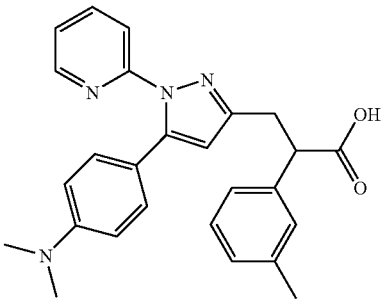

3-[5-(4-Dimethylamino-phenyl)-1-pyridin-2-yl-1H-pyrazol-3-yl]-2-m-tolyl-propionic acid HPLC: R$_t$=3.90 (Method B). MS (ESI): mass calculated for C$_{26}$H$_{26}$N$_4$O$_2$, 426.21; m/z found, 427.2 [M+H]$^+$. $^1$H NMR (500 MHz, CDCl$_3$): 8.38 (d, J=6.3 Hz, 1H), 7.76 (td, J=7.4, 1.2 Hz, 1H), 7.40 (d, J=8.2 Hz, 1H), 7.24-7.18 (m, 4H), 7.11-7.07 (m, 3H), 6.22 (s, 1H), 4.14 (dd, J=9.6, 5.5 Hz, 1H), 3.56 (dd, J=15.0, 9.6 Hz, 1H), 3.12 (dd, J=15.0, 5.5 Hz, 1H), 3.08, (s, 6H), 2.34 (s, 3H).

Example 79

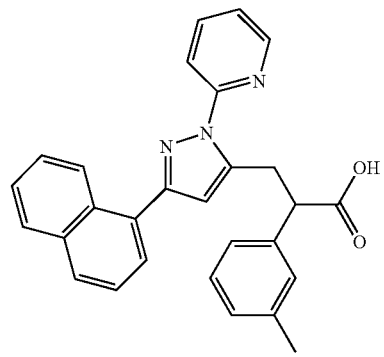

3-(5-Naphthalen-1-yl-2-pyridin-2-yl-2H-pyrazol-3-yl)-2-m-tolyl-propionic acid

HPLC: R$_t$=3.36 (Method B). MS (ESI): mass calculated for C$_{28}$H$_{23}$N$_3$O$_2$, 433.18; m/z found, 434.2 [M+H]$^+$. $^1$H NMR (500 MHz, CDCl$_3$): 8.44 (d, J=4.9 Hz, 1H), 8.25 (s, 1H), 8.09 (d, J=8.2 Hz, 1H), 8.03 (d, J=8.5 Hz, 1H), 7.89-7.82 (m, 4H), 7.50-7.46 (m, 2H), 7.28-7.18 (m, 4H), 7.09 (d, J=6.8 Hz, 1H), 6.64 (s, 1H), 4.34 (dd, J=9.0, 5.7 Hz, 1H), 3.94 (dd, J=14.8, 9.0 Hz, 1H), 3.66 (dd, J=14.8, 5.7 Hz, 1H), 2.34 (s, 3H).

Example 80

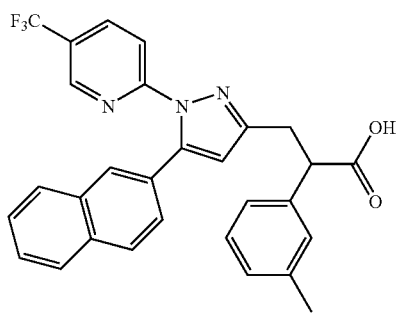

3-[5-Naphthalen-2-yl-1-(5-trifluoromethyl-pyridin-2-yl)-1H-pyrazol-3-yl]-2-m-tolyl-propionic acid HPLC: R$_t$=3.41 (Method B). MS (ESI): mass calculated for C$_{29}$H$_{22}$F$_3$N$_3$O$_2$, 501.17; m/z found, 520/522 [M+H$_3$O]$^+$. $^1$H NMR (500 MHz, CDCl$_3$): 8.45 (s, 1H), 7.89-7.74 (m, 6H), 7.66 (d, J=8.5 Hz, 1H), 7.54-7.48 (m, 2H), 7.28-7.19 (m, 3H), 7.12-7.11 (m, 1H), 6.33 (s, 1H), 4.16 (dd, J=9.6, 5.7 Hz, 1H), 3.60 (dd, J=15.0, 9.6 Hz, 1H), 3.15 (dd, J=15.0, 5.7 Hz, 1H), 2.35 (s, 3H).

Example 81

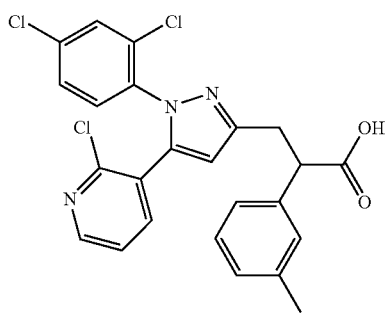

3-[5-(2-Chloro-pyridin-3-yl)-1-(2,4-dichloro-phenyl)-1H-pyrazol-3-yl]-2-m-tolyl-propionic acid MS (ESI): mass calculated for C$_{24}$H$_{18}$Cl$_3$N$_3$O$_2$, 485.05; m/z found, 486/488 [M+H]$^+$. $^1$H NMR (500 MHz, CDCl$_3$): 8.38 (d, J=2.0 Hz, 1H), 7.70-7.67 (m, 2H), 7.59-7.53 (m, 2H), 7.25-7.19 (m, 2H), 7.13 (s, 1H), 7.04 (d, J=8.8 Hz, 1H), 6.88 (d, J=7.6 Hz, 1H), 6.04 (s, 1H), 3.95 (dd, J=7.0, 4.6 Hz, 1H), 3.62 (dd, J=17.0, 4.6 Hz, 1H), 3.00 (dd, J=17.0, 7.0 Hz, 1H), 2.34 (s, 1H).

Example 82

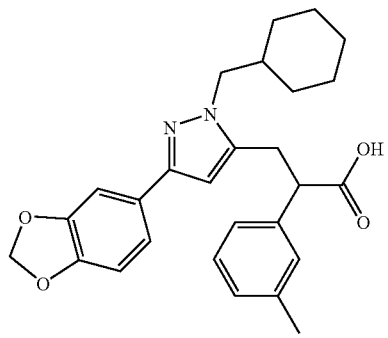

3-(5-Benzo[1,3]dioxol-5-yl-2-cyclohexylmethyl-2H-pyrazol-3-yl)-2-m-tolyl-propionic acid MS (ESI): mass calculated for C$_{27}$H$_{30}$N$_2$O$_4$, 446.22; m/z found, 447.2 [M+H]$^+$. $^1$H NMR (500 MHz, CDCl$_3$): 7.30-7.25 (m, 2H), 7.21-7.20 (m, 2H), 7.16-7.15 (m, 2H), 6.82 (d, J=8.2 Hz, 1H), 6.22 (s, 1H), 3.96-3.86 (m, 3H), 3.43 (dd, J=16.0, 9.3 Hz, 1H), 2.99 (dd, J=16.0, 5.7 Hz, 1H), 2.36 (s, 3H), 1.72-1.53 (m, 5H), 1.21-1.12 (m, 3H), 0.98-0.92 (m, 2H).

Example 83

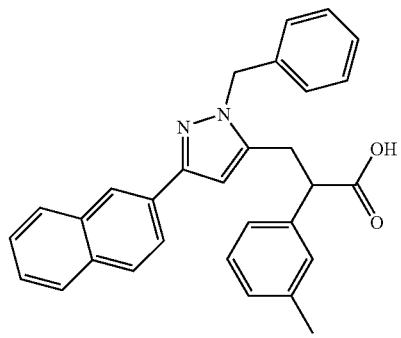

3-(2-Benzyl-5-naphthalen-2-yl-2H-pyrazol-3-yl)-2-m-tolyl-propionic acid

MS (ESI): mass calculated for C$_{30}$H$_{26}$N$_2$O$_2$, 446.20; m/z found, 447.8 [M+H]$^+$. $^1$H NMR (500 MHz, CDCl$_3$): 8.17 (s, 1H), 7.84-7.78 (m, 4H), 7.46-7.44 (m, 2H), 7.29-7.24 (m, 3H), 7.18 (t, J=7.6 Hz, 1H), 7.09-7.06 (m, 3H), 7.01-6.99 (m, 2H), 6.47 (s, 1H), 5.36 (AB syst., Jab=16 Hz, 2H), 3.74 (dd, J=8.7, 6.3 Hz, 1H), 3.39 (dd, J=15.0, 8.7 Hz, 1H), 2.92 (dd, J=15.0, 6.3 Hz, 1H), 2.29 (s, 3H).

Example 84

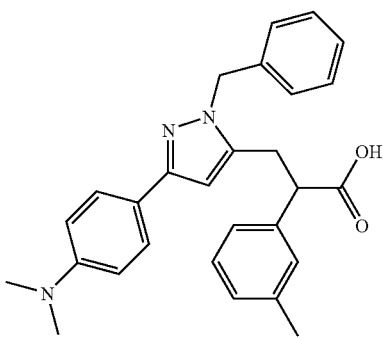

3-[2-Benzyl-5-(4-dimethylamino-phenyl)-2H-pyrazol-3-yl]-2-m-tolyl-propionic acid MS (ESI): mass calculated for $C_{28}H_{29}N_3O_2$, 439.23; m/z found, 440.7 [M+H]$^+$. $^1$H NMR (500 MHz, CDCl$_3$): 7.38 (d, J=8.5 Hz, 2H), 7.31-7.25 (m, 5H), 7.20 (t, J=8.0 Hz, 1H), 7.10-7.06 (m, 3H), 7.01-7.00 (m, 2H), 6.37 (s, 1H), 5.33 (AB syst., Jab=16.0 Hz, 2H), 3.73 (dd, J=9.2, 5.7 Hz, 1H), 3.38 (dd, J=15.7, 9.2 Hz, 1H), 3.13 (s, 6H), 2.88 (dd, J=15.4, 5.7 Hz, 1H), 2.31 (s, 3H).

Example 85

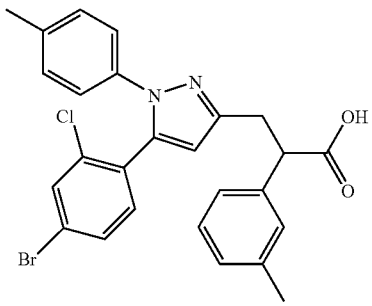

3-[5-(4-Bromo-2-chloro-phenyl)-1-p-tolyl-1H-pyrazol-3-yl]-2-m-tolyl-propionic acid HPLC: R$_t$=4.30 (Method A). MS (ESI): mass calculated for $C_{26}H_{22}BrClN_2O_2$, 508.06; m/z found, 509/511 [M+H]$^+$. $^1$H NMR (500 MHz, CDCl$_3$): 7.53 (d, J=1.9 Hz, 1H), 7.32 (dd, J=8.2, 1.9 Hz, 1H), 7.22 (t, J=7.4 Hz, 1H), 7.17-7.15 (m, 2H), 7.11-7.06 (m, 3H), 7.03-6.98 (m, 3H), 6.20 (s, 1H), 4.08 (dd, J=9.0, 6.3 Hz, 1H), 3.55 (dd, J=14.8, 9.0 Hz, 1H), 3.18 (dd, J=14.8, 6.3 Hz, 1H), 2.34 (s, 3H), 2.31 (s, 3H).

Example 86

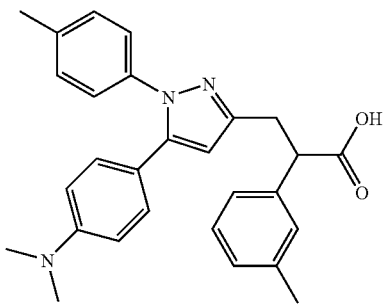

3-[5-(4-Dimethylamino-phenyl)-1-p-tolyl-1H-pyrazol-3-yl]-2-m-tolyl-propionic acid HPLC: R$_t$=1.26 (Method H). MS (ESI): mass calculated for $C_{28}H_{29}N_3O_2$, 439.23; m/z found, 440.2 [M+H]$^+$. $^1$H NMR (400 MHz, CDCl$_3$): 7.30 (s, 3H), 7.24-7.20 (m, 3H), 7.13-7.07 (m, 2H), 6.97 (d, J=8.3 Hz, 2H), 6.67 (d, J=8.3 Hz, 2H), 6.13 (s, 1H), 4.01 (dd, J=9.3, 6.1 Hz, 1H), 3.50 (dd, J=14.9, 9.3 Hz, 1H), 3.07 (dd, J=14.9, 6.1 Hz, 1H), 2.36 (s, 3H), 2.34 (s, 3H).

Example 87

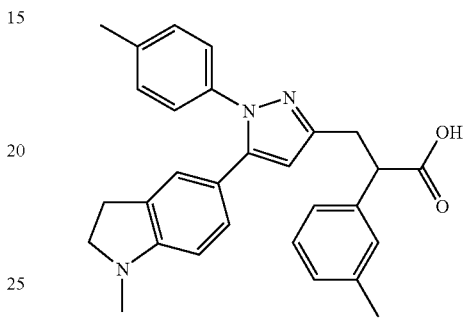

3-[5-(1-Methyl-2,3-dihydro-1H-indol-5-yl)-1-p-tolyl-1H-pyrazol-3-yl]-2-m-tolyl-propionic acid.

HPLC: R$_t$=3.71 (Method A). MS (ESI): mass calculated for $C_{29}H_{29}N_3O_2$, 451.23; m/z found, 452.3 [M+H]$^+$. $^1$H NMR (500 MHz, CDCl$_3$): 7.26-7.10 (m, 8H), 6.94-6.89 (m, 2H), 6.56 (d, J=8.2 Hz, 1H), 6.20 (s, 1H), 4.13 (dd, J=9.6, 5.5 Hz, 1H), 3.54 (dd, J=14.8, 9.6 Hz, 1H), 3.48 (t, J=8.2 Hz, 2H), 3.13 (dd, J=14.8, 5.5 Hz, 1H), 2.96 (t, J=8.2 Hz, 2H), 2.85 (s, 3H), 2.34 (s, 3H).

Example 88

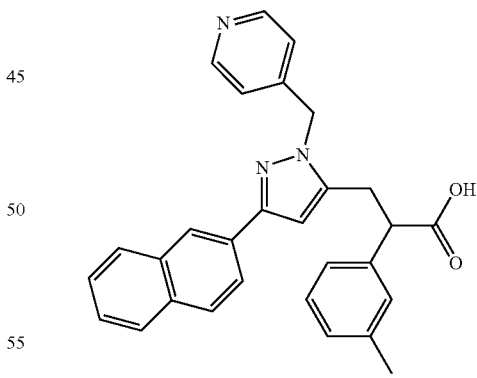

3-(5-Naphthalen-2-yl-2-pyridin-4-ylmethyl-2H-pyrazol-3-yl)-2-m-tolyl-propionic acid MS (ESI): mass calculated for $C_{29}H_{25}N_3O_2$, 447.19; m/z found, 448.3 [M+H]$^+$. $^1$H NMR (400 MHz, CDCl$_3$): 8.56-8.55 (m, 2H), 8.17 (s, 1H), 7.86-7.78 (m, 4H), 7.48-7.44 (m, 2H), 7.32-7.31 (m, 2H), 7.17 (t, J=7.8 Hz, 2H), 7.07-7.04 (m, 3H), 6.70 (s, 1H), 5.52 (AB syst., Jab=17.9 Hz, 2H), 3.97 (dd, J=:9.8, 4.8 Hz, 1H), 3.31 (dd, J=15.0, 9.8 Hz, 1H), 2.92 (dd, J=15.0, 4.8 Hz, 1H), 2.27 (s, 3H).

Example 89

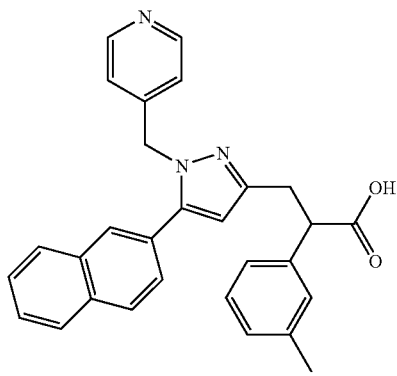

3-(5-Naphthalen-2-yl-1-pyridin-4-ylmethyl-1H-pyrazol-3-yl)-2-m-tolyl-propionic acid MS (ESI): mass calculated for $C_{29}H_{25}N_3O_2$, 447.19; m/z found, 448.3 [M+H]+. $^1$H NMR (400 MHz, CDCl$_3$): 8.65-8.64 (m, 2H), 7.89-7.86 (m, 2H), 7.80-7.70 (m, 1H), 7.70 (s, 1H), 7.56-7.52 (m, 2H), 7.30-7.19 (m, 6H), 7.13-7.11 (m, 2H), 6.36 (s, 1H), 5.51 (s, 1H), 4.13 (dd, J=10.1, 5.0 Hz, 1H), 3.55 (dd, J=14.6, 10.1 Hz, 1H), 3.38 (s, 1H), 3.10 (dd, J=14.6, 5.0 Hz, 1H), 2.33 (s, 3H).

Example 90

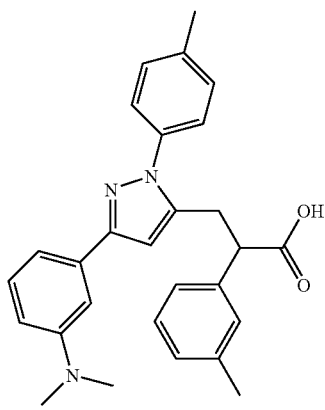

3-[5-(3-Dimethylamino-phenyl)-2-p-tolyl-2H-pyrazol-3-yl]-2-m-tolyl-propionic acid HPLC: R$_t$=3.16 (Method A). MS (ESI): mass calculated for $C_{28}H_{29}N_3O_2$, 439.23; m/z found, 440.3 [M+H]+. $^1$H NMR (400 MHz, CDCl$_3$): 7.64 (t, J=1.7 Hz, 1H), 7.50 (d, J=7.7 Hz, 1H), 7.39 (t, J=8.0 Hz, 1H), 7.28-7.24 (m, 4H), 7.19-7.12 (m, 2H), 7.07-7.05 (m, 1H), 7.01-7.00 (m, 2H), 3.83 (dd, J=9.0, 6.3 Hz, 1H), 3.43 (dd, J=15.5, 9.0 Hz, 1H), 3.11 (s, 3H), 2.99 (dd, J=15.5, 6.3 Hz, 1H), 2.42 (s, 3H), 2.29 (s, 3H).

Example 91

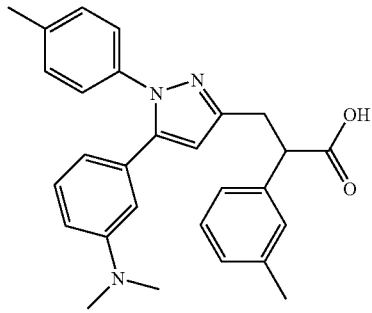

3-[5-(3-Dimethylamino-phenyl)-1-p-tolyl-1H-pyrazol-3-yl]-2-m-tolyl-propionic acid HPLC: R$_t$=3.48 (Method A). MS (ESI): mass calculated for $C_{28}H_{29}N_3O_2$, 439.23; m/z found, 440.4 [M+H]+. $^1$H NMR (400 MHz, CDCl$_3$): 7.36-7.33 (m, 2H), 7.23-7.19 (m, 3H), 7.15-7.09 (m, 7H), 6.36 (s, 1H), 4.10 (dd, J=9.9, 5.4 Hz, 1H), 3.54 (dd, J=14.7, 9.9 Hz, 1H), 3.11 (dd, J=14.9, 5.4 Hz, 1H), 2.97 (s, 6H), 2.34 (s, 6H).

Example 92

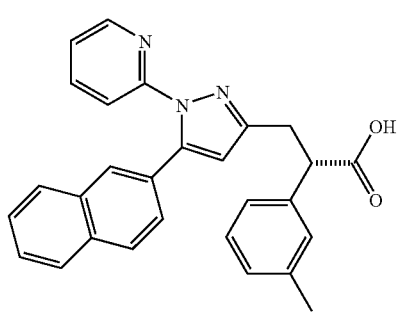

(S)-3-(5-Naphthalen-2-yl-1-pyridin-2-yl-1H-pyrazol-3-yl)-2-m-tolyl-propionic acid HPLC: R$_t$=5.95 (Method J). MS (ESI): mass calculated for $C_{28}H_{23}N_3O_2$, 433.18; m/z found, 434.1 [M+H]+. $^1$H NMR (400 MHz, CDCl$_3$): 7.81-7.74 (m, 5H), 5.52-7.50 (m, 2H), 7.26-7.09 (m, 7H), 6.39 (s, 1H), 4.18 (dd, J=10.2, 4.9 Hz, 1H), 3.62 (dd, J=14.8, 10.2 Hz, 1H), 3.12 (dd, J=14.8, 4.9 Hz, 1H), 2.34 (s, 3H).

Example 93

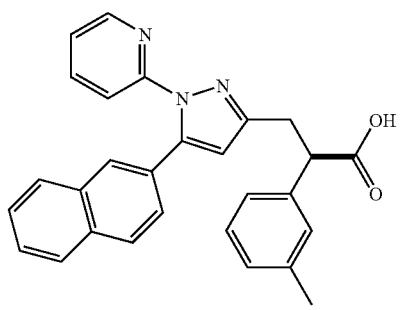

(R)-3-(5-Naphthalen-2-yl-1-pyridin-2-yl-1H-pyrazol-3-yl)-2-m-tolyl-propionic acid HPLC: R$_t$=3.95 (Method J). MS (ESI): mass calculated for $C_{28}H_{23}N_3O_2$, 433.18; m/z found, 434.1 [M+H]+. $^1$H NMR (400 MHz, CDCl$_3$): 7.81-7.74 (m, 5H), 5.52-7.50 (m, 2H), 7.26-7.09 (m, 7H), 6.39 (s, 1H), 4.18 (dd, J=10.2, 4.9 Hz, 1H), 3.62 (dd, J=14.8, 10.2 Hz, 1H), 3.12 (dd, J=14.8, 4.9 Hz, 1H), 2.34 (s, 3H).

Example 94

Amination

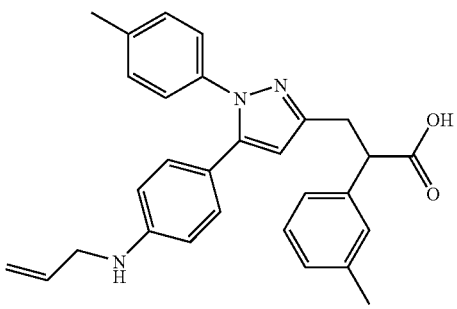

3-[5-(4-Allylamino-phenyl)-1-p-tolyl-1H-pyrazol-3-yl]-2-m-tolyl-propionic acid

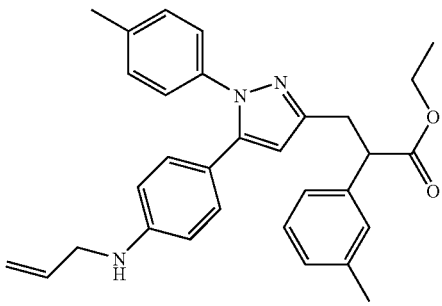

A. 3-[5-(4-Allylamino-phenyl)-1-p-tolyl-1H-pyrazol-3-yl]-2-m-tolyl-propionic acid ethyl ester To a mixture of $Pd_2$(dibenzylideneacetone)$_3$ (4 mg, 0.004 mmol, 1 mol %), 2-(di-tert-butylphosphino)biphenyl (6 mg, 0.02 mmol, 5 mol %) and $K_3PO_4$ (130 mg, 0.61 mmol, 1.5 equiv) was added a solution of 3-[5-(4-bromo-phenyl)-1-p-tolyl-1H-pyrazol-3-yl]-2-m-tolyl-propionic acid ethyl ester (Example 77, Step C; 200 mg, 0.4 mmol) in toluene (0.6 mL) followed by allylamine (0.030 mL, 0.48 mmol, 1.2 equiv). The resulting mixture was stirred at 110° C. for 12 h and then cooled to room temperature. Ethyl acetate (2 mL) and water (3 mL) were added, and the resulting aqueous layer was back-extracted with EtOAc (3×2 mL). The combined organic layers were washed with brine (3 mL), and then dried (MgSO$_4$). The solvent was evaporated under reduced pressure, and the residue was purified by chromatography (silica gel, 25% ethyl acetate/hexanes) to afford the desired compound (90 mg, 47%). HPLC: $R_t$=3.19 (Method B). MS (ESI): mass calculated for $C_{31}H_{33}N_3O_2$, 479.26; m/z found, 480.3 [M+H]$^+$. $^1$H NMR (500 MHz, CDCl$_3$): 7.29 (s, 1H), 7.27-7.04 (m, 7H), 6.96 (d, J=8.5 Hz, 2H), 6.49 (d, J=8.5 Hz, 2H), 6.07 (s, 1H), 5.96-5.89 (m, 1H), 5.29-5.25 (m, 1H), 5.18-5.16 (m, 1H), 4.20-4.14 (m, 1H), 4.10-4.02 (m, 2H), 3.76-3.75 (m, 2H), 3.52-3.45 (m, 1H), 3.08 (dd, J=14.5, 6.0 Hz, 1H), 2.34 (s, 6H), 1.19 (t, J=7.1 Hz, 1H).

B. 3-[5-(4-Allylamino-phenyl)-1-p-tolyl-1H-pyrazol-3-yl]-2-m-tolyl-propionic acid To a solution of 3-[5-(4-allylamino-phenyl)-1-p-tolyl-1H-pyrazol-3-yl]-2-m-tolyl-propionic acid ethyl ester (90 mg, 0.2 mmol) was added LiOH (14 mg, 0.58 mmol, 3 equiv) in 2:1 THF/H$_2$O (1 mL). After 3 h at 45° C., the mixture was purified by preparative reversed-phase HPLC (acetonitrile/water) to afford the desired compound (70 mg, 77 %). MS (ESI): mass calculated for $C_{29}H_{29}N_3O_2$, 451.23; m/z found, 452.6 [M+H]$^+$. $^1$H NMR (500 MHz, CDCl$_3$): 7.21-7.03 (m, 8H), 6.93 (d, J=8.8, 2H), 6.26 (s, 1H), 5.88-5.83 (m, 1H), 5.29-5.24 (m, 2H), 4.06 (dd, J=10.4, 5.1 Hz, 1H), 3.79(d, J=6.3 Hz, 2H), 3.54 (dd, J=15.0, 10.4 Hz, 1H), 3.09 (dd, J=15.0 5.1 Hz, 1H), 2.33 (s, 3H), 2.32 (s, 3H).

The compounds of Examples 95-101 were made according to the synthetic methods outlined in Example 94 and Scheme L.

Example 95

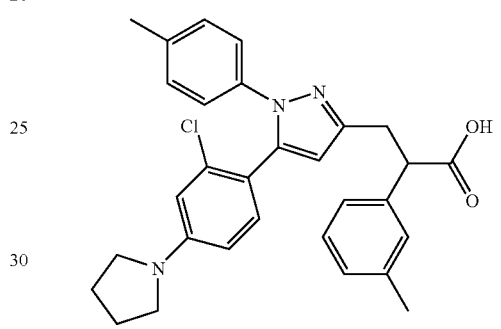

3-[5-(2-Chloro-4-pyrrolidin-1-yl-phenyl)-1-p-tolyl-1H-pyrazol-3-yl]-2-m-tolyl-propionic acid HPLC: $R_t$=4.35 (Method A). MS (ESI): mass calculated for $C_{30}H_{30}ClN_3O_2$, 499.20; m/z found, 500.10 [M+H]$^+$. $^1$H NMR (500 MHz, CDCl$_3$): 7.23-7.15 (m, 3H), 7.10-7.05 (m 5H), 6.89 (d, J=8.8 Hz, 1), 6.49 (d, J=2.5 Hz, 1H), 6.32 (dd, J=8.8, 2.5 Hz, 1H), 6.15 (s, 1H), 4.12 (d, J=9.0, 6.0 Hz, 1H), 3.55 (dd, J=14.8, 9.0 Hz, 1H), 3.26-3.24 (m, 4H), 3.18 (dd, J=14.8, 6.0 Hz, 1H), 2.33 (s, 3H), 2.30 (s, 3H), 2.07-1.99 (m, 4H).

Example 96

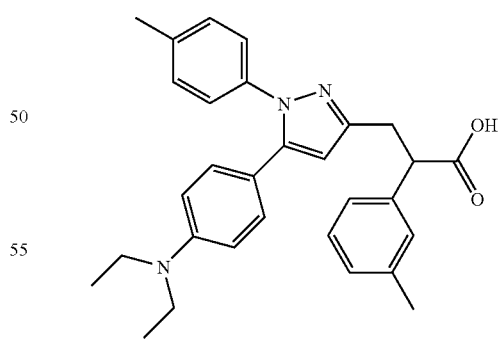

3-[5-(4-Diethylamino-phenyl)-1-p-tolyl-1H-pyrazol-3-yl]-2-m-tolyl-propionic acid HPLC: $R_t$=3.21 (Method A). MS (ESI): mass calculated for $C_{30}H_{33}N_3O_2$, 467.26; m/z found, 468.3 [M+H]$^+$. $^1$H NMR (500 MHz, CDCl$_3$): 7.26-7.16 (m, 8H), 7.09-7.08 (m, 4H), 6.22 (s, 1H), 4.08 (dd, J=9.3, 6.0 Hz, 1H), 3.52 (dd, J=14.8, 9.3 Hz, 1H), 3.44 (q, J=7.1 Hz, 4H), 3.11 (dd, J=14.8 6.0 Hz, 1H), 2.34 (s, 3H), 2.32 (s, 3H), 1.09 (t, J=7.1 Hz).

Example 97

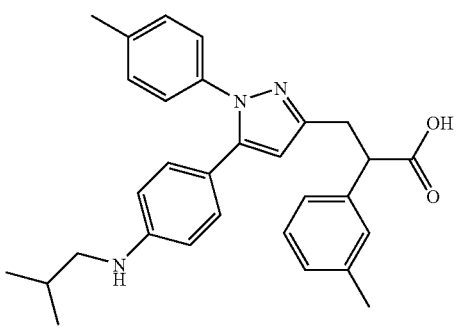

3-[5-(4-Isobutylamino-phenyl)-1-p-tolyl-1H-pyrazol-3-yl]-2-m-tolyl-propionic acid HPLC: $R_t$=4.02 (Method A). MS (ESI): mass calculated for $C_{30}H_{33}N_3O_2$, 467.26; m/z found, 468.3 [M+H]$^+$. $^1$H NMR (500 MHz, CDCl$_3$): 7.20-6.99 (m, 8H), 6.98 (d, J=8.8 Hz, 2H), 6.81 (d, J=8.5 Hz, 2H), 6.17 (s, 1H), 4.07 (dd, J=9.9, 5.5 Hz, 1H), 3.52 (dd, J=14.8, 9.9 Hz, 1H), 3.08 (dd, J=14.8, 5.5 Hz, 1H), 2.96 (d, J=7.1 Hz, 2H), 2.32 (s, 3H), 2.31 (s, 3H), 1.95-1.92 (m, 1H), 0.96 (d J=6.5 Hz, 6H).

Example 98

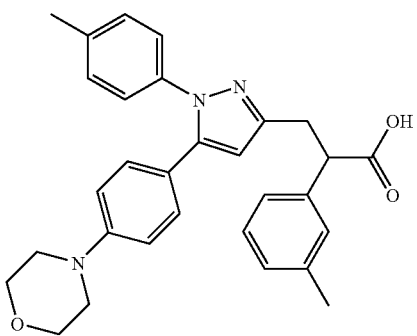

3-[5-(4-Morpholin-4-yl-phenyl)-1-p-tolyl-1H-pyrazol-3-yl]-2-m-tolyl-propionic acid HPLC: $R_t$=3.86 (Method A). MS (ESI): mass calculated for $C_{30}H_{31}N_3O_3$, 481.24; m/z found, 482.2 [M+H]$^+$. $^1$H NMR (500 MHz, CDCl$_3$): 7.21-7.09 (m, 8H), 7.07 (d, J=8.8 Hz, 2H), 6.89 (d, J=8.8 Hz, 2H), 6.21 (s, 1H), 4.08 (dd, J=9.3, 5.8 Hz, 1H), 3.89-3.87 (m, 4H), 3.54 (dd, J=14.8, 9.3 Hz, 1H), 3.23-3.22 (m, 4H), 3.13 (dd, J=14.8, 5.8 Hz, 1H), 2.35 (s, 3H), 2.33 (s, 3H).

Example 99

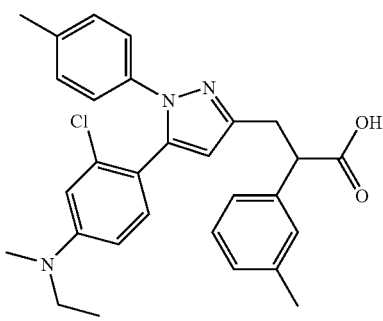

3-{5-[2-Chloro-4-(ethyl-methyl-amino)-phenyl]-1-p-tolyl-1H-pyrazol-3-yl}-2-m-tolyl-propionic acid HPLC: $R_t$=4.13 (Method A). MS (ESI): mass calculated for $C_{29}H_{30}ClN_3O_2$, 487.20; m/z found, 488.1 [M+H]$^+$. $^1$H NMR (500 MHz, CDCl$_3$): 7.24-7.15 (m, 3H), 7.10-7.07 (m, 5H), 6.96 (d. J=8.7 Hz, 1H), 6.77 (d, J=2.4 Hz, 1H), 6.62 (dd, J=8.7, 2.4 Hz, 1H), 6.19 (s, 1H), 4.12 (dd, J=9.3, 6.0 Hz, 1H), 3.56 (dd, J=14.8, 9.3 Hz, 1H), 3.39 (q, J=7.1 Hz, 2H), 3.18 (dd, 14.8, 6.0 Hz, 1H), 2.94 (s, 3H), 2.34 (s, 3H), 2.31 (s, 3H), 1.13 (t, J=7.1 Hz, 3H).

Example 100

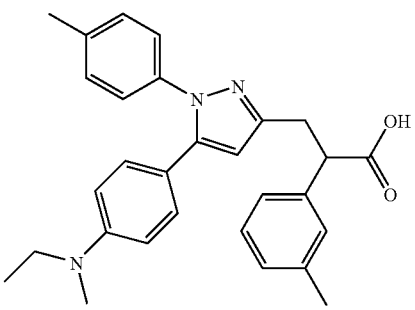

3-{5-[4-(Ethyl-methyl-amino)-phenyl]-1-p-tolyl-1H-pyrazol-3-yl}-2-m-tolyl-propionic acid HPLC: $R_t$=3.29 (Method A). MS (ESI): mass calculated for $C_{29}H_{31}N_3O_2$, 453.24; m/z found, 454.3 [M+H]$^+$. $^1$H NMR (400 MHz, CDCl$_3$): 7.26-7.08 (m, 12H), 6.23 (s, 1H), 4.09-4.05 (m, 1H), 3.52 (dd, J=14.9, 9.3 Hz, 1H), 3.44 (q, J=7.1 Hz, 2H), 3.11 (dd, J=14.9, 6.1 Hz, 1H), 3.06 (s, 3H), 2.35 (s, 3H), 2.32 (s, 3H), 1.12 (t, J=7.1 Hz, 3H).

Example 101

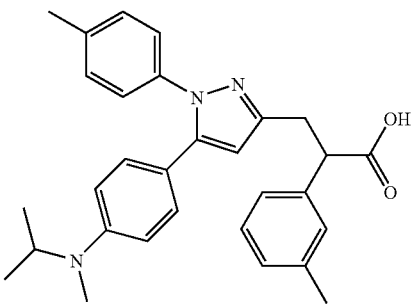

3-{5-[4-(Isopropyl-methyl-amino)-phenyl]-1-p-tolyl-1H-pyrazol-3-yl}-2-m-tolyl-propionic acid HPLC: $R_t$=4.06 (Method A). MS (ESI): mass calculated for $C_{30}H_{33}N_3O_2$, 467.26; m/z found, 468.3 [M+H]$^+$. $^1$H NMR (400 MHz, CDCl$_3$): 7.34 (d, J=8.8 Hz, 2H), 7.26-7.06 (m, 10H), 6.26 (s, 1H), 4.09 (dd, J=9.6, 5.9 Hz, 1H), 3.81-3.78 (m, 1H), 3.53 (dd, J=14.9, 9.6 Hz, 1H), 3.12 (dd, J=14.9, 5.9 Hz, 1H), 3.11 (s, 3H), 2.36 (s, 3H), 2.33 (s, 3H), 1.28 (d, J=6.6 Hz, 6H).

Example 102

Amidation

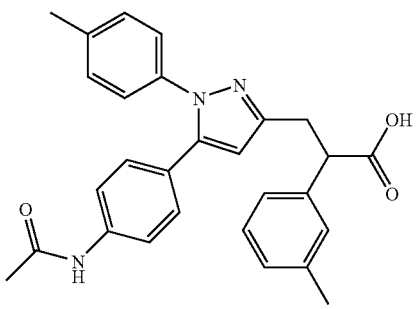

3-[5-(4-Acetylamino-phenyl)-1-p-tolyl-1H-pyrazol-3-yl]-2-m-tolyl-propionic acid

To a solution of 3-[5-(4-bromo-phenyl)-1-p-tolyl-1H-pyrazol-3-yl]-2-m-tolyl-propionic acid ethyl ester (Example 77, Step C; 100 mg, 0.2 mmol) in dioxane (0.6 mL) was added CuI (3 mg, 0.02 mmol, 10 mol %), (1R,2R)-N,N-dimethyl-cyclohexane-1,2-diamine (0.003 mL, 0.02 mmol, 10 mol %), $K_2CO_3$ (55 mg, 0.40 mmol, 2.0 equiv) and N-methylformamide (15 mg, 0.26 mmol, 1.3 equiv). The mixture was stirred at 110° C. for 14 h, and then cooled to 45° C. prior to the addition of a solution of LiOH (28 mg, 1.2 mmol, 3 equiv) in 2:1 THF/$H_2O$ (1 mL). After 3 h at 45° C., the reaction mixture was purified by preparative reversed-phase HPLC (acetonitrile/water) to afford the title compound (50 mg, 50%). HPLC: $R_t$=3.62 (Method A). MS (ESI): mass calculated for $C_{28}H_{27}N_3O_3$, 453.21; m/z found, 454.3 [M+H]$^+$. $^1$H NMR (500 MHz, CDCl$_3$): 7.43-7.39 (m, 3H), 7.25-7.17 (m, 3H), 7.10-7.06 (m, 6H), 6.24 (s, 1H), 4.09 (dd, J=10.0, 5.2 Hz, 1H), 3.53 (dd, J=15.0, 10.0 Hz, 1H), 3.13-3.09 (dd, J=15.0, 5.2 Hz, 1H), 2.34 (s, 6H), 2.16 (S, 3H).

The compounds of Examples 103 and 104 were made according to the synthetic methods outlined in Example 102 and Scheme L.

Example 103

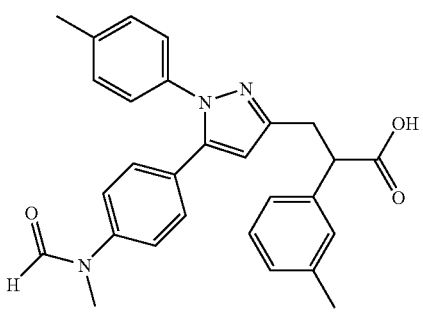

3-{5-[4-(Formyl-methyl-amino)-phenyl]-1-p-tolyl-1H-pyrazol-3-yl}-2-m-tolyl-propionic acid HPLC: $R_t$=3.64 (Method A). MS (ESI): mass calculated for $C_{28}H_{27}N_3O_3$, 453.21; m/z found, 454.3 [M+H]$^+$. $^1$H NMR (500 MHz, CDCl$_3$): 8.50 (s, 1H), 7.25-7.08 (m, 8H), 7.19 (d, J=8.8 Hz, 2H), 7.07 (d, J=8.5 Hz, 2H), 6.24 (s, 1H), 4.11 (dd, J=9.6, 5.7 Hz, 1H), 3.55 (dd, J=15.0, 9.6 Hz, 1H), 3.30 (s, 3H), 3.14 (dd, J=15.0, 5.7 Hz, 1H), 2.36 (s, 3H), 2.24 (s, 3H).

Example 104

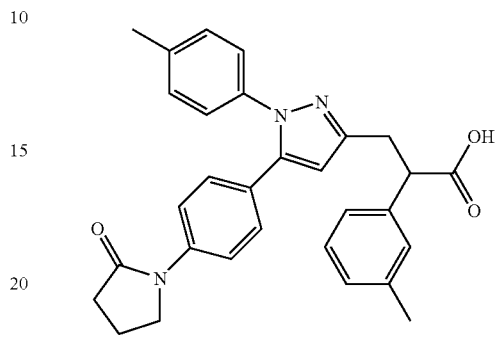

3-{5-[4-(2-Oxo-pyrrolidin-1-yl)-phenyl]-1-p-tolyl-1H-pyrazol-3-yl}-2-m-tolyl-propionic acid HPLC: $R_t$=3.75 (Method A). MS (ESI): mass calculated for $C_{30}H_{29}N_3O_3$, 479.22; m/z found, 480.3 [M+H]$^+$. $^1$H NMR (500 MHz, CDCl$_3$): 7.54 (d, J=8.8 Hz, 2H), 7.24-7.09 (m, 8H), 7.14 (d, J=8.8 Hz, 2H), 6.20 (s, 1H), 4.10(dd, J=9.3, 5.7 Hz, 1H), 3.83 (t, J=7.0 Hz, 2H), 3.54 (dd, J=15.0, 9.3 Hz, 1H), 3.13 (dd, J=15.0, 5.7 Hz, 1H), 2.62 (t, J=8.2 Hz, 2H), 2.37 (s, 3H), 2.24 (s, 3H), 2.16 (quintet, J=8.0, 7.0 Hz, 2H).

Example 105

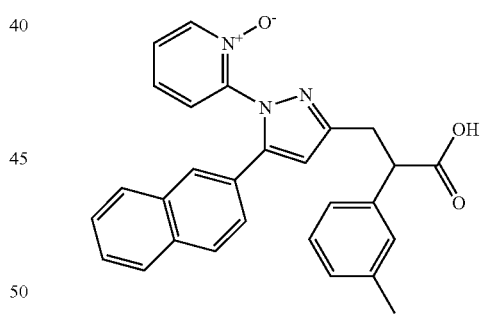

3-[5-Naphthalen-2-yl-1-(1-oxy-pyridin-2-yl)-1H-pyrazol-3-yl]-2-m-tolyl-propionic acid To a solution of 3-(5-naphthalen-2-yl-1-pyridin-2-yl-1H-pyrazol-3-yl)-2-m-tolyl-propionic acid (Example 52; 10 mg, 0.02 mmol) in THF (0.6 mL) was added m-chloroperbenzoic acid (7 mg, 0.03 mmol, 1.5 equiv). The reaction mixture was stirred at room temperature for 3 h, and then diluted with $CH_2Cl_2$ (2 mL). A solution of 1 N NaOH (1 mL) was added, and the resulting aqueous layer was back-extracted with $CH_2Cl_2$ (2×2 mL). The combined organic layers were washed with brine (2 mL), dried (MgSO$_4$), and concentrated under reduced pressure. The residue was purified by preparative reversed-phase HPLC (acetonitrile/water) to afford the title compound (6 mg, 60%). HPLC: $R_t$=1.17 (Method H). MS (ESI): mass calculated for $C_{28}H_{23}N_3O_3$, 449.17; m/z found, 450.1 [M+H]$^+$. $^1$H NMR (500 MHz, CDCl$_3$): 8.25 (s, 1H), 7.78-7.69 (m, 5H), 7.48-7.39 (m, 4H), 7.35-7.30 (m, 1H), 7.30-7.20 (m, 3H), 7.10 (d, J=6.3 Hz, 1H), 4.14 (dd, J=10.0, 5.7 Hz, 1H), 3.59 (dd, J=15.0, 10.0, 1H), 3.12 (dd, J=15.0, 5.7 Hz, 1H), 2.34 (s, 3H).

Example 106

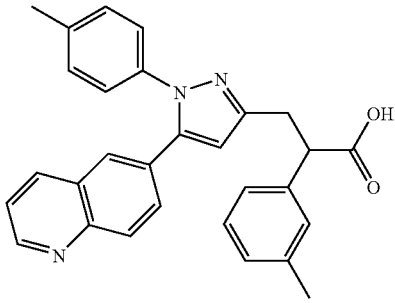

3-(5-Quinolin-6-yl-1-p-tolyl-1H-pyrazol-3-yl)-2-m-tolyl-propionic acid

To a solution of 3-[5-(4-allylamino-phenyl)-1-p-tolyl-1H-pyrazol-3-yl]-2-m-tolyl-propionic acid ethyl ester (Example 94, Step A; 70 mg, 0.15 mmol) in ethanol (1 mL) was added 10% Pd/C (26 mg) and methanesulfonic acid (0.01 mL, 0.15 mmol, 1 equiv). The mixture was stirred at 65° C. for 2 h. The catalyst was removed by filtering the reaction mixture through a CELITE® pad, and the pad was rinsed with EtOH (1.5 mL). The combined filtrates were concentrated under reduced pressure. The crude residue was dissolved in 1:1 THF/H$_2$O (1.5 mL), and LiOH was added (10 mg, 0.45 mmol, 3 equiv). After 3 h at 45° C., the mixture was purified by preparative reversed-phase HPLC (acetonitrile/water) to afford the title compound (26 mg, 35%) along with 3-[5-(4-amino-phenyl)-1-p-tolyl-1H-pyrazol-3-yl]-2-m-tolyl-propionic acid (20 mg, 35%). HPLC: $R_t$=3.18 (Method A). MS (ESI): mass calculated for $C_{29}H_{25}N_3O_2$, 447.19; m/z found, 448.2 [M+H]$^+$. $^1$H NMR (400 MHz, CDCl$_3$): 8.43 (d, J=8.5 Hz, 1H), 8.25 (d, J=8.8 Hz, 1H), 7.85 (d, J=1.7 Hz, 1H), 7.68 (dd, J=8.3, 4.8 Hz, 1H), 7.59 (dd, J=8.8, 1.7 Hz, 1H), 7.26-7.23 (m, 2H), 7.12 (s, 4H), 6.42 (s, 1H), 4.17 (dd, J=9.8, 5.3 Hz, 1H), 3.58 (dd, J=14.9, 9.8 Hz, 1H), 3.17 (dd, J=14.9, 5.3 Hz, 1H), 2.36 (s, 3H).

Example 107

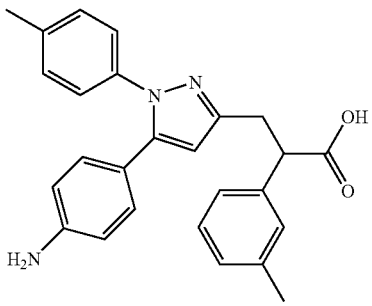

3-[5-(4-Amino-phenyl)-1-p-tolyl-1H-pyrazol-3-yl]-2-m-tolyl-propionic acid

Prepared according to the synthetic methods outlined in Example 106. HPLC: $R_t$=3.16 (Method A). MS (ESI): mass calculated for $C_{26}H_{25}N_3O_2$, 411.19; m/z found, 412.2 [M+H]$^+$. $^1$H NMR (400 MHz, CDCl$_3$): 7.30 (s, 2H), 7.24-7.21 (m, 2H), 7.13-7.07 (m, 4H), 6.97 (d, J=8.3 Hz, 2H), 6.67 (d, J=6.8 Hz, 2H), 6.13 (s, 1H), 4.01 (dd, J=9.3, 6.0 Hz, 1H), 3.49 (dd, J=14.6, 9.3 Hz, 1H), 3.07 (dd, J=14.6, 6.0 Hz, 1H), 2.34 (s, 6H).

Example 108

Preparation of Alkenes

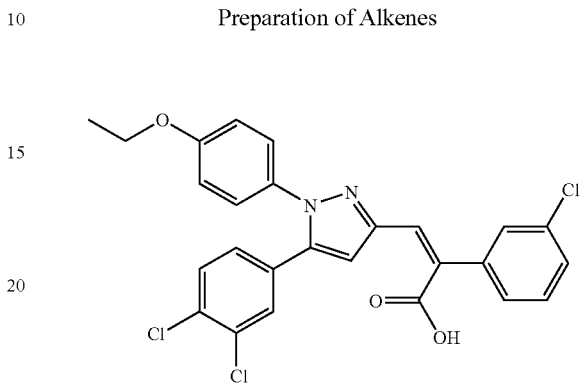

(Z)-2-(3-Chloro-phenyl)-3-[5-(3,4-dichloro-phenyl)-1-(4-ethoxy-phenyl)-1H-pyrazol-3-yl]-acrylic acid A. 5-(3,4-Dichloro-phenyl)-1-(4-ethoxy-phenyl)-1H-pyrazole-3-carbaldehyde To a solution of Dess-Martin periodinane (2.0 g, 4.6 mmol, 2.0 equiv) in CH$_2$Cl$_2$ (10 mL) was added a solution of [5-(3,4-dichloro-phenyl)-1-(4-ethoxy-phenyl)-1H-pyrazol-3-yl]-methanol (prepared by the method of Example 1, Steps A-C; 0.84 g, 2.3 mmol) in CH$_2$Cl$_2$ (10 mL). The reaction mixture was stirred overnight at room temperature. Then the reaction was quenched with 1 M NaOH (10 mL), and the resulting mixture was stirred until the layers separated. The aqueous layer was back-extracted with CH$_2$Cl$_2$ (3×10 mL). The combined organic layers were washed with 1 M NaOH (20 mL) then H$_2$O (20 mL), dried (MgSO$_4$), and concentrated to provide the pure aldehyde as a dark brown oil (0.59 g, 1.6 mmol, 70%). TLC (silica gel, 1:1 EtOAc/hexanes): $R_f$=0.62. MS (ESI): mass calculated for $C_{18}H_{14}Cl_2N_2O_2$, 360.04; m/z found, 361 [M+H]$^+$. $^1$H NMR (400 mHz, CDCl$_3$): 10.05 (s, 1H), 7.38-7.36 (m, 2H), 7.25-7.21 (m, 2H), 7.0 (s, 1H), 7.0-6.97 (m, 1H), 6.93-6.91 (m, 2H), 4.06 (q, J=7.0 Hz), 1.44 (t, J=7.0 Hz, 3H).

B. 2-(3-Chloro-phenyl)-3-[5-(3,4-dichloro-phenyl)-1-(4-ethoxy-phenyl)-1H-pyrazol-3-yl]-acrylic acid, E and Z stereoisomers To a mixture of 5-(3,4-dichloro-phenyl)-1-(4-ethoxy-phenyl)-1H-pyrazole-3-carbaldehyde (0.33 g, 0.91 mmol) and 3-chlorophenyl acetic acid (0.23 g, 1.4 mmol) was added acetic anhydride (0.8 mL) and TEA (0.8 mL). The mixture was allowed to stir overnight at room temperature. The TEA was removed under reduced pressure, and the resulting mixture was purified on silica gel (MPLC, 0-5% MeOH/CH$_2$Cl$_2$) to provide exclusively the E acrylic acid as a brown foam (0.21 g, 46%). The foam was then dissolved in CHCl$_3$ (10 mL), and the solution was placed in quartz tubes and subjected to uv light overnight. The solvent was removed to provide a 1:1 mixture of E and Z stereoisomers. The stereoisomers were separated by preparative reversed-phase HPLC (acetonitrile/water) to afford the pure Z (0.033 g, 0.064 mmol, 15%) and E acrylic acids (0.043 g, 0.084 mmol, 20%). Z stereoisomer: TLC (silica gel, 9:1 CH$_2$Cl$_2$/MeOH): R$_f$=0.26. HPLC: R$_t$=7.35 (Method I). MS (ESI): mass calculated for C$_{26}$H$_{19}$Cl$_3$N$_2$O$_3$, 512.05; m/z found, 511/513 [M–H]$^-$. $^1$H NMR (400 mHz, CDCl$_3$): 7.49-7.47 (m, 1H), 7.39-7.31 (m, 5H), 7.19-7.16 (m, 2H), 7.05(s, 1H), 6.99-6.96 (m, 1H), 6.90-6.86 (m, 2H), 4.04 (q, J=7.0 Hz) 6.72 (s, 1H), ): 1.44 (t, J=7.0 Hz, 3H).

Example 109

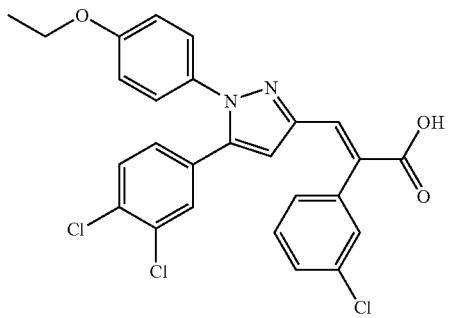

(E)-2-(3-Chloro-phenyl)-3-[5-(3,4-dichloro-phenyl)-1-(4-ethoxy-phenyl)-1H-pyrazol-3-yl]-acrylic acid HPLC: R$_t$=8.58. MS (ESI): mass calculated for C$_{26}$H$_{25}$N$_3$O$_2$, 512.0; m/z found, 513 [M+H]$^+$. $^1$H NMR (400 mHz, CDCl$_3$): 8.09 (s, 1H), 7.30 (m, 3H), 7.24 (m, 2H), 7.14 (m, 3H), 6.86 (m, 2H), 6.79 (m, 1H), 5.53 (s, 1H), 4.03 (q, J=7.0 Hz, 2H), 1.42 (t, J=7.0 Hz, 3H).

Example 110

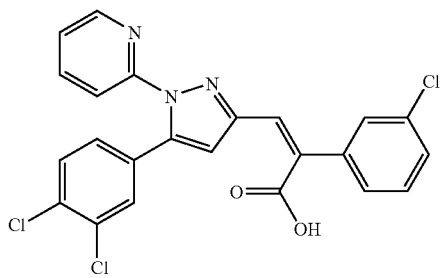

(Z)-2-(3-Chloro-phenyl)-3-[5-(3,4-dichloro-phenyl)-1-pyridin-2-yl-1H-pyrazol-3-yl]-acrylic acid This compound was prepared as described for the 4-ethoxyphenyl analog in EXAMPLE 108 substituting [5-(3,4-dichloro-phenyl)-1-pyridin-2-yl-1H-pyrazol-3-yl]-methanol (prepared by the method of Example 1, Steps A-C) for[5-(3,4-dichloro-phenyl)-1-(4-ethoxy-phenyl)-1H-pyrazol-3-yl]-methanol in Step A. TLC (silica gel, 9:1 CH$_2$Cl$_2$/MeOH): R$_f$=0.19. HPLC: R$_t$=5.63 (Method I). MS (ESI): mass calculated for C$_{23}$H$_{14}$Cl$_3$N$_3$O$_2$, 469.02; m/z found, 468/469 [M–H]$^-$. $^1$H NMR (400 mHz, CDCl$_3$): 8.26-8.25 (m, 1H), 7.79-7.77 (m, 1H), 7.58-7.56 (m, 1H), 7.47-7.46 (m, 1H), 7.37-7.22 (m, 6H), 7.02 (s, 1H), 7.00-6.98 (m, 1H), 6.74 (s, 1H).

Example 111

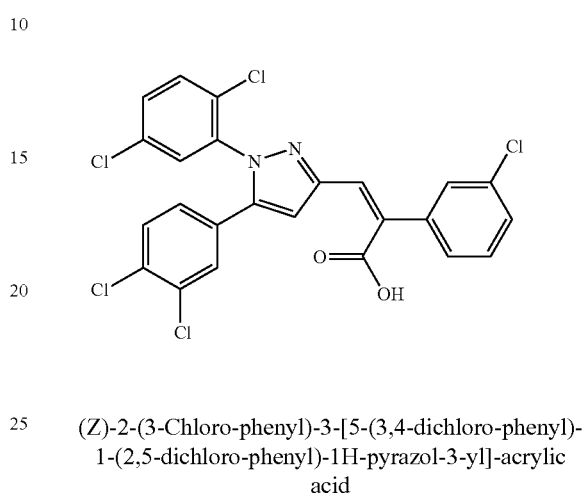

(Z)-2-(3-Chloro-phenyl)-3-[5-(3,4-dichloro-phenyl)-1-(2,5-dichloro-phenyl)-1H-pyrazol-3-yl]-acrylic acid This compound was prepared as described for the 4-ethoxyphenyl analog in EXAMPLE 108 substituting [5-(3,4-dichloro-phenyl)-1-(2,5-dichloro-phenyl)-1H-pyrazol-3-yl]-methanol for [5-(3,4-dichloro-phenyl)-1-(4-ethoxy-phenyl)-1H-pyrazol-3-yl]-methanol in Step A. TLC (silica gel, 9:1 CH$_2$Cl$_2$/MeOH): R$_f$=0.23. HPLC: R$_t$=7.95 (Method I). MS (ESI): mass calculated for C$_{24}$H$_{13}$Cl$_5$N$_2$O$_2$, 535.94; m/z found, 535/537 [M–H]$^-$. $^1$H NMR (400 mHz, CDCl$_3$): 7.51-7.49 (m, 2H), 7.45-7.32 (m, 7H), 7.07 (s, 1H), 6.97-6.94 (m, 1H), 6.82 (s, 1H).

Example 112

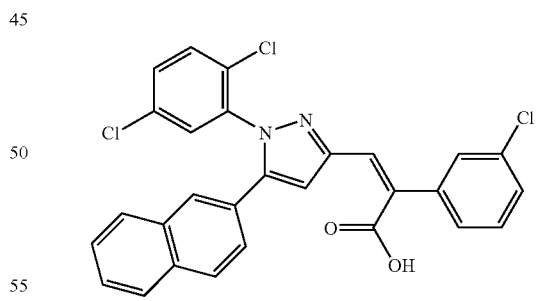

(Z)-2-(3-Chloro-phenyl)-3-[1-(2,5-dichloro-phenyl)-5-naphthalen-2-yl-1H-pyrazol-3-yl]-acrylic acid HPLC: R$_t$=5.28 (Method I). MS (ESI): mass calculated for C$_{28}$H$_{17}$Cl$_3$N$_2$O$_2$, 518.04; m/z found, 519/521 [M+H]$^+$. $^1$H NMR (500 MHz, CDCl$_3$): 7.83-7.72 (m, 4H), 7.54-7.51 (m, 4H), 7.42-7.38 (m, 4H), 7.35-7.33 (m, 2H), 7.11 (s, 1H), 6.87 (s, 1H).

Example 113

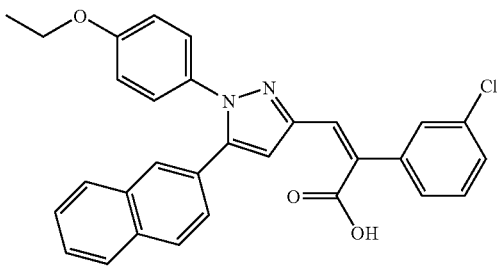

(Z)-2-(3-Chloro-phenyl)-3-[1-(4-ethoxy-phenyl)-5-naphthalen-2-yl-1H-pyrazol-3-yl]-acrylic acid HPLC: $R_t$=5.23 (Method I). MS (ESI): mass calculated for $C_{30}H_{23}ClN_2O_3$, 494.14; m/z found, 495.1 [M+H]$^+$. $^1$H NMR (500 MHz, CDCl$_3$): 7.84-7.83 (m, 2H), 7.80-7.77 (m, 2H), 7.56-7.52 (m, 2H), 7.49-7.48 (m, 1H), 7.39-7.37 (m, 1H), 7.33-7.32 (m, 2H), 7.26-7.24 (m, 3H), 7.08 (s, 1H), 6.86 (d, J=9.0 Hz, 2H), 6.77 (s, 1H), 4.03 (q, J=7.1 Hz, 2H), 1.41 (t, J=7.1 Hz, 1H).

Example 114

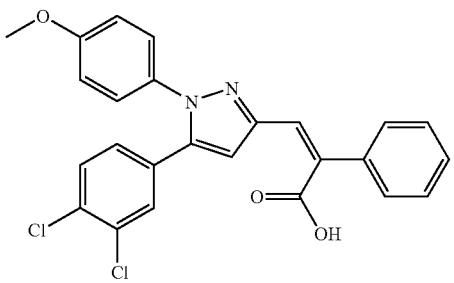

(Z)-3-[5-(3,4-Dichloro-phenyl)-1-(4-methoxy-phenyl)-1H-pyrazol-3-yl]-2-phenyl-acrylic acid HPLC: $R_t$=10.60 (Method A). MS (ESI): mass calculated for $C_{25}H_{18}Cl_2N_2O_3$, 464.07; m/z found, 465.1 [M+H]$^+$. $^1$H NMR (500 MHz, CDCl$_3$): 7.50-7.48 (m, 2H), 7.39-7.35 (m, 5H), 7.23 (d, J=9.0 Hz, 2H), 7.06 (s, 1H), 6.99 (dd, J=8.2, 1.9 Hz, 1H), 6.91 (d, J=9.0 Hz, 2H), 6.70 (s, 1H), 3.85 (s, 3H).

Example 115

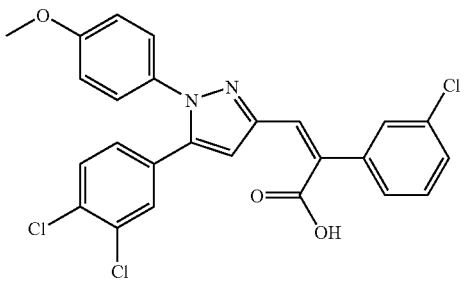

(Z)-2-(3-Chloro-phenyl)-3-[5-(3,4-dichloro-phenyl)-1-(4-methoxy-phenyl)-1H-pyrazol-3-yl]-acrylic acid HPLC: $R_t$=10.50 (Method A). MS (ESI): mass calculated for $C_{25}H_{17}Cl_3N_2O_3$, 498.03; m/z found, 499.0 [M+H]$^+$. $^1$H NMR (500 MHz, CDCl$_3$): 7.47 (br s, 1H), 7.41 (s, 2H), 7.39-7.37 (m, 1H), 7.35 (s, 2H), 7.22 (d, J=9.0 Hz, 2H), 7.04 (s, 1H), 7.00 (dd, J=8.2, 2.2 Hz, 1H), 6.92 (d, J=9.0 Hz, 2H), 6.70 (s, 1H), 3.85 (s, 3H).

Example 116

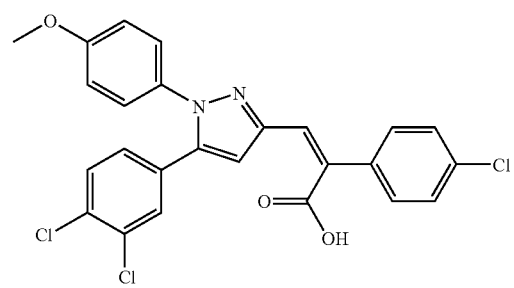

(Z)-2-(4-Chloro-phenyl)-3-[5-(3,4-dichloro-phenyl)-1-(4-methoxy-phenyl)-1H-pyrazol-3-yl]-acrylic acid HPLC: $R_t$=10.50 (Method A). MS (ESI): mass calculated for $C_{25}H_{17}Cl_3N_2O_3$, 498.03; m/z found, 499.0 [M+H]$^+$. $^1$H NMR (500 MHz, CDCl$_3$): 7.43-7.40 (m, 4H), 7.36 (d, J=8.8 Hz, 2H), 7.22 (d, J=9.0 Hz, 2H), 7.02 (s, 1H), 6.99 (dd, J=8.2, 2.2 Hz, 1H), 6.92 (d, J=9.0 Hz, 2H), 6.70 (s, 1H), 3.85 (s, 3H).

Example 117

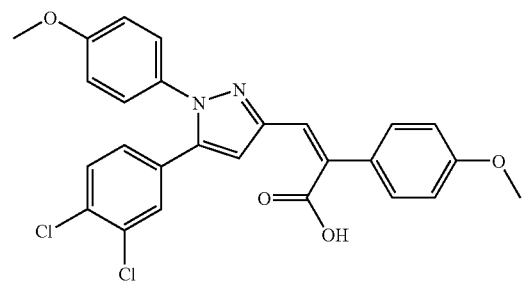

(Z)-3-[5-(3,4-Dichloro-phenyl)-1-(4-methoxy-phenyl)-1H-pyrazol-3-yl]-2-(4-methoxy-phenyl)-acrylic acid HPLC: $R_t$=5.60 (Method A). MS (ESI): mass calculated for $C_{26}H_{20}Cl_2N_2O_4$, 494.08; m/z found, 495.0 [M+H]$^+$. $^1$H NMR (500 MHz, CDCl$_3$): 7.44 (d, J=8.8 Hz, 2H), 7.40 (d, J=2.2 Hz, 1H), 7.38 (d, J=8.5 Hz, 1H), 7.21 (d, J=9.0 Hz, 2H), 7.00 (s, 1H), 6.96 (dd, J=8.5, 1.9 Hz, 1H), 6.9? (d, J=8.8 Hz, 2H), 6.91 (d, J=8.8 Hz, 2H), 6.68 (s, 1H), 3.85 (s, 3H), 3.84 (s, 3H).

Example 118

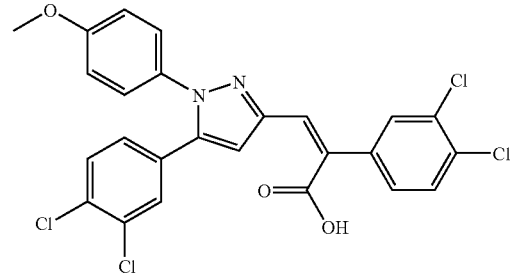

(Z)-2-(3,4-Dichloro-phenyl)-3-[5-(3,4-dichloro-phenyl)-1-(4-methoxy-phenyl)-1H-pyrazol-3-yl]-acrylic acid HPLC: $R_t$=6.20 (Method A). MS (ESI): mass calculated for $C_{25}H_{16}Cl_4N_2O_3$, 531.99; m/z found, 533.0 [M+H]$^+$. $^1$HNMR (500 MHz, CDCl$_3$): 7.58 (d, J=1.9 Hz, 1H), 7.45 (d, J=8.5 Hz, 1H), 7.41-7.39 (m, 2H), 7.32 (dd, J=8.5, 2.2 Hz, 1H), 7.22 (d, J=9.0 Hz, 2H), 7.03 (s, 1H), 6.99 (dd, J=8.2, 1.9 Hz, 1H), 6.93 (d, J=9.0 Hz, 2H), 6.71 (s, 1H), 3.86 (s, 3H).

Example 119

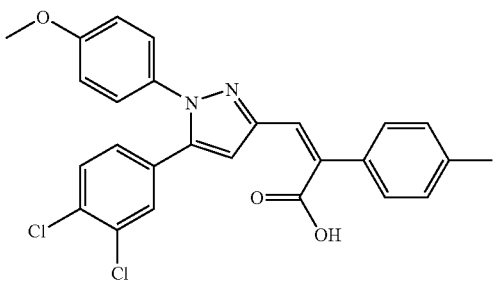

(Z)-3-[5-(3,4-Dichloro-phenyl)-1-(4-methoxy-phenyl)-1H-pyrazol-3-yl]-2-p-tolyl-acrylic acid HPLC: $R_t$=6.94 (Method A). MS (ESI): mass calculated for $C_{26}H_{20}Cl_2N_2O_3$, 478.09; m/z found, 479.1 [M+H]$^+$. $^1$H NMR (500 MHz, CDCl$_3$): 7.40-7.38 (m, 4H), 7.22-7.19 (m, 4H), 7.03 (s, 1H), 6.99 (dd, J=8.2, 1.9 Hz, 1H), 6.91 (d, J=9.0 Hz, 2H), 6.69 (s, 1H), 3.85 (s, 3H), 2.38 (s, 3H).

Example 120

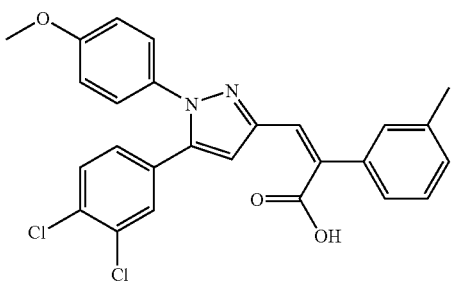

(Z)-3-[5-(3,4-Dichloro-phenyl)-1-(4-methoxy-phenyl)-1H-pyrazol-3-yl]-2-m-tolyl-acrylic acid HPLC: $R_t$=6.79 (Method A). MS (ESI): mass calculated for $C_{26}H_{20}Cl_2N_2O_3$, 478.09; m/z found, 479.1 [M+H]$^+$. $^1$H NMR (500 MHz, CDCl$_3$): 7.40 (d, J=2.2 Hz, 1H), 7.38 (d, J=8.2 Hz, 1H), 7.30-7.28 (m, 3H), 7.21 (d, J=9.0 Hz, 2H), 7.18-7.15 (m, 1H), 7.04 (s, 1H), 6.99 (dd, J=8.2, 1.9 Hz, 1H), 6.91 (d, J=9.0 Hz, 2H), 6.70 (s, 1H), 3.85 (s, 3H), 2.39 (s, 3H).

Example 121

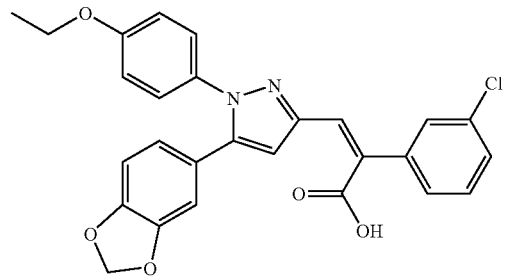

(Z)-3-[5-Benzo[1,3]dioxol-5-yl-1-(4-ethoxy-phenyl)-1H-pyrazol-3-yl]-2-(3-chloro-phenyl)-acrylic acid HPLC: $R_t$=6.38 (Method I). MS (ESI): mass calculated for $C_{27}H_{21}ClN_2O_5$, 488.11; m/z found, 489.1 [M+H]$^+$. $^1$H NMR (500 MHz, CDCl$_3$): 7.48 (br s, 1H), 7.36-7.35 (m, 1H), 7.31-7.30 (m, 2H), 7.23 (d, J=9.0 Hz, 2H), 7.02 (s, 1H), 6.89 (d, J=9.0 Hz, 2H), 6.79 (d, J=7.9 Hz, 1H), 6.75 (dd, J=8.2, 1.6 Hz, 1H), 6.67 (d, 1.6 Hz, 1H), 6.58 (s, 1H), 6.00 (s, 2H), 4.06 (q, J=6.9 Hz, 2H), 1.44 (t, 6.9 Hz, 3H).

Example 122

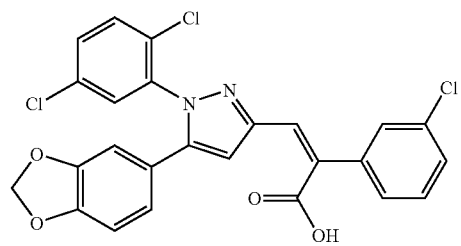

(Z)-3-[5-Benzo[1,3]dioxol-5-yl-1-(2,5-dichloro-phenyl)-1H-pyrazol-3-yl]-2-(3-chloro-phenyl)-acrylic acid A. 5-Benzo[1,3]dioxol-5-yl-1-(2,5-dichloro-phenyl)-1H-pyrazole-3-carbaldehyde To a solution of Dess-Martin periodinane (2.3 g, 5.5 mmol, 2.0 equiv) in CH$_2$Cl$_2$ (10 mL) was added a solution of [5-benzo[1,3]dioxol-5-yl-1-(2,5-dichloro-phenyl)-1H-pyrazol-3-yl]-methanol (prepared by the method of Example 1, Steps A-C; 1.0 g, 2.8 mmol) in CH$_2$Cl$_2$ (10 mL). The reaction mixture was stirred overnight at room temperature. Then the reaction was quenched with 1 M NaOH (10 mL), and the resulting mixture was stirred until the layers separated. The aqueous layer was back-extracted with CH$_2$Cl$_2$ (3×10 mL). The combined organic layers were washed with 1 M NaOH (20 mL) then H$_2$O (20 mL), dried (MgSO$_4$), and concentrated to provide the pure aldehyde (1.04 g, 2.8 mmol, 99%). HPLC: $R_t$=5.35 (Method B). MS (ESI): mass calculated for $C_{17}H_{10}Cl_2N_2O_3$, 360.01; m/z found, 361 [M+H]+. 1H NMR (400 mHz, $CDCl_3$): 10.05 (s, 1H), 7.50-7.43 (m, 1H), 7.25-7.21 (m, 2H), 7.7-7.26 (m, 1H), 6.96 (s, 1H), 6.74-6.72 (m, 1H), 6.68-6.65 (m, 2H), 5.97 (s, 2H).

B. 3-[5-Benzo[1,3]dioxol-5-yl-1-(2,5-dichloro-phenyl)-1H-pyrazol-3-yl]-2-(3-chloro-phenyl)-acrylic acid, E and Z stereoisomers To a mixture of 5-benzo[1,3]dioxol-5-yl-1-(2,5-dichlorophenyl)-1H-pyrazole-3-carbaldehyde (0.20 g, 0.55 mmol) and 3-chlorophenyl acetic acid (0.19 g, 0.82 mmol) was added acetic anhydride (1.0 mL) and TEA (1.0 mL). The mixture was allowed to stir overnight at room temperature. The TEA was removed under reduced pressure, and the resulting mixture was purified on silica gel (MPLC, 0-5% MeOH/$CH_2Cl_2$) to provide exclusively the E acrylic acid as a brown foam (0.14 g, 49%). The foam was then dissolved in $CHCl_3$ (10 mL), and the solution was placed in quartz tubes and subjected to uv/vis light overnight. The solvent was removed to provide a 1:1 mixture of E and Z stereoisomers. The stereoisomers were separated by preparative reversed-phase HPLC (acetonitrile/water) to afford the pure Z (0.02 g, 0.04 mmol, 15%) and E acrylic acids (0.03 g, 0.04 mmol, 20%). Z stereoisomer: HPLC: $R_t$=5.86 (Method I). MS (ESI): mass calculated for $C_{25}H_{15}Cl_3N_2O_4$, 512.01; m/z found, 513.0 [M+H]+. 1H NMR (500 MHz, $CDCl_3$): 7.48 (br s, 1H), 7.45 (br s, 1H), 7.43 (s, 2H), 7.38-7.36 (m, 1H), 7.32-7.31 (m, 2H), 7.06 (s, 1H), 6.75 (d, J=8.5 Hz, 1H), 6.69 (s, 1H), 6.68 (d, J=8.2 Hz, 2H), 5.99 (s, 2H).

Example 123

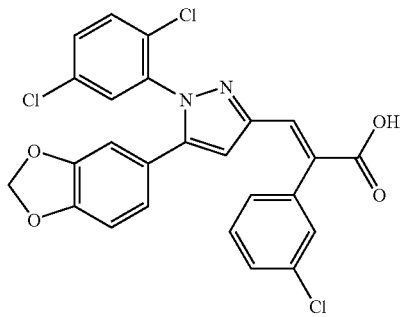

(E)-3-[5-Benzo[1,3]dioxol-5-yl-1-(2,5-dichloro-phenyl)-1H-pyrazol-3-yl]-2-(3-chloro-phenyl)-acrylic acid HPLC: $R_t$=4.82 (Method I). MS (ESI): mass calculated for $C_{25}H_{15}Cl_3N_3O_2$, 512.0; m/z found, 513 [M+H]+. 1H NMR (500 mHz, $CDCl_3$): 8.05 (s, 1H), 7.43-7.34 (m, 3H), 7.26-7.24 (m, 4H), 6.65 (d, J=8.5 Hz, 1H), 6.45-6.43 (m, 2H), 5.93 (s, 2H), 5.49 (s, 1H).

Example 124

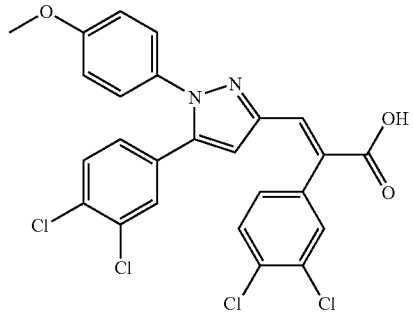

(E)-2-(3.4-Dichloro-phenyl)-3-[5-(3,4-dichloro-phenyl)-1-(4-methoxy-phenyl)-1H-pyrazol-3-yl]-acrylic acid HPLC: $R_t$=6.22 (Method I). MS (ESI): mass calculated for $C25H_{16}Cl_4N_2O_3$, 531.99; m/z found, 532.9 [M+H]+. 1H NMR (500 MHz, $CDCl_3$): 8.09 (s, 1H), 7.54 (d, J=8.2 Hz, 1H), 7.47 (d, J=1.9 Hz, 1H), 7.33 (d, J=8.2 Hz, 1H), 7.21 (dd, J=8.2, 1.9 Hz, 1H), 7.15 (s, 1H), 7.14 (d, J=9.0 Hz, 2H), 6.88 (d, J=9.0 Hz, 2H), 6.83 (dd, J=8.5, 2.2 Hz, 1H), 5.68 (s, 1H), 3.83 (s, 3H).

Example 125

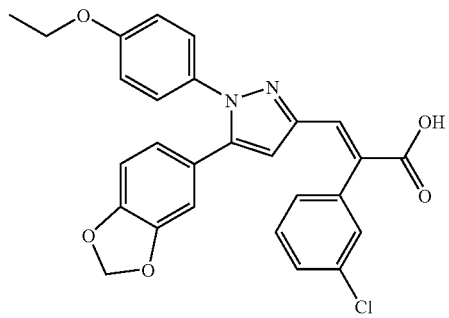

(E)-3-[5-Benzo[1,3]dioxol-5-yl-1-(4-ethoxy-phenyl)-1H-pyrazol-3-yl]-2-(3-chloro-phenyl)-acrylic acid HPLC: $R_t$=6.28 (Method I). MS (ESI): mass calculated for $C_{27}H_{21}ClN_2O_5$, 488.11; m/z found, 489.1 [M+H]+. 1H NMR (500 MHz, $CDCl_3$): 8.09 (s, 1H), 7.40-7.38 (m, 3H), 7.26-7.23 (m, 1H), 7.16 (d, J=9.0 Hz, 2H), 6.85 (d, J=8.8 Hz, 2H), 6.68 (d, J=7.9 Hz, 1H), 6.50 (dd, J=7.9, 1.6 Hz, 1H), 6.45 (d, J=1.6 Hz, 1H), 5.93 (s, 2H), 5.46 (s, 1H), 4.03 (q, J=6.9 Hz, 2H), 1.42 (t, J=6.9 Hz, 3H).

Example 126

Reduction

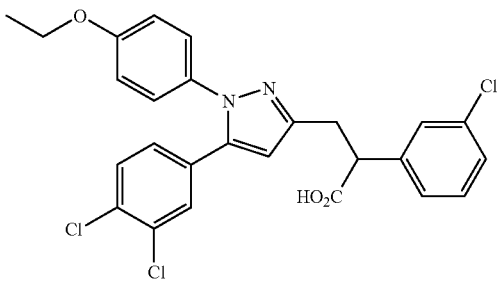

2-(3-Chloro-phenyl)-3-[5-(3,4-dichloro-phenyl)-1-(4-ethoxy-phenyl)-1H-pyrazol-3-yl]-propionic acid To a solution of 2-(3-chloro-phenyl)-3-[5-(3,4-dichloro-phenyl)-1-(4-ethoxy-phenyl)-1H-pyrazol-3-yl]-acrylic acid (Example 108, Step B; 0.043 g, 0.084 mmol) in EtOH (5 mL) was added tosylhydrazine (0.22 g, 1.2 mmol). To the light yellow solution was added a mixture of NaOAc (0.098 g, 1.2 mmol) in $H_2O$ (1 mL). The resulting mixture was heated to 100° C. overnight, then cooled to rt, diluted with $H_2O$ (10 mL), and extracted with $CH_2Cl_2$ (3×10 mL). The combined organic layers were dried ($MgSO_4$) and then concentrated to provide a yellow oil. The oil was purified by preparative reversed-phase HPLC (acetonitrile/water) to afford the pure alkane as a colorless oil (10 mg, 23%). TLC (silica gel, 9:1 $CH_2Cl_2$/MeOH): $R_f$=0.43. HPLC: $R_t$=10.7 (Method A). MS (ESI): mass calculated for $C_{26}H_{21}Cl_3N_2O_3$, 514.06; m/z found, 513 [M−H]$^-$. $^1$H NMR (400 mHz, CDCl$_3$): 7.32-7.23 (m, 6H), 7.14-7.10 (m, 2H), 6.92-6.89 (m, 1H), 6.88-6.85 (m, 2H), 6.23 (s, 1H), 4.03 (q, J=6.9 Hz, 2H), 4.04-4.00 (m, 1H), 3.50 (dd, J=6.7, 14.7 Hz, 1H), 3.09 (dd, J=8.7, 14.7 Hz, 1H), (1.42 (t, J=7.0 Hz, 3H), The compounds of Examples 127 and 128 were made according to the synthetic methods outlined in Example 126 and Scheme H.

Example 127

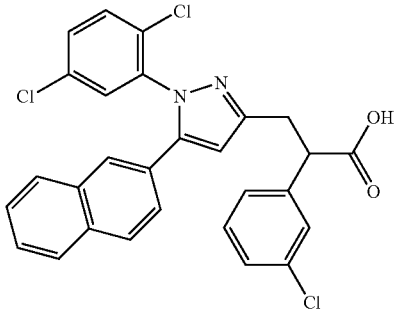

2-(3-Chloro-phenyl)-3-[1-(2,5-dichloro-phenyl)-5-naphthalen-2-yl-1H-pyrazol-3-yl]-propionic acid HPLC: $R_t$=4.77 (Method B). MS (ESI): mass calculated for $C_{28}H_{19}Cl_3N_2O_2$, 520.05; m/z found, 521/523 [M+H]$^+$. $^1$H NMR (400 MHz, CDCl$_3$): 7.79-7.77 (m, 1H), 7.73-7.68 (m, 2H), 7.61-7.60 (m, 1H), 7.48-7.46 (m, 3H), 7.38-7.37 (m, 1H), 7.31-7.26 (m, 4H), 7.20 (dd, J=8.5, 1.8 Hz, 1H), 6.35 (s, 1H), 4.16 (dd, J=8.3, 7.0 Hz, 1H), 3.54 (dd, J=14.8, 8.3 Hz, 1H), 3.19(dd, J=14.8, 7.0 Hz, 1H).

Example 128

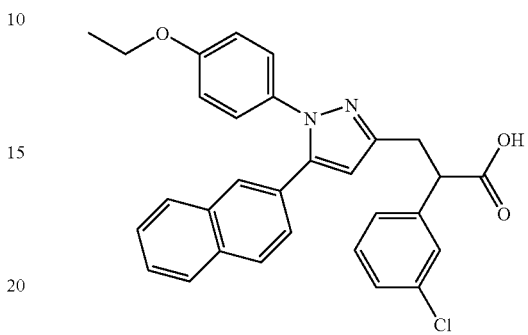

2-(3-Chloro-phenyl)-3-[1-(4-ethoxy-phenyl)-5-naphthalen-2-yl-1H-pyrazol-3-yl]-propionic acid HPLC: $R_t$=5.07 (Method A). MS (ESI): mass calculated for $C_{30}H_{25}ClN_2O_3$, 497.0; m/z 497.1 [M+H]$^+$. $^1$H NMR (500 mHz, CDCl$_3$): 7.80-7.78 (m, 1H), 7.74-7.70 (m, 3H), 7.50-7.48 (m, 2H), 7.39 (s, 1H), 7.28-7.26 (m, 3H), 7.18-7.14 (m, 3H), 6.80 (d, J=8.8 Hz, 2H), 6.36 (s, 1H), 4.16 (dd, J=9.3, 6.0 Hz, 1H), 4.00 (q, J=6.8 Hz, 2H), 3.58 (dd, J=15.0, 9.3 Hz, 1H), 3.19 (dd, J=15.0, 6.0 Hz, 1H), 1.40 (t, J=6.8 Hz, 3H).

The compounds of Examples 129-132 were made according to the synthetic methods outlined in Scheme D.

Example 129

Preparation of Tetrazoles

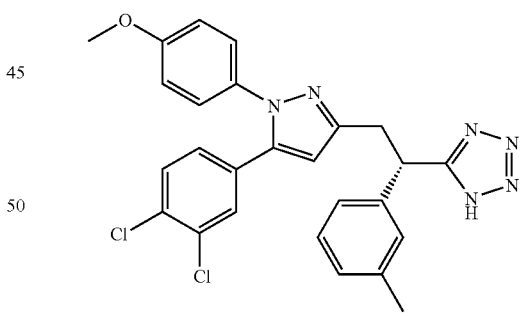

5-{(S)-2-[5-(3,4-Dichloro-phenyl)-1-(4-methoxy-phenyl)-1H-pyrazol-3-yl]-1-m-tolyl-ethyl}-1H-tetrazole A. (S)-N-2-Cyano-ethyl)-3-[5-(3,4-dichloro-phenyl)-1-(4-methoxy-phenyl)-1H-pyrazol-3-yl]-2-m-tolyl-propionamide To a 3-neck round-bottom flask was added (S)-3-[5-(3,4-dichloro-phenyl)-1-(4-methoxy-phenyl)-1H-pyrazol-3-yl]-2-m-tolyl-propionic acid (Example 1; 5.0 g, 9.9 mmol, 1.0 equiv), EDC (4.7 g, 24.7 mmol, 2.5 equiv) and HOBT (3.3 g, 24.7 mmol, 2.5 equiv) under nitrogen. N,N-Dimethylformamide (50 mL) was added, followed by 3-aminopropanenitrile (1.9 g, 24.7 mmol, 2.5 equiv) and diisopropylethylamine (6.8 mL, 39.6 mmol, 4.0 equiv). The reaction mixture was stirred overnight, then was diluted with ethyl acetate (200 mL), washed with 1 N HCl (100 mL), H₂O (100 mL), 10% sodium bicarbonate (100 mL), H₂O (100 mL) then brine (100 mL), and dried (sodium sulfate). The solvent was then removed under reduced pressure yielding the desired amide (5.35 g, 99%), which was used in the next step without purification. HPLC: $R_t$=7.89 (Method A). MS (ESI): mass calculated for $C_{29}H_{26}Cl_2N_4O_2$, 532.14; m/z found, 533.3 [M+H]$^+$. $^1$H NMR (500 MHz, CDCl₃): 7.31-7.30 (m, 2H), 7.23 (t, J=7.4 Hz, 1H), 7.19 (br s, 1H), 7.16-7.14 (m, 3H), 7.10 (d, J=7.4 Hz, 1H), 6.91 (dd, J=8.5, 2.2 Hz, 1H), 6.87 (d, J=9.0 Hz, 2H), 6.20 (s, 1H), 6.09 (t, J=6.0 Hz, 1H), 3.90 (dd, J=9.0, 6.0 Hz, 1H), 3.82 (s, 3H), 3.56-3.50 (m, 2H), 3.35-3.31 (m, 1H), 3.08 (dd, J=14.8, 6.0 Hz, 1H), 2.53-2.46 (m, 2H), 2.35 (s, 3H).

B. 3-(5-{(S)-2-[5-(3,4-Dichloro-phenyl)-1-(4-methoxy-phenyl)-1H-pyrazol-3-yl]-1-m-tolyl-ethyl}-tetrazol-1-yl)-propionitrile A 3-neck round-bottom flask was charged with (S)-N-(2-cyano-ethyl)-3-[5-(3,4-dichloro-phenyl)-1-(4-methoxy-phenyl)-1H-pyrazol-3-yl]-2-m-tolyl-propionamide (4.0 g, 7.5 mmol, 1.0 equiv) and triphenyl phosphine (4.91 g, 18.8 mmol, 2.5 equiv) under nitrogen. Acetonitrile was added, and the mixture was stirred at room temperature until all of the solids dissolved. The solution was then cooled to 0° C., and diisopropyl azodicarboxylate (3.79 mL, 18.8 mmol, 2.5 equiv) was added slowly via syringe. After the resulting mixture had stirred for 5 min, trimethylsilyl azide (3.0 mL, 22.5 mmol, 3 equiv) was added via syringe over 20 min. The reaction mixture was allowed to warm to room temperature and was stirred for 30 min, and then was stirred at 50° C. for 14 h. The mixture was cooled to room temperature, then to 0° C., and a solution of sodium nitrite (685 mg) in water (3.3 mL) was added. After 20 min a solution of cerric ammonium nitrate (5.5 g) in water (15.5 mL) was added, and the resulting mixture was stirred for 30 min. The mixture was then added to water (200 mL), and the resulting solution was extracted with dichloromethane (2×100 mL). The combined extracts were washed with brine (100 mL), dried (Na₂SO₄), and concentrated under reduced pressure. The crude residue was purified by flash chromatography (25% ethyl acetate/dichloromethane) yielding the desired protected tetrazole (2.1 g, 50%). HPLC: $R_t$=8.18 (Method A). MS (ESI): mass calculated for $C_{29}H_{25}Cl_2N_7O$, 557.15; m/z found, 558.3 [M+H]$^+$. $^1$H NMR (500 MHz, CDCl₃): 7.30 (d, J=8.2 Hz, 1H), 7.28-7.25 (m, 3H), 7.17-7.15 (m, 3H), 7.06 (d, J=9.0 Hz, 2H), 6.89-6.86 (m, 3H), 6.24 (s, 1H), 4.75 (dd, J=10.2, 5.3 Hz, 1H), 4.45-4.43 (m, 2H), 3.92 (dd, J=15.2, 10.2 Hz, 1H), 3.83 (s, 3H), 3.42 (dd, J=15.2, 5.3 Hz, 1H), 2.85-2.75 (m, 1H), 2.53-2.49 (m, 1H), 2.34 (s, 3H).

C. 5-{(S)-2-[5-(3,4-Dichloro-phenyl)-1-(4-methoxy-phenyl)-1H-pyrazol-3-yl]-1-m-tolyl-ethyl}-1H-tetrazole To a solution of 3-(5-{(S)-2-[5-(3,4-dichloro-phenyl)-1-(4-methoxy-phenyl)-1H-pyrazol-3-yl]-1-m-tolyl-ethyl}-tetrazol-1-yl)-propionitrile (1.5 g, 2.7 mmol) in dichloromethane (25 mL) was added DBU (2.9 mL, 18.9 mmol, 7.0 equiv), and the mixture was stirred at room temperature for 48 h. Dichloromethane (200 mL) was added, and the resulting mixture was washed with 1 N HCl (2×100 mL) then water (100 mL), dried (Na₂SO₄), and concentrated under reduced pressure. The crude residue was purified by flash chromatography (50% dichloromethane/ethyl acetate) to afford the title compound (1.3 grams, 95%). HPLC: $R_t$=5.31 (Method A). MS (ESI): mass calculated for $C_{26}H_{22}Cl_2N_6O$, 504.12; m/z found, 505.3 [M+H]$^+$. $^1$H NMR (500 MHz, CDCl₃): 7.32 (d, J=8.2 Hz, 1H), 7.28-7.24 (m, 3H), 7.21 (t, J=7.7 Hz, 1H), 7.15 (d, J=8.8 Hz, 2H), 7.08 (d, J=7.7 Hz, 1H), 6.95-6.94 (m, 3H), 6.88 (dd, J=8.5, 2.2 Hz, 1H), 6.18 (s, 1H), 4.85 (dd, J=9.0, 3.6 Hz, 1H), 3.86 (s, 3H), 3.58 (dd, J=14.8, 8.5 Hz, 1H), 3.42 (dd, J=15.4, 3.6 Hz, 1H), 2.31 (s, 3H).

Example 130

Preparation of Tetrazoles

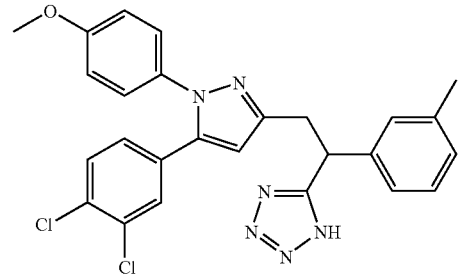

5-{2-[5-(3,4-Dichloro-phenyl)-1-(4-methoxy-phenyl)-1H-pyrazol-3-yl]-1-m-tolyl-ethyl}-1H-tetrazole A. 3-[5-(3,4-Dichloro-phenyl)-1-(4-methoxy-phenyl)-1H-pyrazol-3-yl]-2-m-tolyl-propionitrile To a solution of sodium bis(trimethylsilyl)amide (14.0 mL, 1.0 M solution in THF, 1.0 equiv) in tetrahydrofuran (56.0 mL) at 0° C. was added 3-methylbenzyl cyanide (1.84 g, 14.0 mmol, 1.0 equiv). This mixture was stirred at 0° C. for 30 min then was added to a solution of 3-bromomethyl-5-(3,4-dichloro-phenyl)-1-(4-methoxy-phenyl)-1H-pyrazole (prepared as in Method 1; 5.78 g, 14.0 mmol, 1.0 equiv) in tetrahydrofuran (56.0 mL) and allowed to stir for 2 h. The reaction was quenched with satd aq ammonium chloride (10.0 mL), and the resulting mixture was diluted with water (200 mL), and extracted with diethyl ether (2×100 mL). The combined extracts were dried (Na₂SO₄) and concentrated under reduced pressure. The crude material was purified by flash chromatography (25% ethyl acetate/hexanes) to yield the title intermediate (2.76 g, 43%). HPLC: $R_t$=13.44 (Method G). MS (ESI): mass calculated for $C_{26}H_{21}Cl_2N_3O$, 461.11; m/z found, 462.0 [M+H]$^+$. $^1$H NMR (500 MHz, CDCl₃): 7.36 (d, J=1.9 Hz, 1H), 7.33 (d, J=8.2 Hz, 1H), 7.28 (t, J=7.4 Hz, 1H), 7.24 (s, 1H), 7.23-7.21 (m, 1H), 7.18 (d, J=8.8 Hz, 2H), 7.19-7.16 (m, 1H), 6.95 (dd, J=8.5, 2.2 Hz, 1H), 6.89 (d, J=8.8 Hz, 2H), 6.42 (s, 1H), 4.22 (dd, J=9.6, 6.0 Hz, 1H), 3.83 (s, 3H), 3.30-3.21 (m, 2H), 2.38 (s, 3H).

B. 5-{2-[5-(3,4-Dichloro-phenyl)-1-(4-methoxy-phenyl)-1H-pyrazol-3-yl]-1-m-tolyl-ethyl}-1H-tetrazole To a 48-mL pressure vessel (Chemglass) were added N,N-dimethylformamide (25.0 mL), 3-[5-(3,4-dichloro-phenyl)-1-(4-methoxy-phenyl)-1H-pyrazol-3-yl]-2-m-tolyl-propionitrile (2.76 g, 5.97 mmol, 1.0 equiv), ammonium chloride (1.58 g, 29.8 mmol, 5.0 equiv) and sodium azide (1.94 g, 29.8 mmol, 5.0 equiv). The screw-cap vessel was sealed and then placed in an oil bath heated to 90° C. for 48 h. The reaction mixture was cooled to room temperature, pH-adjusted with formic acid, diluted with water (100 mL), and extracted with ethyl acetate (3×50 mL). The combined extracts were washed with water (3×50 mL) then brine (50 mL), dried ($Na_2SO_4$), and concentrated under reduced pressure. The crude material was purified by flash chromatography (5% methanol/dichloromethane) to yield the title compound (1.9 g, 63%). HPLC: $R_t$=3.09 (Method A). MS (ESI): mass calculated for $C_{26}H_{22}Cl_2N_6O$, 504.12; m/z found, 505.1 [M+H]+. 1H NMR (500 MHz, DMSO-$d_6$): 7.57 (d, J=8.5 Hz, 1H), 7.41 (d, J=2.2 Hz, 1H), 7.23-7.16 (m, 3H), 7.09-7.07 (m, 3H), 7.01 (dd, J=8.5, 2.2 Hz, 1H), 6.96 (d, J=9.0 Hz, 2H), 6.46 (s, 1H), 4.86 (dd, J=9.0, 6.6 Hz, 1H), 3.77 (s, 3H), 3.62 (dd, J=14.8, 9.3 Hz, 1H), 3.35 (dd, J=14.8, 6.6 Hz, 1H), 2.28 (s, 3H).

Example 131

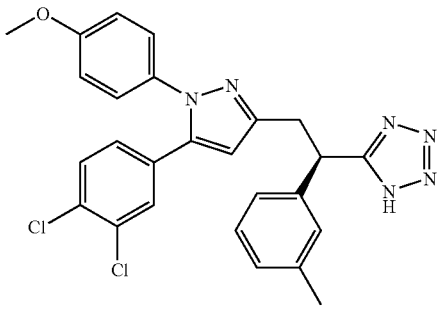

5-{(R)-2-[5-(3,4-Dichloro-phenyl)-1-(4-methoxy-phenyl)-1H-pyrazol-3-yl]-1-m-tolyl-ethyl}-1H-tetrazole This compound was obtained by chiral-HPLC separation of the two enantiomers (Method C) from the racemic mixture prepared in Example 130. HPLC: $R_t$=5.31 (Method A). MS (ESI): mass calculated for $C_{26}H_{22}Cl_2N_6O$, 504.12; m/z found, 505.3 [M+H]+. 1H NMR (500 MHz, CDCl3): 7.32 (d, J=8.2 Hz, 1H), 7.28-7.26 (m, 3H), 7.21 (t, J=7.7 Hz, 1H), 7.15 (d, J=8.8 Hz, 2H), 7.08 (d, J=7.7 Hz, 1H), 6.94 (m, 3H), 6.88 (dd, J=8.5, 2.2 Hz, 1H), 6.18 (s, 1H), 4.85 (dd, J=9.0, 3.6 Hz, 1H), 3.86 (s, 3H), 3.58 (dd, J=14.8, 8.5 Hz, 1H), 3.42 (dd, J=15.4, 3.6 Hz, 1H), 2.31 (s, 3H).

Example 132

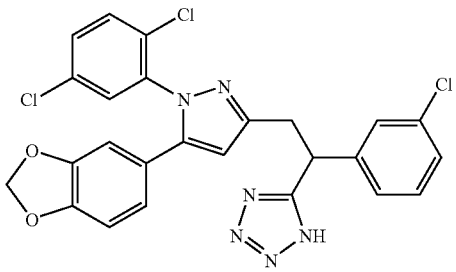

5-[2-[5-Benzo[1,3]dioxol-5-yl-1-(2,5-dichloro-phenyl)-1H-pyrazol-3-yl]-1-(3-chloro-phenyl)-ethyl]-1H-tetrazole This compound was prepared by the procedure described in Example 130, substituting 5-benzo[1,3]dioxol-5-yl-3-bromomethyl-1-(2,5-dichloro-phenyl)-1H-pyrazole (prepared as in Method 1) for 3-bromomethyl-5-(3,4-dichloro-phenyl)-1-(4-methoxy-phenyl)-1H-pyrazole in step A. HPLC: $R_t$=5.21 (Method A). MS (ESI): mass calculated for $C_{25}H_{17}Cl_3N_6O_2$, 538.05; m/z found, 539.0 [M+H]+. 1H NMR (500 MHz, CDCl3): 7.46-7.41 (m, 2H), 7.32 (d, J=2.2 Hz, 1H), 7.26-7.23 (m, 2H), 7.14-7.04 (m, 2H), 6.70 (d, J=7.9 Hz, 1H), 6.57 (dd, J=8.2, 1.9 Hz, 1H), 6.54 (d, J=1.6 Hz, 1H), 6.17 (br s, 1H), 5.96 (s, 2H), 5.02 (dd, J=8.5, 4.4 Hz, 1H), 3.60 (dd, J=15.1, 8.8 Hz, 1H), 3.48 (dd, J=15.1, 4.4 Hz, 1H).

The compounds of Examples 133 and 134 were made according to the synthetic methods outlined in Scheme J.

Example 133

Ester-Arylation

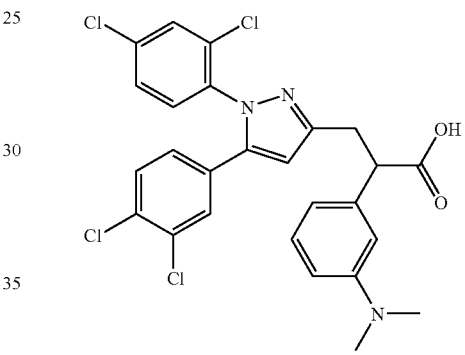

3-[5-(3,4-Dichloro-phenyl)-1-(2,4-dichloro-phenyl)-1H-pyrazol-3-yl]-2-(3-dimethylamino-phenyl)-propionic acid A. 6-(3,4-Dichloro-phenyl)-6-hydroxy-4-oxo-hex-5-enoic acid bis-lithium salt To a 3-neck flask was added diethyl ether (120 mL) and lithium bis(trimethylsilyl)amide (10.0 g, 59.9 mmol, 2.0 equiv) under nitrogen. The slurry was cooled to −78° C., then a solution of 1-(3,4-dichloro-phenyl)-ethanone (11.3 g, 59.9 mmol, 2.0 equiv) in diethyl ether (120 mL) was added dropwise. The mixture was stirred at −78° C. for 30 min, then a solution of succinic anhydride (3.0 g, 29.9 mmol, 1.0 equiv) in diethyl ether (60 mL) was added dropwise. The reaction mixture was stirred at −78° C. for 1 h then allowed to warm to room temperature and stirred 16 h. The resulting precipitate was filtered off, washed with diethyl ether (2×60 mL), and dried yielding a yellow powder (9.48 g, 99%), which was used in the next step without purification or characterization.

B. 3-[5-(3,4-Dichloro-phenyl)-1-(2,4-dichloro-phenyl)-1H-pyrazol-3-yl]-propionic acid To a round-bottom flask was added 6-(3,4-dichloro-phenyl)-6-hydroxy-4-oxo-hex-5-enoic acid bis-lithium salt (9.48 g, 31.3 mmol, 1.0 equiv), 2,4-dichloro-phenyl hydrazine hydrochloride (6.66 g, 31.3 mmol, 1.0 equiv) and EtOH (250 mL) under nitrogen. The mixture was stirred at room temperature for 24 h. The solvent was removed, and the crude residue was partitioned between 5% HCl and diethyl ether (200 mL each). The layers were separated, and the aqueous layer was extracted with diethyl ether (2×100 mL). The combined organic layers were washed with water (100 mL) then brine (100 mL), dried ($Na_2SO_4$), and concentrated under reduced pressure. Purification by flash chromatography (25% ethyl acetate/dichloromethane) afforded the title intermediate (4.5 g, 33%). HPLC: $R_t$=3.04 (Method A). MS (ESI): mass calculated for $C_{18}H_{12}Cl_4N_2O_2$, 427.97; m/z found, 429/431 [M+H]$^+$. $^1$H NMR (500 MHz, DMSO-$d_6$): 12.20 (br s, 1H), 7.82 (d, J=2.2 Hz, 1H), 7.68 (d, J=8.5 Hz, 1H), 7.61-7.59 (m, 2H), 7.50 (d, J=2.2 Hz, 1H), 7.05 (dd, J=8.2, 1.9 Hz, 1H), 6.73 (s, 3H), 2.88 (t, J=7.4 Hz, 2H), 2.64 (t, J=7.4 Hz, 2H).

C. 3-[5-(3,4-Dichloro-phenyl)-1-(2,4-dichloro-phenyl)-1H-pyrazol-3-yl]-propionic acid tert-butyl ester To a 3-neck round bottom flask fitted with an air condenser was added 3-[5-(3,4-dichloro-phenyl)-1-(2,4-dichloro-phenyl)-1H-pyrazol-3-yl]-propionic acid (1.0 g, 2.3 mmol, 1.0 equiv) and toluene (23 mL) under nitrogen. The mixture was heated to 80° C. then N,N-dimethyl-di-tert-butylacetal (2.36 g, 11.6 mmol, 5.0 equiv) was added dropwise (neat). The reaction mixture was heated at 80° C. for 1 h then additional N,N-dimethyl-di-tert-butylacetal (2.36 g, 11.6 mmol, 5.0 equiv) was added. This mixture was stirred at 80° C. for 2 h then cooled to room temperature and partitioned between water (100 mL) and ether (100 mL). The organic layer was washed with 1 M sodium hydroxide (50 mL), water (50 mL) then brine (50 mL), dried ($Na_2SO_4$), and concentrated under reduced pressure. The crude material was then purified by flash chromatography (20% ethyl acetate/hexanes) to afford the desired ester (1.1 g, >99%). HPLC: $R_t$=3.59 (Method A). MS (ESI): mass calculated for $C_{22}H_{20}Cl_4N_2O_2$, 484.03; m/z found, 485.0 [M+H]$^+$. $^1$H NMR (500 MHz, DMSO-$d_6$): 7.81 (d, J=2.2 Hz, 1H), 7.65 (d, J=8.5 Hz, 1H), 7.61-7.59 (m, 2H), 7.48 (d, J=2.2 Hz, 1H), 7.05 (dd, J=8.2, 1.9 Hz, 1H), 6.71 (s, 1H), 2.87 (t, J=7.4 Hz, 2H), 2.61 (t, J=7.4 Hz, 2H), 1.38 (s, 9H).

D. 3-[5-(3,4-Dichloro-phenyl)-1-(2,4-dichloro-phenyl)-1H-pyrazol-3-yl]-2-(3-dimethylamino-phenyl)-propionic acid tert-butyl ester To a mixture of palladium(II) acetate (3 mg, 5 mol %), 2-dicyclohexylphosphino-2'-(N,N-dimethylamino)biphenyl (10 mg, 5 mol %) and lithium bis(trimethylsilyl)amide (0.55 mL, 0.55 mmol, 1.1 equiv, 1.0 M solution in tetrahydrofuran) in toluene (0.5 mL) under nitrogen at −10° C., was added a solution of 3-[5-(3,4-dichloro-phenyl)-1-(2,4-dichloro-phenyl)-1H-pyrazol-3-yl]-propionic acid tert-butyl ester (243 mg, 0.50 mmol, 1.0 equiv) in toluene (1.0 mL). This mixture was stirred at −10° C. for 10 min, then (3-bromo-phenyl)-dimethyl-amine (42 mg, 0.21 mmol, 0.45 equiv) in toluene (0.5 mL) was added. The resulting solution was allowed to warm to room temperature then was heated to 80° C. for 3 h. The reaction mixture was cooled to room temperature, and the reaction was quenched with satd aq ammonium chloride (1.0 mL). Water (10.0 mL) was added, and the resulting mixture was extracted with diethyl ether (2×10 mL). The combined extracts were washed with brine (10 mL), dried ($Na_2SO_4$), and concentrated under reduced pressure. The crude material was purified by reversed-phase HPLC to afford the desired aryl acetic acid ester (20 mg, 16%). MS (ESI): mass calculated for $C_{30}H_{29}Cl_4N_3O_2$, 603.10; m/z found, 604.1 [M+H]$^+$.

E. 3-[5-(3,4-Dichloro-phenyl)-1-(2,4-dichloro-phenyl)-1H-pyrazol-3-yl]-2-(3-dimethylamino-phenyl)-propionic acid 3-[5-(3,4-Dichloro-phenyl)-1-(2,4-dichloro-phenyl)-1H-pyrazol-3-yl]-2-(3-dimethylamino-phenyl)-propionic acid tert-butyl ester (20 mg, 0.03 mmol) was dissolved in 1:1 trifluoroacetic acid/dichloromethane (1.0 mL) and stirred for 2 h. The reaction mixture was concentrated under reduced pressure, and the crude residue was dissolved in 1:1 acetonitrile/water (2.0 mL). The solution was lyopholized to afford the title compound (18 mg, >99%). HPLC: $R_t$=2.60 (Method B). MS (ESI): mass calculated for $C_{26}H_{21}Cl_4N_3O_2$, 547.04; m/z found, 548/550[M+H]$^+$. $^1$H NMR (500 MHz, DMSO-$d_6$): 7.81 (d, J=1.9 Hz, 1H), 7.60-7.58 (m, 3H), 7.45 (d, J=2.2 Hz, 1H), 7.18 (t, J=7.9 Hz, 1H), 7.02 (dd, J=8.5, 2.2 Hz, 1H), 6.78 (m, 3H), 6.64 (s, 1H), 3.96 (dd, J=8.8, 6.6 Hz, 1H), 3.36 (dd, J=15.1, 9.0 Hz, 1H), 2.93 (dd, J=15.1, 6.6 Hz, 1H), 2.91 (s, 6H).

Example 134

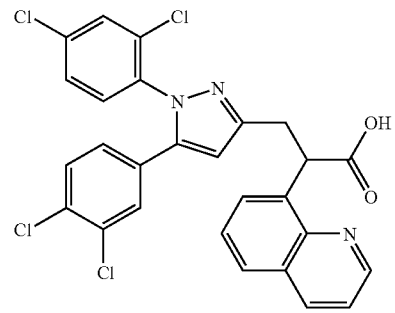

3-[5-(3,4-Dichloro-phenyl)-1-(2,4-dichloro-phenyl)-1H-pyrazol-3-yl]-2-quinolin-8-yl-propionic acid The title compound was prepared as described in Example 133, substituting 8-bromo-quinoline for (3-bromo-phenyl)-dimethyl-amine in Step D. HPLC: $R_t$=2.99 (Method B). MS (ESI): mass calculated for $C_{27}H_{17}Cl_4N_3O_2$, 555.01; m/z found, 556.1 [M+H]$^+$.

The compounds of Examples 135-138 were made according to the synthetic methods outlined in Scheme I.

Example 135

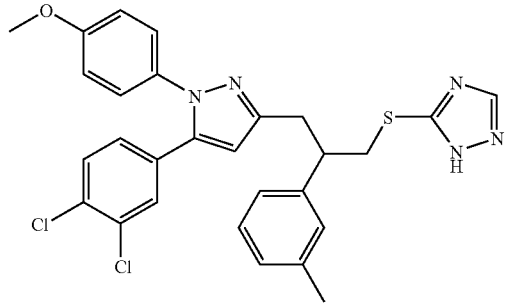

5-{3-[5-(3,4-Dichloro-phenyl)-1-(4-methoxy-phenyl)-1H-pyrazole-3-yl]-2-m-tolyl-propylsulfanyl}-1H-[1,2,4]-triazole

A. 3-[5-(3,4-Dichloro-phenyl)-1-(4-methoxy-phenyl)-1H-pyrazol-3-yl]-2-m-tolyl-propan-1-ol To a 3-neck round-bottom flask charged with nitrogen was added 3-[5-(3,4-dichloro-phenyl)-1-(4-methoxy-phenyl)-1H-pyrazol-3-yl]-2-m-tolyl-propionic acid ethyl ester (see Method 2, product before hydrolysis; 798 mg, 1.57 mmol, 1.0 equiv) and tetrahydrofuran (6.0 mL). The mixture was cooled to -78° C., then diisobutyl aluminum hydride (4.7 mL, 1.0 M solution in tetrahydrofuran) was added dropwise. The reaction mixture was stirred at -78° C. for 30 min then allowed to warm to room temperature and stirred 1 h. The mixture was then poured slowly into a satd aq solution of Rochelle salt (50 mL). Diethyl ether (50 mL) was added, and the resulting mixture was stirred for 3 h. The organic layer was dried ($Na_2SO_4$) and concentrated under reduced pressure to afford 732 mg of the desired alcohol, which was used in the next step without purification.

B. 3-(3-Bromo-2-m-tolyl-propyl)-5-(3,4-dichloro-phenyl)-1-(4-methoxy-phenyl)-1H-pyrazole To a 3-neck round-bottom flask was added phosphorus tribromide (599 mg, 2.77 mmol, 1.5 equiv) and dichloromethane (10 mL). The mixture was cooled to 0° C., then a solution of 3-[5-(3,4-dichloro-phenyl)-1-(4-methoxy-phenyl)-1H-pyrazol-3-yl]-2-m-tolyl-propan-1-ol (690 mg, 1.48 mmol, 1.0 equiv) in dichloromethane (3.0 mL) was added. The reaction mixture was allowed to warm to room temperature then was stirred for 16 h. The resulting mixture was loaded directly onto a silica gel column and purified by chromatography (25% ethyl acetate/hexanes) giving the desired bromide (480 mg, 61%). HPLC: $R_t$=3.80 (Method B). MS (ESI): mass calculated for $C_{26}H_{23}BrCl_2N_2O$, 528.04; m/z found, 529.0 [M+H]$^+$.

C. 5-{3-[5-(3,4-Dichloro-phenyl)-1-(4-methoxy-phenyl)-1H-pyrazole-3-yl]-2-m-tolyl-propylsulfanyl}-1H-[1,2,4]-triazole To a suspension of sodium hydride (4.0 mg, 60% dispersion in oil) in N,N-dimethylformamide (1.0 mL) at 0° C. was added a solution of 2H-[1,2,4]triazole-3-thiol (10.0 mg, 0.1 mmol, 1.1 equiv) in N,N-dimethylformamide (1.0 mL). The mixture was stirred at 0° C. for 30 min then a solution of 3-(3-bromo-2-m-tolyl-propyl)-5-(3,4-dichloro-phenyl)-1-(4-methoxy-phenyl)-1H-pyrazole (48 mg, 0.09 mmol, 1.0 equiv) in N,N-dimethylformamide (1.0 mL) was added. The reaction mixture was brought to room temperature then was stirred for 2 h. The reaction was quenched with satd aq ammonium chloride (1.0 mL), and the resulting mixture was diluted with water (10.0 mL), and extracted with ethyl acetate (3×10 mL). The combined organic layers were washed with water (10 mL) then brine (10 mL), dried ($Na_2SO_4$), and concentrated under reduced pressure. The crude residue was purified by reversed-phase HPLC to yield the title compound (39 mg, 80%). HPLC: $R_t$=3.26 (Method B). MS (ESI): mass calculated for $C_{28}H_{25}Cl_2N_5OS$, 549.12; m/z found, 550.1 [M+H]$^+$. $^1$H NMR (500 MHz, DMSO-$d_6$): 8.32 (br s, 1H), 7.50 (d, J=8.4 Hz, 1H), 7.35 (d, J=2.1 Hz, 1H), 7.07-7.04 (m, 5H), 6.95 (dd, J=8.4, 21. HZ, 2H), 6.89 (d, J=9.0 Hz, 2H), 6.31 (s, 1H), 3.70 (s, 3H), 3.48 (dd, J=12.9, 6.3 Hz, 1H), 3.36 (dd, J=12.7, 8.2 Hz, 1H), 3.26 (m, 1H), 3.07 (dd, J=14.9, 6.4 Hz, 1H), 2.91 (dd, J=14.9, 8.2 Hz, 1H), 2.21 (s, 3H).

Example 136

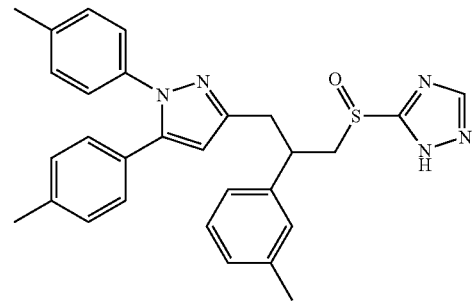

5-[3-(1,5-Di-p-tolyl-1H-pyrazol-3-yl)-2-m-tolyl-propane-1-sulfinyl]-1H-[1,2,4]triazole To a cold (0° C., ice bath) solution of 5-[3-(1,5-di-p-tolyl-1H-pyrazol-3-yl)-2-m-tolyl-propylsulfanyl]-1H-[1,2,4]triazole (177 mg, 0.37 mmol, 1.0 equiv) [prepared by substituting 3-(1,5-di-p-tolyl-1H-pyrazol-3-yl)-2-m-tolyl-propionic acid ethyl ester (see Method 2, product before hydrolysis) for 3-[5-(3,4-dichloro-phenyl)-1-(4-methoxy-phenyl)-1H-pyrazol-3-yl]-2-m-tolyl-propionic acid ethyl ester in Step A of Example 135] in dichloromethane (2.0 mL) was added 3-chloroperoxy benzoic acid (90 mg, 0.41 mmol, 1.1 equiv). The reaction mixture was stirred at 0° C. for 15 min, stirred at 40° C. for 1 h, and then cooled to room temperature and stirred for 16 h. The solvent was evaporated under reduced pressure, and the crude material was purified by reversed-phase HPLC giving the desired sulfinyl triazole (165 mg, 90%). HPLC: $R_t$=2.88 (Method 8). MS (ESI): mass calculated for $C_{29}H_{29}N_5OS$, 495.21; m/z found, 496.2 [M+H]$^+$. $^1$H NMR (500 MHz, DMSO-$d_6$): 8.79 (s, 1H), 7.00-7.23 (m, 12 H), 6.30 (s, 0.5H), 6.14 (s, 0.5H), 3.81 (dd, J=12.5, 3.7 Hz, 0.5H) 3.72(dd, J=12.9, 7.0 Hz, 0.5H), 3.37-3.60 (m, 1.5H), 3.28-3.25 (m, 0.5H), 2.97-3.15 (m, 2.0H), 2.31-2.27 (m, 9H).

Example 137

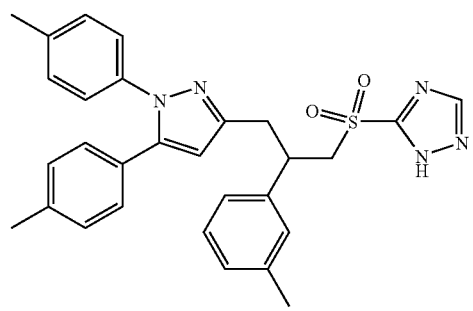

5-[3-(1,5-Di-p-tolyl-1H-pyrazol-3-yl)-2-m-tolyl-propane-1-sulfonyl]-1H-[1,2,4]triazole To a flask was added 5-[3-(1,5-di-p-tolyl-1H-pyrazol-3-yl)-2-m-tolyl-propane-1-sulfinyl]-1H-[1,2,4]triazole (Example 136; 25 mg, 0.05 mmol), hydrogen peroxide (0.15 mL, 30% solution in water) and acetic acid (0.1 ml). The mixture was heated at 50° C. for 24 h and then cooled. Methanol (0.5 mL) and N,N-dimethylformamide (0.5 mL) were added to dissolve the resulting precipitate. This solution was then purified directly by reversed-phase chromatography yielding the title compound (24 mg, 95%). HPLC: $R_t$=2.97 (Method B). MS (ESI): mass calculated for $C_{29}H_{29}N_5O_2S$, 511.20; m/z found, 512.2 [M+H]$^+$. $^1$H NMR (500 MHz, DMSO-d$_6$): 14.87 (br s, 1H), 8.72 (s, 1H), 7.18 (d, J=8.2 Hz, 2H), 7.13 (d, J=8.0 Hz, 2H), 7.08 (d, J=7.0 Hz, 1H), 7.07-7.04 (m, 3H), 7.01-6.99 (m, 3H), 6.95 (d, J=7.4 Hz, 1H), 6.15 (s, 1H), 3.91 (d, J=6.6 Hz, 2H), 3.52-3.49 (m, 1H), 3.08 (dd, J=14.7, 7.6 Hz, 1H) 2.91 (dd, J=14.5, 7.4 Hz, 1H), 2.31 (s, 3H), 2.27 (s, 3H), 2.23 (s, 3H).

Example 138

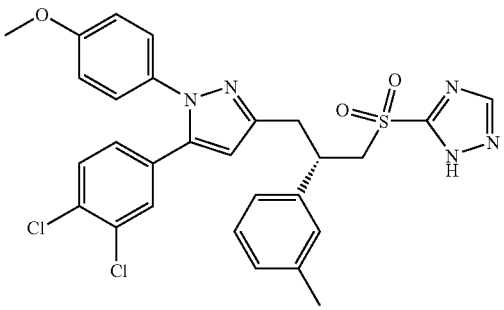

5-{(S)-3-[5-(3,4-Dichloro-phenyl)-1-(4-methoxy-phenyl)-1H-pyrazol-3-yl]-2-m-tolyl-propane-1-sulfonyl}-1H-[1,2,4]triazole The title compound was prepared as outlined in Example 137, substituting the S enantiomer of 3-[5-(3,4-dichloro-phenyl)-1-(4-methoxy-phenyl)-1H-pyrazol-3-yl]-2-m-tolyl-propionic acid ethyl ester [available by chiral separation of ester prepared in Method 2] for the racemic 3-[5-(3,4-dichlorophenyl)-1-(4-methoxy-phenyl)-1H-pyrazol-3-yl]-2-m-tolyl-propionic acid ethyl ester in Step A. HPLC: $R_t$=2.94 (Method B). MS (ESI): mass calculated for $C_{28}H_{25}Cl_2N_5O_3S$, 581.11; m/z found, 582.3 [M+H]$^+$. $^1$H NMR (500 MHz, DMSO-d$_6$): 14.87 (br s, 1H), 8.72 (s, 1H), 7.58 (d, J=8.5 Hz, 1H), 7.43 (d, J=2.2 Hz, 1H), 7.14 (d, J=9.0 Hz, 2H), 7.08 (d, J=7.4 Hz, 1H), 6.96-7.04 (m, 6H), 6.36 (s, 1H), 3.92 (d, J=6.3 Hz, 2H), 3.78 (s, 3H), 3.53-3.50 (m, 1H), 3.09 (dd, J=14.5, 7.4 Hz, 1H), 2.92 (dd, J=14.5, 7.7 Hz, 1H), 2.23 (s, 3H).

Example 139

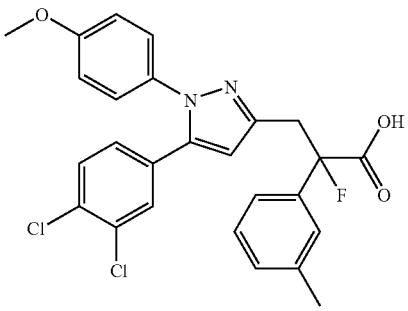

3-[5-(3,4-Dichloro-phenyl)-1-(4-methoxy-phenyl-1H-pyrazol-3-yl]-2-fluoro-2-m-tolyl-propionic acid A. 3-[5-(3,4-Dichloro-phenyl)-1-(4-methoxy-phenyl)-1H-pyrazol-3-yl]-2-fluoro-2-m-tolyl-propionic acid ethyl ester To a round-bottom flask containing lithium bis(trimethylsilyl)amide (0.47 mL, 1.0 M solution in tetrahydrofuran), and tetrahydrofuran (1.5 mL) at 0° C. under nitrogen, was added 3-[5-(3,4-dichloro-phenyl)-1-(4-methoxy-phenyl)-1H-pyrazol-3-yl]-2-m-tolyl-propionic acid ethyl ester (Method 2, product before hydrolysis; 200 mg, 0.39 mmol, 1.0 equiv) in tetrahydrofuran (1.5 mL). The mixture was allowed to stir at 0° C. for 1 h, then a solution of sultam-F (109 mg, 0.51 mmol, 1.5 equiv) in tetrahydrofuran (1.5 mL) was added, and the resulting solution was stirred at 0° C. for 2 h. The reaction was quenched with satd aq ammonium chloride (5 mL), and the resulting mixture was diluted with water (10 mL) and extracted with ethyl acetate (2×10 mL). The combined extracts were washed with water (10 mL) then brine (10 mL), dried (Na$_2$SO$_4$), and concentrated under reduced pressure. The crude residue was purified by reversed-phase HPLC giving the desired alpha-fluoro ester (164 mg, 80%). HPLC: $R_t$=3.66 (Method B). MS (ESI): mass calculated for $C_{28}H_{25}Cl_2FN_2O_3$, 526.12; m/z found, 527.2 [M+H]$^+$.

B. 3-[5-(3,4-Dichloro-phenyl)-1-(4-methoxy-phenyl-1H-pyrazol-3-yl]-2-fluoro-2-m-tolyl-propionic acid The title compound was made as outlined in Method 2 (Scheme A) by hydrolysis of the ester described in Step A. HPLC: $R_t$=3.34. MS (ESI): mass calculated for $C_{26}H_{21}Cl_2FN_2O_3$, 498.09; m/z found, 499.1 [M+H]$^+$. $^1$H NMR (500 MHz, DMSO-d$_6$): 7.59 (d, J=8.2 Hz, 1H), 7.45 (d, J=1.9 Hz, 1H), 7.38-7.36 (m, 2H), 7.33 (t, J=7.4 Hz, 1H), 7.21 (d, J=7.1 Hz, 1H), 7.17 (d, J=8.8 Hz, 2H), 7.07 (dd, J=8.2, 1.9 Hz, 1H), 6.98 (d, J=8.8 Hz, 2H), 6.48 (s, 1H), 3.77 (m, 1H), 3.78 (s, 3H), 3.42 (dd, J=17.0, 15.4 Hz, 1H), 2.35 (s, 3H).

Example 140

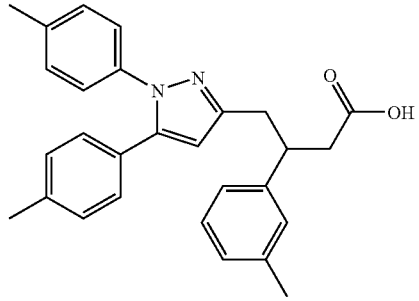

4-(1,5-Di-p-tolyl-1H-pyrazol-3-yl)-3-m-tolyl-butyric acid

A. 4-(1,5-Di-p-tolyl-1H-pyrazol-3-yl)-3-m-tolyl-butyronitrile

To a screw-cap vial were added 3-(3-bromo-2-m-tolyl-propyl)-1,5-di-p-tolyl-1H-pyrazole (prepared by the method of Example 67; 300 mg, 0.65 mmol, 1.0 equiv), sodium cyanide (160 mg, 3.3 mmol, 5.0 equiv) and N,N-dimethylformamide (3.0 mL). The sealed mixture was then heated at 100° C. for 48 h. The reaction mixture was cooled to room temperature, diluted with water (10 mL), and extracted with diethyl ether (3×10 mL). The combined extracts were washed with water (4×10 mL) then brine (10 mL), dried ($Na_2SO_4$), and concentrated under reduced pressure. The crude residue was purified by flash chromatography (25% ethyl acetate/hexanes) giving the desired nitrile (171 mg, 65%). MS (ESI): mass calculated for $C_{28}H_{27}N_3$, 405.22; m/z found, 406.2 $[M+H]^+$.

B. 4-(1,5-Di-p-tolyl-1H-pyrazol-3-yl)-3-m-tolylbutyric acid methyl ester

To a flask were added 4-(1,5-di-p-tolyl-1H-pyrazol-3-yl)-3-m-tolyl-butyronitrile (100 mg, 0.24 mmol), concd sulfuric acid (1.5 mL) and methanol (1.5 mL). The mixture was heated to reflux for 24 h. The reaction mixture was cooled to room temperature, poured into ice (20 g) and neutralized with satd sodium bicarbonate. The resulting solution was extracted with diethyl ether (3×10 mL), and the combined organic extracts were washed with water (10 mL) then brine (10 mL), dried ($Na_2SO_4$), and concentrated under reduced pressure. The crude residue was purified by reversed-phase HPLC yielding the desired ester (86 mg, 82%). HPLC: $R_t$=3.43 (Method B). MS (ESI): mass calculated for $C_{29}H_{30}N_2O_2$, 438.23; m/z found, 439.2 $[M+H]^+$. $^1H$ NMR (500 MHz, $CDCl_3$): 7.19 (t, J=7.4 Hz, 1H), 7.01-7.13 (m, 11H), 6.15 (s, 1H), 3.56 (s, 3H), 3.54-3.52 (m, 1H), 3.11-3.08 (m, 2H), 2.77-2.75 (m, 2H), 2.36 (s, 3H), 2.32 (s, 6H).

C. 4-(1,5-Di-p-tolyl-1H-pyrazol-3-yl)-3-m-tolyl-butyric acid

The title compound was synthesized by Method 2 (Scheme A) by hydrolysis of the ester described in Step B. HPLC: $R_t$=3.14 (Method B). MS (ESI): mass calculated for $C_{28}H_{28}N_2O_2$, 424.22; m/z found, 425.8 $[M+H]^+$. $^1H$ NMR (500 MHz, DMSO-$d_6$): 12.00 (br s, 1H), 6.98-7.19 (m, 12H), 6.23 (s, 1H), 3.39-3.37 (m, 1H), 3.00-2.87 (m, 2H), 2.71 (dd, J=15.5, 5.6 Hz, 1H), 2.56 (dd, J=15.6, 9.4 Hz, 1H), 2.31 (s, 3H), 2.27 (s, 6H).

Example 141

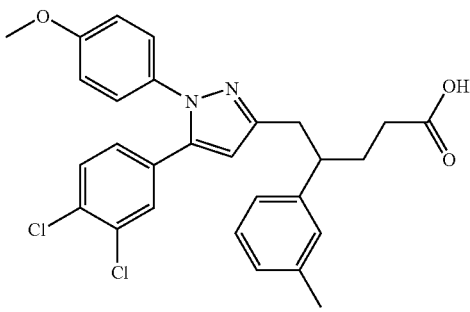

5-[5-(3,4-Dichloro-phenyl)-1-(4-methoxy-phenyl)-1H-pyrazol-3-yl]-4-m-tolyl-pentanoic acid

A. 3-[5-(3,4-Dichloro-phenyl)-1-(4-methoxy-phenyl)-1H-pyrazol-3-yl]-2-m-tolyl-propionaldehyde To a flask containing 3-[5-(3,4-dichloro-phenyl)-1-(4-methoxy-phenyl)-1H-pyrazol-3-yl]-2-m-tolyl-propane-1-ol (prepared by the method of Example 67; 50 mg, 0.11 mmol, 1.0 equiv) and dichloromethane (2.0 mL) was added Dess-Martin reagent (89 mg, 0.21 mmol, 2.0 equiv) in one portion. The reaction mixture was stirred at room temperature for 30 min then poured into satd aq sodium bicarbonate (5.0 mL) containing sodium thiosulfate pentahydrate (5.0 equiv relative to Dess-Martin reagent). The resulting mixture was then diluted with dichloromethane (3.0 mL) and stirred vigorously for 2 h. The resulting organic layer was washed with water (5.0 mL) then brine (5.0 mL), dried ($Na_2SO_4$), and concentrated under reduced pressure, affording the desired aldehyde, which was used in the next step without purification. $R_t$=3.57 (Method B). MS (ESI): mass calculated for $C_{26}H_{22}Cl_2N_2O_2$, 464.11; m/z found, 465.0 $[M+H]^+$.

B. 5-[5-(3,4-Dichloro-phenyl)-1-(4-methoxy-phenyl)-1H-pyrazol-3-yl]-4-m-tolyl-pent-2-enoic acid methyl ester To a suspension of sodium hydride (30 mg, 60% dispersion in oil) in tetrahydrofuran (1.5 mL) at 0° C. was added methyl diethylphosphonoacetate (0.13 mL, 0.69 mmol, 1.0 equiv) neat. The mixture was stirred at 0° C. for 30 min, then a solution of 3-[5-(3,4-dichloro-phenyl)-1-(4-methoxy-phenyl)-1H-pyrazol-3-yl]-2-m-tolyl-propionaldehyde (320 mg, 0.69 mmol, 1.0 equiv) in tetrahydrofuran (1.5 mL) was added. The reaction mixture was allowed to warm to room temperature and was stirred 1 h. The reaction was quenched with 2 mL of water, and the resulting mixture was diluted with satd aq ammonium chloride (10 mL) then extracted with diethyl ether (3×20 mL). The combined extracts were washed with water (20 mL) then brine (20 mL), dried ($Na_2SO_4$), and concentrated under reduced pressure. The crude material was purified by flash chromatography (25% ethyl acetate/hexanes) giving the methyl ester (150 mg, 45%). HPLC: $R_t$=3.70 (Method B). MS (ESI): mass calculated for $C_{29}H_{26}Cl_2N_2O_3$, 520.13; m/z found, 521.2 $[M+H]^+$.

C. 5-[5-(3,4-Dichloro-phenyl)-1-(4-methoxy-phenyl)-1H-pyrazol-3-yl]-4-m-tolyl-pentanoic acid methyl ester To a flask containing ethyl acetate (1.0 mL), ethanol (1.0 mL) and a catalytic amount of Raney nickel was added 5-[5-(3,4-dichloro-phenyl)-1-(4-methoxy-phenyl)-1H-pyrazol-3-yl]-4-m-tolyl-pent-2-enoic acid methyl ester (92 mg, 0.17 mmol). The reaction mixture was stirred under $H_2$ (~1 atm) for 2 h and then filtered through a CELITE® pad. The filtrate was concentrated under reduced pressure, and the crude residue was purified by reversed-phase HPLC giving the desired ester (81 mg, 91%). HPLC: $R_t$=3.68 (Method B). MS (ESI): mass calculated for $C_{29}H_{28}Cl_2N_3O_3$, 522.15; m/z found, 523.3 $[M+H]^+$.

D. 5-[5-(3,4-Dichloro-phenyl)-1-(4-methoxy-phenyl)-1H-pyrazol-3-yl]-4-m-tolyl-pentanoic acid The title compound was made by Method 2 (Scheme A) by hydrolysis of the ester of step C. HPLC: $R_t$=10.60 (Method A). MS (ESI): mass calculated for $C_{28}H_{26}Cl_2N_2O_3$, 508.13; m/z found, 509.0 $[M+H]^+$. $H^1$ NMR (500 MHz, DMSO-$d_6$): 11.97 (br s, 1H), 7.57 (d, J=8.5 Hz, 1H), 7.44 (d, J=2.2 Hz, 1H), 7.19 (t, J=7.7 Hz, 1H), 7.15 (d, J=9.0 Hz, 2H), 7.07-7.02 (m, 4H), 6.96 (d, J=9.0 Hz, 2H), 6.42 (s, 1H), 3.77 (s, 3H), 2.92-2.89 (m, 3H), 2.29 (s, 3H), 2.00-1.99 (m, 3H), 1.80-1.77 (m, 1H).

General Experimental Details:

NMR spectra were obtained on a Bruker model DPX300 (300 MHz), DPX400 (400 MHz), or DPX500 (500 MHz) spectrometer. Chemical shifts are reported in ppm downfield of the tetramethylsilane reference. The format of the $^1$H NMR data below is: chemical shift (multiplicity, coupling constant J in Hz, integration).

IR spectra were collected on a 2000 FTIR Perkin-Elmer Spectrophotometer.

Mass spectra were obtained on an Agilent series 1100 MSD using electrospray ionization (ESI) in either positive or negative mode as indicated. The "mass calculated" for a molecular formula is the monoisotopic mass of the compound.

Thin Layer Chromatography (TLC) was performed using silica gel 60 F$_{254}$ pre-coated plates (size, 2.5×7.5 cm; thickness, 250 μm). The reaction products were detected by viewing the plates under a UV lamp (254 nm).

Melting points were determined on either an Electrothermal apparatus or on a Thomas-Hoover capillary melting point apparatus and are uncorrected.

Elemental analysis was performed by QTI (Whitehall, N.J.).

Differential Scanning Calorimetry (DSC) was performed on a Mettler-Toledo DSC instrument.

Reverse Phase HPLC (Method R):
Column: Zorbax Eclipse XDB-C8, 5 mm, 4.6×150 mm;
Flow rate: 0.75 mL/min; λ=220 & 254 nm;
Gradient (Acetonitrile/Water):
1) 8.0 min 1% -99% Acetonitrile
2) 10.0 min 99% Acetonitrile Chiral HPLC (Method S):
Column: Chiralcel AD, 0.46×25 cm;
Mobile Phase: 85:15 Ethanol/Hexane;
Flow rate: 1 mL/min; λ=220 & 254 nm Chiral HPLC (Method T):
Column: Chiralcel AD 0.46×25 cm;
Mobile Phase: 85:15 Ethanol/Hexane with 0.07% TFA;
Flow rate: 1 mL/min; λ=220 & 254 nm Reverse Phase HPLC (Method U):
Column: Zorbax Eclipse XDB-C8, 5 μm, 4.6×150 mm;
Flow rate: 1.0 mL/min; λ=200 & 260 nm;
Gradient (Water/Acetonitrile):
1) 0.0 min 70% -30% Acetonitrile
2) 15.0 min 20% -80% Acetonitrile
3) 24.0 min 20% -80% Acetonitrile
4) 24.5 min 70% -30% Acetonitrile
5) 30.0 min 70% -30% Acetonitrile Example 500

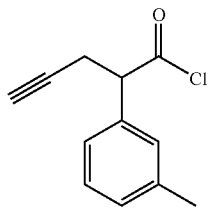

2-m-Tolyl-pent-4-ynoyl chloride

Step 1: 2-m-Tolyl-pent-4-ynoic acid

An oven dried, 1-L, 3-necked, round-bottomed flask was equipped with a magnetic stirring bar, N$_2$ inlet, and a thermometer. The reaction vessel was charged with 39.2 mL (0.280 mol) of N,N-diisopropylamine and 250 mL of anhydrous THF. The solution was cooled to 0° C. and 112 mL of n-BuLi (2.5 M in hexanes, 0.279 mol) was added. After stirring for 30 min, the reaction mixture was cooled to −78° C. and a solution of m-tolylacetic acid (20.0 g, 0.133 mole) in 100 mL of anhydrous THF was added. After 30 min, propargyl bromide (80% wt in toluene, 15.8 mL, 0.146 mole) was added dropwise. After the addition, the reaction mixture was stirred at −78° C. for 2 h. The cooling bath was then removed and the reaction was allowed to warm to rt. Satd. aq. NH$_4$Cl (150 mL) was added, followed by 1 N HCl until pH=2, and the mixture transferred to a separatory funnel with the aid of 200 mL of EtOAc. The layers were separated and the organic layer was washed with H$_2$O (1×100 mL) and brine (1×100 mL), and was dried over MgSO$_4$. After filtration the solvents were evaporated under reduced pressure to obtain a brown solid. The product was purified by recrystallization from hot hexane to obtain the desired acid as a pale brown, crystalline solid (19.5 g, 78%). HPLC (Method R): R$_t$=8.26 min. MS (ES+): mass calculated for C$_{12}$H$_{12}$O$_2$, 188.08; m/z found, 189.09 [M+H]$^+$. $^1$H NMR (400 MHz, CDCl$_3$): 7.19-7.23 (m,1H), 7.08-7.11 (m, 3H), 3.79 (t, J=9.9 Hz, 1H), 2.92 (ddd, J=16.6, 8.6, 2.5 Hz, 1H), 2.61 (ddd, J=16.6, 7.1, 2.5 Hz, 1 H), 2.34 (s, 3H), 1.96 (t, J=2.5 Hz, 1H).

Step 2: 2-m-Tolyl-pent-4-ynoyl chloride

An oven dried, 500-mL, 1-necked round-bottomed flask was equipped with a magnetic stirring bar and N$_2$ inlet. The reaction vessel was charged sequentially with 13 g (0.069 mol) of 2-m-tolyl-pent-4-ynoic acid, 100 mL of CH$_2$Cl$_2$, and 0.1 mL of DMF. Oxalyl chloride (7.3 mL, 0.082 mol) was added dropwise to the reaction. After the addition, the reaction mixture was stirred for 4 h. The solvent and excess reagents were removed by evaporation under reduced pressure to provide a brown oil. Bulb-to-bulb distillation under reduced pressure (167° C./5 Torr gave the desired acid chloride as a pale orange oil (12.8 g, 90%). HPLC (Method R): R$_t$ of methyl ester (quenching in MeOH)=9.35 min. $^1$H NMR (400 MHz, CDCl$_3$): 7.15-7.18 (m, 1H), 7.08-7.11 (m, 2H), 4.18 (t, 1H, J=7.5Hz), 2.97 (ddd, J=16.6, 8.6, 2.5 Hz, 1H), 2.61 (ddd, J=16.6, 7.1, 2.5 Hz, 1H), 2.37 (s, 3H), 2.03 (t, J=2.5 Hz, 1H).

Example 501

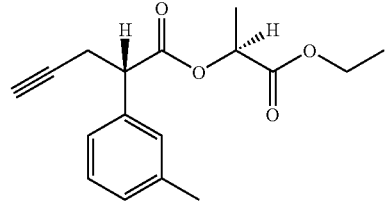

(S)-2-m-Tolyl-pent-4-ynoic acid 1-ethoxycarbonyl-ethyl ester

An oven dried 1-L, 3-necked round-bottomed flask was equipped with a magnetic stirring bar, a rubber septa, and a N$_2$ inlet. The reaction vessel was charged with a solution of 2-m-tolyl-pent-4-ynoyl chloride from Example 500, Step 2 (12.8 g, 61.9 mmol) in 350 mL of toluene via cannula. To this mixture was then added 22.3 mL (0.206 mmol) of N,N-dimethylethylamine. After stirring at rt for about 5 h, the reaction mixture was cooled to −78° C. and 8.6 mL (75 mmol)

of ethyl (S)-(−)-lactate (neat) was added. After the mixture was stirred at this temperature for 4 h, the cooling bath was removed and the reaction mixture was allowed to warm to rt overnight. Water (100 mL) was added and the resulting mixture was transferred to a separatory funnel. The layers were separated and the organic layer was washed with H$_2$O (100 mL) and dried over MgSO$_4$. After filtration, the solvents were evaporated under reduced pressure. The crude product thus obtained was purified by filtration through a pad of silica gel to obtain the lactate ester as a yellow oil (16.1 g, 90%). The product was found to be predominantly one diastereoisomer (82% de by $^1$H NMR). HPLC (Method R): R$_t$=9.84 min. MS (ES+): mass calculated for C$_{17}$H$_{20}$O$_4$, 288.14; m/z found, 289.14 [M+H]$^+$. $^1$H NMR (400 MHz, CDCl$_3$): 7.20-7.25 (m, 1H), 7.10-7.15 (m, 3H), 5.12 (dd, J=10.4, 7.0 Hz, 1H), 4.06 (dd, J=14.4, 7.0 Hz, 2H), 3.84 (t, J=8.0 Hz), 2.95 (ddd, J=16.6, 8.6, 2.8 Hz, 1H), 2.66 (ddd, J=16.6, 7.1, 2.8 Hz, 1H), 2.37 (s, 3H), 1.97 (t, J=2.5 Hz, 1H), 1.48 (d, J=7.0 Hz, 3H), 1.11 (t, J=7.3 Hz, 3H).

Example 502

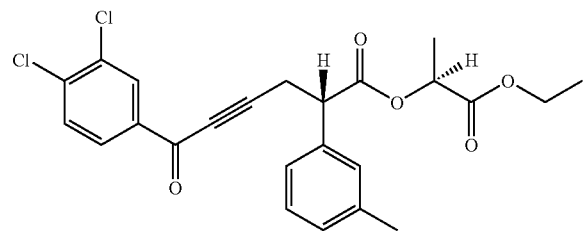

(S)-6-(3,4-Dichloro-phenyl)-6-oxo-2-m-tolyl-hex-4-ynoic acid 1-ethoxycarbonyl-ethyl ester An oven dried, 1-L, 1-necked round-bottomed flask was equipped with a magnetic stirring bar and a N$_2$ inlet. The reaction vessel was charged sequentially with 14.3 g (0.068 mol) of 3,4-dichlorobenzoyl chloride (solid), a solution of 16.5 g of (S)-2-m-tolyl-pent-4-ynoic acid 1-ethoxycarbonyl-ethyl ester from Example 501 (57.2 mmol) in 75 mL of anhydrous THF, and 75 mL of anhydrous toluene. N$_2$ was bubbled through the solution for about 5 min. The catalysts PdCl$_2$(PPh$_3$)$_2$ (0.10 g, 0.086 mmol) and CuI (0.10 g, 0.52 mmol) were added, followed by 15 mL (13.8 g, 0.138 mol) of N-methylmorpholine (NMM). The reaction mixture was stirred at rt for 28 h when TLC indicated almost complete consumption of starting materials. Water was added (200 mL) and the mixture transferred to a separatory funnel with the aid of 200 mL of EtOAc. The layers were separated and the organic layer was washed with H$_2$O (2×50 mL) and dried over MgSO$_4$. After filtration, the solvents were evaporated and the dark residue obtained was purified by pad filtration on silica gel to yield the acetylenic ketone as a yellow oil (21 g, 80%). HPLC (Method R): R$_t$=11.09 min. MS (ES+): mass calculated for C$_{21}$H$_{18}$Cl$_2$O$_3$, 460.08; m/z found, 461.09 [M+H]$^+$. $^1$H NMR (400 MHz, CDCl$_3$): 8.03 (d, J=2.0 Hz, 1H), 7.65 (dd, J=8.3, 2.0 Hz, 1H), 7.45 (d, J=8.3 Hz, 1H), 7.25-7.29 (bm, 1H), 7.13-7.16 (m, 3H), 5.13 (dd, J=10.4, 7.0 Hz, 1H), 4.10 (dd, J=14.4, 7.2 Hz, 2H), 3.95 (t, J=8.0 Hz), 3.22 (dd, J=16.6, 7.6 Hz, 1H), 3.04 (dd, J=16.6, 8.0 Hz, 1H), 2.37 (s, 3H), 1.48 (d, J=7.0 Hz, 3H), 1.15 (t, J=73 Hz, 3H).

Example 503

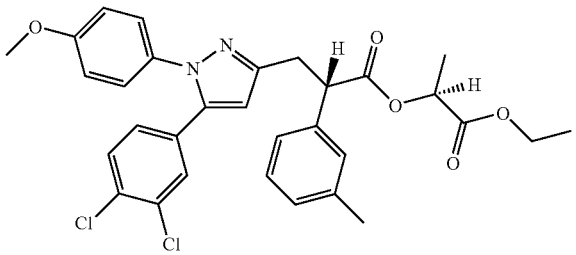

(S)-3-[5-(3,4-Dichloro-phenyl)-1-(4-methoxy-phenyl)-1H-pyrazol-3-yl]-2-m-tolyl-propionic acid 1-ethoxycarbonyl-ethyl ester To a stirred solution of (S)-6-(3,4-dichloro-phenyl)-6-oxo-2-m-tolyl-hex-4-ynoic acid 1-ethoxycarbonyl-ethyl ester from Example 502 (15.5 g, 0.0336 mol) in THF (150 mL) was added Cs$_2$CO$_3$ (8.8 g, 0.027 mol) followed by 4-methoxyphenyl hydrazine HCl (6.5 g, 0.037 mol). The resulting slurry was stirred at rt overnight and then slowly quenched with 1 N HCl until pH 2-3. The mixture was transferred to a separatory funnel and extracted with EtOAc (3×75 mL). The combined organic layers were washed with brine, dried over Na$_2$SO$_4$, filtered and concentrated to an oil. The crude oil was purified by pad filtration on silica gel using EtOAc/hexanes to obtain the pyrazole as mixture of two regioisomers in 4:1 ratio (18.6 g, 95%). Chiral HPLC (Method S): R$_t$ (R,S)=5.6 min; (S,S)= 6.3 min. $^1$H NMR (400 MHz, CDCl$_3$): 7.31-7.07 (m, 8H), 6.91-6.86 (m, 3H), 6.23 (s, 1H), 5.13 (dd, J=10.4, 7.0 Hz, 1H), 4.16 (m, 1H), 4.07 (dd, J=14.4, 7.2 Hz, 2H), 3.82 (s, 3H), 3.51 (dd, J=14.9, 9.6 1H), 3.04 (dd, J=14.9, 6.3 Hz, 1H), 2.37 (s, 3H), 1.42 (d, J=7.0 Hz, 3H), 1.12 (t, J=7.3 Hz, 3H).

Example 504

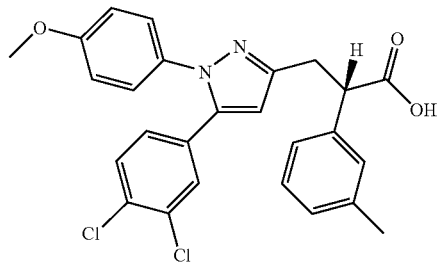

(S)-3-[5-(3,4-Dichloro-phenyl)-1-(4-methoxy-phenyl)-1H-pyrazol-3-yl]-2-m-tolyl-propionic acid A 500-mL, 1-necked round-bottomed flask equipped with a magnetic stirring bar was charged with (S)-3-[5-(3,4-dichloro-phenyl)-1-(4-methoxy-phenyl)-1H-pyrazol-3-yl]-2-m-tolyl-propionic acid 1-ethoxycarbonyl-ethyl ester from Example 503 (18.5 g. 0.0318 mol), as a 4:1 mixture of regioisomers, in 150 mL of acetic acid. After the addition of 2 N HCl (25 mL), the reaction mixture was heated at 85° C. using an oil bath. After 4 h, when TLC indicated complete hydrolysis of the lactate ester, the heating source was removed and reaction flask cooled to rt. The mixture was concentrated under reduced pressure to remove most of acetic acid, and then 250 mL of EtOAc was added. The EtOAc solution was then washed with H₂O (50 mL) and brine (50 mL), and then dried over Na₂SO₄. The solvents were removed under reduced pressure to obtain the crude acid as a brown oil (15 g, 98%). HPLC (Method E) indicated the product to be a mixture of 2 regioisomers in a 4:1 ratio. Chiral HPLC (Method S): $R_t$ (S isomer)=8.1 min (enantiomeric ratio of 1:9 R/S). This mixture was subjected to the next step without any additional purification. MS (ES+): mass calculated for $C_{26}H_{22}Cl_2N_2O_3$, 480.10; m/z found, 480.8 [M+H]⁺. ¹H NMR (400 MHz, CDCl₃): 7.31-7.09 (m, 8H), 6.91-6.86 (m, 3H), 6.21 (s, 1H), 4.12-4.08 (dd, J=5.8, 9.6 Hz, 1H), 3.82 (s, 3H), 3.54-3.49 (dd, J=9.6, 14.9 Hz, 1H), 3.13-3.08 (dd, J=5.8, 14.9 Hz, 1H), 2.35 (s, 3H).

Example 505

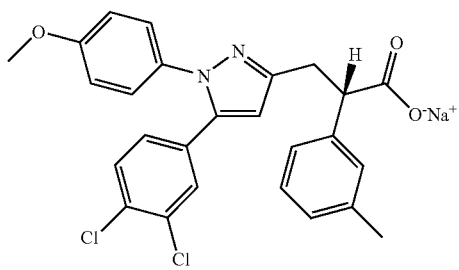

(S)-Sodium; 3-[5-(3,4-dichloro-phenyl)-1-(4-methoxy-phenyl)-1H-pyrazol-3-yl]-2-m-tolyl-propionate A stirred solution of (S)-3-[5-(3,4-dichloro-phenyl)-1-(4-methoxy-phenyl)-1H-pyrazol-3-yl]-2-m-tolyl-propionic acid from Example 504 (15.3 g, 0.0318 mol), as a 4:1 mixture of regioisomers, in THF (150 mL) was cooled to 0° C. After the addition of 3.1 M NaOH, the resulting mixture was stirred for 2 h. The cooling bath was removed and the mixture was concentrated under reduced pressure. The residue was dissolved in 100 mL of THF and CH₃CN (100 mL) was added. The solution was stirred at rt for about 30 min when precipitation started. The mixture was stirred for another 4 h and filtered. The solid sodium salt was collected and dried under vacuum to afford the sodium salt as a white crystalline powder (10 g, 63%). Chiral HPLC (Method T): $R_t$=8.1 min (>99.9% enantiomeric purity). MS (ES+): mass calculated for $C_{26}H_{22}Cl_2N_2O_3$, 481.38; m/z found, 482.2 [M+H]⁺. Mp 280-285° C. Optical rotation $[\alpha]_D$=+58.8 (c 0.1; EtOH). ¹H NMR (500 MHz, D₂O): 7.14-7.10 (m, 2H), 6.99-6.96 (t, J=7.4 Hz, 1H), 6.82-6.80 (d, J=8.2 Hz, 2H), 6.74-6.72 (d, J=7.4 Hz, 1H), 6.0-6.5 (m, 4H), 6.32-6.30 (d, J=8.0 Hz, 1H), 5.60 (s, 1H), 3.82-3.80 (m, 1H), 3.42 (s, 3H), 3.37-3.28 (m, 2H), 2.01 (s, 3H).

Example 506

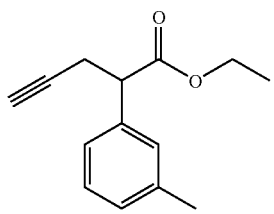

2-m-Tolyl-pent-4-ynoic acid ethyl ester

A 2-L, 3-necked round-bottomed flask was equipped with a magnetic stirring bar, a N₂ inlet, and a thermometer. The reaction vessel was charged with 34.6 mL of N,N-diisopropylamine and 300 mL of anhydrous THF. The solution was cooled to 0° C. and 100 mL of n-butyllithium (2.5 M in hexanes) was added. After the addition, the solution was stirred for 0.5 h and cooled to −78° C. To this solution, 40 mL of ethyl m-tolyl acetate was added (neat). After stirring for 1 h, propargyl bromide (80% wt in toluene, 26.8 mL) was added dropwise (temperature ranged from −75 to −78° C. during addition). The cooling bath was then removed and the solution was allowed to warm to rt overnight. The reaction mixture was quenched by adding satd. aq. NH₄Cl (100 mL) and the resulting mixture was transferred to a separatory funnel with the aid of 100 mL of EtOAc. The layers were separated and the organic layer was washed with brine and dried over MgSO₄. After filtration, the solvents were evaporated under reduced pressure to yield a pale orange oil. Distillation under reduced pressure furnished the desired ester as colorless oil (40 g, 82%). ¹H NMR spectrum of the product thus obtained indicated the presence of about 5% of the starting material. The product was further purified by fractional distillation using a Vigreux column (8 in.). The main fractions distilling between 83 and 85° C. at 500 mTorr were collected to yield the pure ester as a colorless liquid (35 g, 72%). TLC: $R_f$=0.54 (1:4 EtOAc/hexanes). HPLC (Method R): $R_t$=9.75 min. MS (ES+): mass calculated for $C_{14}H_{16}O_2$, 216.12; m/z found, 238.7 [M+Na]⁺. ¹H NMR (400 MHz, CDCl₃): 7.19-7.23 (m, 1H), 7.08-7.11 (m, 3H), 4.09-4.22 (m, 2H), 3.75 (dd, J=8.6, 7.1 Hz, 1H), 2.92 (ddd, J=16.6, 8.6, 2.5 Hz, 1H), 2.61 (ddd, J=16.6, 7.1, 2.5 Hz, 1H), 2.34 (s, 3H), 1.95 (t, J=2.5 Hz, 1H), 1.22 (t, J=7.1 Hz, 3H).

Example 507

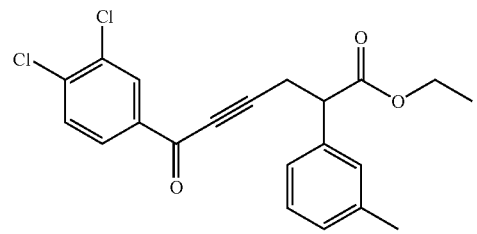

6-(3,4-Dichloro-phenyl)-6-oxo-2-m-tolyl-hex-4-ynoic acid ethyl ester

An oven dried 1-L, 1-necked round-bottomed flask was equipped with a magnetic stirring bar and a N₂ inlet. The reaction vessel was charged sequentially with 17.4 g (83.2 mmol) of 3,4-dichlorobenzoyl chloride (solid), a solution of 15.0 g of 2-m-tolyl-pent-4-ynoic acid ethyl ester from Example 506 (69.4 mmol) in 100 mL of anhydrous THF, and 100 mL of anhydrous toluene. Catalysts PdCl₂(PPh₃)₂ (0.10 g, 0.086 mmol) and CuI (0.10 g, 0.52 mmol) were then added, followed by 15.4 mL (14.2 g, 140 mmol) of NMM. The reaction mixture was stirred at rt for 14 h when TLC indicated almost complete consumption of the starting material. Water (100 mL) and EtOAc (100 mL) were added to the reaction and the mixture was transferred to a separatory funnel. The layers were separated and the organic layer was washed with H₂O (2×100 mL), brine (50 mL), and dried over MgSO₄. After filtration, the solvents were evaporated to yield a yellow oil.

The crude product was purified by silica gel column chromatography (column: 14 cm OD, 12 cm in height; eluent: 1:9 EtOAc/hexanes) to obtain the acetylenic ketone as a pale yellow oil (19 g, 69%). TLC (1:4 EtOAc/hexanes): $R_f$=0.49. HPLC (Method R): $R_t$=11.09 min. MS (ES+): mass calculated for $C_{21}H_{18}Cl_2O_3$, 388.06; m/z found, 389.18 [M+H]$^+$. $^1$H NMR (400 MHz, CDCl$_3$): 8.03 (d, J=2.0 Hz, 1H), 7.65 (dd, J=8.3, 2.0 Hz, 1H), 7.45 (d, J=8.3 Hz, 1H), 7.25-7.29 (bm, 1H), 7.13-7.16 (m, 3H), 4.12-4.25 (m, 1H), 3.88 (t, J=7.8 Hz, 1H), 3.16(dd, J=17.2, 7.6 Hz, 1H), 2.98 (dd, J=17.2, 7.8 Hz, 1H), 2.35 (s, 3H), 1.20 (t, J=7.4 Hz, 3H).

Example 508

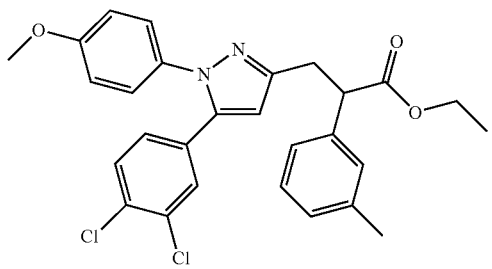

3-[5-(3,4-Dichloro-phenyl)-1-(4-methoxy-phenyl)-1H-pyrazol-3-yl]-2-m-tolyl-propionic acid ethyl ester To a stirred solution of 6-(3,4-dichloro-phenyl)-6-oxo-2-m-tolyl-hex-4-ynoic acid ethyl ester from Example 507 (9.55 g, 0.0245 mol) in THF (125 mL) was added Cs$_2$CO$_3$ (8.8 g, 0.027 mol) followed by 4-methoxyphenyl hydrazine HCl (6.50 g, 0.0372 mol). The resulting slurry was stirred at rt overnight and then was slowly quenched with 1 N HCl until pH 2-3. The mixture was transferred to a separatory funnel and extracted with EtOAc (3×75 mL). The combined organic layers were washed with brine, dried over Na$_2$SO$_4$, filtered and concentrated to an oil. The crude oil was purified by filtration chromatography (silica gel column: 14 cm OD, 10 cm in height, 10 to 30% EtOAc/hexanes). The desired fractions were combined to afford 9.46 g (76%) of the pyrazole ester as dark-orange oil. Chiral HPLC (Method S): $R_t$ (R enantiomer)=5.6 min; $R_t$ (S enantiomer)=6.3 min. MS (ES+): mass calculated for $C_{28}H_{26}Cl_2N_2O_3$, 509.44; m/z found, 510.9 [M+H]$^+$. $^1$H NMR (400 MHz, CDCl$_3$): 7.31-7.07 (m, 8H), 6.91-6.86 (m, 3H), 6.19 (s, 1H), 4.22-4.01 (m, 3H), 3.82 (s, 3H), 3.54-3.48 (dd, J=14.9, 9.6 Hz, 1H), 3.11-3.06 (dd, J=14.9, 6.0 Hz, 1H), 2.35 (s, 3H), 1.20-1.16 (t, J=7.3 Hz, 3H).

Example 509

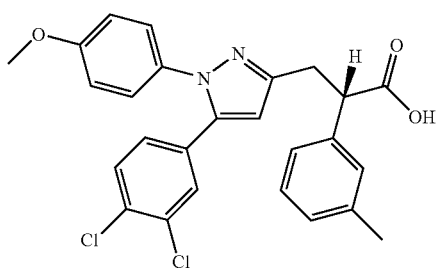

(S)-3-[5-(3,4-Dichloro-phenyl)-1-(4-methoxy-phenyl)-1H-pyrazol-3-yl]-2-m-tolyl-propionic acid To a stirred solution of the Altus catalyst #8 (10.0 g) in phosphate buffer (pH 7, 500 mL) was slowly added 3-[5-(3,4-dichloro-phenyl)-1-(4-methoxy-phenyl)-1H-pyrazol-3-yl]-2-m-tolyl-propionic acid ethyl ester from Example 508 (10.0 g, 0.0196 mol) in IPA/toluene (40 mL/15 mL) for over 30 min to form a slurried reaction mixture. The reaction was monitored at 2 day intervals using chiral HPLC. After 24 days, the reaction mixture was adjusted to pH 1-2 using 1 N HCl, and then EtOAc (300 mL) was added. The mixture was stirred vigorously for 1 h. The emulsion was filtered through a pad of CELITE®, washing with EtOAc (75 mL). The filtrate was transferred to a separatory funnel and the layers were separated. The aqueous layer was extracted with EtOAc (2×75 mL). The combined organic layers were dried over Na$_2$SO$_4$, filtered and concentrated to an oil. The crude oil was purified by filtration chromatography (silica gel column: 14 cm OD, 10 cm in height, 1% MeOH/20% EtOAc/hexanes). After the unreacted pyrazole ester (4:1 R/S) was recovered (6.0 g, 60%), the eluent was changed to 2-3% MeOH/50% EtOAc/hexanes to obtain the desired pyrazole acid (3.8 g, 40%) as an oil. Chiral HPLC (Method S): $R_1$ (S enantiomer) =8.1 min. MS (ES+): mass calculated for $C_{26}H_{22}Cl_2N_2O_3$, 480.10; m/z found, 480.8 [M+H]$^+$. $^1$H NMR (400 MHz, CDCl$_3$): 7.31-7.09 (m, 8H), 6.91-6.86 (m, 3H), 6.21 (s, 1H), 4.12-4.08 (dd, J=9.6, 5.8 Hz, 1H), 3.82 (s, 3H), 3.54-3.49 (dd, J=14.9, 9.6 Hz, 1H), 3.13-3.08 (dd, J=14.9, 5.8 Hz, 1H), 2.35 (s, 3H).

Example 509a

Enzymatic resolutions were also performed with lipases such as *Mucor miehei*, lyo; *Rhizomucor miehei*; and *Candida cyclindracea*, according to the procedures described in Example 509. The yield in the enzymatic resolutions with lipase *Mucor miehei*, lyo, was substantially the same as that described in Example 509.

Example 510

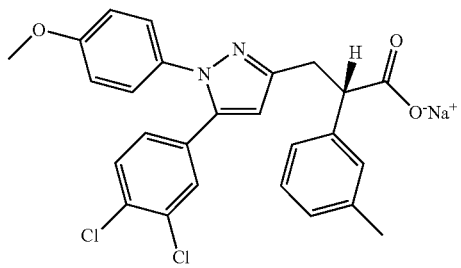

(S)-Sodium; 3-[5-(3,4-dichloro-phenyl)-1-(4-methoxy-phenyl)-1H-pyrazol-3-yl]-2-m-tolyl-propionate To a stirred solution of (S)-3-[5-(3,4-dichloro-phenyl)-1-(4-methoxy-phenyl)-1H-pyrazol-3-yl]-2-m-tolyl-propionic acid from Example 509 (3.8 g, 7.9 mmol) in THF (40 mL) was added 4.4 M NaOH at rt. The mixture was stirred for 60 min, and then was concentrated to an oil under reduced pressure using a rotary evaporator with a bath temperature of 25-30° C. The residue was diluted in THF (25 mL) and CH$_3$CN was added whereupon precipitation occurred. The solids were stirred for 2 h, then were filtered and washed with CH$_3$CN to afford the desired sodium salt (3.34 g, 68%) as a white solid.

Chiral HPLC (Method T): $R_t$=7.1 min (>99.9% enantiomeric purity). MS (ES+): mass calculated for $C_{26}H_{22}Cl_2N_2O_3$, 480.10; m/z found, 481.0 [M+H]$^+$. Mp 280-285° C. Optical rotation $[\alpha]_D$=+58.8 (c0.1; EtOH). $^1$H NMR (500 MHz, $D_2O$): 7.14-7.10 (m, 2H), 6.99-6.96 (t, J=7.4 Hz, 1H), 6.82-6.80 (d, J=8.2 Hz, 2H), 6.74-6.72 (d, J=7.4 Hz, 1H), 6.0-6.5 (m, 4H), 6.31 (d, J=8.0 Hz, 1H), 5.60 (s, 1H), 3.82-3.80 (m, 1H), 3.42 (s, 3H), 3.37-3.28 (m, 2H), 2.01 (s, 3H).

Example 511

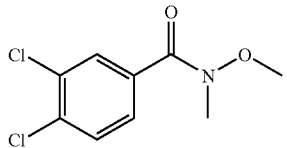

3,4-Dichloro-N-methoxy-N-methyl-benzamide

N,O-Dimethylhydroxylamine hydrochloride (1.48 kg, 14.9 mol) was suspended in EtOAc (16 L) and warmed to 35° C. A solution of 3,4-dichlorobenzoyl chloride (3.00 kg, 13.9 mol) in EtOAc (8 L) was added, followed by addition of DIPEA (5.45 ml, 31.2 mol) while maintaining the temperature below 40° C. The reaction suspension was stirred for 1 h. When TLC analysis confirmed reaction completion by the disappearance of starting material, the reaction mixture was cooled to rt and $H_2O$ (10 L) was added to achieve a clear, biphasic solution. After removing the aqueous layer, the organic layer was dried ($Na_2SO_4$) and concentrated to afford the title compound (3.49 kg, 100%) as an oil. Upon sitting at rt, the product crystallized. IR (KBr pellet): 3445, 3258, 3091.6, 2981.4, 2945.5, 1942.4, 1645.6, 1588.6, 1557.4, 1462.9, 1414.5, 1368, 1386.2,1262, 1209, 1130, 1112.5, 1071.8, 1030.9, 100.9, 893.8. MS (ES+): mass calculated for $C_9H_9Cl_2NO_2$, 233.00; m/z found 234.0 [M+H]$^+$. Mp: 39.5-43.2° C. $^1$H NMR (400 MHz, CDCl$_3$): 7.80 (d, J=2 Hz, 1H), 7.54 (dd, J=8.4, 2.0 Hz, 1H), 7.46 (d, J=8.3 Hz, 1H), 3.54 (s, 3H), 3.34 (s, 3H). $^{13}$C NMR (100 MHz, CDCl$_3$): 167.2, 135.0, 133.9, 132.4, 130.7, 130.2, 127.9, 61.5, 33.7.

Example 512

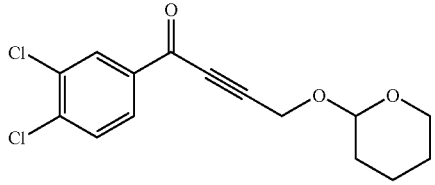

1-(3,4-Dichlorophenyl)-4-[(tetrahydro-2H-pyran-2-yl)oxy]-2-butyn-1-one (2a)

To a mixture of 3,4-dichloro-N-methoxy-N-methyl-benzamide from Example 511 (0.68 g, 2.9 mmol) and tetrahydro-2-(2-propynyloxy)-2H-pyran (0.40 mL, 2.9 mmol) in 3.5 mL of dry THF at −25° C. was added lithium bis(trimethylsilyl)amide (LHMDS, 1 M in THF) between −25° C. and −18° C. The reaction mass was stirred at that temperature range for 1 h. The reaction was quenched with 10 mL of 1 M citric acid and was allowed to warm to 10° C. EtOAc (5 mL) was added and the mass was stirred for 15 min. The pH of the aqueous layer was 5. The layers were separated and the organic layer was concentrated to give a light yellow oil (110%, including residual solvent). HPLC (Method U): $R_t$=15.42 min. MS (ES+): mass calculated for $C_{15}H_{14}Cl_2O_3$, 312.03; m/z found, 325.1 [M+Na]$^+$. $^1$H NMR (400 MHz, CDCl$_3$): 8.19 (d, J=2 Hz, 1H), 7.95 (dd, J=8.4, 2.1 Hz, 1H), 7.57 (d, J=8.4 Hz, 1H), 4.94-4.81 (m, 1H), 4.56 (s, 2H), 3.97-3.82 (m, 1H), 3.71-3.55 (m, 1H), 1.91-1.54 (m, 6H). $^{13}$C NMR (100 MHz, CDCl$_3$): 175.0, 139.0, 136.0, 133.4, 131.4, 131.2, 130.8, 128.3, 97.7, 92, 82.9, 62.2, 54.2, 30.1, 25.2, 18.9.

Example 513

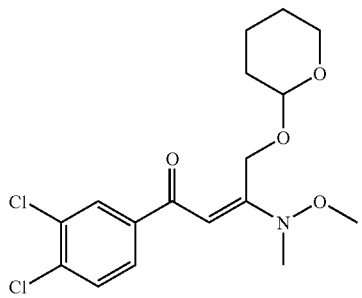

(E)-1-(3,4-Dichlorophenyl)-3-(methoxymethylamino)-4-[(tetrahydro-2H-pyran-2-yl)oxy]-2-buten-1-one MS (ES+): mass calculated for $C_{17}H_{21}Cl_2NO_4$, 373.08; m/z found, 374.1 [M+H]$^+$. $^1$H NMR (400 MHz, CDCl$_3$): 7.95 (d, J=2.1 Hz, 1H), 7.69 (dd, J=8.4, 2.1 Hz, 1H), 7.44 (d, J=8.3 Hz, 1H), 6.12 (s, 1H), 5.13 (d, J=12 Hz, 1H), 4.79-4.77 (m, 1H), 4.76 (d, J=11.5 Hz, 1H), 3.70 (s, 3H), 3.88-3.86 (m, 1H), 3.30 (s, 3H), 1.83-1.50 (m, 3H), 1.49-1.21 (m, 4H).

Example 514

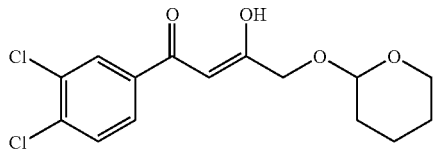

(Z)-1-(3,4-Dichlorophenyl)-3-hydroxy-4-[(tetrahydro-2H-pyran-2-yl)oxy]-2-buten-1-one 3,4-Dichloro-N-methoxy-N-methyl-benzamide (Example 511, 4.90 kg, 20.9 mol) and tetrahydro-2-(2-propynyloxy)-2H-pyran (3.06 kg, 21.4 mol), which was prepared by methods known to those skilled in the art, were dissolved in THF (28.6 L) at rt. After cooling to between −10 and −15° C., LHMDS (1 M in THF, 19.76 kg, 22.19 mol) was added. When HPLC analysis indicated the disappearance of the starting material, the reaction mixture was warmed to 0° C. and 1 M aq. citric acid (34.0 L) was added. Next, EtOAc (20.0 L) was added and the resulting mixture was stirred for 15 min. After removing the aqueous layer, the organic layer was washed with brine (30.0 L) and the desired product was obtained as a solution, which was used in the next step without isolation. HPLC (Method U): $R_t$=16.24 min. MS (ES+): mass calculated for $C_{15}H_{16}Cl_2O_4$, 330.04; m/z found, 331.1 [M+H]$^+$. $^1$H NMR (400 MHz, CDCl$_3$): 15.7 (bs, 1H), 7.99 (d, J=2 Hz, 1H), 7.71 (dd, J=8.4, 2.1 Hz, 1H), 7.53 (d, J=8.4 Hz,1H), 6.45 (s, 1H), 4.72-4.70 (m, 1H), 4.39 (d, J=16.8 Hz, 1H), 4.33 (d, J=16.8 Hz, 1H), 4.28-4.25 (m, 1H), 3.91-3.83 (m,1H), 2.04-1.43 (m, 6H). $^{13}$C NMR (100 MHz, CDCl$_3$): 193.5, 179.2, 135.4, 133.2, 131.9, 129.4, 127.7, 124.8, 97.5, 92.4, 67.1, 61.1, 29.0, 23.9, 17.9.

Example 515

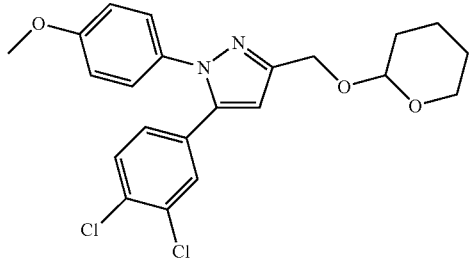

5-(3,4-Dichlorophenyl)-1-(4-methoxyphenyl)-3-[[(tetrahydro-2H-pyran-2-yl)oxy]methyl]-1H-pyrazole 4-Methoxyphenylhydrazine hydrochloride (3.88 kg, 21.8 mol) and K$_2$CO$_3$ (3.21 kg, 23.2 mol) were added to a THF/EtOAc solution containing (Z)-1-(3,4-dichlorophenyl)-3-hydroxy-4-[(tetrahydro-2H-pyran-2-yl)oxy]-2-buten-1-one (Example 514) at 0-10° C. The resultant suspension was stirred and allowed to warm to rt overnight (16 h). When HPLC analysis indicated the disappearance of the starting material, the reaction mixture was filtered. The organic reaction filtrate was washed with 1 M aq. citric acid (34.0 L), followed by 10% aq. NaCl (50.0 L) and the resulting product solution was used in the next synthetic step without isolation. HPLC (Method U): $R_t$=16.22 min. MS (ES+): mass calculated for $C_{22}H_{22}Cl_2N_2O_3$, 432.10; m/z found, 455.1 [M+Na]$^+$. $^1$H NMR (400 MHz, CDCl$_3$): 7.39 (d, J=1.9 Hz, 1H), 7.33 (d, J=8.5 Hz, 1H), 7.19 (dd, J=6.8, 2.2 Hz, 2H), 6.96 (dd, J=8.1, 2.1 Hz, 1H), 6.87 (dd, J=2.1, 7 Hz, 2H), 6.58 (s, 1H), 4.86 (d, J=12 Hz, 1H), 4.83-4.81(m, 1H), 4.60 (d, J=12 Hz, 1H), 3.99-3.84 (m, 1H), 3.82 (s, 3H), 3.78-3.74 (m, 1H), 1.91-1.52 (m, 6H). $^{13}$C NMR (100 MHz, CDCl$_3$): 159.5, 150.7, 141.8, 133.0, 132.7, 130.9, 130.8, 130.6, 128.1, 127.1, 114.7, 107.7, 98.6, 63.2, 62.6, 60.8, 55.9, 30.9, 25.8, 21.4, 19.7, 14.6.

Example 516

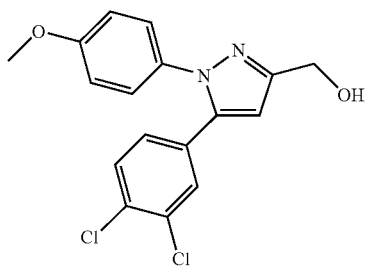

[5-(3,4-Dichlorophenyl)-1-(4-methoxyphenyl)-1H-pyrazol-3-yl]-methanol

A solution of p-toluenesulfonic acid (1.22 kg, 6.28 mol) in methanol (20.0 L) was added to the THF/EtOAc solution of 5-(3,4-dichlorophenyl)-1-(4-methoxyphenyl)-3-[[(tetrahydro-2H-pyran-2-yl)oxy]methyl]-1H-pyrazole (Example 515) at rt and the resulting mixture was stirred overnight (18 h). When HPLC analysis indicated the disappearance of the starting material, the reaction mixture was concentrated to remove methanol. The resulting mixture was washed with 10% aq. NaHCO$_3$ (40.0 L) followed by brine (40.0 L). The organic layer was added to n-heptane and the resultant suspension was filtered, washed, and vacuum dried to afford [5-(3,4-dichlorophenyl)-1-(4-methoxyphenyl)-1H-pyrazol-3-yl]-methanol (4.65 kg, 63.7% over 3 chemical steps) as a solid. Data compared favorably with that obtained for Example 1, Step C.

Example 517

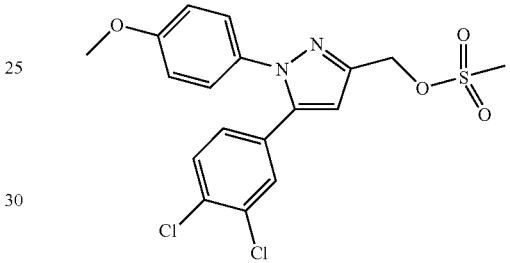

Methanesulfonic acid 5-(3,4-dichlorophenyl)-1-(4-methoxyphenyl)-1H-pyrazol-3-ylmethyl ester Triethylamine (3.25 L, 23.3 mol) was added to a solution containing [5-(3,4-dichlorophenyl)-1-(4-methoxyphenyl)-1H-pyrazol-3-yl]-methanol (Example 516, 5.18 kg, 14.8 mol) in THF (25.2 L) and toluene (6.3 L) at rt under N$_2$. The reaction mixture was heated to 35° C. and methanesulfonyl chloride (1.82 L, 23.5 mol) was added slowly maintaining the temperature between 35-45° C. The reaction mixture was stirred for an additional 2 h at 45° C. When HPLC analysis indicated the disappearance of the starting material, the reaction mixture was cooled to rt and quenched with 10% aq. NaCl (6.3 L). The organic layer was washed with brine (5.0 L) and the desired mesylate was used in solution in the next synthetic step without isolation. Data compared favorably with that obtained for Example 1, Step D.

Example 518

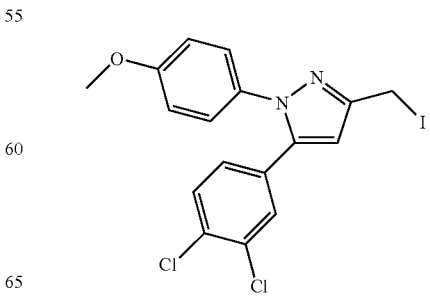

5-(3,4-Dichlorophenyl)-3-iodomethyl-1-(4-methoxyphenyl)-1H-pyrazole

Sodium iodide (4.06 kg, 27.1 mol) was added to the THF/toluene solution of methanesulfonic acid 5-(3,4-dichlorophenyl)-1-(4-methoxyphenyl)-1H-pyrazol-3-ylmethyl ester (Example 517, 6.32 kg, 14.8 mol). The resulting reaction mixture was heated at 40° C. for 6 h and then allowed to cool to rt overnight. When HPLC analysis indicated the disappearance of the starting material, the reaction was quenched with 28% aq. sodium thiosulfate (6.3 L). The organic layer was washed with sat. aq. NaHCO$_3$ (6.3 L), brine (6.3 L), then dried (MgSO$_4$). After filtration to remove the drying agent, the desired product was obtained in a solution, which was used in the next synthetic step without isolation. Chemical characterization data obtained herein for the title compound is not duplicated in this Example in light of the same data given in Example 1, Step E.

Example 519

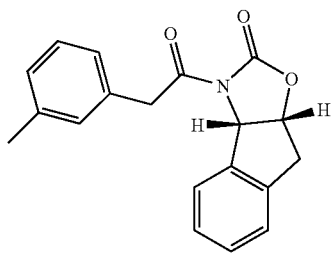

(3aS,8aR)-3-(2-m-Tolyl-acetyl)-3,3a,8,8a-tetrahydro-indeno[1,2-d]oxazol-2-one (3aS-cis)-(−)-3,3a,8,8a-Tetrahydro-2H-indeno[1,2-d]-oxazol-2-one (4.00 kg, 22.8 mol) and m-tolylacetic acid (6.86 kg, 45.7 mol) were stirred in toluene (40.0 L) at rt. Triethylamine (9.25 kg, 91.3 mol) was added, followed by a solution of pivaloyl chloride (5.6 L) in toluene (8 L) and heated at 90° C. for 10 h. When HPLC analysis indicated the disappearance of the starting material, the reaction was cooled to rt and H$_2$O (20.0 L) was added. After removing the aqueous layer, the organic layer was washed with sat. aq. NaHCO$_3$ (20.0 L) followed by brine (20.0 L). The organic layer was vacuum-distilled to a volume of 14 L and n-heptane (70.0 L) was added to precipitate the product. The resultant suspension was filtered, washed, and vacuum dried to afford the desired oxazolone (6.22 kg, 88.6%) as an off-white fluffy solid. Chemical characterization data obtained herein for the title compound is not duplicated in this Example in light of the same data given in Example 1, Step F.

Example 520

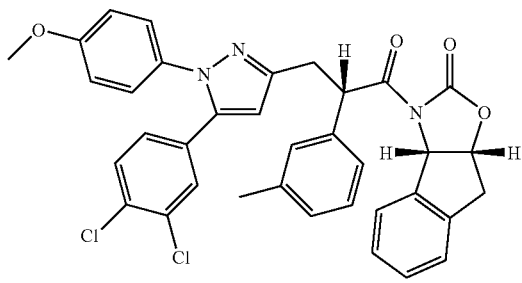

(2S,3aS,8aR)-3-{3-[5-(3,4-Dichlorophenyl)-1-(4-methoxyphenyl)-1H-pyrazol-3-yl]-2-m-tolyl-propionyl}-3,3a,8,8a-tetrahydro-indeno[1,2-d]oxazol-2-one To a stirred solution containing (3aS,8aR)-3-(2-m-tolyl-acetyl)-3,3a,8,8a-tetrahydro-indeno[1,2-d]oxazol-2-one (Example 519, 5.54 kg, 18.0 mol) in THF (22.2 L) was added sodium bis(trimethylsilyl)amide (NaHMDS, 1 M in THF, 19.8 L, 19.8 mol) at <−35° C. The mixture was stirred for 45 min between −35 and −70° C., then treated with the THF/toluene solution containing 5-(3,4-dichlorophenyl)-3-iodomethyl-1-(4-methoxyphenyl)-1H-pyrazole (Example 6, 6.79 g, 14.8 mol). The reaction mixture was stirred at <−35° C. for 2 h, and then was allowed to warm to rt overnight. When HPLC analysis indicated the disappearance of the starting material, the reaction was quenched with H$_2$O (13.6 L). Toluene (10.5 L) was then added and after removing the aqueous layer, the resulting solution of the product oxazolone was used in the next synthetic step without isolation. Chemical characterization data obtained herein for the title compound is not duplicated in this Example in light of the same data given in Example 1, Step G.

Example 521

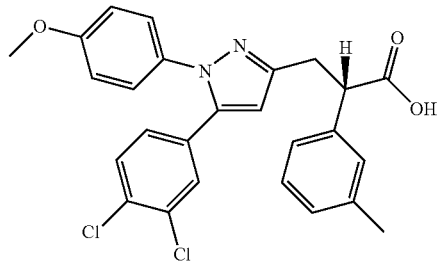

(S)-3-[5-(3,4-Dichloro-phenyl)-1-(4-methoxy-phenyl)-1H-pyrazol-3-yl]-2-m-tolyl-propionic acid To a stirred THF/toluene solution containing 3-{3-[5-(3,4-dichlorophenyl)-1-(4-methoxyphenyl)-1H-pyrazol-3-yl]-2-m-tolyl-propionyl}-3,3a,8,8a-tetrahydro-indeno[1,2-d]oxazol-2-one (Example 520, 9.45 kg, 14.8 mol) at 0-10° C. was added H$_2$O (5.25 L) and 30% hydrogen peroxide (4.35 L, 42.6 mol) followed by 19% aq. LiOH (9.40, 42.6 mol). The reaction mixture was stirred between 0-10° C. for 2 h. When HPLC analysis indicated the disappearance of the starting material, the reaction was quenched between 0-10° C. with 1.5 N sodium meta-bisulfite solution (8.0 L) maintaining the pH at 9-10. The quenched reaction mixture was then acidified to pH 1-2 using 6 N HCl (8.4 L). After removing the aqueous layer, ~60.0 L of the organic phase was removed under reduced pressure, and EtOAc (8.5 L) was added. The resultant suspension was filtered and washed. The filtrate, containing the desired acid, was used directly in the next synthetic step without isolation. Chemical characterization data obtained herein for the title compound is not duplicated in this Example in light of the same data given in Example 1, Step H.

Example 522

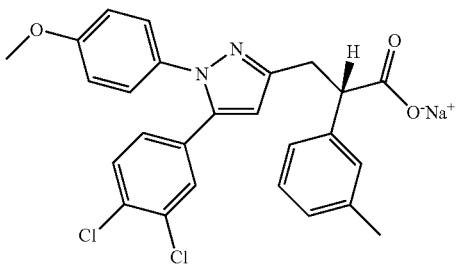

(S)-Sodium; 3-[5-(3,4-dichloro-phenyl)-1-(4-methoxy-phenyl)-1H-pyrazol-3-yl]-2-m-tolyl-propionate To a stirred solution containing (S)-3-[5-(3,4-dichloro-phenyl)-1-(4-methoxy-phenyl)-1H-pyrazol-3-yl]-2-m-tolyl-propionic acid (Example 521, 12.67 kg, 26.34 mol) at rt was added THF (26.5 L) and 4 N NaOH (6.60 L). After stirring for 2 h, the reaction mixture was concentrated to ~55% of the solvent volume and $CH_3CN$ (100.0 L) was added to precipitate the product. The resultant suspension was filtered, washed, and vacuum-dried to afford the desired propionate sodium salt (9.05 kg, 61.0% over 5 chemical steps) as an off-white solid. Christalline; melting point 301.0° C. by DSC. Chemical characterization data obtained herein for the title compound is not duplicated in this Example in light of the same data given in Example 505.

Example 523

Meglumine salt (Table A). The meglumine salt was prepared according to the following procedure: (S)-3-[5-(3,4-Dichloro-phenyl)-1-(4-methoxy-phenyl)-1H-pyrazol-3-yl]-2-m-tolyl-propionic acid was prepared by dilution of (S)-sodium; 3-[5-(3,4-dichloro-phenyl)-1-(4-methoxy-phenyl)-1H-pyrazol-3-yl]-2-m-tolyl-propionate (Example 522) with EtOAc and neutralization of the sodium salt with 3 N aq. HCl. The resulting solution was treated with the appropriate base (1 molar equiv) and stirred. The solution was then partially concentrated and was usually treated with an anti-solvent to obtain a crystalline solid. This crude solid was usually further purified by re-slurrying with an appropriate solvent, filtering, and drying the solids. Upon concentration, an oily solid precipitated. It was triturated with hexanes, collected, and dried overnight at 50° C. under vacuum.

Example 524

Tromethamine salt. The tromethamine salt was prepared according to the procedure described in Example 523. After stirring, the solvent was removed in vacuo. The resultant solids were dissolved in methanol, and concentrated again. The resulting solids were finally re-slurried with 1:1 EtOAc/hexanes at rt. The slurry was filtered and solids were dried under nitrogen. Semicrystalline.

Example 525

Tributylamine salt. The free acid was prepared according to the procedure described in Example 523, and then was concentrated to an oil. This material was solubilized in IPA (50 mL) and t-butylamine was added. The resultant slurry was stirred for 2 h at rt and filtered. The solids were dried at 40° C. overnight under vacuum. Crystalline; melting point 173.29° C. (decomposes), by DSC.

Example 526

Potassium salt. The potassium salt was prepared according to the procedure described in Example 523. After stirring, the solvent was removed in vacuo. The resultant residue was dissolved in toluene, and concentrated again. The resulting residue was triturated with n-heptane to yield an oily solid which was dried at 40° C. under vacuum. Semicrystalline.

Example 527

Ethylene diamine salt. The free acid was prepared according to the procedure described in Example 523, and then was concentrated to an oil. The acid was solubilized in EtOAc and ethylene diamine was added. $CH_3CN$ was added and the resultant slurry was stirred for 2 h. The solids were then filtered and air-dried. Crystalline; melting point 150.45° C., by DSC.

Assay Method

Cell Culture

CHO—K1 cells that had undergone stable transfection with the CCK-1 receptor were grown in DMEM supplemented with L-glutamine (2 mM), penicillin (50 units/mL) and streptomycin (50 μg/mL). Cells were cultured under continuous G418 selection (2 mM) and were harvested using a rubber cell scraper. CHO—K1 cells were sub-cultured a maximum of ten times before being reseeded from the original stocks.

Membrane Preparation

Membranes were prepared from the stably transfected CHO—K1 cells. Frozen cell pellets (−40° C.) were thawed in 14 mL of buffer A (10 mM HEPES, 130 mM NaCl, 4.7 mM KCl, 5 mM MgCl, 1 mM EGTA and 15.4 mg/100 mL bacitracin at pH 7.2), adapted from Harper et al. (Br. J. Pharmacol. (1996) 118, pp 1717-1726). The thawed pellets were homogenized using a Polytron PT-10 (7×1 s). The homogenates were centrifuged for 5 min at 1500 rpm (600× g), and the resulting pellets were discarded. The supernatants were re-centrifuged in order to collect the receptor-membrane pellets (25 min 15,000 rpm; 39,800× g), which were re-suspended in buffer A.

Incubation Conditions

All assays were conducted in 96-well plates (GF/B millipore filter plates) using buffer A, with 0.3 μM PD-134,308, for the dilutions. The CCK-2 receptor ligand was included to eliminate the contribution of this receptor subtype to the binding. For the optimal cell number determination experiments 20 pM [125I]-BH—CCK-8S (50 μL 60 pM solution) was incubated with a range of cell concentrations (2.5×105 to 12.5×105 cells/well) in a total volume of 150 μL. Total binding of [125I]-BH—CCK-8S was determined in the presence of 15 μL of buffer A. Non-specific binding of [125I]-BH—CCK-8S was determined in the presence of 15 μL of 100 μM 2-naphthalenesulphonyl L-aspartyl-(2-phenethyl)amide (2-NAP: see R. A. Hull et al., Br. J. Pharmacol. (1993) 108,pp 734-740), a CCK-1 receptor selective antagonist that is structurally unrelated to the radioligand [125I]-BH—CCK-8S. The assay preparation was incubated for 1 h at 21±3° C., and then the assay was terminated upon rapid filtration of the preparation under reduced pressure. The loaded filters were washed three times using undiluted PBS (100 μL), and then the residues were transferred to 5 mL scintillation tubes. Bound radioactivity was determined using a gamma counter (count time=1 min). From these experiments a cell concentration of 1 pellet in 40 mL of buffer (2.5×106 cells/mL) was chosen for use in other assays (below). To validate the radioligand concentration and incubation time for the assay, saturation and kinetic binding studies were also conducted (see M. F. Morton, The Pharmacological Characterization of Cholecystokinin Receptors in the Human Gastrointestinal Tract. PhD Thesis, University of London, 2000). The affinity of novel compounds was estimated by incubating membrane preparations with 15 μL of competing ligand (0.1 pM-1 mM) for 60 min at 21±3° C. The assay was then terminated according to the procedure outlined above.

Data Analysis

The pKi values were determined using the equation of Cheng and Prusoff (Biochem. Pharmacol. (1973) 22, pp 3099-3108):

$$K_i = \frac{IC_{50}}{1 + \frac{[L]}{K_D}}$$

To circumvent problems associated with computer-assisted data analysis of compounds with low affinity, the data obtained in the current study were weighted according to a method described by Morton (2000). In brief, 100% and 0% specific binding were defined independently using total binding and binding obtained in the presence of a high concentration of the reference antagonist, 2-NAP.

TABLE

| Example | pKi | Example | pKi | Example | pKi |
|---|---|---|---|---|---|
| 1 | 8.0 | 198 | 8.1 | 56 | 7.3 |
| 2 | 8.0 | 208 | 5.5 | 80 | 7.9 |
| 3 | 6.6 | 210 | 7.9 | 92 | 8.2 |
| 4 | 8.0 | 211 | 7.9 | 93 | 6.6 |
| 7 | 8.1 | 221 | 7.8 | 105 | 6.5 |
| 18 | 7.4 | 246 | 7.4 | 47 | 6.7 |
| 19 | 7.5 | 77 | 7.8 | 51 | 8.3 |
| 21 | 6.8 | 106 | 7.2 | 303 | 5.9 |
| 24 | 7.7 | 322 | 7.4 | 305 | 5.7 |
| 26 | 7.1 | 328 | 7.7 | 308 | 7.2 |
| 27 | 8.2 | 334 | 7.0 | 311 | 7.7 |
| 28 | 5.9 | 71 | 7.6 | 48 | 7.1 |
| 29 | 7.4 | 72 | 7.3 | 50 | 7.0 |
| 31 | 6.0 | 261 | 7.9 | 79 | 6.9 |
| 32 | 7.2 | 262 | 7.9 | 82 | 5.9 |
| 37 | 7.7 | 64 | 7.3 | 83 | 7.2 |

TABLE-continued

| Example | pKi | Example | pKi | Example | pKi |
|---|---|---|---|---|---|
| 40 | 8.1 | 65 | 5.7 | 88 | 7.4 |
| 42 | 8.2 | 66 | 7.7 | 90 | 6.1 |
| 43 | 7.0 | 68 | 6.6 | 86 | 8.4 |
| 46 | 7.7 | 74 | 8.2 | 87 | 7.6 |
| 145 | 7.8 | 129 | 7.8 | 91 | 7.9 |
| 148 | 7.8 | 131 | 6.9 | 101 | 7.8 |
| 151 | 6.7 | 132 | 8.0 | 104 | 7.4 |
| 152 | 7.9 | 136 | 8.2 | 349 | 7.1 |
| 153 | 7.8 | 137 | 8.0 | 352 | 7.5 |
| 155 | 8.0 | 138 | 7.5 | 75 | 7.1 |
| 157 | 7.9 | 335 | 7.5 | 110 | 7.9 |
| 167 | 7.9 | 54 | 7.4 | 111 | 8.4 |
| 168 | 8.1 | 58 | 6.3 | 112 | 8.4 |
| 170 | 8.1 | 59 | 8.5 | 115 | 8.2 |
| 177 | 7.9 | 60 | 8.3 | 118 | 8.3 |
| 181 | 7.8 | 271 | 7.8 | 120 | 8.0 |
| 182 | 7.9 | 275 | 7.7 | 121 | 8.1 |
| 189 | 7.4 | 276 | 8.2 | 122 | 8.8 |
| 190 | 8.0 | 287 | 7.7 | 123 | 6.6 |
| 195 | 8.0 | 52 | 8.0 | 124 | 7.4 |
|  |  |  |  | 363 | 6.1 |

Having described the invention in specific detail and exemplified the manner in which may be carried into practice, it will be apparent to those skilled in the art that innumerable variations, applications, modifications, and extensions of the basic principles involved may be made without departing from its spirit or scope. It is to be understood that the foregoing is merely exemplary and the present invention is not to be limited to the specific form or arrangements of parts herein described and shown.

What is claimed is:

1. A compound selected from the group consisting of 3-[5-(3,4-dichloro-phenyl)-1-(4-methoxy-phenyl)-1H-pyrazol-3-yl]-2-m-tolyl-propionate and its sodium salt.

2. (Z)-3-[5-Benzo[1,3]dioxol-5-yl-1-(2,5-dichloro-phenyl)-1H-pyrazol-3-yl]-2-(3-chloro-phenyl)-acrylic acid.

3. 5-{(S)-2-[5-(3,4-Dichloro-phenyl)-1-(4-methoxy-phenyl)-1H-pyrazol-3-yl]-1-m-tolyl-ethyl}-1H-tetrazole.

* * * * *